United States Patent
Griffiths et al.

(10) Patent No.: US 6,492,160 B1
(45) Date of Patent: *Dec. 10, 2002

(54) METHODS FOR PRODUCING MEMBERS OF SPECIFIC BINDING PAIRS

(75) Inventors: Andrew David Griffiths, Cambridge (GB); Samuel Cameron Williams, Cambridge (GB); Peter Michael Waterhouse, Canberra (AU); Ahuva Nissim, Cambridge (GB); Gregory Paul Winter, Cambridge (GB); Kevin Stuart Johnson, Cambridgeshire (GB); Andrew John Hammond Smith, Cambridge (GB)

(73) Assignees: Cambridge Antibody Technology Limited, Cambridgeshire (GB); Medical Research Council, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/104,337

(22) Filed: Jun. 25, 1998

Related U.S. Application Data

(63) Continuation of application No. 08/350,260, filed on Dec. 5, 1994, now Pat. No. 5,962,255, which is a continuation-in-part of application No. 08/307,619, filed as application No. PCT/GB93/00605 on Mar. 24, 1993, now Pat. No. 5,733,743, and a continuation-in-part of application No. 08/150,002, filed as application No. PCT/GB92/00883 on May 15, 1992, now Pat. No. 5,871,907.

(30) Foreign Application Priority Data

May 15, 1991 (GB) .............................................. 9110549
Mar. 24, 1992 (GB) .............................................. 9206318

(51) Int. Cl.⁷ ................................................. C12N 7/01
(52) U.S. Cl. ............................... 435/235.1; 435/320.1; 530/387.3; 530/388.1
(58) Field of Search .................... 435/235.1, 320.1, 435/6; 530/387.3, 388.1

(56) References Cited

U.S. PATENT DOCUMENTS

| | | | |
|---|---|---|---|
| 4,190,495 A | 2/1980 | Curtiss, III | ................. 435/440 |
| 4,816,397 A | 3/1989 | Bass et al. | ................. 435/69.1 |
| 4,946,778 A | 8/1990 | Ladner et al. | ............. 435/69.6 |
| 5,223,409 A | 6/1993 | Ladner et al. | ............. 435/69.7 |

FOREIGN PATENT DOCUMENTS

| | | |
|---|---|---|
| AU | B 27617/88 | 7/1989 |
| EP | 0 324 162 A1 | 12/1988 |
| WO | WO 88/06630 | 9/1988 |
| WO | WO 88/09344 | 12/1988 |
| WO | WO 90/02809 | 3/1990 |
| WO | WO 90/05144 | 5/1990 |
| WO | WO 90/14424 | 11/1990 |
| WO | WO 90/14430 | 11/1990 |
| WO | WO 90/14443 | 11/1990 |
| WO | WO 91/10737 | 7/1991 |
| WO | WO 91/17271 | 11/1991 |
| WO | WO 92/01047 | 1/1992 |
| WO | WO 92/06204 | 4/1992 |
| WO | WO 92/09690 | 6/1992 |
| WO | WO 92/18619 | 10/1992 |
| WO | WO 92/20791 | 11/1992 |

OTHER PUBLICATIONS

Bass et al., "Hormone Phage: An Enrichment Method for Variant Proteins With Altered Binding Properties," *Proteins*, 8(4):309–314 (1990).

de la Cruz et al., "Immunogenicity and Epitope Mapping of Foreign Sequences via Genetically Engineered Filamentous Phage," *J. Biol. Chem.*, 263(9):4318–4322 (Mar. 25, 1988).

Huse et al., "Generation of a Large Combinatorial Library of the Immunoglobulin Repertoire in Phage Lambda," *Science*, 246:1275–1281 (1989).

Kang et al., "Linkage of Recognition and Replication Functions by Assembly Combinatorial Antibody Fab Libraries Along Phage Surface," *Proc. Nat'l Acad. Sci., USA*, 88(10):4364–4366 (May 15, 1991).

McCafferty et al., "Phage Antibodies: Filamentous Phage Displaying Antibody Variable Domains," *Nature*, 348:552–554 (1990).

Milstein, C., "The Croonian Lecture, 1989. Antibodies: A Paradigm for the Biology of Molecular Recognition," *Proc. R. Soc. London, B. Biol. Sci.*, 239:1–16 (1990).

Parmley & Smith, "Antibody–selectable Filamentous fd Phage Vectors: Affinity Purification of Target Genes," *Gene*, 73(2):305–318 (Dec. 20, 1988).

Short et al., "Lambda ZAP: A Bacteriophage Lambda Expression Vector with In Vivo Excision Properties," *Nucleic Acids Research*, 16(15):7583–7600 (Aug. 11, 1988).

Smith, "Filamentous Fusion Phage: Novel Expression Vectors that Display Cloned Antigens on the Virion Surface," *Science*, 228(4705):1315–1317 (Jun. 14, 1985).

Tsunetsugu–Yokota et al., "Expression of an Immunogenic Region of HIV by a Filamentous Bacteriophage Vector," *Gene*, 99(2):261–265 (Mar. 15, 1991).

(List continued on next page.)

Primary Examiner—James Ketter
(74) Attorney, Agent, or Firm—Marshall, Gerstein & Borun.

(57) ABSTRACT

Methods, recombinant host cells and kits are disclosed-for the production of members of specific binding pairs (sbp), e.g. antibodies, using display on the surface of secreted replicable genetic display packages (rgdps), e.g. filamentous phage. To produce a library of great diversity recombination occurs between first and second vectors comprising nucleic acid encoding first and second polypeptide chains of sbp members respectively, thereby producing recombinant vectors each encoding both a first and a second polypeptide chain component of a sbp member. The recombination may take place in vitro or intracellularly and may be site-specific, e.g. involving use of the loxP sequence and mutants thereof. Recombination may take place after prior screening or selecting for rgdps displaying sbp members which bind complementary sbp member of interest.

36 Claims, 34 Drawing Sheets

OTHER PUBLICATIONS

Winter & Milstein, "Man–made Antibodies," *Nature*, 349(6307):293–299 (Jan. 24, 1991).

Abremski et al., "Studies on the Properties of P1 Site–Specific Recombination: Evidence for Topologically Unlinked Products following Recombination," *Cell*, 32:1301–1311 (Apr., 1983).

Better et al., "*Escherichia coli* Secretion of an Active Chimeric Antibody Fragment," *Science*, 240:1041–1043 (1988).

Boyd, A.C., "Turbo Cloning: A Fast, Efficient Method for Cloning PCR Products and Other Blunt–ended DNA Fragments into Plasmids," *Nucleic Acids Research*, 21(4):817–821 (1993).

Clonetech, *cDNA & Genomic Libraries*, Clontech Laboratories, Inc., Palo Alto, California, USA, pp. 75–96 & 192 (1995/1996).

Cregg et al., "Short Communication: Use of Site–Specific Recombination to Regenerate Selectable Markers," *Mol. Gen. Genet.*, 219:320–323 (1989).

Dale et al., "Gene Transfer with Subsequent Removal of the Selection Gene from the Host Genome," *Proc. Nat'l Acad. Sci., USA*, 88:10558–10562 (Dec., 1991).

Dower et al., "High Efficiency Transformation of *E. coli* by High Voltage Electroporation," *Nucleic Acids Research*, 16(13):6127–6145 (1988).

Fukushige et al., "Genomic Targeting with a Positive–selection lox Integration Vector Allows Highly Reproducible Gene Expression in Mammalian Cells," *Proc. Nat'l Acad. Sci.*, 89:7905–7909.

Griffiths et al., "Isolation of High Affinity Human Antibodies Directly from Large Synthetic Repertoires," *EMBO J.*, 13(14):3245–3260 (1994).

Hoess et al., "The Cre–lox Recombination System," *Nucleic Acids and Molecular Biology*, vol. 4, Eckstein et al., (Eds.), Springer–Verlag Berlin Heidelberg, pp. 99–109 (1990).

Hoess et al., "The Role of the loxP Spacer Region in P1 Site–Specific Recombination," *Nucleic Acids Research*, 14(5):2287–2300 (1986).

Landy, A., "Mechanistic and Structural Complexity in the Site–specific Recombination Pathways of Int and FLP," *Current Opinion in Genetics and Development*, 3:699–707 (1993).

Lane et al., "Epitope Mapping Using Bacteriophage Peptide Libraries," *Curr. Opin. Immunol.*, 5:268–271 (1993).

Neidhardt, F.C., (Ed.), *Escherichia coli* and *Salmonella typhimurium*, Cellular & Molecular Biology, American Society of Microbiology, Washington, D.C., pp. 1034–1043, 1054–1060, 1061–1070 (1987).

Orban et al., "Tissue– and Site–Specific DNA Recombination in Transgenic Mice," *Proc. Nat'l Acad. Sci., USA*, 89:6861–6865 (Aug., 1992).

Palazzolo et al., "Phage Lambda cDNA Cloning Vectors for Subtractive Hybridization, Fusion–protein Synthesis and Cre–loxP Automatic Plasmid Subcloning," *Gene*, 88:25–36 (1990).

Parmley et al., "Filamentous Fusion Phage Cloning Vectors for the Study of Epitopes and Design of Vaccines," *Adv. Exp. Med. Biol.* 215–218 (1989).

Peakman et al., "Highly Efficient Generation of Recombinant Baculoviruses by Enzymatically Mediated Site–Specific In Vitro Recombination," *Nucleic Acids Research*, 20(3):495–500 (1992).

Präve, P., (Ed.), *Fundamentals of Biotechnology*, VCH, Weinheim, Germany, pp. 307–308 (1987).

Qian et al., "Reactions between Half– and Full–FLP Recombination Target Sites," *J. Biol. Chem.*, 267(11):7794–7805 (Apr. 15, 1992).

Sambrook et al., "Transformation of *E. coli* by High–voltage Electroporation Electrotransformation," *Molecular Cloning, A Laboratory Manual*, Second Edition, Cold Spring Harbor Laboratory Press, Cold Spring Harbor, New York, p. 1.75 (1989).

Siest et al., "Application of Gene Transfer Technologies to the Production of Enzyme Reference Materials: Example of Gamma–Glutamyltransferase," *Clin. Chem.*, 39:1573–1589 (1993).

Skerra et al., "Assembly of a Functional Immunoglobulin $F_v$ Fragment in *Escherichia coli*," *Science*, 240:1038–1041 (1988).

Waterhouse et al., "Combinatorial Infection and In Vivo Recombination: A Strategy for Making Large Phage Antibody Repertoires," *Nucleic Acids Research*, 21(9):2265–2266 (1993).

Gage et al., "A Cell–Free Recombination System for Site–Specific Integration of Multigenic Shuttle Plasmids into the Herpes Simplex Type 1 Genome," *J. of Virology*, 66(9):5509–5515 (Sep., 1992).

Hoekstra et al., "A Tn3 Derivative That Can Be Used to Make Short In–Frame Insertions Within Genes," *Proc. Nat'l Acad. Sci., USA*, 88:5457–5461 (Jun., 1991).

Maruyama and Brenner, "A Selective λ Phage Cloning Vector With Automatic Excision of the Insert in a Plasmid," *Gene*, 120:135–141 (1992).

Russell et al., "Directed Excision of a Transgene from the Plant Genome," *Mol. Genet. Gene.*, 234:49–59 (1992).

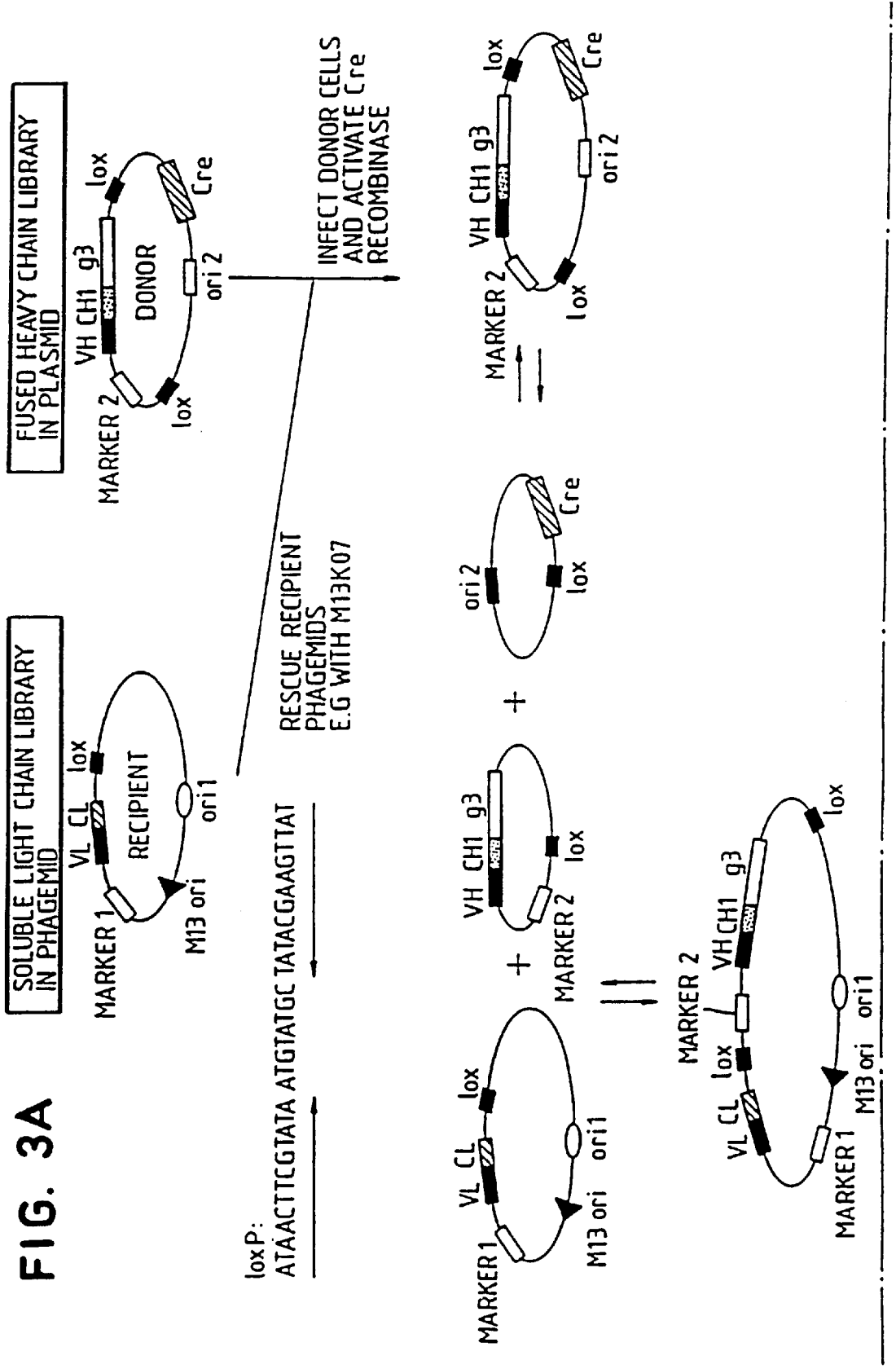

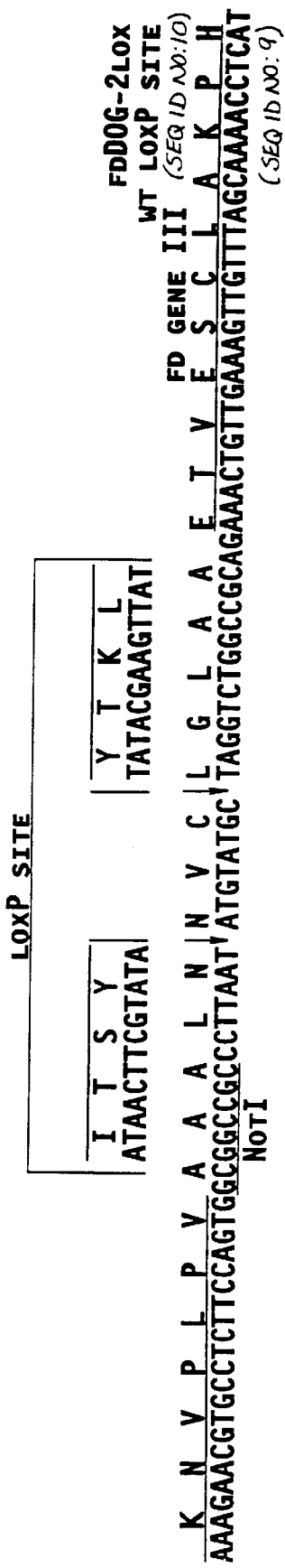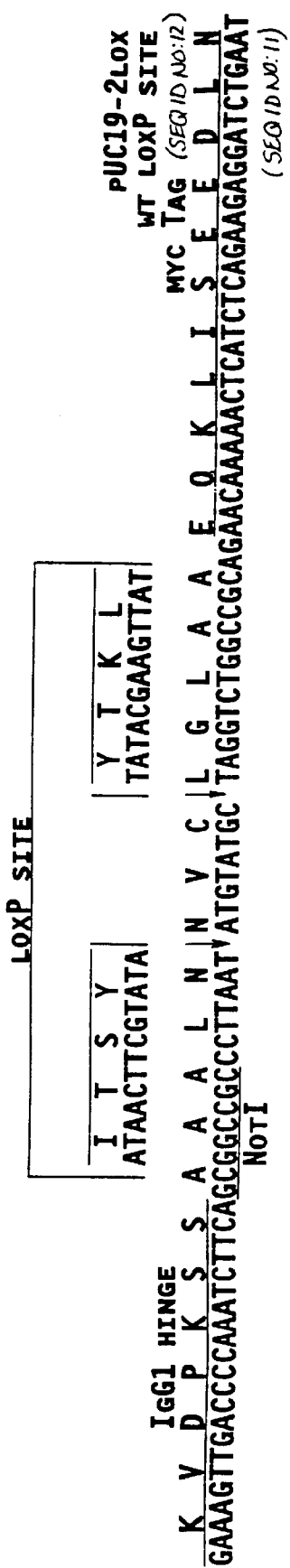
FIG. 4B

```
C KAPPA                          LoxP SITE
  G  E  C  *  *         |ATAACTTCGTATA|       |TATACGAAGTTAT|                          FdDOG-2Lox
GGAGAGTGTTAATAAGGGCGGCCAAAGCTTCCTTAAT↓ATGTATAC\TAGGTCGCATGCAAATTCTATTTCAAGGAGACAGTCATAATGAAA   LoxP 511 SITE
                       AscI HindIII        #                                          LEADER
                                                                                       M  K
                                                      R.B.S.                  (SEQ ID NO:7)

LoxP SITE
                       |ATAACTTCGTATA|       |TATACGAAGTTAT|                          PUC19-2Lox
AACAGCTATGACCATGATTACGCCAAGCTTCCTTAAT↓ATGTATAC\TAGGTCGCATGCAAATTCTATTTCAAGGAGACAGTCATAATGAAA   LoxP 511 SITE
                      HindIII          #                                              LEADER
                                                                                       M  K
                                                     R.B.S.                    (SEQ ID NO:8)

FIG. 4B-1
```

FIG. 5A
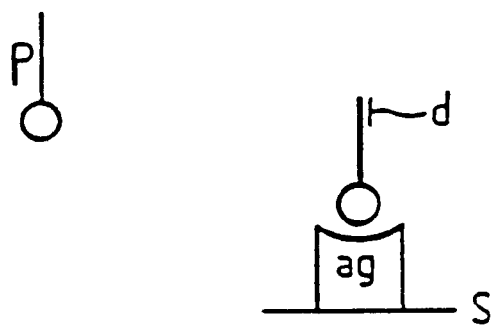
FIG. 5B
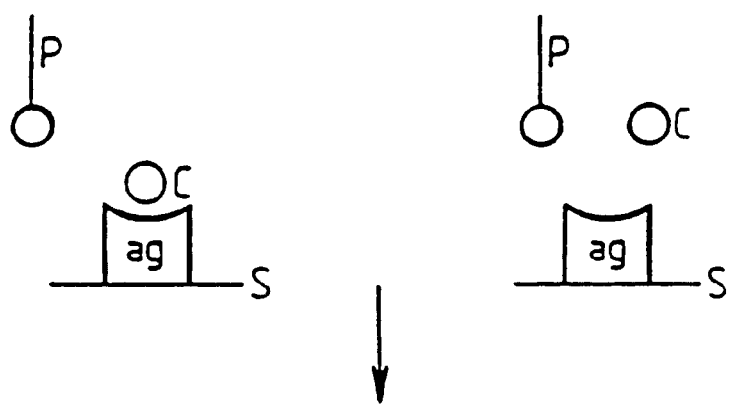

Fig 6A  V_H

CDR1  CDR2  CDR3
FR1 FR2 FR3 FR4

V Y Y C A R              W G Q G T L
GTG TAT TAC TGT GCA AGA (NNT/G)$_{4-12}$ TGG GGC CAA GGT ACC CTG

Fig. 6B  V_K

CDR1  CDR2  CDR3
FR1 FR2 FR3 FR4

T   F C
Y Y C Q K Y N S A              
TAT TAC TGT CAA AAG TAT AAC AGT GCC CNN (NNT/G)$_{0-2}$ ACG TTC GGC

Fig. 6C  Vλ

CDR1  CDR2  CDR3
FR1 FR2 FR3 FR4

V   F G
Y Y C C S Y A G S Y              
TAT TAC TCC TCA TAT CCA CCC ACC TAC (NNT/G)$_{0-3}$ GTA TTC GGC

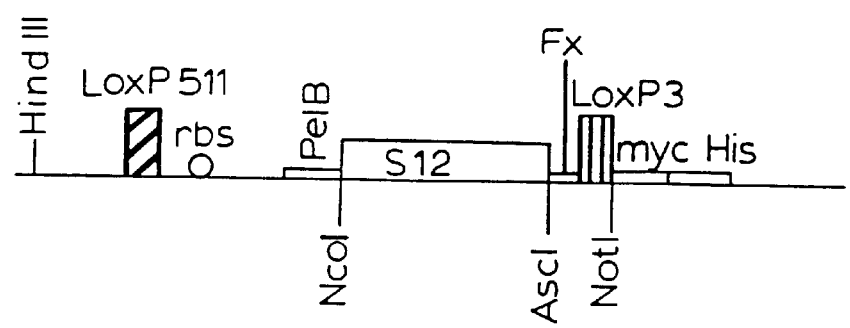
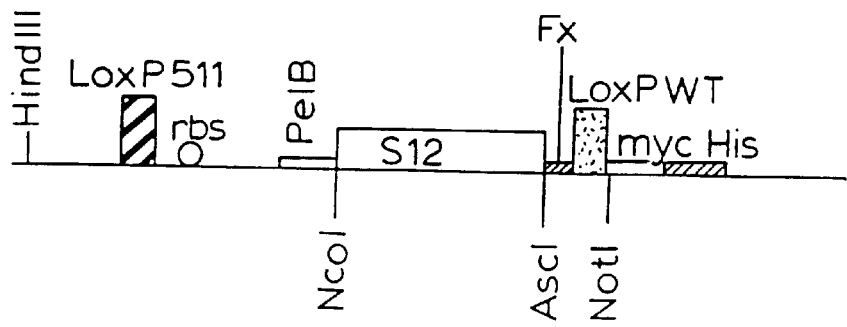
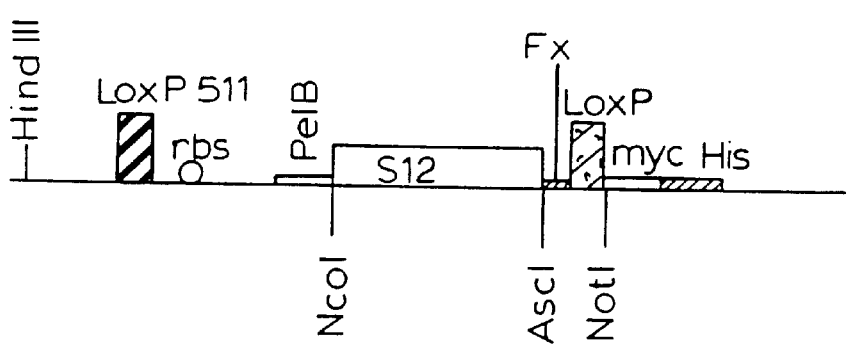
Fig. 19C

METHODS FOR PRODUCING MEMBERS OF SPECIFIC BINDING PAIRS

CROSS REFERENCE TO RELATED APPLICATIONS

This application is a continuation of U.S. Ser. No. 08/350,260 filed Dec. 5, 1994, issued as U.S. Pat. No. 5,962,255, which in turn is a continuation-in-part of U.S. Ser. No. 08/307,619 filed Sep. 16, 1994, issued as U.S. Pat. No. 5,733,743, which in turn is a 371 application of PCT/GB93/00605 filed Mar. 24, 1993, now abandoned, and a continuation-in-part of U.S. Ser. No. 08/150,002 filed March 31, 1994, issued as U.S. Pat. No. 5,871,907, and which in turn is a 371 application of PCT/GB92100883, filed May 15, 1992. Additionally, this application claims priority under 35 U.S.C. Section 119 of application No. 9110549.4 filed May 15, 1991 in Great Britain, application No. 9206318.9 filed Mar. 24, 1992 in Great Britain, and PCT/GB91/01134 filed Jul. 10, 1991, now abandoned.

FIELD OF THE INVENTION

The present invention relates to methods for producing members of specific binding pairs (sbp). In particular, the present invention relates to methods for producing members of specific binding pairs involving recombination between vectors which comprise nucleic acid encoding polypeptide chain components of sbp members.

BACKGROUND OF THE INVENTION

Structurally, the simplest antibody (IgG) comprises four polypeptide chains, two heavy (H) chains and two light (L) chains inter-connected by disulphide bonds. The light chains exist in two distinct forms called kappa (K) and lambda (λ). Each chain has a constant region. (C) and a variable region (V). Each chain is organized into a series of domains. The light chains have two domains, corresponding to the C region and the other to the V region. The heavy chains have four domains, one corresponding to the V region and three domains (1,2 and 3) in the C region. The antibody has two arms (each arm being a Fab region), each of which has a VL and a VH region associated with each other. It is this pair of V regions (VL and VH) that differ from one antibody to another (owing to amino acid sequence variations), and which together are responsible for recognising the antigen and providing an antigen binding site (ABS). In even more detail, each V region is made up from three complementarity determining regions (CDR) separated by four framework regions (FR). The CDR's are the most variable part of the variable regions, and they perform the critical antigen binding function.

The CDR regions are derived from many potential germ line sequences via a complex process involving recombination, mutation and selection.

It has been shown that the function of binding antigens can be performed by fragments of a whole antibody. Example binding fragments are (i) the Fab fragment consisting of the VL, VH, CL and CH1 domains; (ii) the Fd fragment consisting of the VH and CH1 domains; (iii) the Fv fragment consisting of the VL and VH domains of a single arm of an antibody, (iv) the dAb fragment (Ward et al., Nature 341:544–546 (1989)) which consists of a VH domain; (v) isolated CDR regions; and (vi) F(ab')₂ fragments, a bivalent fragment comprising two Fab fragments linked by a disulphide bridge at the hinge region.

Although the two domains of the Fv fragment are coded for by separate genes, it has proved possible to make a synthetic linker that enables them to be made as a single protein chain (known as single chain Fv (scFv));

Bird et al., Science 242:423–426 (1988); Huston et al., Proc. Natl. Acad. Sci., USA 85:5879–5883 (1988)) by recombinant methods. These scFv fragments were assembled from genes from monoclonals that had been previously isolated.

Bacteriophage have been constructed that express and display at their surface a large biologically functional binding molecule (e.g. antibody fragments, and enzymes and receptors) and which remain intact and infectious. This is described in WO 92/01047, the disclosure of which is herein incorporated by reference. Readers of the present document are urged to consult WO 92/01047 for detailed explanation of many of the procedures used in the experiments described herein. The applicants have called the structure which comprises a virus particle and a binding molecule displayed at the viral surface a "package". Where the binding molecule is an antibody, an antibody derivative or fragment, or a domain that is homologous to an immunoglobulin domain, the applicants call the package a "phage antibody" (pAb). However, except where the context demands otherwise, where the term phage antibody is used generally, it should also be interpreted as referring to any package comprising a virus particle and a biologically functional binding molecule displayed at the viral surface.

pAbs have a range of applications in selecting antibody genes encoding antigen binding activities. For example, pAbs could be used for the cloning and rescue of hybridomas (Orlandi et al., Proc. Natl. Acad. Sci. USA, 86:3833–3837 (1989)), and in the screening of large combinatorial libraries (such as found in Huse et al., Science 246:1275–1281 (1989)). In particular, rounds of selection using pAbs may help in rescuing the higher affinity antibodies from the latter libraries. It may be preferable to screen small libraries derived from antigen-selected cells (Casali et al., Science 234:476–479 (1986)) to rescue the original VH/VL pairs comprising the Fv region of an antibody. The use of pAbs may also allow the construction of entirely synthetic antibodies. Furthermore, antibodies may be made which have some synthetic sequences e.g. CDRs, and some naturally derived sequences. For example, V-gene repertoires could be made in vitro by combining un-rearranged V genes, with D and J segments. Libraries of pAbs could then be selected by binding to antigen, hyper-mutated in vitro in the antigen-binding loops or V domain framework regions, and subjected to further rounds of selection and mutagenesis.

The demonstration that a functional antigen-binding domain can be displayed on the surface of phage, has implications beyond the construction of novel antibodies. For example, if other protein domains can be displayed at the surface of a phage, phage vectors could be used to clone and select genes by the binding properties of the displayed protein. Furthermore, variants of proteins, including epitope libraries built into the surface of the protein, could be made and readily selected for binding activities. In effect, other protein architectures might serve as "nouvelle" antibodies.

The technique provides the possibility of building antibodies from first principles, taking advantage of the structural framework on which the antigen binding loops fold. In general, these loops have a limited number of conformations which generate a variety of binding sites by alternative loop combinations and by diverse side chains. Recent successes in modelling antigen binding sites augurs well for de novo design. In any case, a high resolution structure of the antigen is needed. However, the approach is attractive for making e.g. catalytic antibodies, particularly for small substrates. Here side chains or binding sites for prosthetic groups might be introduced, not only to bind selectively to the transition state of the substrate, but also to participate directly in bond making and breaking. The only question is whether. the antibody architecture, specialised for binding, is the best starting point for building catalysts.

Genuine enzyme architectures, such as the triose phosphate isomerase (TIM) barrel, might be more suitable. Like antibodies, TIM enzymes also have a framework structure (a barrel of β-strands and α-helices) and loops to bind substrate. Many enzymes with a diversity of catalytic properties are based on this architecture and the loops might be manipulated independently on the frameworks for design of new catalytic and binding properties. The phage selection system as provided by the present disclosure can be used to select for antigen binding activities and the CDR loops thus selected, used on either an antibody framework or a TIM barrel framework. Loops placed on a e.g. a TIM barrel framework could be further modified by mutagenesis and subjected to further selection.

One class of molecules that could be useful in this type of application are receptors. For example, a specific receptor could be displayed on the surface of the phage such that it would bind its ligand. The receptor could then be modified by, for example, in vitro mutagenesis and variants having higher binding affinity for the ligand selected. The selection may be carried out according to one or more of the formats described below.

Alternatively, the phage-receptor could be used as the basis of a rapid screening system for the binding of ligands, altered ligands, or potential drug candidates. The advantages of this system namely of simple cloning, convenient expression, standard reagents and easy handling makes the drug screening application particularly attractive. In the context of this discussion, receptor means a molecule that binds a specific, or group of specific, ligand(s). The natural receptor could be expressed on the surface of a population of cells, or it could be the extracellular domain of such a molecule (whether such a form exists naturally or not), or a soluble molecule performing a natural binding function in the plasma, or within a cell or organ.

Another possibility, is the display of an enzyme molecule or active site of an enzyme molecule on the surface of a phage (see examples 11, 12, 30, 31, 32 and 36 of WO 92/01047). Once the phage enzyme is expressed, it can be selected by affinity chromatography, for instance on columns derivatized with transition state analogues. If an enzyme with a different or modified specificity is desired, it may be possible to mutate an enzyme displayed as a fusion on bacteriophage and then select on a column derivatised with an analogue selected to have a higher affinity for an enzyme with the desired modified specificity.

Although throughout this application, the applicants discuss the possibility of screening for higher affinity variants of pAbs, they recognise that in some applications, for example low affinity chromatography (Ohlson, S. et al Anal. Biochem. 169, p204–208 (1988)), it may be desirable to isolate lower affinity variants.

pAbs also allow the selection of antibodies for improved stability. It has been noted for many antibodies, that yield and stability are improved when the antibodies are expressed at 30° C. rather than 37° C. If pAbs are displayed at 37° C., only those which are stable will be available for affinity selection. When antibodies are to be used in vivo for therapeutic or diagnostic purposes, increased stability would extend the half-fife of antibodies in circulation.

Although stability is important for all antibodies and antibody domains selected using phage, it is particularly important for the selection of Fv fragments which are formed by the non-covalent association of VH and VL fragments. Fv fragments have a tendency to dissociate and have a much reduced half-life in circulation compared to whole antibodies. Fv fragments are displayed on the surface of phage, by the association of one chain expressed as a gene m protein fusion with the complementary chain expressed as a soluble fragment. If pairs of chains have a high tendency to dissociate, they will be much less likely to be selected as pAbs. Therefore, the population will be enriched for pairs which do associate stably. Although dissociation is less of a problem with Fab fragments, selection would also occur for Fab fragments which associate stably. pAbs allow selection for stability to protease attack, only those pAbs that are not cleaved by proteases will be capable of binding their ligand and therefore populations of phage will be enriched for those displaying stable antibody domains.

The technique of displaying binding molecules on the phage surface can also be used as a primary cloning system. For example, a cDNA library can be constructed and inserted into the bacteriophage and this phage library screened for the ability to bind a ligand. The ligand/binding molecule combination could include any pair of molecules with an ability to specifically bind to one another e.g. receptor/ligand, enzyme/substrate (or analogue), nucleic acid binding protein/nucleic acid etc. If one member of the complementary pair is available, this may be a preferred way of isolating a clone for the other member of the pair.

The first functional antibody molecules to be expressed on the surface of filamentous phage were single-chain Fv's (scFv), ed because heavy and light chain variable domains, normally on two separate proteins, are covalently joined by a flexible linker peptide. Alternative expression strategies have also been successful. Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each fab molecule assemble post-translationally and the dimer is incorporated into the phage particle via linkage of one of the chains to g3p.

More recent cloning has been performed with 'phagemid' vectors which have ca. 100-fold higher transformation efficiencies than phage DNA. These are plasmids containing the intergenic region from filamentous phages which enables single-stranded copies of the phagemid DNA to be produced, and packaged into infectious filamentous particles when cells harbouring them are infected with 'helper' phages providing the phage components in trans. When phagemids contain gIII fused to an antibody gene (e.g. pHEN-1), the resulting fusion protein is displayed on the phagemid particle (Hoogenboom et al., *Nucleic Acids Res.* 19(1S):4133–4137 (1991)). Multi-subunit proteins on the surface of filamentous phage: methodologies for displaying antibody (Fab) heavy and light chains. Efficient strategies have been developed for cloning antibody genes, a factor which becomes most important when dealing with large numbers of different antibody fragments such as repertoires.

The cloning vector fd-DOG-1 was used in early work with phage antibody repertoires in which scFv fragments were derived from spleen mRNA of mice immunised with the hapten oxazalone (Clackson et al., *Nature* 352:624–628 (1991)). Making antibody fragments using phage display libraries. VH and VL domains were separately amplified then linked at random via a short DNA fragment encoding the scFv linker peptide to produce a library of approximately $10^5$ different clones. This was panned against the immunising antigen to select combinations of VH and VL which produced functional antibodies. Several binders were isolated, one in particular having an affinity not far below that of the best monoclonal antibodies produced by conventional hybridoma technology.

In a mouse, at any one time there are approximately $10^7$ possible H chains and $10^5$ possible L chains, making a total of $10^{12}$ possible VH:VL combinations when the two chains are combined at random (these figures are estimates and simply provide a rough guide to repertoire size). By these figures, the above mouse library sampled only 1 in $10^7$ of the possible VH:VL combinations. It is likely that good affinity antibodies were isolated in the work described in the preceeding paragraph because the spleen cells derived from an immunised donor in which B cells capable of recognising the antigen are clonally expanded and producing large quantities of Ig mRNA. The low library complexity in this experiment is partly due to the intrinsically low transformation efficiency of phage DNA compared to plasmid (or phagemid).

Marks et al. (Marks et al., By-Passing Immunization: Human Antibodies from V-Gene Libraries Displayed on Phage. *J. Mol. Biol.* 222:581–597 (1991)) and WO92/01047 describe construction of an antibody repertoire from unimmunised humans cloned in the phagemid pHEN-1. This library, consisting of $3 \times 10^7$ clones has so far yielded specific antibodies to many different antigens. These antibodies tend to have the moderate affinities expected of a primary immune response, demonstrating that usable antibodies to a range of structurally diverse antigens can indeed be isolated from a single resource.

New binders can be created from clones isolated from phage antibody libraries using a procedure called 'chain-shuffling'. In this process one of the two chains is fixed and the other varied. For example, by fixing the heavy chain from the highest affinity mouse anti-OX phage antibody and recloning the repertoire of light chains alongside it, libraries of $4 \times 10^7$ were constructed. Several new OX-binders were isolated, and the majority of these had light chains that were distinct from those first isolated and considerably more diverse. These observations reflect the fact that a small library is sufficient to tap the available diversity when only one chain is varied, a useful procedure if the original library was not sufficiently large to contain the available diversity.

The size of the library is of critical importance. This is especially true when attempting to isolate antibodies from a naive human repertoire, but is equally relevant to isolation of the highest affinity antibodies from an immunised source.

It is clear that while phage display is an exceptionally powerful tool for cloning and selecting antibody genes, we are tapping only the tiniest fraction of the potential diversity using existing technology. Transformation efficiencies place the greatest limitation on library size with $10^9$ being about the limit using current methods. Rough calculations suggest that this is several orders of magnitude below the target efficiency; more rigourous analysis confirms it.

Perelson and Oster have given theoretical consideration to the relationship between size of the immune repertoire and the likelihood of generating an antibody capable recognising a given epitope with greater than a certain threshold affinity, K. The relationship is described by the equation:

$$P = e^{-N(p[K])}$$

Where P=probability that an epitope is not recognised with an affinity above the threshold value K by any antibody in the repertoire, N=number of different antibodies in the repertoire, and p[K]=probability that an individual antibody recognises a random epitope with an affinity above the threshold value K In this analysis p[K] is inversely proportional to affinity, although an algorithm describing this relationship precisely has not been deduced. Despite this, it is apparent that the higher the affinity of the antibody, the lower its p[K] and the larger the repertoire needs to be to achieve a reasonable probability of isolating that antibody. The other important feature is that the function is exponential; as shown in FIG. 1, a small change in library size can have either a negligible or a dramatic effect on the probability of isolating an antibody with a given p[K] value, depending upon what point on the curve is given by the library size.

WO 92/01047 and WO92/20791 (also incorporated herein by reference) describe how the limitations of transformation efficiency (and therefore the upper limit on library size) can be overcome by use of other methods for introducing DNA into cells, such as infection. In one configuration, heavy and light chain genes are cloned separately on two different replicons, at least one of which is capable of being incorporated into a filamentous particle. Infectious particles carrying one chain are infected into cells harbouring the complementary chain; infection frequencies of >90% can be readily achieved. Heavy and light chains are then able to associate post-translationally in the periplasm and the combination displayed on the surface of the filamentous particle by virtue of one or both chains being connected to g3p. For example, a library of $10^7$ heavy chains is cloned as an unfused population in a phagemid, and $10^7$ light chains are cloned as g3 fusions in fd-DOG-1. Both populations are then expanded by growth such that there are $10^7$ of each heavy chain-containing cell and $10^7$ copies of each light chain phage. By allowing the phage to infect the cells, $10^7 \times 10^7 = 10^{14}$ unique combinations can be created, because there are $10^7$ cells carrying the same heavy chain which can each be infected by $10^7$ phage carrying different light chains. When this is repeated for each different heavy chain clone then one ends up with up to $10^{14}$ different heavy/light combinations in different cells. This strategy is outlined in FIG. 2, which shows the heavy chain cloned as g3 fusions on phage and the light chains expressed as soluble fragments from a phagemid. Clearly, the reverse combination, light chains on phage, heavy chain on phagemid, is also tenable.

In the configuration shown in FIG. 2, fd-DOG 'rescues' the phagemid so that both phage and phagemid DNA is packaged into filamentous particles, and both types will have paired heavy and light chains on their surface, despite having the genetic information for only one of them. For a given antigen or epitope, the vast majority of the heavy and light chain pairings will be non-functional (i.e. will not bind that antigen or epitope), so that selection on antigen will have the effect of vastly reducing the complexity of the heavy and light chain populations. After the first round of selection the clones are re-assorted, for example by infecting fresh host cells and selecting for both replicons. After several rounds of antigen selection and recovery of the two replicons, the considerably reduced heavy and light chain populations can be cloned onto the same replicon and analysed by conventional means. Selection from the, say, $10^{14}$ combinations produces a population of phages displaying a particular combination of H and L chains having the desired specificity. The phages selected however, will only contain DNA encoding one partner of the paired H and L chains. Selection for the two replicons may be as follows. Vectors of the H chain library may encode tetracycline resistance, with vectors of the L chain library encoding ampicillin resistance. The sample elute containing the population is divided into two portions. A first portion is grown on e.g. tetracycline plates to select those bacteriophage containing DNA encoding H chains which are involved in the desired antigen binding. A second portion is grown on e.g. ampicillin plates to select those bacteriophage containing phagemid DNA encoding L chains which are involved in the desired antigen binding. A set of colonies from individually isolated clones e.g. from the tetracycline plates are then used to infect specific colonies e.g. from the ampicillin plates. This results in bacteriophage expressing specific combinations of H and L chains which can then be assayed for antigen binding.

One technical problem with the use of separate replicons for VL and VH chains is so-called 'interference' between filamentous phage origins of replication carried on different replicons as a result of competition for the same replication machinery.

Procedures have been described which work on the principle of first reducing the complexity of a repertoire then recloning one or both chains of the reduced population (WO92/20791). The present invention provides a different approach.

TERMINOLOGY

Much of the terminology discussed in this section has been mentioned in the text where appropriate.

Specific Binding Pair (sbp)

This describes a pair of molecules (each being a member of a specific binding pair) which are naturally derived or synthetically produced. One of the pair of molecules, has an area on its surface, or a cavity which specifically binds to, and is therefore defined as complementary with a particular spatial and polar organisation of the other molecule, so that the pair have the property of binding specifically to each other. Examples of types of specific binding pairs are antigen-antibody, biotin-avidin, hormone-hormone receptor, receptor-ligand, enzyme-substrate, IgG-protein A.

Multimeric Member

This describes a first polypeptide which will associate with at least a second polypeptide, when the polypeptides are expressed in free form and/or on the surface of a substrate. The substrate may be provided by a bacteriophage. Where there are two associated polypeptides, the associated polypeptide complex is a-dimer, where there are three, a trimer etc. The dimer, trimer, multimer etc or the multimeric member may comprise a member of a specific binding pair.

Example multimeric members are heavy domains based on an immunoglobulin molecule, light domains based on an immunoglobulin molecule, T-cell receptor subunits.

Replicable Genetic Display Package (Rgdp)

This describes a biological particle which has genetic information providing the particle with the ability to replicate. The particle can display on its surface at least part of a polypeptide. The polypeptide can be encoded by genetic information native to the particle and/or artificially placed into the particle or an ancestor of it. The displayed polypeptide may be any member of a specific binding pair e.g. heavy or light chain domains based on an immunoglobulin molecule, an enzyme or a receptor etc.

The particle may be a virus e.g. a bacteriophage such as fd or M13 or other viruses.

Package

This describes a replicable genetic display package in which the particle is displaying a member of a specific binding pair at its surface. The package may be a bacteriophage which displays an ,antigen binding domain at its surface. This type of package has been called a phage antibody (pAb).

Antibody

This describes an immunoglobulin whether natural or partly or wholly synthetically produced. The term also covers any protein having a binding domain which is homologous to. an immunoglobulin binding domain. These proteins can be derived from. natural sources, or partly or wholly synthetically produced.

Example antibodies are the immunoglobulin isotypes and the Fab, $F(ab^1)_2$, scFv, Fv, dAb, Fd fragments.

Immunoglobulin Superfamily

This describes a family of polypeptides, the members of which have at least one domain with a structure related to that of the variable or constant domain of immunoglobulin molecules. The domain contains two β-sheets and usually a conserved disulphide bond (see A. F. Williams and A. N. Barclay, *Ann. Rev Immunol.* 6:381–405 (1988)).

Example members of an immunoglobulin superfamily are CD4, platelet derived growth factor receptor (PDGFR), intercellular adhesion molecule. (ICAM). Except where the context otherwise dictates, reference to immunoglobulins and immunoglobulin homologs in this application includes members of the immunoglobulin superfamily and homologs thereof.

Homologs

This term indicates polypeptides having the same or conserved residues at a corresponding position in their primary, secondary or tertiary structure. The term also extends to two or more nucleotide sequences encoding the homologous polypeptides.

Example homologous peptides are the immunoglobulin isotypes.

Functional

In relation to a sbp member displayed on the surface of a rgdp, means that the sbp member is presented in a folded form in which its specific binding domain for its complementary sbp member is the same or closely analogous to its native configuration, whereby it exhibits similar specificity with respect to the complementary sbp member. In this respect, it differs from the peptides of Smith et al, supra, which do not have a definite folded configuration and can assume a variety of configurations determined by the complementary members with which they may be contacted.

Genetically Diverse Population

In connection with sbp members or polypeptide components thereof, this is referring not only to diversity that can exist in the natural population of cells or organisms, but also. diversity that can be created by artificial mutation in vitro or in vivo.

Mutation in vitro may for example, involve random mutagenesis using oligonucleotides having random mutations of the sequence desired to be varied. In vivo mutagenesis may for example, use mutator strains of host microorganisms to harbour the DNA (see Example 38 of WO 92/01047). The word "population" itself may be used to denote a plurality of e.g. polypeptide chains, which are not genetically diverse i.e. they are all the same.

Domain

A domain is a part of a protein that is folded within itself and independently of other parts of the same protein and independently of a complementary binding member.

Folded Unit

This is a specific combination of an α-helix and/or β-strand and/or β-turn structure. Domains and folded units contain structures that bring together amino acids that are not adjacent in the primary structure.

Free Form

This describes the state of a polypeptide which is not displayed by a replicable genetic display package.

Conditionally Defective

This describes a gene which does not express a particular polypeptide under one set of conditions, but expresses it under another set of conditions. An example is a gene containing an amber mutation expressed in non-suppressing or suppressing hosts respectively.

Alternatively, a gene may express a protein which is defective under one set of conditions, but not under another set. An example is a gene with a temperature sensitive mutation.

Suppressible Translational Stop Codon

This describes a codon which allows the translation of nucleotide sequences downstream of the codon under one set of conditions, but under another set of conditions translation ends at the codon. Example of suppressible translational stop codons are the amber, ochre and opal codons.

Mutator Strain

This is a host cell which has a genetic defect which causes DNA replicated within it to be mutated with respect to its parent DNA. Example mutator strains are NR9046mutD5 and NR9046 mut T1 (see Example 38 of WO92/01047).

Helper Phage

This is a phage which is used to infect cells containing a defective phage genome and which functions to complement the defect. The defective phage genome can be a phagemid or a phage with some function encoding gene sequences removed. Examples of helper phages are M13KO7, M13KO7 gene III no. 3; and phage displaying or encoding a binding molecule fused to a capsid protein.

Vector

This is a DNA molecule, capable of replication in a host organism, into which a gene is inserted to construct a recombinant DNA molecule.

Phage Vector

This is a vector derived by modification of a phage genome, containing an origin of replication for a bacteriophage, but not one for a plasmid.

Phagemid Vector

This is a vector derived by modification of a plasmid genome, containing an origin of replication for a bacteriophage as well as the plasmid origin of replication.

Secreted

This describes a rgdp or molecule that associates with the member of a sbp displayed on the rgdp, in which the sbp member and/or the molecule, have been folded and the package assembled externally to the cellular cytosol.

Repertoire of Rearranged Immunoglobulin Genes

A collection of naturally occurring nucleotides e.g. DNA sequences which encoded expressed immunoglobulin genes in an animal. The sequences are generated by the in vivo rearrangement of e.g. V, D and J segments for H chains and e.g. the V and J segments for L chains. Alternatively the sequences may be generated from a cell line immunised in vitro and in which the rearrangement in response to immunisation occurs intracellularly. The word "repertoire" is used to indicate genetic diversity.

Library

A collection of nucleotide e.g. DNA, sequences within clones;

or a genetically diverse collection of polypeptides, or specific binding pair members, or polypeptides or sbp members displayed on rgdps capable of selection or screening to provide an individual polypeptide or sbp members or a mixed population of polypeptides or sbp members.

Repertoire of Artificially Rearranged Immunoglobulin Genes

A collection of nucleotide e.g. DNA, sequences derived wholly or partly from a source other than the rearranged immunoglobulin sequences from an animal. This may include for example, DNA sequences encoding VH domains by combining unrearranged V segments with D and J segments and DNA sequences encoding VL domains by combining V and J segments.

Part or all of the DNA sequences may be derived by oligonucleotide synthesis.

Secretory Leader Peptide

This is a sequence of amino acids joined to the N-terminal end of a polypeptide and which directs movement of the polypeptide out of the cytosol.

Eluant

This is a solution used to breakdown the linkage between two molecules. The linkage can be a non-covalent or covalent bond(s). The two molecules can be members of a sbp.

Derivative

This is a substance which derived from a polypeptide which is encoded by the DNA within a selected rgdp. The derivative polypeptide may differ from the encoded polypeptide by the addition, deletion, substitution or insertion of amino acids, or by the linkage of other molecules to the encoded polypeptide. These changes may be made at the nucleotide or protein level. For example the encoded polypeptide may be a Fab fragment which is then linked to an Fc tail from another source. Alternatively markers such as enzymes, flouresceins etc may be linked to e.g. Fab, scFv fragments.

SUMMARY OF THE INVENTION

According to one aspect of the present invention there is provided a method for producing specific binding pair (sbp) members, which method comprises:

causing or allowing recombination between (a) first vectors comprising nucleic acid encoding a population of a first polypeptide chain of a specific binding pair member and (b) second vectors comprising nucleic acid encoding a population of a second polypeptide chain of a specific binding pair member, at least, one of said populations being genetically diverse, the recombination resulting in recombinant vectors each of which comprises nucleic acid encoding a said first polypeptide chain and a said second polypeptide chain. The sbp member may be "multimeric". The sbp member may be a single chain, e.g. a scFv antibody fragment, as disclosed herein.

The first vectors may each encode a fusion of a said first polypeptide chain and a component of a replicable genetic display package (rgdp), the recombination resulting in recombinant. vectors each of which comprises nucleic acid encoding a said fusion and a said second polypeptide chain. The fusion and a said second polypeptide chain. The recombinant vectors may be capable of being packaged into rgdps using said rgdp component.

One or other or both of the populations of first and second polypeptide chains may be genetically diverse. Where both are genetically diverse, the recombinant vectors will represent an enormously diverse repertoire of sbp members. Either or both of the populations may be genetically diverse but restricted compared with the full repertoire available, perhaps by virtue of a preceding selection or screening step. A library of nucleic acid encoding a restricted population of polypeptide chains may be the product of selection or screening'using rgdp display.

According to another aspect of the invention there is provided a method of producing multimeric specific binding pair (sbp) members, which method comprises:

(i) expressing from a vector in recombinant host organism cells a population of a first polypeptide chain of a specific binding pair member fused to a component of a replicable genetic display package (rgdp) which thereby displays said polypeptide chains at the surface of rgdps, and combining said population with a population of a second polypeptide chain of said specific binding pair member by causing or allowing first and second polypeptide chains to come together to form a library of said multimeric specific binding pair members displayed by rgdps, said population of second polypeptide chains not being expressed from the same vector as said population of first polypeptide chains, at least one of said populations being genetically diverse and expressed from nucleic acid that is capable of being packaged using said rgdp component, whereby the genetic material of each said rgdp encodes a polypeptide chain of a said genetically diverse population;

(ii) selecting or screening rgdps formed by said expressing to provide an individual sbp member or a mixed population of said sbp members associated in their respective rgdps with nucleic acid encoding a polypeptide chain thereof;

(iii) obtaining nucleic acid from a selected or screened rgdp, the nucleic acid obtained being one of (a) nucleic acid encoding a first polypeptide chain, (b) nucleic acid encoding a second polypeptide chain, and (c) a mixture of (a) and (b);

(iv) producing a recombinant vector by causing or allowing recombination between (a) a vector comprising nucleic acid obtained in step (iii) encoding a first polypeptide chain and a vector comprising nucleic acid encoding a second polypeptide chain, or (b) a vector comprising nucleic acid encoding a first polypeptide chain and a vector comprising nucleic acid obtained in step (iii) encoding a second polypeptide chain.

The recombination may take place intracellularly or in vitro, although it is preferable that it takes place in recombinant host cells. This is discussed elsewhere, but briefly this may involve introducing a library of vectors including nucleic acid encoding first (or second) polypeptide chain components of sbp member into host cells harbouring a library of vectors comprising nucleic acid encoding second (or first) polypeptide chain components of sbp members.

Following the recombination the polypeptide fusions (first polypeptide chains fused to a rgdp component) and the second polypeptide chains may be expressed, producing rgdps which display at their surface said first and second polypeptide chains and which each comprise nucleic acid encoding a said first polypeptide chain and a said second polypeptide chain, by virtue of the packaging of the recombinant vectors into rgdps. This expression may therefore produce an extremely diverse library of sbp members displayed on rgdp. In one embodiment, the rgdps displaying sbp member are pAbs (i.e. phage displaying antibodies or antibody fragments or derivatives), and those which bind antigen of interest may be selected using their binding capability. Since each pAb contains within it nucleic acid encoding both polypeptide chains of the antibody displayed on its surface, pAbs selected by binding to an antigen of interest will provide nucleic acid encoding an antibody which binds that antigen. The nucleic acid may be isolated from the selected pAbs and used in subsequent obtention of desired antibodies, after any amplification and cloning required in a given case.

The recombination may be promoted by inclusion in the vectors of sequences at which site-specific recombination will occur. This enables accurate design of the resultant recombinant vectors. For instance, a sequence at which site-specific recombination will occur may be position in the nucleic acid which encodes a polypeptide linker which joins the two domains of a single chain sbp member. The single chain sbp member may consist of an immunoglobulin VH domain linked to an immunoglobulin VL domain. VH and VL domains may associate to form an antigen binding site. The resultant recombinant vector may then comprise nucleic acid encoding a single chain Fv derivative of an immunoglobulin resulting from recombination between first and second vectors. (Note: a single chain sbp member, such as a scFv fragment or derivative of an antibody, may be considered to be multimeric (dimeric) because it consists of two polypeptide chain domains, such as VL and VH of an antibody.)

The sequences at which site-specific recombination will occur may be loxP sequences obtainable from coliphage P1, with site-specific recombination catalysed by Cre-recombinase, also obtainable from coliphage P1. The site-specific recombination sequences used may be derived from a loxP sequence obtainable from coliphage P1.

The Cre-recombinase used may be expressible under the control of a regulatable promoter.

In order to increase the efficiency of the method, increasing the proportion of productive recombination leading to the resultant recombinant vectors desired, each vector may include two site-specific recombination sequences each of which is different from other. The sequences should then be such that recombination will take place between like sequences on different vectors but not between the different sequences on the same vector.

Site-specific recombination sequences which are different may recombine inefficiently on the same vector. Preferably, recombination takes place preferentially between first site-specific recombination sequences on different vectors and between second site-specific recombination sequences on different vectors compared with a first site-specific recombination sequence and a second site-specific recombination sequence on the same vector.

Each of the first vectors and each of the second vectors may include a first site-specific recombination sequence and a second site-specific recombination sequence different from the first, site-specific recombination taking place preferentially between first site-specific recombination sequences on different vectors and between second site-specific recombination sequences on different vectors compared with a first site-specific recombination sequence and a second site-specific recombination sequence on the same vector.

The first site-specific recombination sequence may be loxP obtainable from coliphage P1 and the second site-specific recombination sequence a mutant loxP sequence, or vice versa. Potentially, both the first and second site-specific recombination sequences may be mutants, as long as the first sequence will not recombine with the second sequence as efficiently as first sequences will recombine with each other and second sequences will recombine with each other. Others include loxP 1, loxP 2, loxP 3, and loxP 4, whose sequences are shown in Table 8. Suitable sites may be selected on the basis of ability for like sites to recombine on different vectors preferentially over unlike sites on the same vector.

A third site-specific recombination sequence may be used in addition to and different from the first and second. Provided the third site-specific recombination sequence has a frequency of recombination with the first site-specific recombination sequence which is low compared with the frequency of recombination between first site-specific recombination sequences and a frequency of recombination with the second site-specific recombination sequence which is low compared with the frequency of recombination between second site-specific recombination sequences, the presence of the third site will not interfere with successful recombination between first sites and between second sites. The third site may be used in a further recombination step following the first, e.g. to transfer recombined sequences encoding first and second polypeptide chains of an sbp member from the recombinant vector into a further vector, e.g. for expression and/or fusion to nucleic acid encoding a component of and rgdp. Alternatively, the third site may be used in "chain shuffling".

Thus, the present invention provides a method comprising causing or allowing recombination between (a) first vectors comprising nucleic acid encoding a specific binding pair (sbp) member and (b) second vectors, the vectors comprising site-specific recombination sequences and the site-specific recombination sequences of the first vectors flanking the nucleic acid encoding a specific binding pair member. The first vectors may comprise nucleic acid encoding a genetically diverse population of sbp members, as disclosed. As discussed above, the second vectors may comprise nucleic acid for expression of the sbp member following recombination and may comprise nucleic acid for expression of a fusion of the sbp member and a component of a rgdp.

While the first and second site-specific recombination sequences may flank the nucleic acid encoding the sbp member, a third site-specific recombination sequence (as discussed) may'separate nucleic acid encoding each of two chains of the sbp member. A vector comprising such a construct may be provided by recombination between (i) vectors comprising nucleic acid encoding a first polypeptide chain flanked by two site-specific recombination sequences wherein one is a said first site-specific recombination sequence and the other is a said third site-specific recombination sequence and (ii) vectors comprising nucleic acid encoding a second polypeptide chain flanked by two site-specific recombination sequences wherein one is a said third site-specific recombination sequence and the other is a said second site-specific recombination sequence and further comprising a said first site-specific recombination sequence, recombination taking place preferentially between first site-specific recombination sequences on different vectors and between third site-specific recombination sequences on different vectors compared with a first site-specific recombination sequence and a third site-specific recombination sequence on the same vector.

Where three site-specific recombination sequences are used they may be selected from the group consisting of loxP, loxP 511, loxP 1, loxP 2, loxP 3, and loxP 4, whose sequences are shown in Table 8.

A suitable mutant loxP sequence is loxP 511.

The first vectors may be phages or phagemids and the second vectors plasmids, or the first vectors may be plasmids and the second vectors phages or phagemids.

In one embodiment, the recombination is intracellular and takes place in a bacterial host which replicates the recombinant vector preferentially over the first vectors and the second vectors. This may be used to enrich selection of successful recombination events. The intracellular recombination may take place in a bacterial host which replicates plasmids preferentially over phages or phagemids, or which replicates phages or phagemids preferentially over plasmids. For instance, the bacterial host may be a PolA strain of $E.$ $coli$ or of another gram-negative bacterium. PolA cells are unable to support replication of plasmids, but can support replication of filamentous phage and phagemids (plasmids containing filamentous phage intergenic regions). So, for instance, if the first vectors are plasmids containing a first marker gene, and the second vectors are phage or phagemids containing a second marker gene, selection for both markers will yield recombinant vectors which are the product of a successful recombination event, since recombination transferring the first marker from plasmid must take place in order for that marker to be replicated and expressed.

Nucleic acid from one or more rgdp's may be taken and used in a further method to obtain an individual sbp member or a mixed population of sbp members, or polypeptide chain components thereof, or encoding nucleic acid therefor.

The present invention also provides a kit for use in carrying out methods provided, having:

(i) a first vector having a restriction site for insertion of nucleic acid encoding or a polypeptide component of an sbp member, said restriction site being in the 5'end region of the mature coding sequence of a phage capsid protein, with a secretory leader sequence upstream of said site which directs a fusion of the capsid protein and sbp polypeptide to the periplasmic space of a bacterial host; and (ii) a second vector having a restriction site for insertion of nucleic acid encoding a second said polypeptide chain, at least one of the vectors having an origin of replication for single-stranded bacteriophage, the vectors having sequences at which site-specific recombination will occur.

The kit may contain ancillary components needed for working the method.

Also provided by the present invention are recombinant host cells harbouring a library of first vectors each comprising nucleic acid encoding a first polypeptide chain of a sbp member fused to a component of a secretable replicable genetic display package (rgdp) and second vectors each comprising nucleic acid encoding a second polypeptide chain of a sbp member, the first vectors or the second vectors or both being capable of being packaged into rgdps using the rgdp component, and the vectors having sequences at which site-specific recombination will occur.

According to another aspect of the present invention there is provided a population of rgdps each displaying at its surface a sbp member and each containing nucleic acid which encodes a first and a second polypeptide chain of the sbp member displayed at its surface and which includes a site-specific recombination sequence.

According to another aspect of the invention there is provided a population of rgdps each displaying at its surface a sbp member and each containing nucleic acid which comprises a combination of (i) nucleic acid encoding a first polypeptide chain of a sbp member and (ii) nucleic acid encoding a second poypeptide chain of a sbp member, the population containing $10^{10}$ or more combinations of (i) and (ii). Such a population exceeds in size the maximum which is achievable using available techniques. The present invention enables production of enormously diverse libraries or populations of rgdps displaying sbp members. The nucleic acid encoding a first polypeptide chain of a sbp member may have, for instance, $10^7$ different sequences throughout the population. Where the nucleic acid encoding a second polypeptide chain of a sbp member also has such a genetic diversity throughout the population, the number of different combinations of nucleic acid encoding first and second polypeptide chains is immense.

Embodiments of the present invention will now be described in more detail by way of example only and not by way of limitation, with reference to the figures.

BRIEF DESCRIPTION OF THE FIGURES

FIGS. 3A and 3B illustrate the use of sites specific recombination for construction of polycombinantorial libraries.

FIGS. 4A and 4A-1 show replicons generated by Cre mediated recombination between the acceptor phage vector fdDOG-2lox (A) and the donor plasmid vector pUC19-2lox (B). A is based on fd-tet-DOG1, with Vk from the mouse anti-phOx antibody NQ10.12.5 linked to a human Ck constant domain, and VH from the mouse anti-TNFa antibody linked to a human Cm1 constant domain. B is based on pUC19, with VH of NQ10.12.5 linked to the human Cg1 constant domain. Within *E. coli* an equilibrium between the six vectors develops due to the reversible nature of recombination in the lox-Cre system. Ribosome-binding sites (small open circles), c-myc peptide tag (myc), phage fd gene III leader peptide sequence (Lg3), pelB leader peptide sequence (LpelB), fd phage gene III (gIII) and locations of oligonucleotides used for hybridisation and screening are indicated.

FIGS. 4B and 4B-1 shows the sequence across the wild-type loxP and mutant loxP 511 sites present in fdDOG-2lox (A) and pUC19-2lox (B). The inverted repeats in the loxP sites are boxed and the position of the point mutation in the mutant loxP 511 site is indicated (#), as are the ribosome-binding sites (r.b.s.). Note that the wild-type loxP sites are in frame to ensure that the heavy chains immediately upstream can be fused to gene III for display on phage.

FIGS. 5A and 5B show schematically, selection techniques which utilise the unique properties of pAbs; FIG. 5A shows a binding/elution system; and FIG. 5B shows a competition system (p=pAb; ag=antigen to which binding by pAb is required; c=competitor population e.g. antibody, pAb, ligands; s=substrate (e.g. plastic beads etc); d=detection system.

FIG. 6 shows (A) The repertoire of heavy chains (>$10^8$ different clones) which was built from 49 cloned $V_H$ segments (Tomlinson et al., *J. Mol. Biol.*, 227:776–798 (1992); Nissim et al., *EMBO J.*, 13:692–698 (1994)), with CDR3 loops of 4–12 residues of random sequence. (B) The repertoire of κ light chains (9×$10^4$ clones) which was built from 26 cloned $V_k$ segments (Cox et al., *Eur. J. Immunol.*, in press (1994)) with CDR3 loops of 8–10 residues that included 1, 2 or 3 residues of random sequence in all cases. DPK-4 is shown by way of example. (C) The repertoire of λ light chains (7.4×$10^5$ clones) which was built from 21 cloned $V_\lambda$ segments (Williams et al., *Eur. J. Immunol.*, 23: 1456–1461 (1993)), with CDR3 loops of 8–13 residues that included 0, 1, 2, 3, 4 or 5 residues of random sequence. DPL-12 is shown by way of example. CDR, complementarity determining region; FR, framework region.

FIG. 8 shows the characterisation of Fab fragments against 4 antigens of the kringle-serine protease family— hepatocyte growth factor/scatter factor (HGF/SF), plasmin, urokinase-type plasminogen activator (u-PA), or tissue-type plasminogen activator (t-PA)—as members of a family of related proteins. Using ELISA, binding of "polyclonal" phage was detected after three rounds of selection, and proved to be specific, despite homologies between the members of this family.

FIG. 9 shows the use of human germline V-gene segments. Frequencies of use of human $V_H$, $V_k$ and $V_\lambda$ segments from the synthetic repertoire (A, C, E), or from natural antibodies (B, D, F). Frequencies (f) are plotted as % of total. V-gene usage was compiled for the synthetic antibodies from Table 3, and for natural antibodies, from the 292 rearranged $V_H$ genes in the database described in Tomlinson et al., *J. Mol. Biol.*, 227:776–798 (1992), from the 236 rearranged $V_k$ genes in the database described in Cox et al., *Eur. J. Immunol.*, in press (1994), and from a database of 110 rearranged $V_\lambda$ genes taken from the "Entrez" sequence database (release 8.0; National Center for Biotechnological Information). $V_H$ segments are listed by DP numbers (Tomlinson et al., *J. Mol. Biol.*, 227:776–798 (1992)), $V_k$ segments by DPK numbers (Cox et al., *Eur. J. Immunol.*, in press (1994)), and $V_\lambda$ segments by DPL numbers (Williams et al., *Eur. J. Immunol.*, 23:1456–1461 (1993)). All V-gene segments listed were included in the synthetic repertoire except those marked (·). $V_H$-gene segments (located on chromosome 15 or 16) which are not used in vivo (I. M. Tomlinson et al., manuscript submitted), but which were included in the synthetic repertoire are indicated (#).

FIG. 10 shows the distribution of CDR3 lengths. Length distribution of CDR3 loops in human $V_H$, $V_k$ and $V_\lambda$ chains from the synthetic repertoire (A, C, E), or from natural antibodies (B, D, F). Frequencies (f) are plotted as % of total. Data were compiled as in the description of FIG. 4, except that for natural rearranged $V_H$ genes the data were taken from the 177 human genes described by Wu et al., *Proteins*, 16: 1–7 (1993). All CDR lengths listed were included in the synthetic repertoire except for those marked (#).

Figure 11:
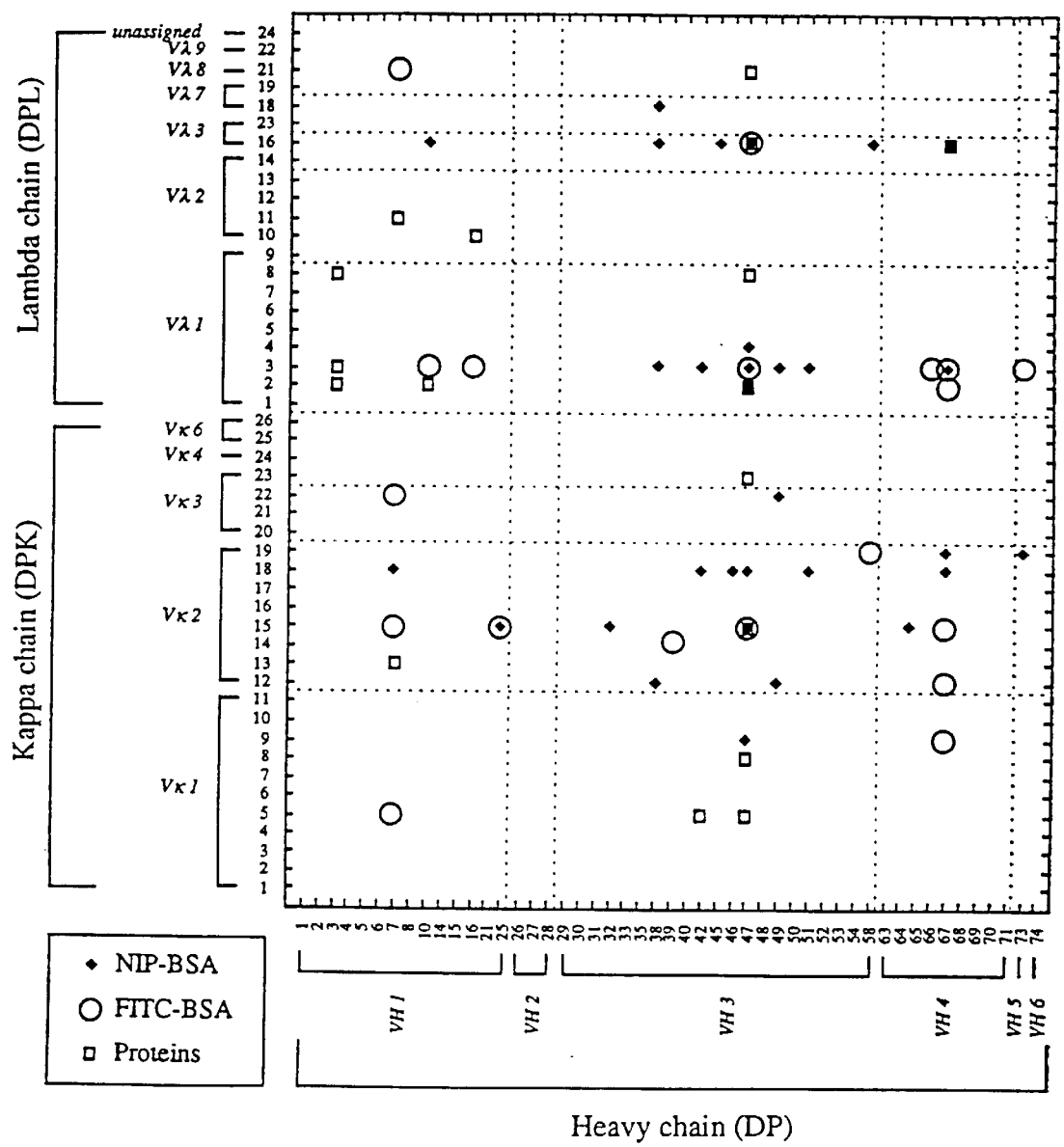

FIG. 11 shows the pairings of heavy and light chain V-gene segments in the synthetic repertoire. Data were compiled and are listed as described for FIG. 4. Fab fragments binding NIP-BSA are indicated by black diamonds; Fab fragments binding FITC-BSA by open circles; and Fab fragments binding antibody NQ11/7.22, plasmin, u-PA, t-PA or HGF/SF by open squares.

Figure 12:
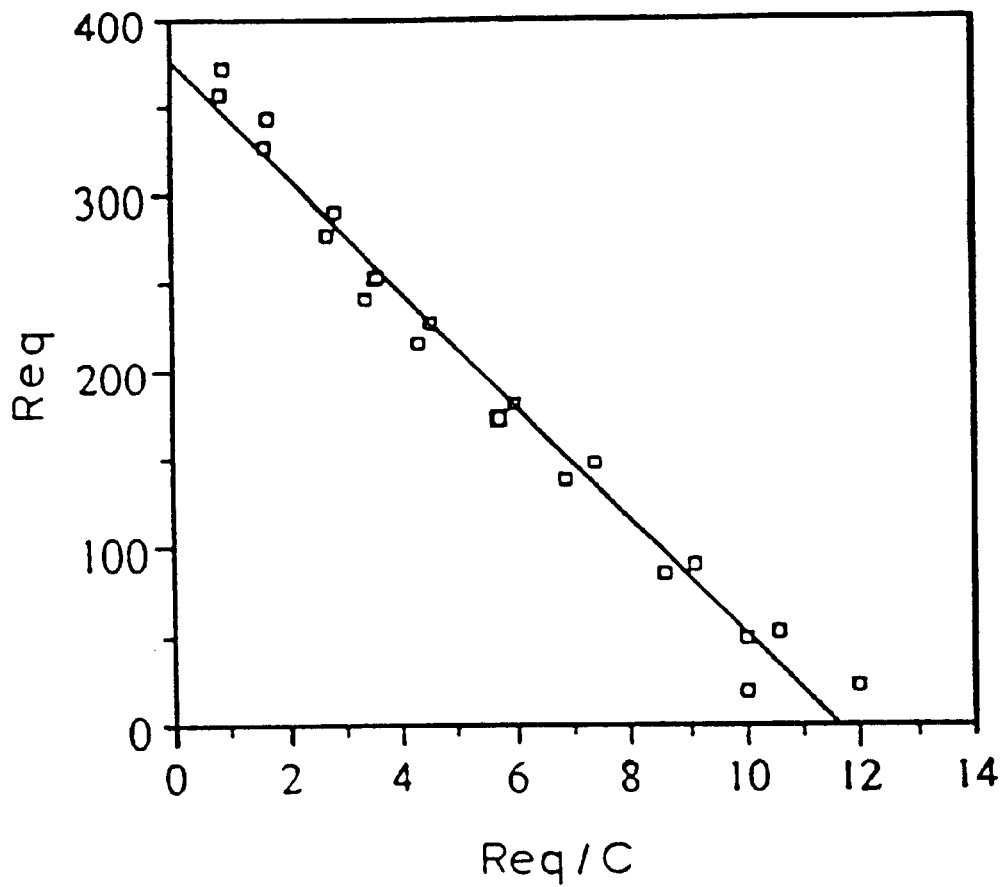

FIG. 12 shows the analysis of affinity of Fab NML1 by SPR.

Figure 13A:
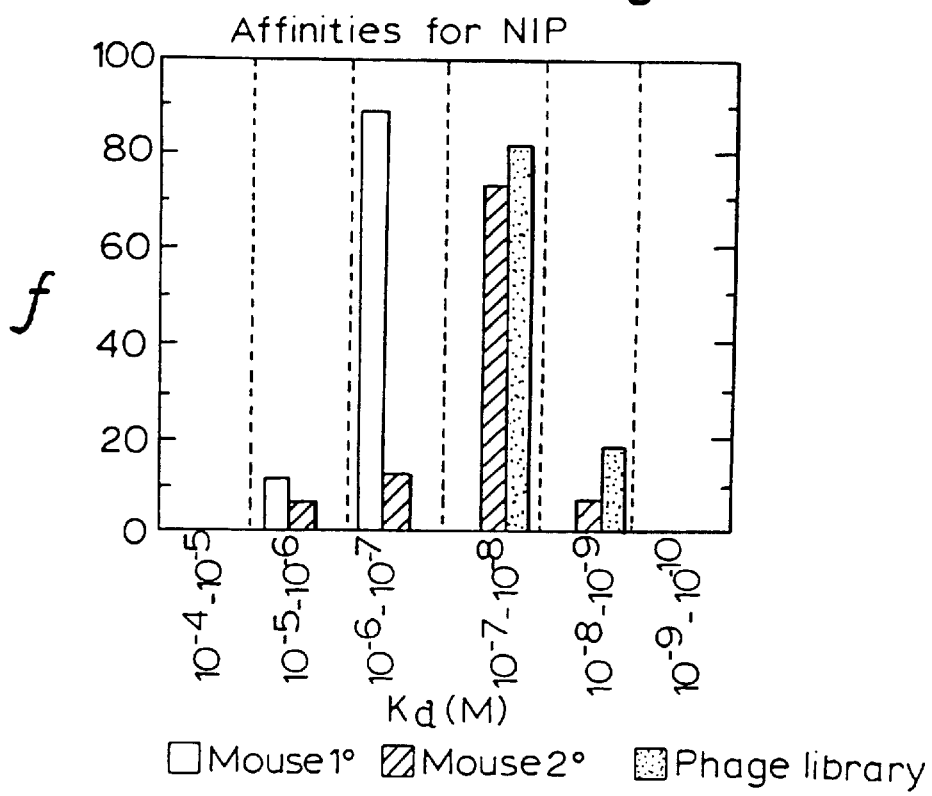
Figure 13B:
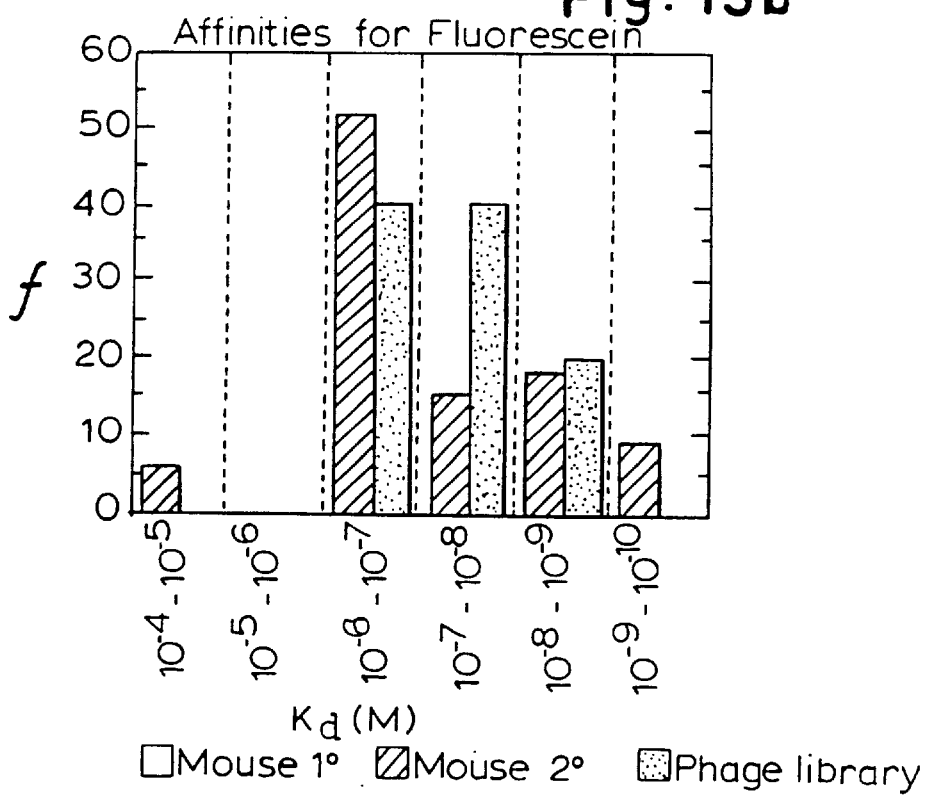

FIG. 13 shows affinities for synthetic antibodies and mouse monoclonal antibodies. Affinity data for the Fab fragments from the synthetic repertoire were compiled from Table 4A. (A) Antibodies binding to NIP; data on the mouse immune response were taken from (Mariuzza et al., *Molec. Immunol.*, 18:847–855 (1981); Cumano et al., *EMBO J.*, 5:2459–2468 (1986); Lucisano-Valim et al., *Clin. Exp. Immunol.*, 84:1–8 (1991)). (B) Antibodies binding fluorescein; data on the mouse immune response were taken from (Kranz et al., *Molec. Immunol.*, 18:889–898 (1981); Kranz et al., *J. Biol. Chem.*, 257:6987–6995 (1982); Reinitz et al., *Molec. Immunol.*, 21:775–784 (1984); Bates et al., *Molec. Immunol.*, 22:871–877 (1985); Bedzyk et al., *Molec. Immunol.*, 23:1319–1328 (1986); Denzin et al., *J. Biol. Chem.*, 267:8925–8931 (1992)).

Figure 14:
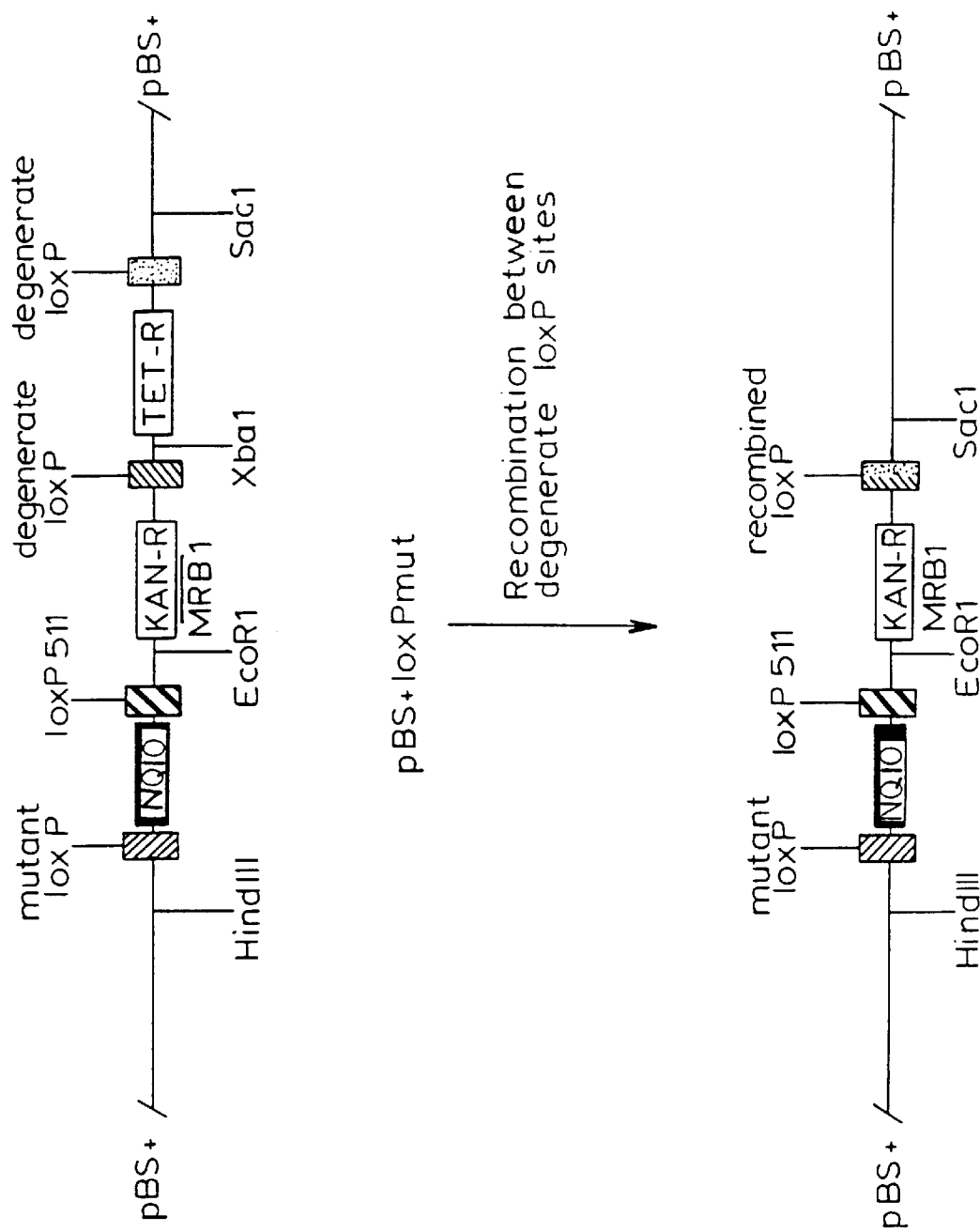

FIG. 14 shows recombination between degenerate loxP sites in the construct pBS+loxP mut. If there is recombination between the two degenerate loxP sites the tetracyclin resistance gene is deleted and the cells become tetracyclin sensitive.

Figure 15:
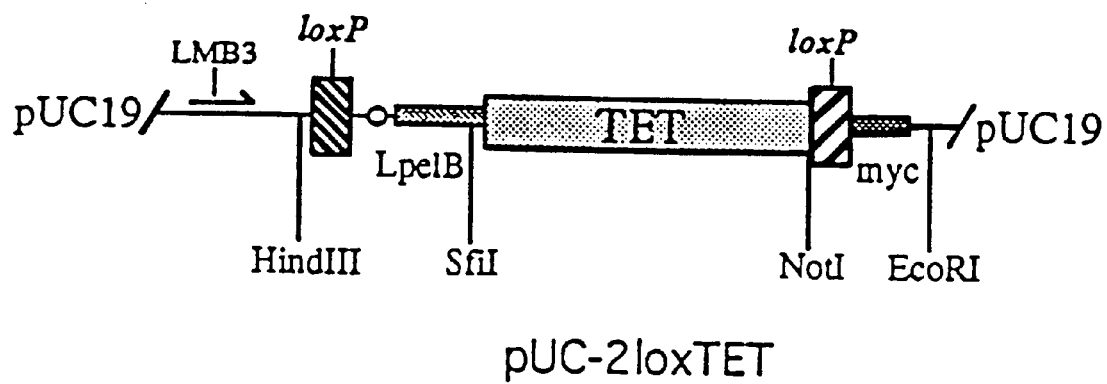

FIG. 15 shows the construct pUC-2loxTET where the tetracyclin gene is flanked by two loxP sites which are varied to test recombinatin between them.

Figure 16:
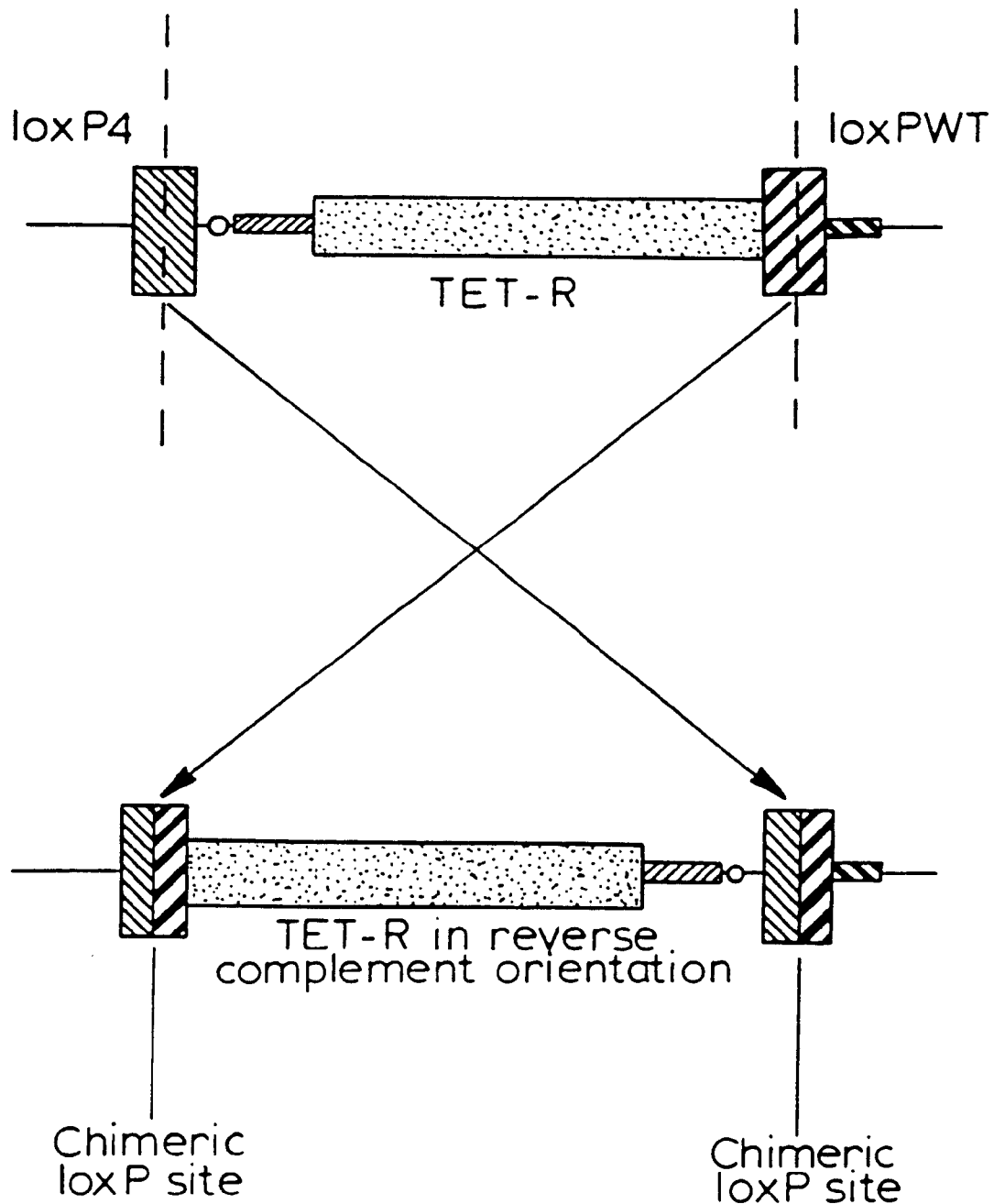

FIG. 16 shows the inversion event which occurs between loxP 4 and WT in pUC-2loxTET.

Figure 17:
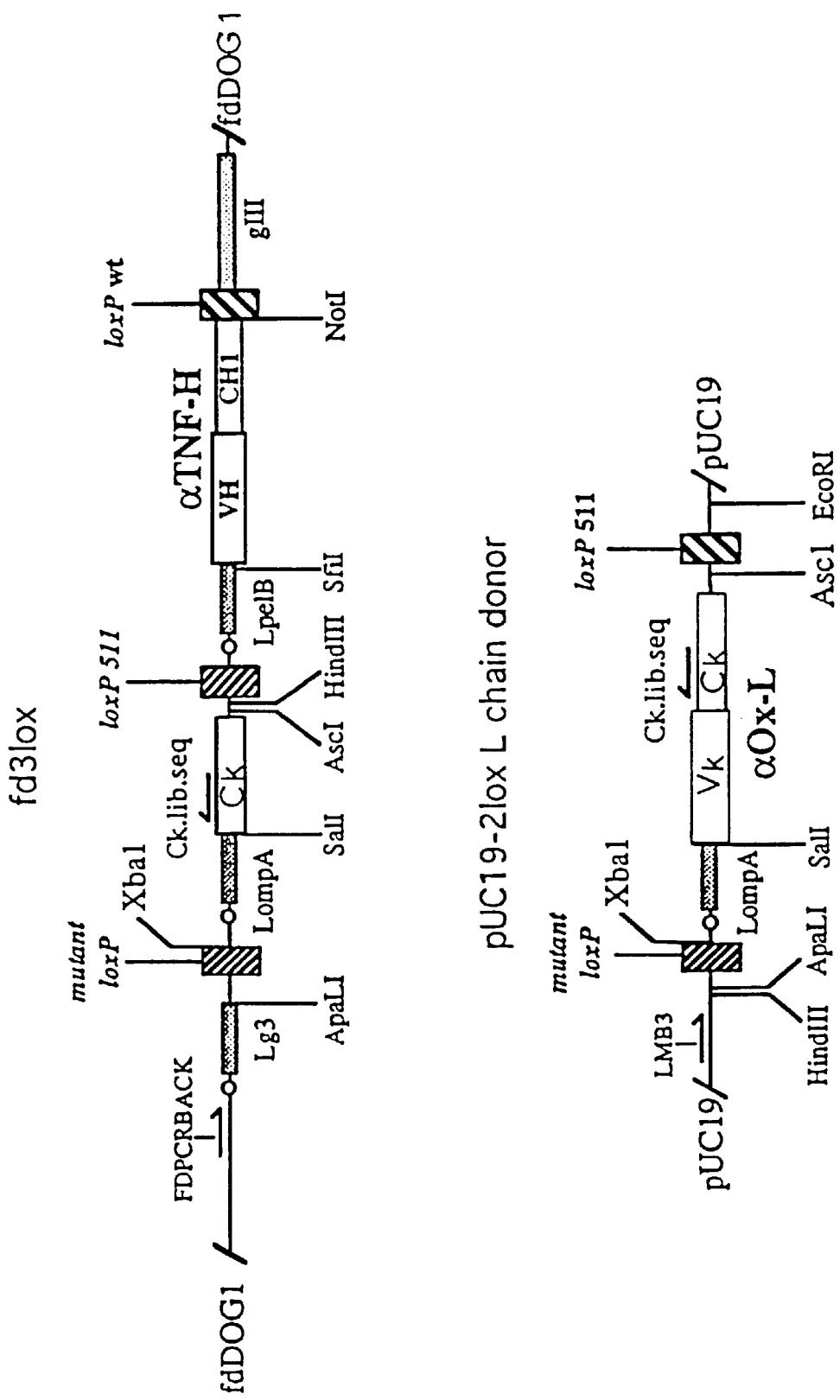

FIG. 17 The 2-loxP system described in example 1 was adapted to include a third loxP site at the 5' end of the Ck gene which replaced the anti-phOx light chain from NQ10.12.5. A donor vector was also created containing light chain from NQ10.12.5 flanked at the 5' end by the new loxP site, and at the 3' end by loxP 511. Four versions of this system were created corresponding to each of the new loxP sites 1, 2, 3, and 4 where both fd3lox and the pUC19-2lox light chain donor had the same mutant loxP sites.

Figure 18:
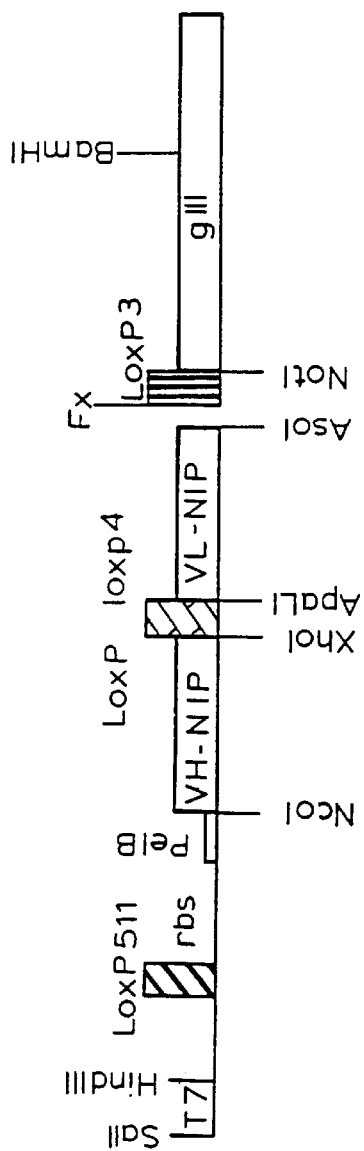

FIG. 18 is a schematic diagram of fd containing scFv with loxP 1 or loxP 4 sequence as linker. T7 is a T7 promoter introduced into the HindIII site. Fx is factor X cleavage site. rbs is a ribosome binding site.

FIG. 19 shows pUC and fd vector constructs described in example 7.

Figure 19A:
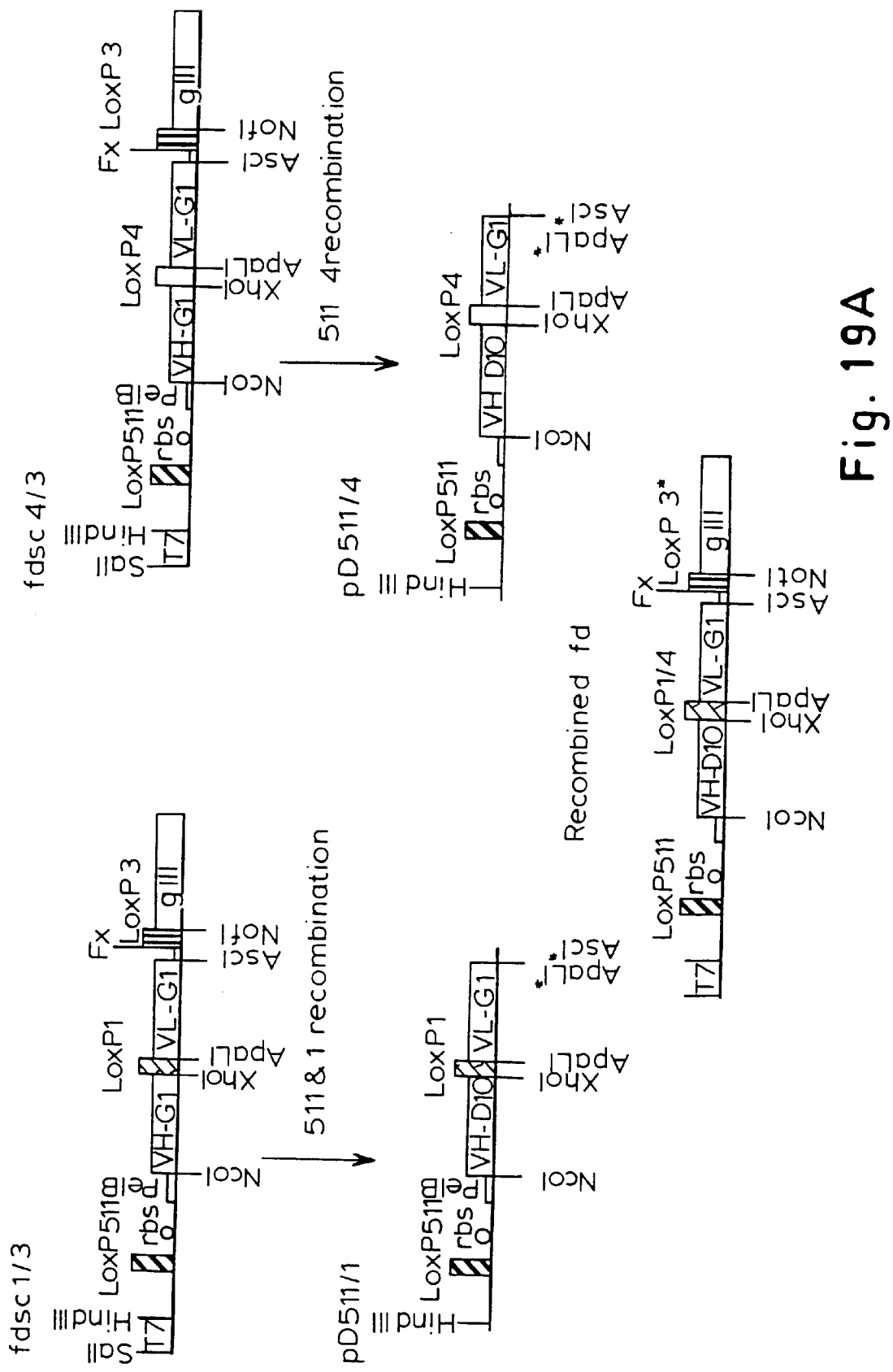

FIG. 19a shows the recombination experiment between the loxP site in fdSc1/3 or fdSc4/3 encoding a single chain Fv with a loxP 1 or loxP 4 linker with the donor vectors pD511/1 and pD511/4. * indicates a loxP 3 site in between the VL and gene III, which was changed to loxP WT in the case of fdSc4/WT or loxP 1 in the case of fdSc4/1. Recombination for fddSc4/WT and fdSc4/1 was tested as for fdSc1/3 and fdSc4/3 except that loxP 3 was exchanged accordingly.

Figure 19B:
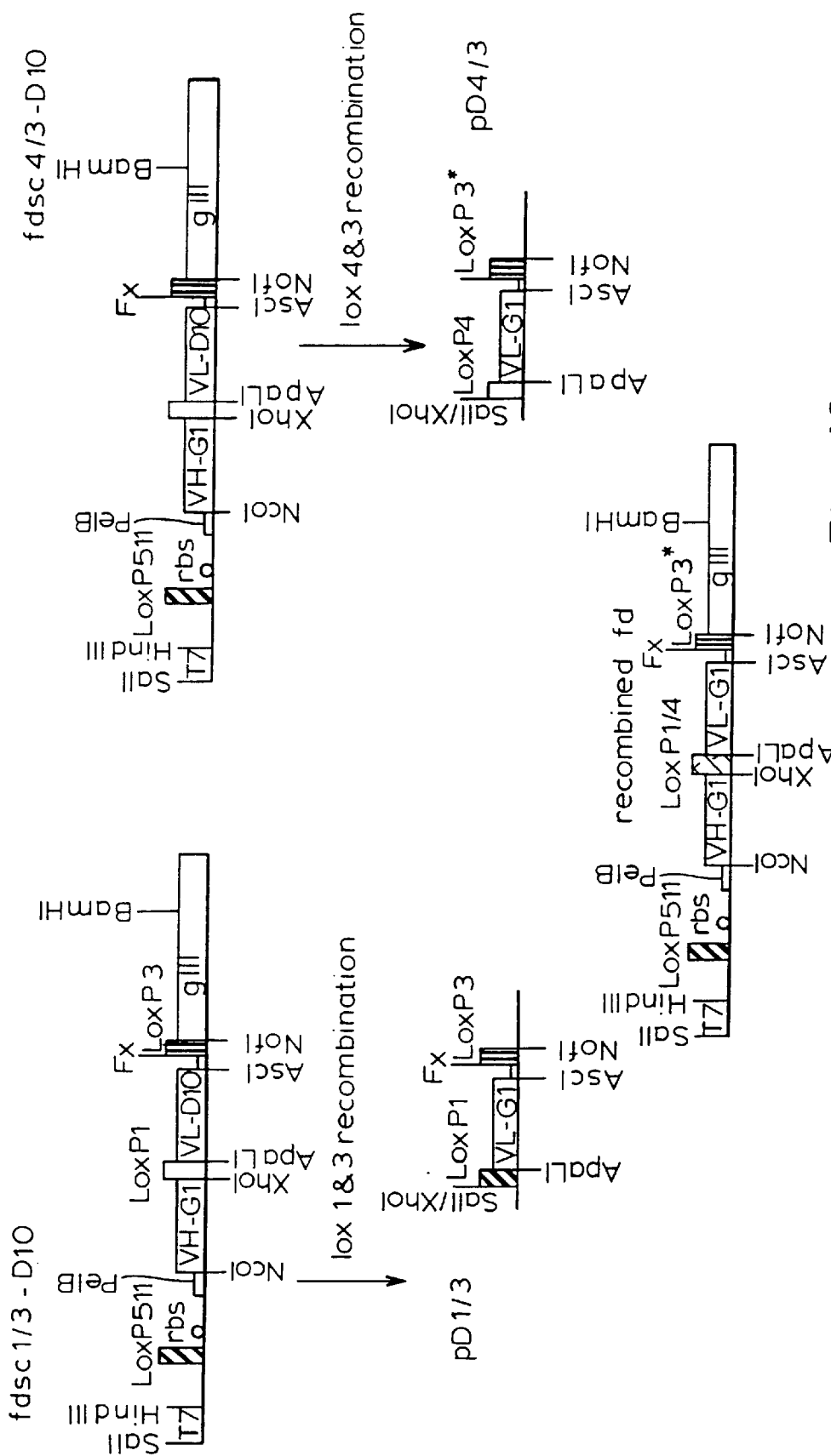

FIG. 19b shows recombination between the fd1/3-D10 and fd4/3-D10 acceptor molecules and VL domains encoded on the donor vectors pD1/3 and p4/3. The loxP 3 site of the p4/3 donor was changed to loxP 1 or loxP WT to give the vectors pD4/wt and pD4/1 respectively. The loxP 3 site of the pfd4/3D-10 acceptor was changed to loxP 1 or loxP WT to give the vectors fdSc4/1-D10 and fdSc4/WT-D10 respectively.

FIG. 19c shows the pUC, expression vectors pEX511/3; pEX511/WT and pEX511/1 for subcloning for expression.

FIG. 20 shows recombination efficiencies in experiments described in example 7. The loxP sites loxP WT, loxP 511, loxP 4, loxP 1, and loxP 3 are indicated by WT, 511, 4, 1, and 3. The percentages refer to the efficiencies of recombination between the corresponding identical loxP sites on donor and acceptor vectors.

DETAILED DESCRIPTION

Disclosed here are methods useful for preparing extremely diverse libraries of specific binding pair members, such as antibody heavy and light chains. Heavy and light chains cloned on separate replicons may be introduced into host cells. The heavy and light chain genes are recombined onto the same replicon such that the final number of combinations created is the number of heavy chains multiplied by the number of light chains. Recombination can occur in vivo or in vitro. Preferably, the recipient replicon is capable of being incorporated into an rgdp such that functional combinations of heavy and light chain genes can be selected. Such a format is particularly advantageous for construction of extremely diverse libraries of antibody heavy and light chains, for example, from unimmunised donors, immunised donors or a repertoire of an artificially rearranged immunoglobulin gene or genes, and is also convenient for chain-shuffling, mutagenesis, humanising and CDR 'imprinting'. As used herein in respect of vectors, the term "acceptor" or "recipient" refers to the vector which gains nucleic acid from what is termed the "donor" vector. Nucleic acid encoding, e.g. a first polypeptide chain of an sbp member, may pass from the "donor" vector to the "acceptor" or "recipient" vector upon recombination. As shown in the figures, the vector following recombination corresponds to the "acceptor" or "recipient" vector comprising the "donor" nucleeotide sequence (e.g. encoding said first polypeptide chain) from the donor vector. Other nucleic acid from the donor vector does not appear in the recombinant vector.

These methods can also be applied to other proteins in which two or more subunits assemble to create a functional oligomer.

The genes for both subunits present on two separate replicons can be brought together onto the same rgdp such that favourable combinations of subunit genes may be isolated directly without recourse to extensive recloning. This may be achieved by recombination between the replicons once they have been introduced into the same cell. In a preferred configuration, recombination events are effected such that the genes for one of the chains is recombined onto a recipient replicon which contains the gene for a partner chain. Preferably, the recipient replicon is capable of being packaged into an rgdp. Most preferably, the genes encoding one or more of the subunits is fused to a capsid gene such as gIII in order that the functional multimer can be displayed on the surface of the rgdp.

A variety of recombination systems are known, and many of these could be harnessed in such a way as to effect recombination between replicons. Example recombination systems include general recombination, transposition and site-specific recombination.

General recombination is a process whereby genetic exchange occurs between DNA segments that share some homology, and is also known as 'homologous recombination'. It is the principal mechanism by which genetic material is transferred between chromosones, and in *E. coli* the process is catalysed by the rec BCD enzyme (In "*Escherichia coli* and *Salmonella typhimurium*. Cellular and Molecular Biology." (1987) pp. 1034–1043, Neidhart, F. C., Editor-in-Chief, American Society for Microbiology). A general recombination mechanism could be used to transfer genes from one replicon to the other if, for example, the rgdp genome has a gene for one of the chains and a 'dummy' partner chain gene such that recombination would have to occur to replace the dummy gene on the rgdp replicon with the functional gene on the second replicon in order to produce a functional pairing.

Transposition could also be used to effect transfer of genetic information from one replicon to another (In "*Escherichia coli* and *Salmonella typhimurium*, Cellular and Molecular Biology." (1987) pp. 1061–1070. Neidhart, F. C. Editor-in-Chief, American Society for Microbiology). Transposons such as Tn 3 and Tn 10 are DNA segments that have also been called 'jumping genes' and 'selfish DNA' and are found on plasmids and in the *E. coli* chromosome. Transposon structure is variable, but usually comprises recombinase genes flanked by repeated DNA sequences; the recombinase(s) together with host factors catalyse insertion of the transposon into sites on the chromosome, by a mechanism which usually results in a duplication of site at which the transposon has inserted. Insertion by some transposons can be highly site-specific wheras others insert essentially at random. For the purpose of transferring genes from one replicon to another, the donor gene could be incorporated within a highly site-specific transposon such as Tn 7. The recipient plasmid would be engineered to contain the target DNA sequence.

One of the most fully understood site-specific recombination systems is that used in integration and excision of bacteriophage lambda (In "*Escherichia coli* and *Salmonella typhimurium*, Cellular and Molecular Biology." (1987). pp. 1054–1060, Neidhart, F. C. Editor-in-Chief, American Society for Microbiology). This bacteriophage can follow two developmental pathways once inside the cell: lysis or lysogeny. The lysogenic pathway involves integration of the lambda genome into the chromosome of the infected bacterium; integration is the result of a site-specific recombination between a ca. 240 bp sequence in the bacteriophage called att P and a 25 bp site in the bacterial chromosome called att B. The integration event is catalysed by a host encoded factor called IHF and a phage encoded enzyme called Int recombinase, which recognises a 15 bp region common to the two att sites. The integrated DNA is flanked by sequences derived from att B and att P, and these are called att L and att R. The integration event is reversible and is catalysed by Int, IHF and a second bacteriophage encoded enzyme, Xis. It is envisaged that this system could be used for sequence transfer between replicons within *E. coli*. For example, the donor gene could be flanked by att L and att R sites such that when Int and Xis proteins are provided in the host cell, recombination between att L and att R sites would create a circular DNA segment containing the donor gene and a recreated att B site. This circular segment could then recombine with an att P site engineered into the recipient plasmid.

An alternative site-specific recombination system is the loxP/Cre recombinase system of coliphage P1 (Hoess, R. H. and Abremski, K. (1990) The Cre-lox recombination system. In 'Nucleic Acids and Molecular Biology.' Eckstein, F. and Lilley, D. M. J. eds. Vol 4, pp99–109, Springer-Verlag, Berlin, Heidelberg). Cre-recombinase catalyses a highly specific recombination event at sequences called lox, loxP, the recombination site in phage P1 consists of two 13 bp inverted repeats separated by an 8 bp non-symmetrical core. For the work described in this application, the loxP/Cre system was chosen of the alternatives available because the recombination is highly sequence-specific, very efficient and occurs at a short target site that is readily incorporated into cloning vectors.

Figure 3B:
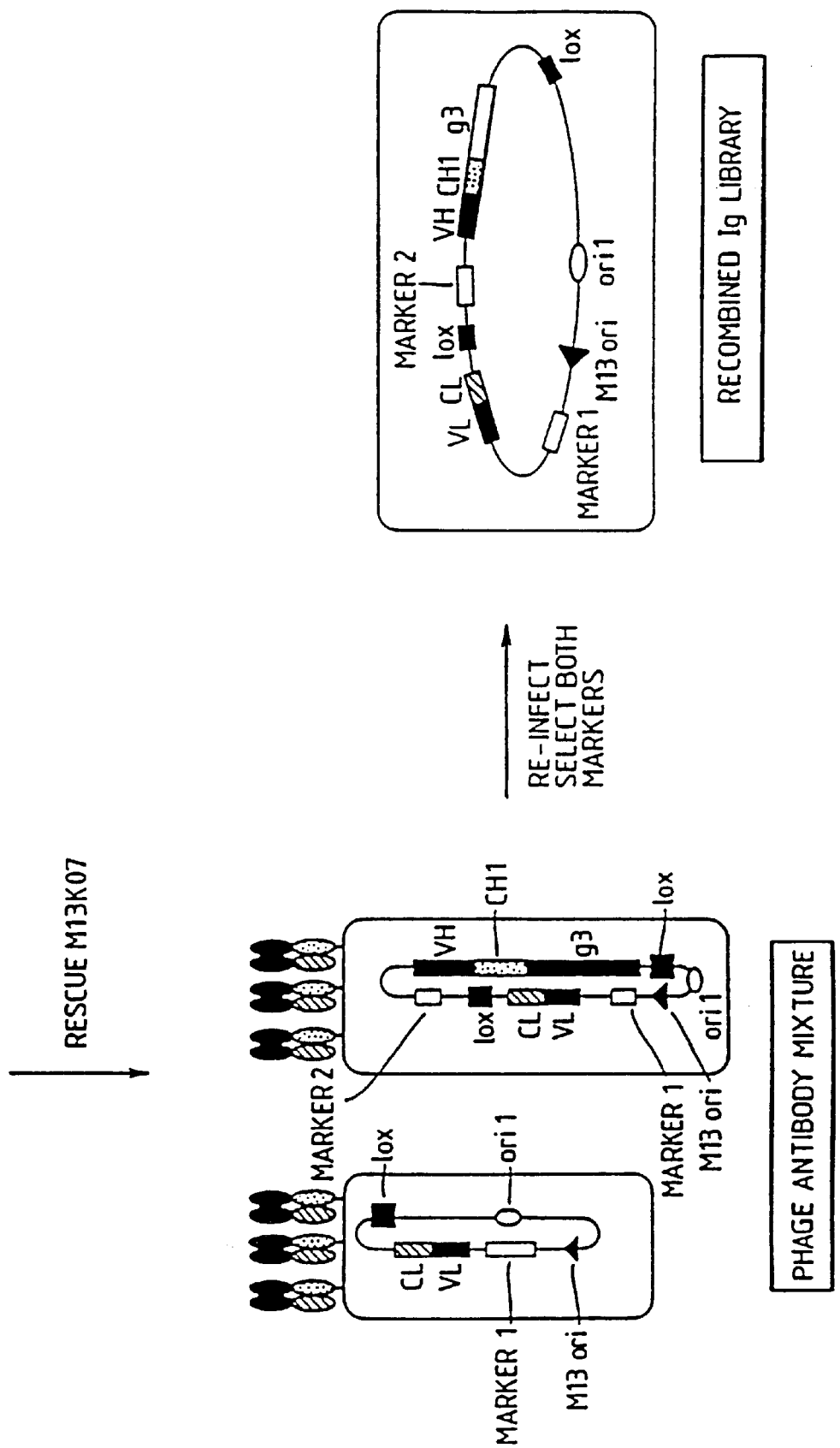

In the example outlined in FIGS. 3A–3B soluble light chain is cloned onto a phagemid containing a single loxP site. The heavy chains are cloned onto a plasmid as g3 fusions. Alongside the g3 fusion is the gene for a selectable marker, and the heavychain/g3/marker sequence flanked by two loxP sites. This plasmid also contains the Cre recombinase on a regulatable promoter and has an origin of double-stranded replication that is compatible with that on the phagemid in addition to that on the helper phage e.g. p15A, RSF 1010 and col E1 origins will co-exist in the same cell. The phagemids are then infected into cells containing the donor plasmid and the Cre recombinase promoter induced, so that recombination between the loxP sites occurs inside infected cells. Some of these recombination events will lead to the heavychain/g3/marker sequences transferring as a block onto the phagemid at its single loxP site. Phagemids are then rescued with a helper phage such as M13KO7 (see WO92/01047) and the resulting phagemid particles either directly selected on antigen or infected into fresh host cells and grown with selection for the presence of both markers; one from the phagemid itself and the other from the heavychain/g3/marker block.

The source of the Cre recombinase to catalyse the recombination between the loxP sites may be P1 phage used to infect bacteria containing the DNA sequences to be recombined as described in examples 1 to 3 or cloned recombinase encoded on a plasmid under the control of a regulatable promoter as described in example 4. It is preferable that this Cre recombinase expressing plasmid is present within the host cell, such as E. coli TG1, into which the DNA sequences to be recombined are transformed or infected. It is essential in this case that the plasmid on which the Cre recombinase is encoded has a different origin of replication from the replicons on which the DNA to be recombined is encoded. In example 5 we describe the construction of a plasmid with a pACYC origin which expresses Cre recombinase.

In example 4, a library was constructed where a repertoire of VH genes encoded on a plasmid with a ColE1 origin was recombined with Vκ and Vλ genes encoded on a phage vector with a phage fd origin, the recombination catalysed by Cre recombinase encoded on a plasmid with a pACYC origin. These three origins of replication are compatible, so all three plasmids may coexist in the same, cell. The recombination mechanism is illustrated FIGS. 4A, 4A-1, 4B, and 4B-1.

The use of site-specific recombination to bring genes onto the same replicon may be extended to creation of a continuous coding sequence on the same replicon, for example to construct single-chain Fv molecules. There is a single open reading frame in the loxP sequence that could be incorporated into an scFv linker which would then be a substrate for Cre-catalysed site-specific recombination. Placement of such modified scFv linker sequences at one or both ends of the genes to be fused can then result in creation of continuous open reading frames in vivo or in vitro when Cre recombinase is provided.

As with other site-specific recombination systems, Cre-catalysed recombination is reversible such that productive recombinants form only a fraction of the recombinants. Selection of productive rearrangements may be facilitated by use of a polA strain of bacteria, preferably E. coli or other gram negative bacterium. These cells are deficient in DNA polymerase I and are unable to support replication of plasmids (Johnston, S. and Ray, D. S. 1984, supra.). However, they are able to support replication of filamentous phage and plasmids containing filamentous phage intergenic regions. If Cre-catalysed recombination is performed in polA bacteria, by selecting for the presence of both selectable markers in the same pol A cell successful recombination events are enriched, since recombination must take place for the second marker gene to be replicated and expressed. The resulting cells then contain the complete repertoire and can be propagated as cells and infected with helper phage to produce phagemids containing the genes for both chains and expressing them on their surface.

Another way of enriching for productive recombination events is to employ mutant loxP sites. Several mutants of the loxP sequence are known, and these are compromised with respect to their ability to recombine with each other and the wild-type loxP sequence (Hoess, R. H., Wierzbicki, A. and Abremski, K. (1986) Nucl. Acids Res. 14, 2287–2300). For example, loxP 511 has a G->A point mutation in the central 8 bp segement, with the result that it will only recombine with other loxP 511 sites, but not the wild-type loxP sequence (Hoess, R. H., Wierzbicki, A. and Abremski, K. (1986) supra). Placement of wild-type and mutant loxP sequence combinations can direct which recombination events are possible: their use is described in example 1. Other mutant loxP sites are known but their abilities to recombine with each other and the wild-type loxP sequence have not been extensively characterised, presumably loxP 511 is not unique. Provision of different mutant loxP sites in the vectors would permit even greater control over the occurance of recombination events perhaps leading to more complex, controllable and efficient recombination strategies being possible.

Further, loxP sites which can be used for recombination have been derived as described in example 6 and are shown in Table 8. The availability of these loxP sites has allowed the construction of a vector system including 3 lox sites. This 3lox system offers two additional features compared to the 2lox system of example 1:

(i) Chain shuffling of light and heavy chain genes for affinity maturation of antibody fragments (see Marks, et al. "By-passing immunization: building high affinity human antibodies by chain shuffling." Bio/Technology 10:779–783 (1992)) is facilitated since one chain may be kept constant and a library of light chains or VHCH1 heavy chains recombined with it using an appropriate donor vector. For example, a clone specific for an antigen may be isolated where the gene for a VHCH1 region of a Fab fragment is located between loxP 511 and loxP WT of fd3lox and the gene for the original light chain is located between the mutant loxP site, e.g. loxP 4, and loxP 511 of fd3lox (see FIG. 15). A library of light chains may then be shuffled with the VHCH1 heavy chain region kept constant by recombining the fd3lox clone with a library of light chain genes on a pUC19 2lox donor vector which are located between the loxP 4 site and the loxP 511 site (as in FIG. 15). The library of light chains is now encoded in the fd3lox vector and Fab fragments with e.g. improved affinity can be selected from the phage displayed Fab fragment repertoire. Similarly, if a repertoire of antibody fragments displayed on phage is selected for binding to antigent to give a pool of selected fragments, a pool of one chain may be kept constant and a library of light chains or VHCH1 heavy chains recombined with it using an appropriate donor vector. The fact that the heavy and light chain gene elements are flanked by different pairs of loxP sequences means that, for instance, a light chain shuffle may be sequentially followed by a heavy chain shuffle.

(ii) The transfer of light and heavy chain gene pairs which have been selected on the surface of filamentous bacteriophage for binding to antigen into a soluble expression vector for expression of soluble Fab fragments, which at present needs to be done by cloning using restriction enzymes, is also facilitated. The transfer by recombination may be achieved by creating an expression vector containing a new mutant loxP site such as loxP 4 and the WT site and by recombination between these two sites and the corresponding sites on the other vector, e.g. fd3lox. The inversion that occurs between loxP 4 and WT (see example 6) should make this process more efficient. If the loxP sites generated are non-functional, then the gene pairs should become 'locked' into the reverse complement orientation, thus driving the recombination event between. the two vectors towards completion i.e., with most of the gene pairs contained in the expression vector.

The use of three different lox sites also allows, for example, the recombination of three sequences in order. One sequence to be recombined may be flanked by loxP and loxP 511, a second sequence by loxP 511 and loxP 3. These sequences could then be recombined into a third replicon containing a third DNA sequence and three lox sites. The lox sites could be arranged for expression of the three sequences separately or continuously.

Naturally, these principles may be extended to any recombination system (e.g. other than loxP) where three different recombination sites are available. As with loxP, the three sites used may be any combination of sites where like sites combine with like but are unable to recombine with unlike. Thus, a wild-type and two mutants may be used, or indeed three mutants may be used. The use of site-specific recombination to bring genes onto the same replicon. may be used for the creation of a continuous coding sequence on the same replicon, for example to construct single-chain Fv molecules. There is a single open reading frame in the loxP sequence that could be incorporated into a scFv linker which would then be a substrate for Cre-catalysed site-specific recombiantion. The availability of further loxP sites as described in example further sequences for linkers when site-specific recombination creates a continuous coding sequence on the same replicon, e.g. encoding a single chain Fv fragment. The opening reading frames present in the loxP sites would lead to the different linkers shown in FIG. 18 when they are used to link together two sequences. The linkers derived from loxP 1 and loxP 4 are shown in example 7 to allow expression of single chain Fv molecules and to be functional. The locP sites in the gene encoding the single chain molecule are shown to be utilisable in the construction of new single chain Fv molecules and in shuffling of VH and V1 domains. The same methodology could be used to link other pairs of polypeptides to form a member of a specific binding pair, for instance Vα and Vβ chains of a T-cell receptor could be brought together to form a single chain T-cell receptor molecule.

The presence of target DNA sequences for site-specific recombination in the vectors has utility for subsequent manipulation of the genes. Naturally occurring or artificially introduced loxP sequences in the genomes of prokaryotic and eukaryotic organisms can be used as target sites for insertion of genes. Moreover, since Cre-catalysed recombination occurs readily in vitro, rapid and efficient transfer of genes in vitro, for example between different vectors, is also contemplated (Boyd, A. C., *Nuc. Acids Res.* 21:817–821 (1993)).

It will be apparent that the concept of using two or more replicons to generate diversity is not confined to display of multimers on the surface of filamentous bacteriophages. For example, bacteria could be used as the replicable genetic display package. For example, Fuchs et al. have shown that functional antibody can be displayed on the surface of *E. coli* by fusion to peptidoglycan-associated lipoprotein (Fuchs et al., 9:1369–1373 (1991)). Klauser et al. describe transport of a heterologous protein to the surface of *E. coli* by fusion to Neisseria IgA protease (Klauser et al., *EMBO* 9:1991–1999 (1990)). Other surface proteins such as pili, ompA or the surface-exposed lipoprotein Tra T could also be used, and gram positive organisms such as lactobacilli. and streptococci employed. Cloning and expression in eukaryotic organisms is also contemplated.

Alternative cloning strategies are possible when cells are used in place of phage. For example, replicons can be introduced into the cells by conjugation, in addition to transformation and infection. Moreover, one or more genes can be recombined or transposed into the chromosome reducing the limitation of having to use compatible replicons.

The polycombinatorial concept is also particularly advantageous for mutagenesis experiments by allowing far greater numbers of mutant progeny to be produced. For example, if the genes encoding a multimeric peptide or polypeptide are mutated at a total of 10 amino acid positions, to incorporate any amino acid at these positions, then the total number of combinations is $20^{10}$=>$1.024 \cdot 10^{13}$. This figure is way beyond the reach of standard cloning formats, but can be achieved using the approaches described here.

The methods described here are applicable to multimeric proteins other than antibodies, such a T cell receptors, CD3 and insulin receptor. Libraries of proteins having more than two different and diverse subunits can be created by, for example, more than one cycle of infection. Cells containing one of the subunits are infected with phage containing the second subunit and the resulting population infected a second time with a compatible phage carrying the third subunit. The invention may also be applied to combining two libraries of peptide displayed on phage to give a library of longer peptides. Rather than VH and VL domains being expressed as a continuous reading frame, linked by amino acids encoded by the loxP sequence as in example 7, two separate peptide libraries, each encoding for example 10 amino acids, may be cloned into separatee replicons and recombined using a loxP site which then encodes amino acids which link the two peptide elibraries to form a recombined library of, for example, 32 amino acid peptides. The constructs may be designed so that a continuous open reading frame is formed. Instead of loxP sites, or sites derived from loxP, other site-specific recombination sequences containing an open reading frame may be used.

In some cases, it is advantageous to express all components of the multimer as g3 fusions. This will have the benefit stabilising weak interactions between seperate chains, e.g. VHg3 and VLg3 to create phage or phagemid particles with both VH and VL fused to g3 on the same particle, or stabilising polypeptides which interact weakly, or polypeptides which only associate in the presence of ligand.

The numbers of combinations possible with the polycombinatorial approach is limited only by the number of clones present in each of the repertoires, and, in the specific instance of using phage supplying one chain to infect cells containing the other, by the numbers of phage and cells that can be produced. The use of more sophisticated methods, for example fermentation technology, will allow even greater numbers of combinations to be accessed.

The nucleic acid encoding first and second polypeptide components of antibodies may be derived from the repertoire of an immunised or unimmunised animal or human, or from an artificially rearranged immunoglobulin gene or genes. Artificial rearrangement of immunoglobulin genes may involve joining of germ-line V segments in vitro to J segments and, in the case of VH domains, D segments. Any of the V, D and J segments may be synthetic. The joining may use a PCR-based process which may use primers which have a region of random sequence to introduce sequence diversity into the product, artificially rearranged immunoglobulin genes.

Filamentous F-specific bacteriophages are among the suitable examples of the type of phage which provide a vehicle for the display of binding molecules e.g. antibodies and antibody fragments and derivatives thereof, on their surface and facilitate subsequent selection and manipulation.

The F-specific phages (e.g. fl, fd and M13) have evolved a method of propagation which does not kill the host cell and they are used commonly as vehicles for recombinant DNA (Kornberg, A., DNA Replication, W. H. Freeman and Co., San Francisco, 1980). Gene III of phage fd is attractive for the insertion of biologically active foreign sequences. There are however, other candidate sites including for example gene VIII and gene VI. The protein encoded by gene III has several domains (Pratt et al., *Virology* 39:42–53 (1969), Grant et al., *J. Biol. Chem.* 256:539–546 (1981) and Armstrong et al., *FEBS Lett.* 135:167–172 (1981)).

The gene coding sequences for biologically active antibody fragments have been inserted into the gene III region of fd to express a large fusion protein. An initial vector used was fd-tet (Zacher, A. N., et al., *Gene* 9:127–140 (1980)) a tetracycline resistant version of fd bacteriophage that can be propagated as a plasmid that confers tetracycline resistance to the infected *E. coli* host. The applicants chose to insert after the signal sequence of the fd gene III protein for several reasons. In particular, the applicants chose to insert after amino acid 1 of the mature protein to retain the context for the signal peptidase cleavage. To retain the structure and function of gene III itself, the majority of the original amino acids are synthesized after the inserted immunoglobulin sequences. The inserted immunoglobulin sequences were designed to include residues from the switch region that links VH-VL to CH1-CL (Lesk, A., and Chothia, C., *Nature* 335:188–190 (1988)).

By manipulating gene III of bacteriophage fd, one can construct a bacteriophage that displays on its surface large biologically functional antibody, enzyme, and receptor molecules whilst remaining intact and infectious. Furthermore, the phages bearing antibodies of desired specificity, can be selected from a background of phages not showing this specificity.

The sequences coding for a population of antibody molecules and for insertion into the vector to give expression of antibody binding functions on the phage surface can be derived from a variety of sources. For example, immunised or non-immunised rodents or humans, and from organs such as spleen and peripheral blood lymphocytes. The coding sequences are derived from these sources by techniques familiar to those skilled in the art (Orlandi et al., supra (1989); Larrick et al., supra (1989); Chiang et al., *Bio Techniques* 7:360–366 (1989); Ward et al., supra (1989); Sastry et al., supra (1989)).

In standard recombinant techniques for the production of antibodies, an expression vector containing sequences coding for the antibody polypeptide chains is used to transform e.g. *E. coli*. The antibody polypeptides are expressed and detected by use of standard screening systems. When the screen detects an antibody polypeptide of the desired specificity, one has to return to the particular transformed *E. coli* expressing the desired antibody polypeptide. Furthermore, the vector containing the coding sequence for the desired antibody polypeptide then has to be isolated for use from *E. coli* in further processing steps.

In the present invention however, the desired antibody polypeptide when expressed, is already packaged with its gene coding sequence. This means that when the an antibody polypeptide of desired specificity is selected, there is no need to return to the original culture for isolation of that sequence. Furthermore, in previous methods in standard recombinant techniques, each clone expressing antibody needs to be screened individually. The present application provides for the selection of clones expressing antibodies with desired properties.

Herein we show in example 3 the construction of a large human synthetic phage display library by recombination and the selection of high affinity human antibodies. A highly diverse combinatorial repertoire has been constructed in vivo using V-gene segments as building blocks. We first created highly diverse repertoires of heavy and light chains entirely in vitro from a bank of human V-gene segments and then, by recombination of the repertoires in bacteria, generated a large (close to $6.5 \times 10^{10}$) synthetic repertoire of Fab fragments displayed on filamentous phage. From this repertoire we isolated Fab fragments which bound to a range of different antigens and haptens, and with binding affinities comparable to those of antibodies from a secondary immune response in mice (up to 4 nM). In example 4, we show the construction by recombination in the loxP format of a large phage display repertoire of Fab fragments derived from the tonsils of unimmunised human and selection of antibodies. A library of $8.24 \times 10^{11}$ clones was prepared and antibodies selected against human self antigens.

Because a rgdp (e.g. a pAb) displays a member of a specific binding pair (e.g. an antibody of monoclonal antigen-binding specificity) at the surface of a relatively simple replicable structure also containing the genetic information encoding the member, rgdps (e.g. pAbs), that bind to the complementary member of the specific binding pair (e.g. antigen) can be recovered very efficiently by either eluting off the complementary member using for example diethylamine, high salt etc and infecting suitable bacteria, or by denaturing the structure, and specifically amplifying the sequences encoding the member using PCR. That is, there is no necessity to refer back to the original bacterial clone that gave rise to the pAb.

Selection Formats and Affinity Maturation

Individual rgdps e.g. pAbs expressing the desired specificity e.g. for an antigen, can be isolated from the complex library using the conventional screening techniques (e.g. as described in Harlow, E., and Lane, D., supra (1988); Gherardi et al. *J. Immunol. Meth.* 126:61–68 (1990)).

Other selection techniques, described and illustrated in WO 92/01047, are practicable only because of the unique properties of rgdps. The general outline of some screening procedures is illustrated in FIG. 5 using pAbs as an example type of rgdp.

The population/library of pAbs to be screened could be generated from immunised or other animals; or be created in vitro by mutagenising pre-existing phage antibodies (using techniques well-known in the art such as oligonucleotide. directed mutagenesis (Sambrook et al., *Molecular Cloning a Laboratory Manual*, Cold Spring Harbor Laboratory Press (1989)). This population can be screened in one or more of the formats described below with reference to FIGS. 5A–5B, to derive those individual pAbs whose antigen binding properties are different from sample c.

Binding Elution

FIG. 5A shows antigen (ag) bound to a solid surface (s) the solid surface (s) may be provided by a petri dish, chromatography beads, magnetic beads and the like. The population/library of pAbs is then passed over the (ag), and those individuals p that bind are retained after washing, and optionally detected with detection system. A detection system based upon anti-fd antisera is illustrated in more detail in example 4 of WO 92/01047. If samples of bound population p are removed under increasingly stringent conditions, the binding. affinity represented in each sample will increase. Conditions of increased stringency can be obtained, for example, by increasing the time of soaking or changing the pH of the soak solution, etc.

Competition

Referring to FIG. 5B antigen (ag) can be bound to a solid support (s) and bound to saturation by the original binding molecule (c). If a population of mutant pAb (or a set of unrelated pAbs) is offered to the complex, only those that have higher affinity for antigen ag than c will bind. In most examples, only a minority of population c will be displaced by individuals from population p. If c is a traditional antibody molecule, all bound material can be recovered and bound p recovered by infecting suitable bacteria and/or by use of standard techniques such as PCR.

An advantageous application is where ag is used as a receptor and c the corresponding ligand. The recovered bound population p is then related structurally to the receptor binding site/and or ligand. This type of specificity is known to be very useful in the pharmaceutical industry.

Another advantageous application is where ag is an antibody and c its antigen. The recovered bound population p is then an anti-idiotype antibody which have numerous uses in research and the diagnostic and pharmaceutical industries.

At present it is difficult to select directly for anti-idiotype antibodies. pAbs would give the ability to do this directly by binding pAb libraries (e.g. a naive library) to B cells (which express antibodies on their surface) and isolating those phage that bound well.

In some instances it may prove advantageous to pre-select population p. For example, in the anti-idiotype example above, p can be absorbed against a related antibody that does not bind the antigen.

However, if c is a pAb, then either or both c and p can advantageously be marked in some way to both distinguish and select for bound p over bound c. This marking can be physical, for example, by pre-labelling p with biotin; or more advantageously, genetic. For example, c can be marked with an EcoB restriction site, whilst p can be marked with an EcoK restriction site (see Carter et al., *Nucl. Acids Res.* 13:4431–4443 (1985)). When bound p+c are eluted from the antigen and used to infect suitable bacteria, there is restriction (and thus no growth) of population c (i.e. EcoB restricting bacteria in this example). Any phage that grew, would be greatly enriched for those individuals from p with higher binding affinities. Alternatively, the genetic marking can be achieved by marking p with new sequences, which can be used to specifically amplify p from the mixture using PCR.

Since the bound pAbs. can be amplified using for example PCR or bacterial infection, it is also possible to rescue the desired specificity even when insufficient individuals are bound to allow detection via conventional techniques.

The preferred method for selection of a phage displaying a protein molecule with a desired specificity or affinity will often be elution from an affinity matrix with a ligand (e.g. example 21 of WO 92/01047). Elution with increasing concentrations of ligand should elute phage displaying binding molecules of increasing affinity. However, when e.g. a pAb binds to its antigen with high affinity or avidity (or another protein to its binding partner) it may not be possible to elute the pAb from an affinity matrix with molecule related to the antigen. Alternatively, there. may be no suitable specific eluting molecule that can be prepared in sufficiently high concentration. In these cases it is necessary to use an elution method which is not specific to e.g. the antigen-antibody complex. Some of the non-specific elution methods generally used reduce phage viability for instance, phage viability is reduced with time at pH12 (Rossomando, E. F. and Zinder N. D., *J. Mol.Biol.* 36:387–399 (1968)). There may be interactions between e.g. antibodies and affinity matrices which cannot be disrupted without completely removing phage infectivity. In these cases a method is required to elute phage which does not rely on disruption of e.g. the antibody—antigen interaction. A method was therefore devised which allows elution of bound pAbs under mild conditions (reduction of a dithiol group with dithiothreitol) which do not disrupt phage structure (example 47 of WO 92/01047).

This elution procedure is just one example of an elution procedure under mild conditions. A particularly advantageous method would be to introduce a nucleotide sequence encoding amino acids constituting a recognition site for cleavage by a highly specific protease between the foreign gene inserted, in this instance a gene for an antibody fragment, and the sequence of the remainder of gene III. Examples-of such highly specific proteases are Factor X and thrombin. After binding of the phage to an affinity matrix and elution to remove non-specific binding phage and weak binding phage, the strongly bound phage would be removed by washing the column with protease under conditions suitable for digestion at the cleavage site. This would cleave the antibody fragment from the phage particle eluting the phage. These phage would be expected to be infective, since the only protease site should be the one specifically introduced. Strongly binding phage could then be recovered by infecting e.g. *E. coli* TG1 cells.

An alternative procedure to the above is to take the affinity matrix which has retained the strongly bound pAb and extract the DNA, for example by boiling in SDS solution. Extracted DNA can then be used to directly transform *E. coli* host cells or alternatively the antibody encoding sequences can be amplified, for example using PCR with suitable primers such as those disclosed herein, and then inserted into a vector for expression as a soluble antibody for further study or a pAb for further rounds of selection.

Another preferred method for selection according to affinity would be by binding to an affinity matrix containing low amounts of ligand.

If one wishes to select from a population of phages displaying a protein molecule with a high affinity for its ligand, a preferred strategy is to bind a population of phage to an affinity matrix which contains a low amount of ligand. There is competition between phage, displaying high affinity and low affinity proteins, for binding to the ligand on the matrix. Phage displaying high affinity protein is preferentially bound and low affinity protein is washed away. The high affinity protein is then recovered by elution with the ligand or by other procedures which elute the phage from the affinity matrix (example 35 of WO 92/01047 demonstrates this procedure).

In summary then, for recovery of the packaged DNA from the affinity step, the package can be simply eluted, it can be eluted in the presence of a homologous sbp member which competes with said package for binding to a complementary sbp member; it could be removed by boiling, it could be removed by proteolytic cleavage of the protein; and other methods will be apparent to those skilled in the art e.g. destroying the link between the substrate and complementary sbp member to release said packaged DNA and sbp member. At any rate, the objective is to obtain the DNA from the package so that it can be used directly or indirectly, to express the sbp member encoded thereby.

The efficiency of this selection procedure for pAbs and the ability to create very large libraries means that the immunisation techniques developed to increase the proportion of screened cells producing antibodies of interest will not be an absolute requirement. The technique allows the rapid isolation of binding specificities e.g. antigen-binding specificities, including those that would be difficult or even unobtainable by conventional techniques, for example, catalytic or anti-idiotypic antibodies. Removal of the animal altogether is now possible, once a complete library of the immune repertoire has been constructed.

The structure of the pAb molecule can be used in a number of other applications, some examples of which are:

Signal Amplification

Acting as a molecular entity in itself, rgdps e.g. pAbs combine the ability to bind a specific molecule e.g. antigen with amplification, if the major coat protein is used to attach another moiety. This moiety can be attached via immunological, chemical, or any other means and can be used, for example, to label the complex with detection reagents or cytotoxic molecules for use in vivo or in vitro.

Physical Detection

The size of the rgdps e.g. pAbs can be used as a marker particularly with respect to physical methods of detection such as electron microscopy and/or some biosensors, e.g. surface plasma resonance.

Diagnostic Assays

The rgdps e.g. pAbs also have advantageous uses in diagnostic assays, particularly where separation can be effected using their physical properties for example centrifugation, filtration etc.

EXAMPLE 1

In Vivo Recombination of Antibody Genes Between Replicons Using Cre/Lox

This example illustrates using the Cre/loxP system to transfer antibody genes between two replicons in the same cell. Here, recombination must occur to produce a functional pairing of antibody genes.

Figure 4A:
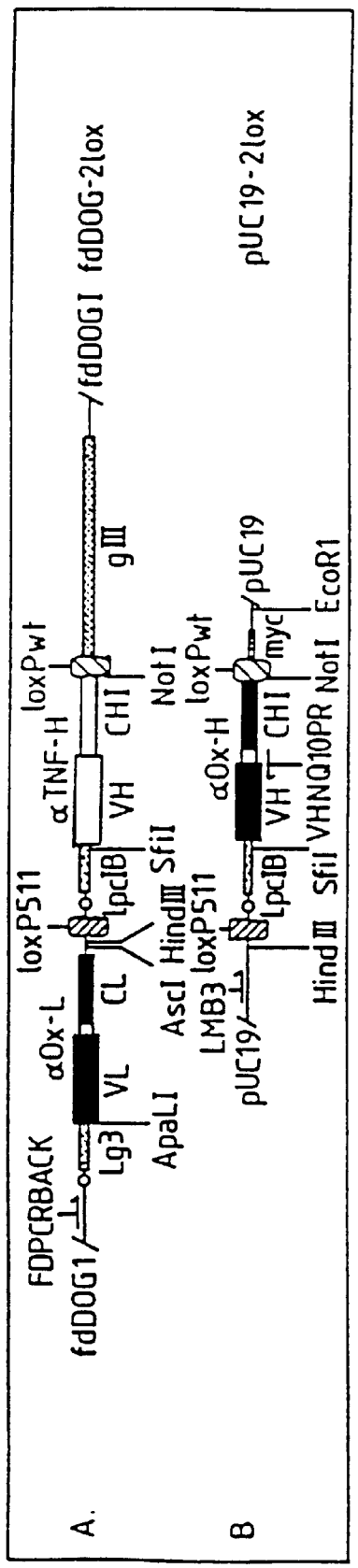
Figures 1, 4A:
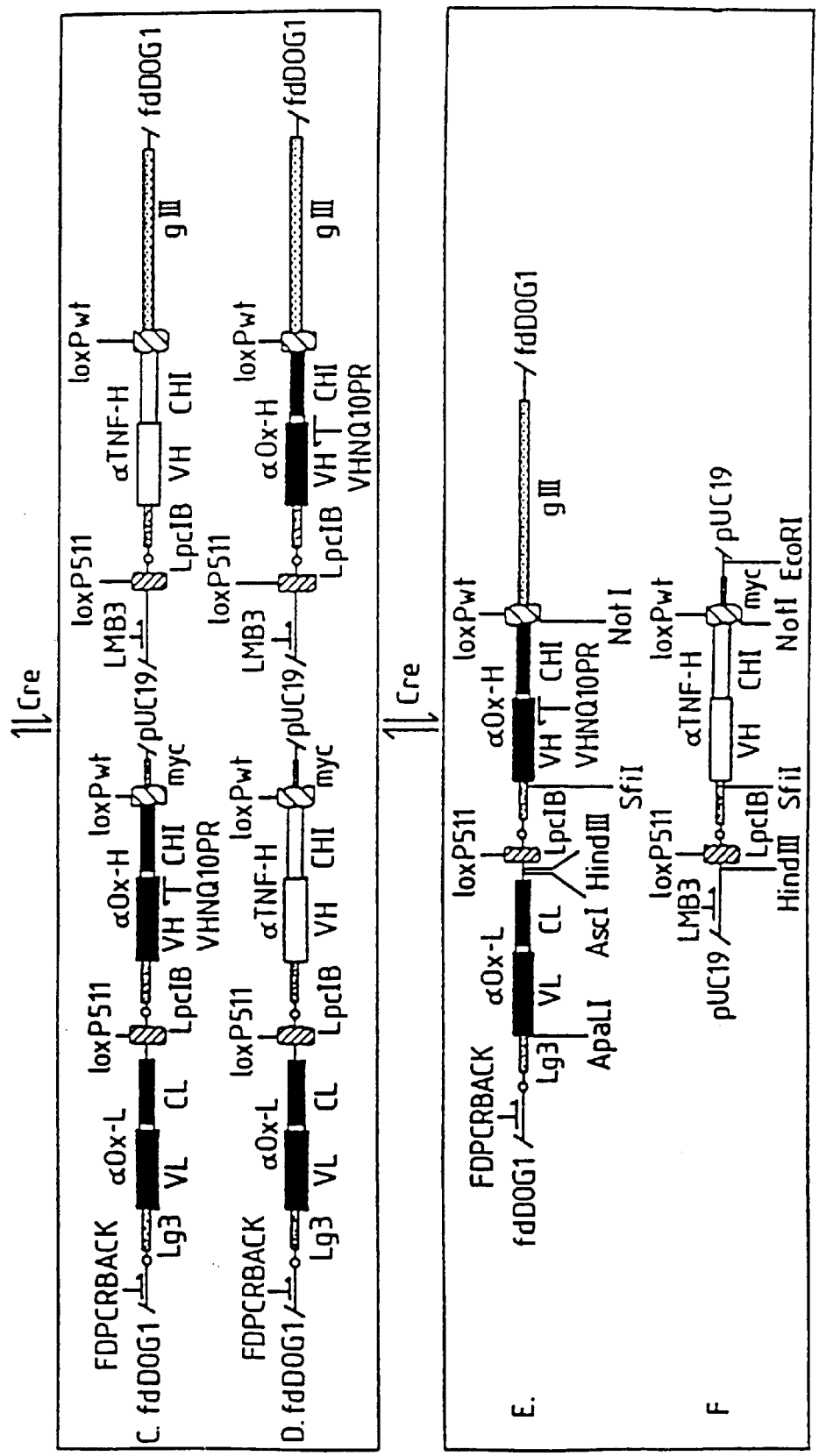

Two constructs were made: an "acceptor" fd phage vector, fdDOG-2lox (A) and a "donor" plasmid vector, pUC19-2lox (B) (see FIG. 4A and legend). A encodes the light chain of a first antibody (and the heavy chain from a second, different antibody): B encodes the heavy chain of the first antibody. In both vectors the VH genes are flanked by two loxP sites (see FIG. 4A). To avoid deletion of the VH genes in the presence of Cre, one of the loxP sites is wild-type but the other contains a G to A point mutation within the 8 bp spacer region loxP 511 (Hoess, R. H., Wierzbicki, A. and Abremski, K., supra (1986)). The wild-type loxP site and. the mutant loxP 511 site do not recombine with each other in the same vector, but will, as shown below, recombine with sites of matching sequence in different vectors. When Cre recombinase is provided in vivo by infecting the E. coli with phage P1Cm cl.100 (Rosner, J. L., Virology, 48:679–689 (1972), A and B can co-integrate by recombination between either mutant or wild-type loxP sites to create chimaeric plasmids C or D respectively (see FIG. 4A-1). Further recombination can then occur between the two wild-type or the two mutant loxP sites, to generate the original vectors (A and B) (see FIG. 4A) or two new vectors (E and F) (see FIG. 4A-1). The heavy chains of A and B are therefore exchanged, and E now encodes the Fab fragment of the first antibody for display as a fusion to the N-terminus of the phage gene 3 protein (g3p).

a) Construction of fdDOG-2lox and pUC19-2lox Vectors

FdDOG-2lox and pUC19-2lox vectors were derived from fdDOG-1 and pUC19 respectively (WO 92/01047 and WO 92120791; fdDOG-1 previously called fdCAT-2). The cloning sites of these vectors were engineered using a combination of site-directed mutagenesis and ligation of double-stranded synthetic oligonucleotides using standard molecular biology techniques (Sambrook, J., Fritsch, E. F. and Maniatis, T., *Molecular Cloning-A Laboratory Manual*, Cold Spring Harbor Laboratory, New York (1990)).

These constructs were used to produce donor plasmid B and acceptor phage A depicted in FIG. 4A. Plasmid B contains the VH gene of the anti-phOx (2-phenyloxazol-5-one) hybridoma NQ10.12.5 (Griffiths, G. M., Berek, C., Kaartinen, M. and Milstein, C., *Nature*, 312:271–275 (1984)) linked to a human Cg1 segment, and cloned into pUC19-2lox as an Sfi 1-Not 1 fragment. Acceptor phage A contains the VL partner of the anti-phOx hybridoma NQ10.12.5 linked to a human Ck1 segment cloned into fdDOG-2lox as an Apa LI-Asc I fragment. Acceptor phage A also contains a VH segment from an anti-Tumour Necrosis Factor antibody (Rathjen, D. A., Furphy, L. J. and Aston, R., *Br. J. Cancer*, 65:852–856 (1992)) linked to a human Cm1 segment, and cloned into fdDOG-2lox as an Sfi 1-Not 1 fragment.

Both A and B constructs were transformed into *E. coli* TG1, construct A conferring resistance to tetracyclin, construct B conferring resistance to ampicillin.

(b) Preparation of Infectious Acceptor Phage Particles (Construct A)

Phage particles were harvested from the medium of construct B clones grown overnight in 2×YT containing tetracycline, as described in PCT WO 92/01047, example 6.

(c) In vivo Cre-Catalysed Recombination

In vivo Cre-catalysed recombination was performed as follows:

1. *E. coli* containing'the plasmid pUC19-2lox were grown, shaking at 37° C. in 2 ml 2×TY medium with 100 mg/ml ampicillin and 1% glucose to an O.D.600 nm of 0.4.

2. $5 \times 10^9$ transducing units (tu) fdDOG-2lox phage were added (a ten-fold excess over bacteria) and incubation continued at 37° C. without shaking for 30 min.

3. $5 \times 10^9$ pfu phage P1Cm cl.100 (confers chloramphenicol resistance; Rosner, J. L. (1972) et. supra.) were added and incubation continued for a further 30 min. at 37° C. 40 ml of this culture were then added to 2 ml 2×TY, 100 mg/ml ampicillin, 12.5 mg/ml tetracycline, 12.5 mg/ml chloramphenicol, 1% glucose. The culture was shaken for 40 hours at 30° C.

4. About $10^{10}$ tu phage fd particles (including recombinant phage) were harvested from the culture supernatant by centrifuging out bacteria at 13000×g for 5 min. and passing the supernatant through a 0.45 mm sterile filter (Minisart, Sartorius).

In order to sample the recombined population, $10^3$ tu of the above fd particles were infected into fresh *E. coli* TG1 and plated on 2×TY agar containing 12.5 mg/ml tetracycline then incubated at 37° C. overnight. Ninety six well seperated colonies were transferred to a 96 well microtitre tray containing 100 ml/well 2×TY containing 12.5 mg/ml tetracycline and grown at 37° C. overnight. This plate was used as a master stock which was then screened by several techniques to identify which recombination events had occurred:

(1) ELISA, to identify clones producing phage that bind to phOx-BSA (to identify vector E).

(2) Replica plating, to find clones resisitant to both ampicillin and tetracycline (to identify vectors C and D).

(3) Colony hybridisation, with a radiolabelled oligonucleotide VHNQ10PR which binds specifically to CDR3 of NQ10.12.5 VH (to identify vectors C, D and E).

(4) PCR, with oligonucleotides FDPCRBACK and VHNQ10PR (to identify vectors C and E).

(5) PCR, with oligonucleotides LMB3 and VHNQ10PR (to identify vector D).

(d) ELISA to Identify phOX Binders (Vector E)

1. Coat plate (Falcon 3912) with 100 µl of phOX-BSA (14:1 substitution) per well at 10 µg/ml, in PBS. Leave overnight at room temp.
2. Rinse wells 3× with PBS, and block with 200 µl per well of 2% Marvel/PBS, for 2 hs at 37° C.
3. Rinse wells 3× with PBS, then add 25 µl 10% Marvel/PBS to all wells.
4. Add 100 µl culture supernatant to the appropriate wells. Mix, leave 2 hrs room temp.
5. Wash out wells 3 times with PBS, 0.05% Tween 20 and 3 times with PBS. Add 100 ml sheep anti-M13 antiserum diluted 1:1000 in 2% Marvel/PBS into each well. Incubate at room temp. for 1.5 hrs.
6. Wash out wells with 3 times with PBS, 0.05% Tween 20 and 3 times with PBS. Pipette 100 µl of 1:5000 dilution of anti-sheep IgG antibody (peroxidase-conjugated, Sigma). Incubate at room temp. for 1.5 hrs.
7. Discard 2nd antibody, and wash wells 3 times with PBS, 0.05 % Tween 20 and 3 times with PBS.
8. Add one 10 mg ABTS (2,2'-azino bis (3-ethylbenzthiazoline-6-sulphonic acid), diammonium salt) tablet to 20 ml 50 mM citrate buffer, pH 4.5. (50 mM citrate buffer, pH 4.5 is made by mixing equal volumes 50 mM trisodium citrate and 50 mM citric acid).
9. Add 20 µl 30% hydrogen peroxide to the above solution immediately before dispensing.
10. Add 100 µl of the above solution to each well. Leave room temp. 30 min.
11. Quench by adding 50 µl 3.2 mg/ml sodium fluoride. Read optical density (O.D.) at 405 nm.

Note 1: 'Marvel' is dried milk powder. PBS is 5.84 g NaCl, 4.72 g $Na_2HPO_4$ and 2.64 g $NaH_2PO_4.2H20$, pH 7.2, in 1 liter.

68 of the 96 clones were found to be positive in the ELISA (O.D. 405 nM>1.0); 71% of the tetracycline resistant clones therefore correspond to vector E (FIG. 4A-1) since they encode functional anti-phOX Fab fragments on phage.

Replica Plating to Identify Vectors C and D

Cells from the master plate were inoculated onto a 2×YT agar plate containing 100 mg/ml ampicillin, 12.5 mg/ml tetracycline and 1% glucose, using a 96 pin device. The plate was incubated at 37° C. overnight. Five colonies had grown up the next day indicating that 5/96 clones had the structures shown in C or D.

Colony Hybridization to Identify Vectors C, D and E

Colony hybridisation was performed with the array using standard techniques as described in Sambrook et al. (1989, supra.). The probe used was a radiolabelled oligonucleotide VHNQ10PR which binds specifically to CDR3 of NQ10.12.5 VH.

73 of the 96 colonies were positive and therefore correspond to vectors C, D or E.

(g) PCR Screening to Identify Vectors C and E

PCR reactions were performed essentially as described in example 11, WO 92/01047. Cells from each of the 96 clones were carefully transferred using a toothpick into 20 ml sterile water in a 0.5 ml centrifuge tube. The samples were then placed in a boiling water bath for 5 minutes and 2 ml of this used as template for each 20 ml PCR reaction. Thirty cycles of amplification were performed each of 94° C. 1 minute, 50° C. 1 minute and 72° C. 2 minutes, using primers FDPCRBACK and VHNQ10PR. PCR reaction products were resolved on 1% TAE agarose gels (Sambrook et al. (1989) supra.). Of the 96 clones tested, 72 clones gave a ca. 1Kb PCR fragment and were thus scored as positive. These clones correspond to vectors C and E.

PCR Screening to Identify Vector D

A second set of PCR reactions were performed on cells from the array as described above, this time using primers LMB3 and VHNQ10PR.

Only 1 of the 96 clones gave a ca. 400 bp PCR fragment and was thus scored as vector D.

Analysis of Recombinants

The preceding experiments show that of the 96 tetracycline resistant clones that were sampled, 23 were vector A, 4 vector C, 1 vector D and 68 vector E. All 68 vector E clones produced phage which bound to phOx-BSA, but the remaining 28 clones did not (as expected). Thus, 70% of all tetracycline resistant clones corresponded to vector E, which encodes functional anti-phOx Fabs for display on phage.

The process is very efficient, and should allow the creation and use of extremely large combinatorial repertoires.

EXAMPLE 2

Creation of an Extremely Large Combinatorial Library Using in vivo Recombination This example describes construction of an extremely large library of V-genes from unimmunised donors, using the in vivo recombination strategy outlined in the previous example. Many of the procedures detailed below have been previously described (Marks, J et al. (1991) et supra.).

(a) Preparation of cDNA Template 500 ml of blood, containing approximately $10^8$ B-lymphocytes, was obtained from 2 healthy volunteers. The white cells were separated on Ficoll and RNA was prepared using a modified method (Cathala et al., *DNA*, 2:329 (1983)). Three first strand cDNA syntheses were made as described by Marks et al (1991, supra.) from RNA corresponding to $2.5 \times 10^7$ B-cells, using HuIgMFOR constant region primer for the heavy chains, and HuCKFORCYS for kappa light chains and HuCLFORCYS for lambda light chains (Table 1).

(b) PCR of Heavy Chains and Construction of Heavy Chain Repertoire

VH genes were PCR-amplified using the HuIgMFOR primer in conjunction with each of the HuVHBACK primers individually. Six separate PCR amplifications were performed each of 50 µl reaction volume containing 5 µl of the supernatant from the cDNA synthesis using the HUIGMFOR primer, 20 pmol total concentration of the BACK primers, 20 pmol concentration of the FORWARD primer, 250 µM dNTPs, 10 mM KCl, 10 mM (NH4)2SO4, 20 mM Tris.HCl (pH 8.8), 2.0 mM MgCl2, 100 mg/ml BSA and 1 µl (1 unit) Vent DNA polymerase (New England Biolabs). The reaction mixture was overlaid with mineral (paraffin) oil and subjected to 30 cycles of amplification using a Techne PHC-2 thermal cycler. The cycle was 94° C. for 1 minute (denaturation), 57° C. for 1 minute (annealing) and 72° C. for 2.5 minutes (extension). The products were purified on a 1.0% agarose gel, isolated from the gel using Geneclean (Bio-101) and resuspended in 25 μl of $H_2O$. The six products were then pooled and 'pullthrough' PCR reactions performed to attach Sfi I and Not I restriction sites.

Pull through reactions were set up with . the primers HUVHBACKSfi (equimolar mix of all 6 primers) and HUCMLFONO. 50 ml reactions of containing 5 μl of the pooled PCR products from the previous step were amplified using the same conditions as for the primary PCR except that 25 cycles of amplification were used. The resulting fragments were digested with Sfi I and Not I, gel-purified, and the fragments ligated to Sfi I and Not I-cut pUC19-2lox using previously described procedures (Sambrook, J. et al. (1989) et supra; PCT WO 92/01047). The ligation mixes were phenol-chloroform extracted prior to electroporation into TG1 cells (Marks et al. supra (1991)). Briefly, the ligated DNA was resuspended in 20 μl of water, and 2.5 μl samples were electroporated into 50 μl aliquots of electrocompetent E. coli TG1. Cells were grown in SOC for 1 hr and then plated on 2YT agar with 100 μg/ml ampicillin and 1% glucose (2YTAG) in 243×243 mm dishes (Nunc) then grown overnight at 30° C. Colonies were scraped off the plates into 2YTAG containing 15% glycerol for storage at −70° C. as library stocks.

The heavy chain repertoire was calculated to have ca. $1 \times 10^7$ independant recombinants, which by Bst NI fingerprinting was shown to be extremely diverse (PCT WO 92/01047).

PCR of Light Chains and Construction of Kappa and Lambda-Chain Repertoires

Kappa and lambda-chain genes were amplified separately. Kappa chain genes were amplified using an equimolar mixture of the 12 SYNKB primers in conjunction with HuCKFORCYS (Table 1). l-chain genes were amplified from the cDNA synthesis using an equimolar mix of the 8 DPVL primers in conjunction with the HUCLFORCYS primer. In each case 50 μl reaction mixtures were prepared containing 5 μl of the supernatant from the appropriate cDNA synthesis, 20 pmol total concentration of the BACK primers, 20 pmol concentration of the FORWARD primers, 250 μM dNTPs, 10 mM KCl, 10 mM (NH4)2SO4, 20 mM Tris.HCl (pH 8.8), 2.0 mM MgCl2, 100 mg/ml BSA and 1 μl (1 unit) Vent DNA polymerase (New England Biolabs). The reaction mixture was overlaid with mineral (paraffin) oil and subjected to 30 cycles of amplification using a Techne thermal cycler. The cycle was 94° C. for 1 minute (denaturation), 57° C. for 1 minute (annealing) and 72° C. for 2.5 minutes (extension). The products were purified on a 1% agarose gel, isolated from the gel by Geneclean (Bio-101) and resuspended in 25 μl of $H_2O$.

Pull through reactions were now performed on each of the two light chain preparations. kappa-chain genes were amplified using an equimolar mixture of the 12 SYNKBApa primers in conjunction with either HUCKFORCYSNOT. lambda-chain genes were amplified using an equimolar mixture of the 8 DPVLApa primers in conjunction with HUCLFORCYSNOT. Pullthrough conditions were performed as for the primary light chain PCRs above except that 25 cycles of amplification were used.

Kappa and lambda-chain repertoires were processed seperately. In each case, PCR products were digested with Apa LI and Not I and ligated into Apa LI-Not I-cut fdDOG-2lox (prepared using the standard format), the ligation mixes were purified by phenol extraction and ethanol precipitated prior to electroporation into TG1 as above, except that transformed cells were plated on 2YT agar with 12.5 μg/ml tetracycline in 243×243 mm dishes (Nunc) then grown overnight at 30° C. Colonies were scraped off the plates into 2YT containing 15% glycerol for storage at −70° C. as library stocks.

The kappa and lambda-chain repertoires were calculated to have ca. $1 \times 10^6$ independent recombinants; again, Bst NI fingerprinting indicates that both libraries were extremely diverse.

(d) In Vivo Recombination of Heavy and Light Chains

The kappa and lambda-chain repertoires were separately recombined with the heavy chain repertoire using a scale-up of the procedure described in example 1.

O.D. at 600 nm was used to calculate the cell density of the stocks scraped from the plates, using the algorithm $O.D.600_{nm}$ of $1.0 = 5 \times 10^8$ cells. Approximately $1 \times 10^{10}$ cells from each of the kappa and lambda-chain repertoires in fdDOG-2lox were inoculated into 1 liter volumes of 2×YT containing 12.5 μg/ml tetracycline and grown for 30 hrs at 37° C. with rapid shaking. Phage particles were harvested from the clarified growth medium as described in PCT WO 92/01047, example 6, and stocks adjusted to ca. $1 \times 10^{12}$ TU ml-1.

$1 \times 10^{11}$ cells from the heavy chain repertoire were inoculated into 2×1 liter volumes 2YTAG in 2.5 L shake flasks and grown at 37° C. with rapid shaking until the cultures reached an $O.D._{600nm}$ of 0.4 ml$^{-1}$. $5 \times 10^{12}$ fdDOG-2lox kappa and lambda fdDOG-2lox phage were added (a tenfold excess over bacteria) and incubation continued at 37° C. without shaking for 30 min. $5 \times 10^{12}$ pfu phage P1Cm cl.100 were then added and incubation continued for a further 30 min. at 37° C. The cultures were then centrifuged at 4,000× g-for 15 minutes at 4° C. and the supernatant poured off. The cell pellets were resuspended in 1 liter of 2×TY, 100 mg/ml ampicillin, 12.5 mg/ml tetracycline, 12.5 mg/ml chloramphenicol, 1% glucose and the cultures shaken for 40 hours at 30° C. Phage fd particles (including recombinant phage) were harvested from the culture supernatant by centrifuging out bacteria at 13000×g for 15 minutes and the particles. PEG precipitated.

The recombined library phage were then resuspended in 10 mM TRIS-HCl (pH 8.0), 1 mM EDTA and adjusted to $1 \times 10^{12}$ TU ml-1: this stock represents the library. These phage are selected on antigen, reinfected into fresh E. coli and recovered by plating on 2×YT agar containing 12.5 μg/ml tetracycline. Growth of selected phages. is achieved by culture in 2×YT containing 12.5 μg/ml tetracycline (no other antibiotics necessary—see FIG. 4, construct E), and phages bearing functional antibodies recovered from the growth medium.

Note: Sbp members and encoding nucleic acid therefor obtained using the present invention may be used in the production of derivatives. The term derivative is discussed above.

EXAMPLE 3

Construction of a Large Human Synthetic Phage Display Library by Recombination in the loxP Format and the Selection of High Affinity Human Antibodies In this example, the construction of a highly diverse combinatorial repertoire in vivo using V-gene segments as building blocks is described. First, highly diverse repertoires of heavy and light chains were created entirely in vitro from a bank of human V-gene segments and then, by recombination of the repertoires in bacteria, generated a large (close to $6.5 \times 10^{10}$) synthetic repertoire of Fab fragments displayed on filamentous phage. From this repertoire Fab fragments. were isolated which bound to a range of different antigens and haptens, and with binding affinities comparable to those of antibodies from a secondary immune response in mice (up to 4 nM).

The vast majority of heavy. and light chain segments were used in vivo and encoded part, or all, of each CDR3 loop by random sequence. To make the repertoire as large as possible bacteria harbouring a "donor" heavy chain repertoire (on a plasmid) were infected with an "acceptor" light chain repertoire (on phage). The two chains were combined on the same (phage) replicon within the bacterium by Cre catalysed recombination at loxP sites. This process, termed "combinatorial infection", generates a large number of heavy and light chain combinations, potentially as large as the. number of bacteria that have been infected. The repertoire was characterised by the properties of the selected Fab fragments.

Construction of a Large Synthetic Repertoire in the loxP Format

Heavy and light chain repertoires were built from the majority of human V-gene segments as described in FIG. 6. Neither the single segment of the Vk7 subgroup, nor the few segments from the Vλ families 4, 5, or 6, were included in the repertoire. Segments rarely used in vivo, for example light chain segments (DPK 2, 7, 10, 12, 17, 19, 20, 23 and 25) from the distal $V_k$ locus (Cox et al., *Eur. J. Immunol.*, in press (1994)), were represented equally in the synthetic repertoire. Some of the $V_H$-gene segments (DP-1, -12, -30, -39, -40, -44, -45 and -69) included in the repertoire are now known to be located on chromosome 15 or 16, and therefore outside the functional locus (Tomlinson et al., *Human Mol. Gen.* in press (1994)). The light chain repertoire was cloned into "acceptor" fd phage (tetracycline resistant), with a "dummy" heavy chain (FIG. 7A), and the heavy chain repertoire into "donor" plasmid (ampicillin resistant) (FIG. 7B). The repertoires, >$10^8$ heavy chains and >$8\times10^5$ light chains, were combined by infection of *E. coli* harbouring the donor heavy chains with fd phage carrying the light chains. If every heavy chain were paired with every light chain, this would generate a repertoire of >$8\times10^{13}$ antibodies. The culture was then co-infected with bacteriophage P1 (chloramphenicol resistant), which provides the Cre recombinase (example 1), leading to $6.5\times10^{10}$ colonies resistant. to ampicillin, tetracycline and chloramphenicol (for summary, see Table 5). After growth of the cultures, the fd phage were used to infect *E. coli*. 28% of the acceptor phage were shown to have acquired a heavy chain from the donor vector.

As there are multiple copies of plasmid and phage replicons in each bacterial cell when Cre recombinase is delivered by phage P1 infection, and at least 60 phage are produced per bacterium after overnight growth, each bacterium should yield at least one phage containing the heavy chain from the donor vector and therefore we estimate that the repertoire contains close to $6.5\times10^{10}$ different phage antibodies, with up to 60 copies of each.

The generation of this large library is described in more detail below:

Vectors

Figure 7A:
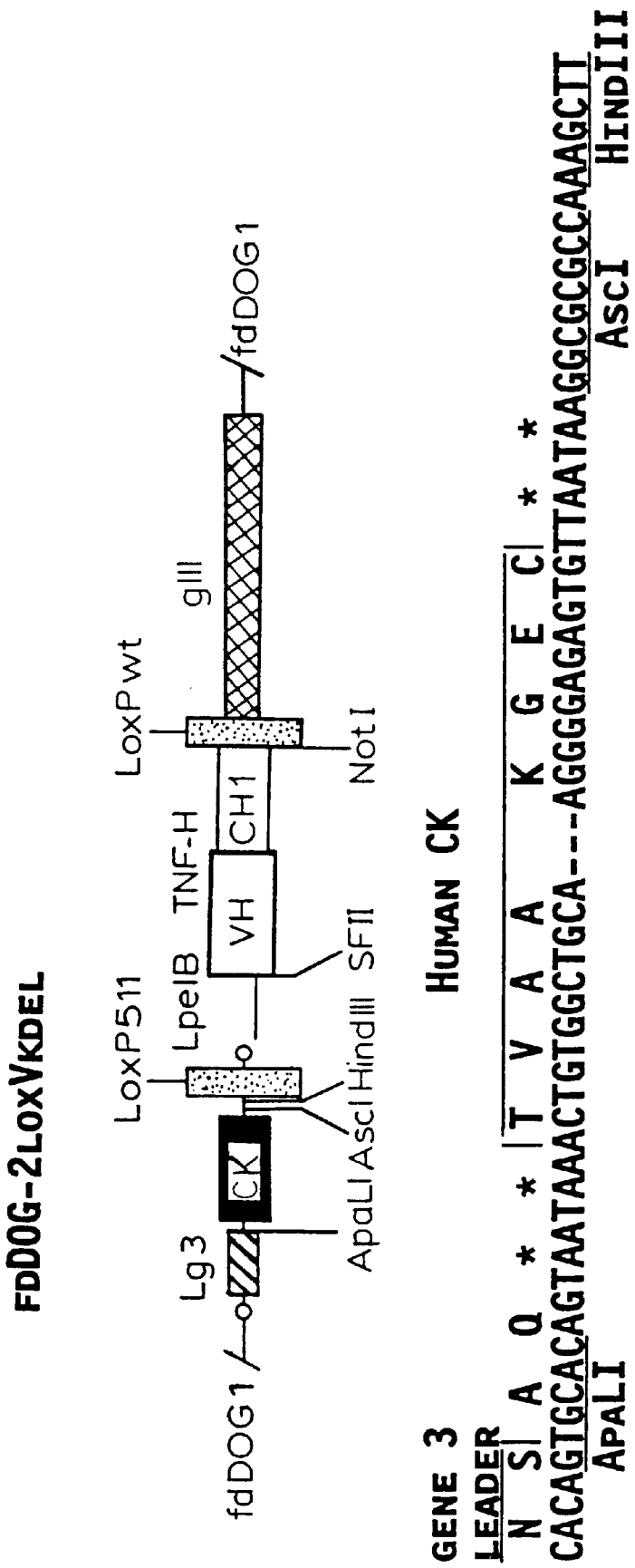
FIG. 7 shows: (A) The fd phage "acceptor" vector fdDOG-2loxVkdel. Light chain genes ($V_k$-$C_k$ and $V_\lambda$-$C_\lambda$) are cloned into this vector as ApaLI-AscI fragments. (B) The plasmid "donor" vector pUC19-2loxVHdel. Heavy chain variable region genes ($V_H$-genes) are cloned into this vector as NcoI-XhoI fragments. (C) The phagemid expression vector pUC119His6mycXba. Heavy and light chain genes encoding Fabs are cloned into this vector as XbaI-NotI fragments. Other features are marked as follows: sequences encoding Lg3, gene III leader sequence; LpelB, pelB leader sequence; Cκ, human kappa light chain -constant region; VH, heavy chain variable region; CH1, first heavy chain constant domain (human Cμ1 in fdDOG-2loxVkdel and human Cγ1 in pUC19-2loxVHdel); αTNF-H, the $V_H$-gene of the mouse anti-TNFα antibody mAb32 (Rathjen et al., *Br. J. Cancer*, 65:852–856 (1992)) linked to a human Cμ1 constant domain gene; gIII, fd phage gene III; loxP WT, wild-type loxP site (Hoess et al., *Proc. Natl. Acad. Sci. USA*, 79:3398–3402 (1982)); loxP 511, a mutant loxP site with a single point mutation (Hoess et al., *Nucleic Acids Res.*, 14:2287–2300 (1986)); myc, peptide from c-myc recognised by the monoclonal antibody 9E10 (Munro et al., *Cell*, 46:291–300 (1986); His6, six histidines.
Figure 7B:
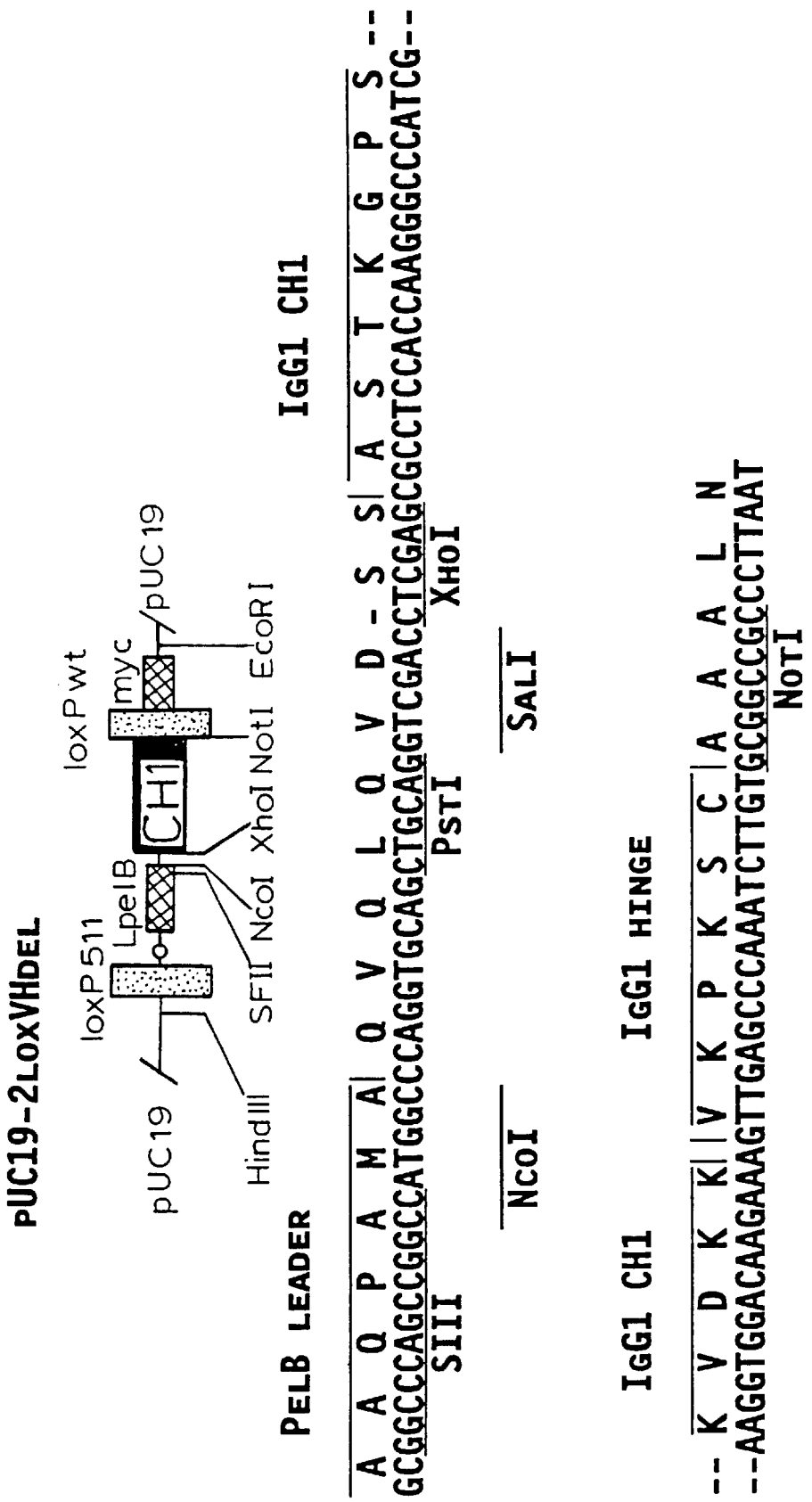
Figure 7C:
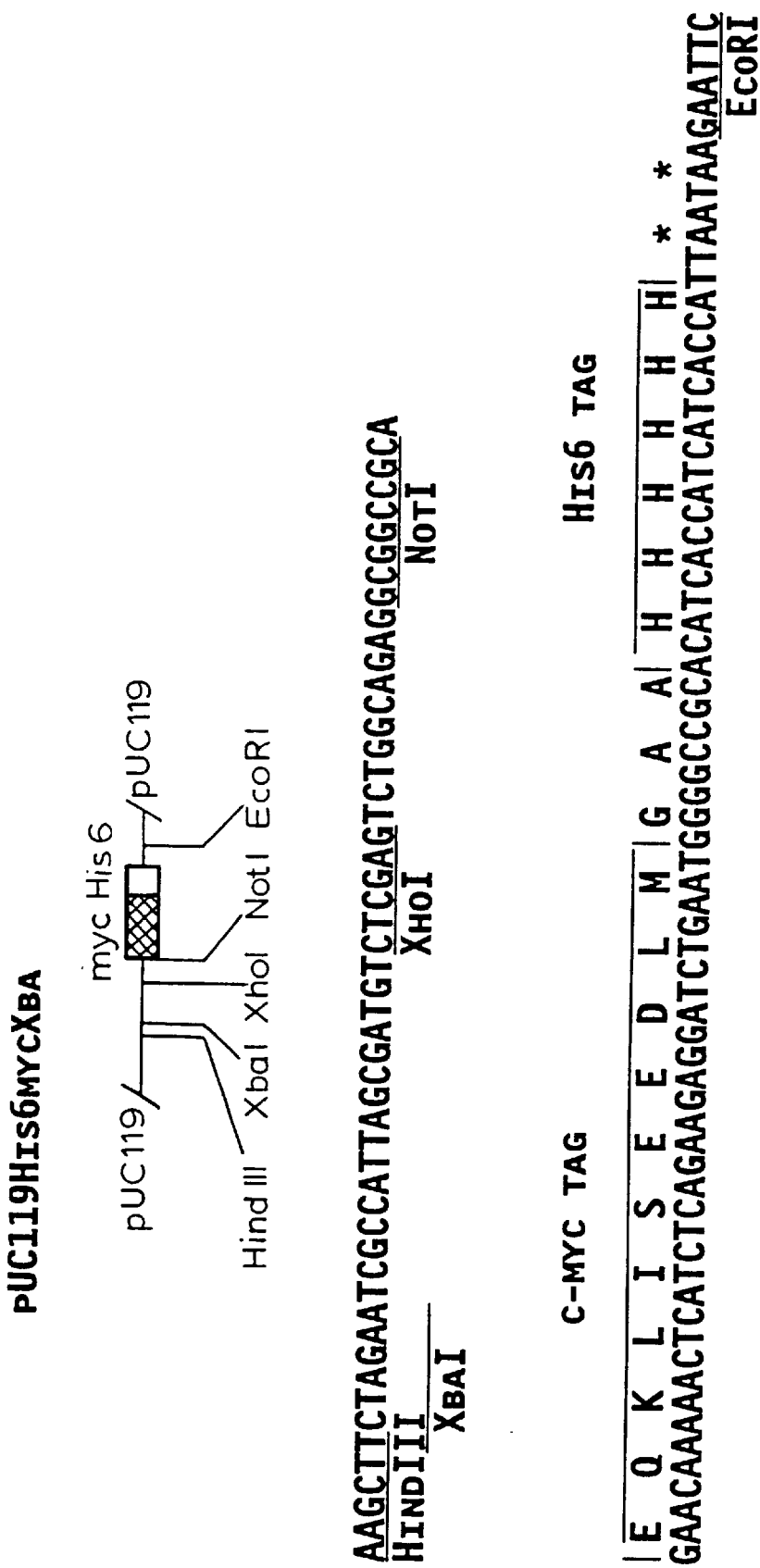

The "acceptor" vector, into which light chain repertoires are cloned, fdDOG-2loxVkdel, is identical to fdDOG-2lox (Example 1) except that the light chain variable region gene has been deleted (FIG. 7A). The "donor" vector, into which heavy chain repertoires are cloned, pUC19-2loxVHdel, is identical to pUC19-2lox (Example 1) except that the heavy chain variable region gene has been deleted (FIG. 7B). The vector for expression of soluble Fab fragments, pUC119His6mycXba, is a derivative of pUC119 (Vieira, J.

and Messing, J., *Meth. Enzymol.*, 153:3–11 (1987)), in which the polylinker has been replaced by the sequence shown in FIG. 7C.

Construction of Synthetic Heavy Chain Repertoires

A diverse repertoire of rearranged $V_H$-genes has previously been built in vitro (Nissim et al., *EMBO J.*, 13:692–698 (1994)), from a bank of 49 cloned $V_H$-gene segments (Tomlinson et al., *J. Mol. Biol.*, 227:776–798 (1992)) (one of the 50 segments (DP-20) included in the repertoire of Nissim et al., *EMBO J.*, 13:692–698 (1994) was a pseudogene). To these segments completely randomised CDR3 regions (Kabat et al., *Sequences of Proteins of Immunological Interest*, 5th edit., U.S. Dept. of Health and Human Services, Bethesda (1991)) were appended, varying in size between 4 and 12 residues (FIG. 6A). This cloned repertoire, with >$10^8$ different clones, was re-amplified using PCR with primers pUC-reverse and JH-Xho-FOR (Table 6A), the DNA was cut with NcoI and XhoI, and ligated into pUC19-2loxVHdel. The ligation mixture was electroporated (Dower et al., *Nucleic Acids Res.*, 16:6127–6145 (1988)) into *E. coli* TG1 (Gibson, T. J., *PhD Thesis*, University of Cambridge (1984)) to create the library pUC19-2loxVHlib, and in total $5\times10^8$ clones were obtained. Diversity was confirmed by BstNI fingerprinting (Clackson et al., *Nature*, 352:624–628 (1991)) and sequencing of 24 independent clones. All these clones were found to be different.

Construction of Synthetic Kappa Chain Repertoires

The human $C_k$ gene was amplified from the vector pSW1/FabD1.3 (Skerra et al., *Anal. Biochem.*, 196:151–155 (1991)) by PCR with Taq polymerase using primers CkFOR and CkLink (Table 6B1) which introduce a consensus human $J_k$ segment at the 5'-end of the Ck gene and two stop codons (TAA) and an AscI site at the 3'-end. The reaction mixture (50 μl) was cycled 25 times (94° C. for 1 min, 60° C. for 1 min, 72° C. for 1 min). The amplified $C_k$ gene was purified using Magic PCR Preps (Promega) and resuspended in 50 μl water.

In parallel, 26 human germline $V_k$ gene segments with open reading frames (DPK1-26), which had been cloned from the genomic DNA of a single individual (Cox et al., *Eur. J. Immunol.*, in press (1994)), were individually amplified with Back primers that introduce an ApaLI site at the 5'-end (see Table 6B2) and Forward primers that append a portion of the $J_k$ segment to the 3'-end (see Table 6B3). For each segment three independent PCR reactions were performed with different Forward primers to construct CDR3 regions (Kabat et al., *Sequences of Proteins of Immunological Interest*, 5th edit., U.S. Dept. of Health and Human Services, Bethesda (1991)) of length 8, 9 or 10 residues that included 1, 2, or 3 residues of random sequence (FIG. 6B). For each gene, a 50 μl PCR reaction was performed using Taq polymerase and toothpicked frozen glycerol stocks of *E. coli* infected with the appropriate M13 clone as template. Reactions were cycled 25 times (94° C. for 1 min, 60° C. for 1 min, 72° C. for 1 min). The Forward primers (Table 6B3) introduced length and sequence diversity into CDR3 corresponding to that observed in vivo (Kabat et al., *Sequences of Proteins of Immunological Interest*, 5th edit., U.S. Dept. of Health and Human Services, Bethesda (1991)).

The amplified $V_k$-genes were each joined to the amplified $C_k$ gene using PCR (Horton et al., *Gene*, 77:61–68 (1989)). Assembly PCR reactions (25 μl) used Taq polymerase, 1 μl of amplified $C_k$ and 0.8 μl of the $V_k$ gene PCR reaction from above. The appropriate $V_k$ Back primer was used for each gene (Table 6B2) together with $C_k$ FOR (Table 6B1) and the reaction cycled 30 times (94° C. for 1 min, 55° C. for 1 min, 72° C. for 2 min).

The PCR assembly reactions for each $V_k$ gene were checked by agarose gel electrophoresis, then pooled with the other $V_k$ genes according to CDR3 length, and the $V_k$-$C_k$ genes purified using Magic PCR Preps. The pooled DNA was then cut with ApaLI and AscI and digested DNA (approx. 6 μg) purified from a 1.5% low-melting-point agarose gel using Magic PCR Preps. Approx. 1 μg of the purified and cut $V_k$-$C_k$ DNA from each pool was ligated in a 60 μl volume with 1200 units of T4 DNA ligase (New England Biolabs) to approx. 5 μg of digested fdDOG-2loxVkdel vector (previously electroeluted from a 0.8% agarose gel (Sambrook et al., *Molecular cloning-a laboratory manual*, Cold Spring Harbor Laboratory, New York (1990)). DNA was purified from the ligation mixture using Geneclean II (Bio 101), resuspended in 30 μl water, and electroporated (Dower et al., *Nucleic Acids Res.*, 16:6127–6145 (1988)) into four 50 μl aliquots of *E. coli* TG1. Cells were grown in 1 ml 2×TY broth containing 1% glucose for 1 hour and then plated in 243mm×243 mm dishes (Nunc) on TYE (Miller, J. H., *Experiments in Molecular Genetics*, Cold Spring Harbor Lab. Press, Cold Spring Harbor, N.Y. (1972)) medium with 12.5 μg/ml tetracycline (TYE-TET). After overnight incubation at 37° C., colonies were scraped off the plates into 7 ml of 2×TY broth (Miller, J. H., *Experiments in Molecular Genetics*, Cold Spring Harbor Lab. Press, Cold Spring Harbor, N.Y. (1972)) containing 15% (v/v) glycerol for storage at −70° C.

The frequency of inserts was checked by PCR for each of the three pools and found to be 90% for CDR3 of 8 residues, 100% for CDR3 of 9 residues and 87% for CDR3 of 10 residues. The number of clones with light chains could then be calculated as $9.9\times10^3$ (CDR3 of 8 residues), $1.5\times10^4$ (CDR3 of 9 residues), $6.5\times10^4$ (CDR3 of 10 residues). Sequence diversity was confirmed by sequencing 8 clones of each CDR3 length; all clones were found to be different. The pools were then combined, to create the library fdDOG-2loxVklib, corresponding to $9.0\times10^4$ light chains.

Construction of Synthetic Lambda Chain Repertoires

The human Cλ2 gene (Vasicek et al., *J. Exp. Med.*, 172:609–20 (1990)) was amplified from genomic DNA by PCR with Taq polymerase using primers CL2BACK1 and CL2FOR1 (Table 6C1) based in the regions flanking the Cλ2 exon. The EcoR1 and HindIII sites in CL2FOR1 and CL2BACK1 respectively were used to clone the PCR product into M13mp19 (Yanisch-Perron et al., *Gene*, 33:103–119 (1985)).

21 $V_\lambda$ germline gene segments with open reading frames, previously cloned in M13mp19 (Williams, S. C. and Winter, G., *Eur. J. Immunol.*, 23:1456–1461 (1993)), were individually amplified using PCR and Taq polymerase with back primers (Table 6C2) which anneal to framework 1 (FR1) and introduce a 5' ApaL1 site, and forward primers (Table6C3) which append a portion of the Jλ2 gene (Vasicek et al., *J. Exp. Med.*, 172:609–20 (1990)) to CDR3. CDR3 loops (Kabat et al., *Sequences of Proteins of Immunological Interest*, 5th edit., U.S. Dept. of Health and Human Services, Bethesda (1991)) of 8–13 residues that included 0, 1, 2, 3, 4 or 5 residues of random sequence were encoded by the forward primers (FIG. 6C). The number of residues of random sequence included was designed to match the pattern of V-gene rearrangement seen in vivo and varied with the different $V_\lambda$ segments used.

Each synthetically rearranged $V_\lambda$ gene was individually joined to the human Cλ12 gene by PCR with Taq polymerase (Horton et al., *Gene*, 77:61–68 (1989)). Each 50 μl PCR assembly reaction contained approx. 1 ng of M13mp19 containing the Cλ2 gene, approx. 0.1 μg of the $V_\lambda$ gene, the appropriate (FR1) back primer (25 pmol) (Table 6C2), the back primer CL2BACK2 (2.5 pmol) (Table 6C1), which contains the 3'sequence of the Jλ2 gene linked to the 5' sequence of the C12 gene, and the forward primer HUCλFORCYSASCNOT (25 pmol) (Table 6C1) which appends 2 stop codons (TAA) followed by an AscI site to the 3' of the Cλ2 gene. Reactions were cycled 30 times (94° C. for 1 min., 65° C. for 1 min., 72° C. for 2 min.).

The PCR assembly reactions were combined into a single pool and the $V_\lambda$ genes digested and ligated into fdDOG-2loxVkdel as described for the $V_k$-$C_k$ gene pools (see above), thus creating the library fdDOG-2loxVλlib. 92%. of clones were found to carry inserts of the correct size, corresponding to a repertoire size of $7.4\times10^5$ λ light chains. 33 clones were sequenced to confirm the presence of each $V_\lambda$ segment. AU the sequences were different.

Combinatorial Infection and In Vivo Recombination

To create a large combinatorial repertoire of heavy and light chains on an fd phage vector we used the strategy of combinatorial infection and in vivo recombination (Example 1). This system uses the lox-Cre site-specific recombination system of bacteriophage P1 (Sternberg et al., *J. Mol. Biol.*, 150:467–486 (1981); Hoess et al., *Nucleic Acids Res.*, 14:2287–2300 (1986)) to bring together heavy and light chain genes onto the same replicon.

Phage P1 lysates were made by thermal induction (Rosner, J. L., *Virology*, 48:679–689 (1972)). *E. coli* C600 Su (Appleyard, R. K., *Genetics*, 39:440–452 (1954)) harbouring phage P1Cm c1.100 r⁻m⁻ (Yarmolinsky et al., *J. Bacteriol.*, 171:4785–4791 (1989)) were grown in a 2 liter baffled flask containing 1 liter 2×TY, 25 μg/ml chloramphenicol, 10 mM $MgSO_4$ with vigorous shaking at 30° C. to $O.D._{600nm}$ of 0.6. The temperature was then raised quickly to 42° C. by shaking in a 70° C. water bath and then shaking continued for a further 35 min. in a 40° C. water bath.

Shaking was then continued at 37° C. until lysis was visible (usually about 1.5 to 2 hours). The culture was then spun at 5000×g for 15 min. at 4° C. and 100 μl chloroform added to the supernatant. P1 phage titres were measured by adding serial dilutions of the lysate to mid-log phase *E. coli* TG1 (Gibson, T. J., PhD thesis, University of Cambridge (1984)) grown in 2×TY broth containing 5 mM $CaCl_2$, the mixture incubated for 30 min. at 30° C. to allow infection and then plated on TYE medium (Miller, J. H., *Experiments in Molecular Genetics*, Cold Spring Harbor Lab. Press, Cold Spring Harbor, N.Y. (1972)) containing 30 μg/ml chloramphenicol. Chloramphenicol resistant colonies were counted after 24 hour incubation at 30° C. The P1 titre of the lysate used for this library was $3\times10^9$ transducing units (t.u.) per ml.

$10^9$ *E. coli* TG1, harbouring the library of synthetic $V_k$ genes (or the library of synthetic $V_\lambda$ genes) cloned in fdDOG-2loxVkdel, were used to inoculate 1 liter of 2×TY broth containing 12.5 μg/ml tetracycline (2×TY-TET) and the culture shaken for 20 hours at 30° C. in two 500 ml aliquots in 2 liter baffled Erlenmeyer flasks. Phage were purified from the supernatant by precipitation with polyethylene glycol (McCafferty et al., *Nature*, 348:552–554 (1990)), resuspended in PBS (phosphate buffered saline: 25 mM $NaH_2PO_4$, 125 mM NaCl, pH 7.0) and filtered through a 0.45 μm sterile filter (Minisart, Sartorius). Phage were titred by infecting exponential phase *E. coli* TG1 (30 min., 37° C.) and plating on TYE-TET. Yields were typically $10^{10}$ t.u. per ml of culture.

At various points during the recombination procedure aliquots of bacteria were removed and serial dilutions plated on TYE plates supplemented with 1% glucose and containing a variety of different antibiotics (100 μg/ml ampicillin; 15 μg/ml tetracycline; 30 μg/ml chloramphenicol). From the number of colony forming units (c.f.u.) the overall repertoire size could be calculated. These points are indicated in the protocol below and the results are summarised in Table 5.

Approx. $10^9$ *E. coli* TG1 harbouring the library of synthetic heavy chain genes cloned in pUC19-2loxVHdel (pUC19-2loxVHlib; see above) were used to inoculate 100 ml 2×TY broth containing 100 μg/ml ampicillin and 1% (w/v) glucose (2×TY-AMP-GLU). An aliquot of bacteria was plated for c.f.u. determination (see Table 5, sample point 1) and the rest of the culture grown overnight at 30° C. An aliquot of bacteria was then plated for c.f.u. determination (see Table 5, sample point 2). Two 5 ml aliquots of the overnight culture were then used to inoculate two 500 ml aliquots of 2×TY-AMP-GLU in 2 liter Erlenmeyer flasks and the cultures grown, shaking, at 37° C. to an $O.D._{600nm}$ of 0.5.

$2\times10^{12}$ t.u. $V_k$ library in fdDOG-2loxVkdel were added to one of the above cultures and $2\times10^{12}$ t.u. $V_\lambda$ library in fdDOG-2loxVkdel were added to the other culture. Each culture was immediately split into 5×100 ml aliquots and each aliquot mixed with 1 liter of 2×TY-AMP-GLU, prewarmed to 37° C. These cultures were then incubated at 37° C., without shaking for 30 min., and then with shaking until an $O.D._{600nm}$ of 0.4 was reached (about 30 min.). An aliquot of bacteria from the kappa infection and another from the lambda infection were plated for c.f.u. determination (see Table 5, sample point 3).

$CaCl_2$ was then added to a final concentration of 5 mM and 200 ml phage P1Cm cl.100 r⁻m⁻ lysate ($6\times10^{11}$ t.u, see above) were added to each 1 liter flask (giving a multiplicity of infection of approx. 1). Incubation was continued at 30° C. for 1 hour, with a short burst of shaking every 15 min. The culture was then centrifuged at 5,000×g for 15 min. and the pellets resuspended in the original volume of 2×TY broth. containing 100 μg/ml ampicillin, 12.5 μg/ml tetracycline, 25 μg/ml chloramphenicol and 1% glucose (i.e. 5 liters for the $V_k$ library and 5 liters for the $V_\lambda$ library). An aliquot of bacteria was plated for c.f.u. determination (see Table 5, sample point 4). The repertoire size was determined to be $6.5\times10^{10}$ from the number of ampicillin, tetracycline and chloramphenicol resistant c.f.u. at this point (see results described below). An aliquot of each culture was also centrifuged at 12,000×g for 5 min. and the supernatant filtered through a 0.45 μm sterile filter (Minisart, Sartorius). The fd phage in the supernatant were titred by infecting exponential phase *E. coli* TG1 (30 min., 37° C.) plating on TYE-TET (see Table 5, sample point 5).

The cultures were incubated overnight at 30° C. with shaking for 24 hours in 2 liter baffled flasks (1 liter medium per flask). An aliquot of bacteria from each culture was plated for c.f.u. determination (see Table 5, sample point 6). The fd phage in the supernatant were also titred by infection of exponential phase *E. coli* TG1 as above (see Table 5, sample point 7). The total yield of fd phage was $4.1\times10^{13}$ t.u. and therefore over 99.9% were propagated from bacteria containing the pUC "donor" vector and phage P1. The cultures were then centrifuged at 5000×g for 15 min. at 4° C. and the fd phage precipitated from the supernatant using polyethylene glycol as (McCafferty et al., *Nature*, 348:552–554 (1990)) and resuspended in a final volume of 10 ml PBS.

Ten 2 liter flasks, each containing 1 liter 2×TY broth were inoculated with *E. coli* TG1 and grown, shaking, at 37° C. until an $O.D._{600nm}$ of 0.4 (approx. $4\times10^{12}$ bacteria) was reached. 2 ml of the above recombined $V_k$ fd phage ($8\times10^{11}$ t.u.) were added to 5 liters of *E. coil* and 2 ml of the above recombined $V_\lambda$ fd phage ($2\times10^{12}$ t.u.) were added to the other 5 liters of *E. coli* and the cultures held at 37° C. for 30 min without shaking and then for 30 min. with shaking. The number of *E. coli* infected with fd phage was determined by plating bacteria on TYE-TET plates to be $1.7\times10^{12}$ ($V_k$ repertoire) and $1.1\times10^{12}$ ($\lambda$ repertoire); this exceeds the estimated repertoire size by over 10-fold hence maintaining library diversity. Tetracycline was then added to 12.5 μg/ml and the culture shaken for 16 hours at 30° C. The $V_k$ culture and the $V_\lambda$ cultures were then centrifuged at 5,000×g for 10 min. and the pellet from each repertoire resuspended in 250 ml 2×TY broth containing 15% glycerol and stored in 15 ml aliquots at −70° C.

Aliquots of the two libraries were also spread on TYE-TET in 243mm×243 mm dishes (Nunc). After overnight incubation at 30° C. the number of colonies on the large plates was calculated from the number of colonies on small TYE-TET plates on which serial dilutions had been spread. Two plates, one containing $3.5\times10^6$ colonies of the $V_k$ library and the other containing $6.4\times10^6$ colonies of the $V_\lambda$ library were selected, and the bacteria scraped into 10 ml 2×TY broth containing 15% glycerol. This stock therefore corresponded to a repertoire of $10^7$ clones.

Assaying the Efficiency of In Vivo Recombination

To test the efficiency of replacement of the anti-TNF heavy chain in the "acceptor" vector (fdDOG-2loxVλlib and fdDOG-2loxVλlib with synthetic heavy chain from the "donor" vector (pUC19-2loxVHlib), 250 individual colonies from each of the $V_\lambda$ and $V_k$ recombined libraries were picked onto TYE-TET plates and grown overnight at 30° C. Colony hybridisation was then performed as in Tomlinson et al., *J. Mol. Biol.*, 227:776–798 (1992), with a primer (TNFCDR3PRB; Table 6) complementary to the CDR3 region of the anti-TNF heavy chain gene found in the "acceptor" vector (fdDOG-2loxVλlib and fdDOG-2loxVklib). Where recombination is successful, the anti-TNF heavy chain gene should be replaced by the synthetic heavy chain from the "donor" vector. Probing of the colonies indicated that only 12 $V_\lambda$ colonies (5%) and 39 $V_k$ colonies (16%) retained the original heavy chain. Probing of 250 colonies from each of the $V_\lambda$ and $V_k$ phage libraries before recombination indicated that, as expected, all colonies harboured the original heavy chain.

Clones lacking the anti-TNF heavy chain gene (42 $V_\lambda$, 48 $V_k$) were screened by PCR (Güssow et al., *Nucleic Acids Res.*, 17:4000 (1989)) for the presence of heavy chains with the primers pelBback and CH1.lib.seq (see Table 6) and for the presence of light chains with the primers fdPCRback and Ck.lib.seq (or Cλ.lib.seq). The probing and PCR screening indicated that in the recombined $V_\lambda$ library, 28% of clones had acquired a heavy chain from the donor vector and also had a lambda light chain gene; 5% were unrecombined fdDOG-2loxVλlib; and 67% had deletions of light chain, heavy chain, or both. For the $V_k$ library, 28 % of clones had acquired a heavy chain from the donor vector and also had a kappa light chain gene; 16% were unrecombined fdDOG-2loxVλlib; and 56% had deletions of light chain, heavy chain, or both. Further cycles of infection (without selection) led to a further decrease in the frequency of phage harbouring heavy and light chain genes, presumably due to competition with deletion phage. Nevertheless, immediately after recombination, for both $V_\lambda$ and $V_k$ repertoires, we can calculate that 28% of all fd phage clones had both heavy and light chain genes and that the heavy chain gene derived from the pUC "donor" vector.

Propagation of Phage From the Recombined Library 5 liters of 2×TY-TET were inoculated with a 15 ml aliquot of the recombined $V_k$ library glycerol stock ($5\times10^{10}$ c.f.u.) and a further 5 liters 2×TY-TET inoculated with a 15 ml aliquot of the recombined $V_\lambda$ library glycerol stock ($1\times10^{11}$ c.f.u.). The cultures were grown, shaking, overnight at 30° C. in baffled flasks (1 liter medium per flask). The cultures were centrifuged at 5,000×g for 15 min. at 4° C. and the fd phage precipitated from the supernatant using polyethylene glycol as (McCafferty et al., Nature, 348:552–554 (1990)) and each repertoire resuspended in a final volume of 10 ml PBS. Total phage yields (from 10 liters) were typically around $10^{14}$ t.u.

Specificity of Selected Antibodies

The repertoire of $6.5\times10^{10}$ phage was selected with a range of antigens, leading to isolation of binding specificities, as summarised in Table 2. The repertoire was selected on all antigens and haptens by panning on antigen coated immunotubes; for the haptens NIP and fluorescein, the phage were also captured with biotinylated NIP-BSA and FITC-BSA and streptavidin-coated paramagnetic beads. This was performed as follows.

Selection of the Recombined Library on Immunotubes

The phage repertoire was panned using immunotubes (Nunc; Maxisorp) coated with each antigen as (Marks et al., J. Mol. Biol., 222:581–597 (1991); Griffiths et al., EMBO J., 12:725–734 (1993)). A range of antigens were used as described in Table 2. Here we have focused on five protein antigens: a mouse monoclonal antibody (NQ11/7.22; (Griffiths et al., Nature, 312:271–275 (1984)); and four proteins belonging to the kringle-serine proteases family (hepatocyte growth factor/scatter factor {HGF/SF}, plasmin, tissue-type plasminogen activator {t-PA} and urokinase-type plasminogen activator {u-PA}). In addition, selection was performed on two haptens conjugated to BSA (fluorescein 5-isothiocyanate {FITC Isomer I} and 3-iodo-4-hydroxy-5-nitrophenyl-acetate {NIP}). FITC conjugated to BSA (FITC-BSA; 11.2 FITC groups per BSA molecule) was purchased from Sigma; NIP conjugated to BSA (NIP-BSA) was synthesised by coupling NIP-caproate-O-succinimide to BSA as (Brownstone et al, Immunology, 10:465–481 (1966)) to give 27.9 NIP groups per BSA molecule. Tubes were coated with 10 μg/ml protein or 100 μg/ml hapten-BSA conjugates in PBS overnight at room temperature.

For the first round of selection 0.5 ml ($6.4\times10^{12}$ t.u.) of the recombined $V_k$ library and 0.5 ml ($7.5\times10^{12}$ t.u.) of the recombined $V_\lambda$ library were used per immunotube. For the first two rounds of selection tubes were washed 10 times with PBS, 0.1% (v/v) Tween 20 and 10 times with PBS. For subsequent rounds of selection tubes were washed 20 times with PBS, 0.1% (v/v) Tween 20 and 20 times with PBS (Griffiths et al., EMBO J., 12:725–734 (1993)). Phage were eluted with 100 mM triethylamine as (Marks et al., J. Mol. Biol., 222:581–597 (1991)). Eluted phage were used to infect 10 ml log phase E. coli TG1 cells and plated on TYE-TET medium in 243×243 mm dishes (Nunc). After incubation overnight at 30° C. the colonies were scraped off the plate into 200 ml 2×TY-TET and incubated, shaking, at 30° C. for approx. 6 hours. The culture was centrifuged at 7000 r.p.m. for 15 min. at 4° C. and the fd phage precipitated from the supernatant using polyethylene glycol as (McCafferty et al., Nature, 348:552–554 (1990)), each repertoire being resuspended in a final volume of 2 ml PBS. The cell pellet was resuspended in 20 ml 2×TY broth containing 15% glycerol and a 2 ml aliquot stored at −70° C.

1 ml of these phage (approx. $10^{12}$ t.u.) were used per immunotube for the next round of selection. The library was subjected to 4 or 5 rounds of growth and selection for each antigen.

Selection of the Recombined Library Using Streptavidin-Coated Paramagnetic Beads The library was also selected using soluble biotinylated, hapten-BSA conjugates and streptavidin-coated paramagnetic beads as (Hawkins et al., J. Mol. Biol., 226:889–896 (1992)) but with some modifications. FITC-BSA (11.2 FITC:BSA) and NIP-BSA (27.9 NIP-BSA) (see above) were biotinylated using Immunopure NHS-SS-Biotin (sulfosuccinimidyl 2-(biotinamido) ethyl-1,3'-dithiopropionate; Pierce) according to the manufacturer's instructions.

For the first round of selection 0.5 ml ($6.4\times10^{12}$ t.u.) of the recombined $V_k$ library and 0.5 ml ($7.5\times10^{12}$ t.u.) of the recombined $V_\lambda$ library were made up to 2.5 ml with PBS and mixed with 2.5 ml PBS containing 4% skimmed milk powder, 50 μl Tween 20, and biotinylated hapten-BSA added to give a final concentration of 50 nM. The mixture was then gently rotated on an inclined wheel for 1 hour at room temperature. 1.5 ml of Dynabeads M-280 coated with Streptavidin (Dynal) (and previously blocked by incubating for 2 hours at 37° C. with PBS containing 2% skimmed milk powder (2% MPBS)) were then added and mixing continued for a further 15 min at room temp. The Dynabeads were then washed a total of 15 times, using a Dynal MPC (Magnetic Particle Concentrator); each wash was with 1 ml PBS or with 1 ml 2% MPBS (every third wash). Phage were eluted from the beads by incubating 5 min. at room temperature in 300 μl PBS, 50 mM dithiothreitol (DTT) and the eluate used to infect 10 ml log phase E. coli TG1 cells and plated on TYE-TET in 243×243 mm dishes (Nunc). Phage were harvested from the plates as above and each repertoire resuspended in a final volume of 2 ml PBS. The cell pellet was resuspended in 20 ml 2×TY broth containing 15% glycerol and a 2 ml aliquot stored at −70° C. (see above).

For the second round (and subsequent rounds) of selection 1 ml of phage (approx. $10^{12}$ t.u.) were mixed with 0.5 ml PBS containing 6% skimmed milk powder, 10 μl Tween 20, and biotinylated hapten-BSA added to give a final concentration of 50 nM. Selection was then as above, except that only 300 μl of streptavidin-coated Dynabeads M-280 were used. The library was subjected to 4 or 5 rounds of growth and selection for each antigen.

ELISA Screening of Repertoire Selections

"Polyclonal" mixtures of phage produced by re-propagation of the library after each round of selection were screened for binding to the antigen used for selection and to other control antigens by ELISA. The phage ELISA was performed essentially as (McCafferty et al., Nature, 348:552–554 (1990)) using 10 μl PEG precipitated phage (approx. $10^{10}$ t.u.), but using for detection horseradish peroxidase conjugated anti-sheep antibody (Sigma) and 3', 3', 5', 5'-tetramethylbenzidine (TMB). Reactions were stopped by the addition of $H_2SO_4$ after 10 min. and readings taken by subtracting the $A_{650nm}$ from the $A_{450nm}$. AU antigens were coated at 10 μg/ml in PBS.

Single tetracycline resistant colonies from infection of E. coli TG1 with eluted phage were also screened to identify those producing antigen-binding phage by ELISA essentially as in Clackson et al., Nature, 352:624–628 (1991) except that phage were grown at 30° C., and detection was as for the polyclonal phage ELISA above.

Selection and Characterization of Fab Fragments

To follow the selection process, E. coli were infected with the eluted phage after each round, and the phage screened for binding to antigen by ELISA, either as a "polyclonal" population, or as phage clones. DNA encoding the Fab fragments was amplified using the polymerase chain reaction from the population of phage after 2–4 rounds of selection, and recloned into plasmid (FIG. 7C) for expression of soluble Fab fragments. Subcloning was performed as follows.

Approx. $10^8$ bacteria harbouring phage fd were taken from the stocks frozen down after the appropriate round of selection (5 µl of a 10-fold dilution of the frozen stock). In general, these bacteria were used as template in a 50 µl PCR reaction and the heavy chain genes amplified by pre-soaking at 94° C. for 10 min. and then cycling 30 times (94° C. for 1 min. 50° C. for 1 min, 72° C. for 2.5 min) using the primers fdSEQ1 and G3LXbaGTGBack (Table 6). The products were run on a 1.3% low melting point agarose gel and purified from the gel using 'Magic PCR Preps' (Promega). The DNA was then cut with XbaI and NotI and ligated into pUC119His6mycXba. The ligation mixture was electroporated (Dower et al., Nucleic Acids Res., 16:6127–6145 (1988)) into E. coli TG1 and plated on TYE medium containing 100 µg/ml ampicillin and 1% glucose (TYE-AMP-GLU) and incubated at 37° C. overnight.

Individual ampicillin resistant colonies were grown in 96-well plates and soluble Fab production induced with isopropyl β-D-thiogalactoside (IPTG) as in Marks et al., J. Mol. Biol., 222:581–597 (1991). Soluble Fab fragments in supernatants were assayed for binding to antigen coated plates by ELISA. All antigens were coated at 10 µg/ml in PBS. Bound Fabs were detected with a mixture of rabbit anti-human λ light chain antibodies and rabbit anti-human κ light chain antibodies (Dako) followed by goat anti-rabbit IgG (whole molecule) peroxidase conjugate (Sigma), or by using a mixture of peroxidase conjugated sheep anti-human κ light chain (free and bound) antibodies and peroxidase conjugated sheep anti-human λ light chain (free and bound) antibodies (The Binding Site). ELISAs were developed with TMB as above.

Each antigen-binding clone was streaked on a TYE-AMP-GLU plate and two individual colonies picked and re-assayed for production of antigen-binding Fab fragments as above. Positive clones were stored in 2×TY, 15% glycerol at −70° C.

Attention was focused on the characterisation of Fab fragments with specificities against the hapten-BSA conjugates of NIP (3-iodo-4-hydroxy-5-nitrophenyl-acetate) and FITC (fluorescein 5-isothiocyanate), as allowed comparisons with the natural immune response to both haptens in mice, and which was facilitated the measurement of binding affinities to the free haptens (by fluorescent quench titrations).

The fragments against hapten-BSA were first screened for binding to the free hapten by competition with fluorescein or NIP-caproic acid (NIP-CAP), or for binding to BSA. Most of the Fab fragments bound to hapten-BSA, but some also bound to BSA, or to free hapten.

Figure 8:
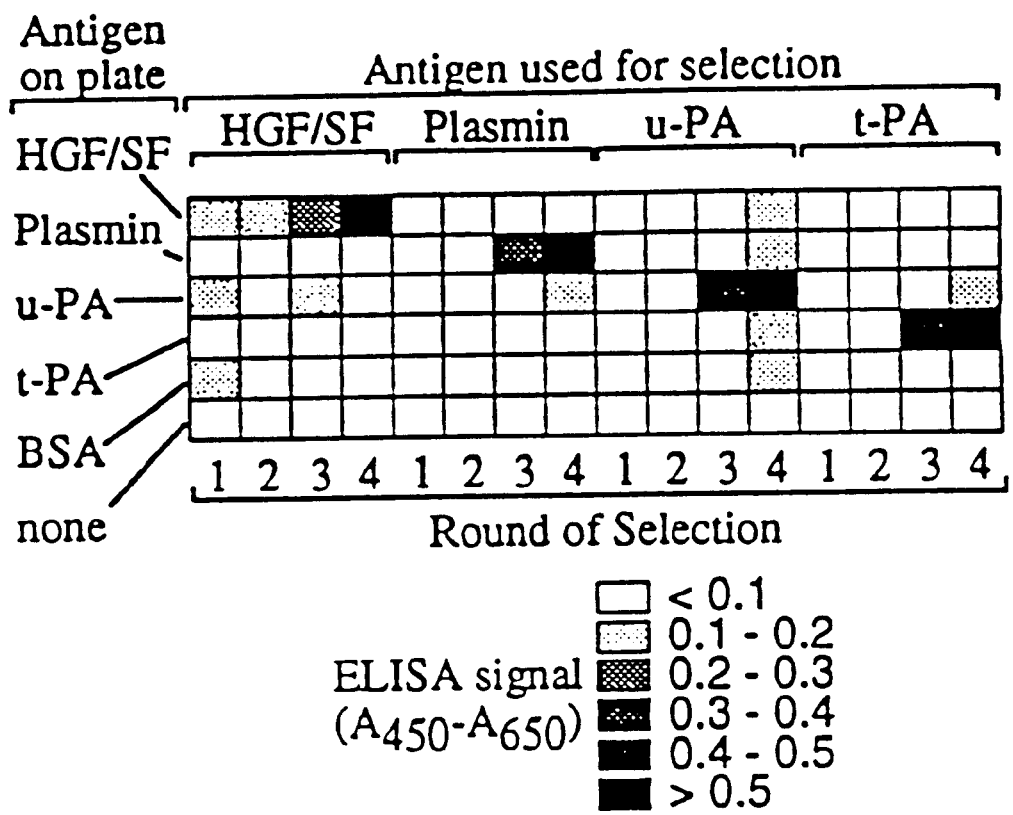
Figure 9A:
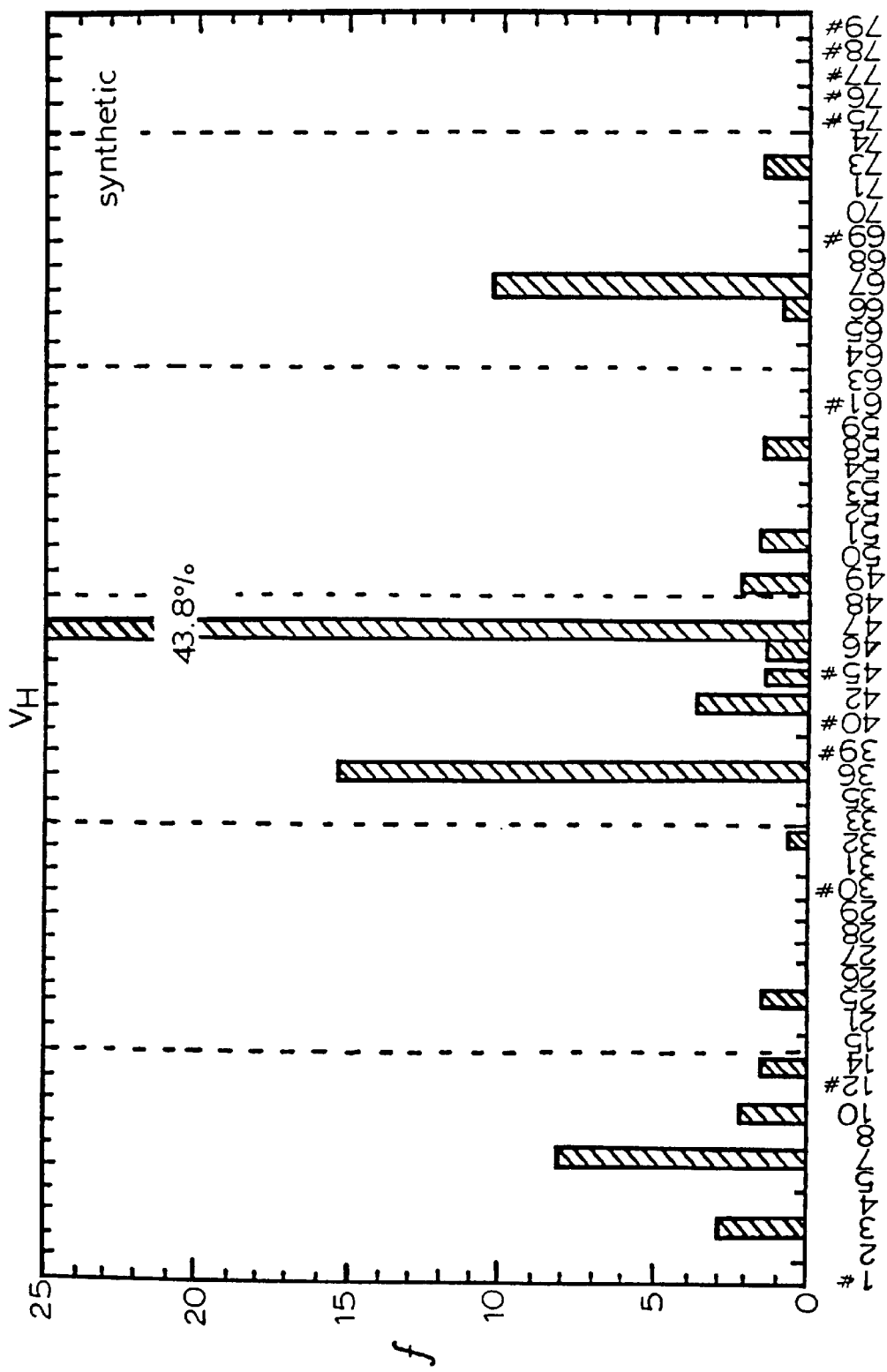
Figure 9B:
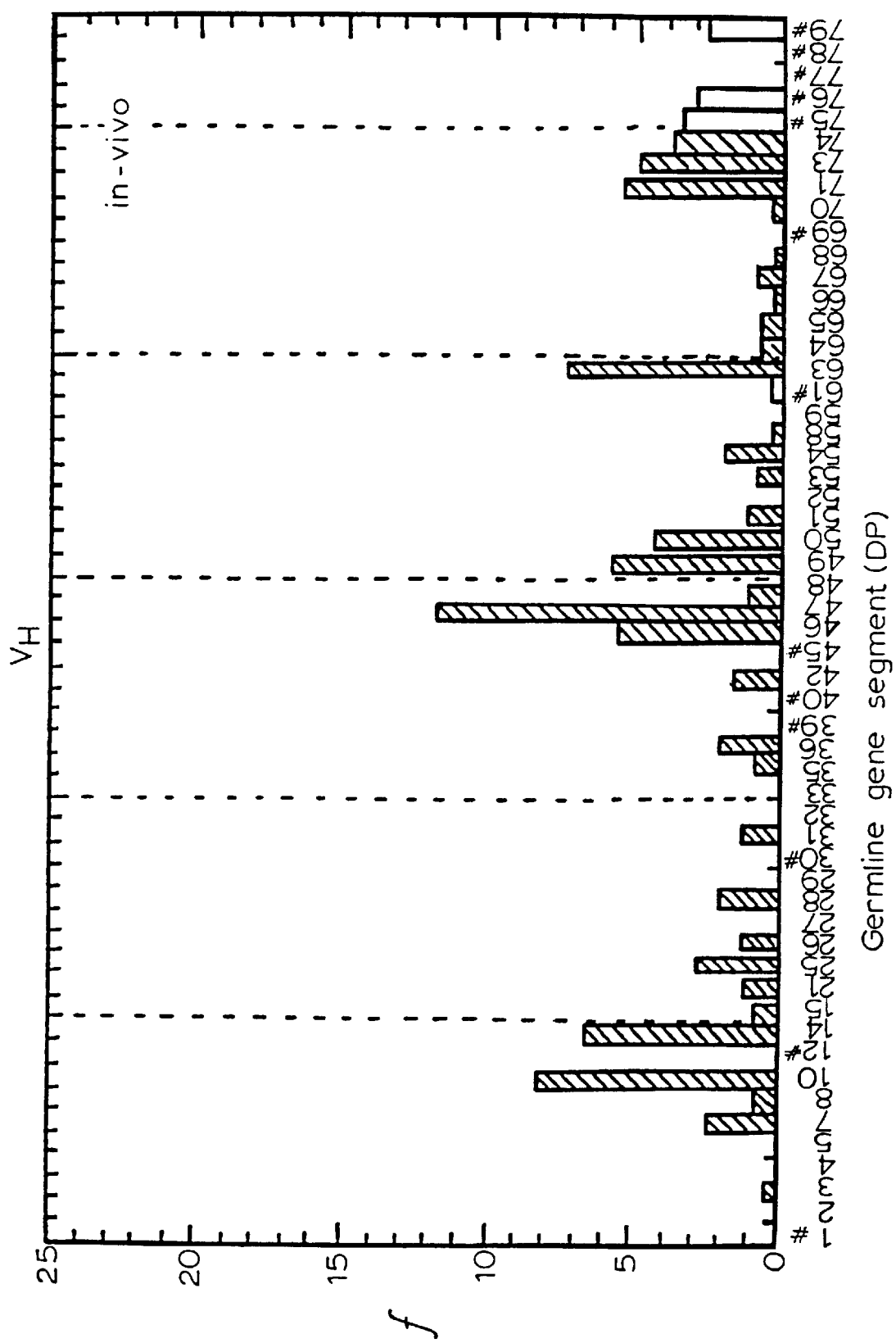
Figure 9C:
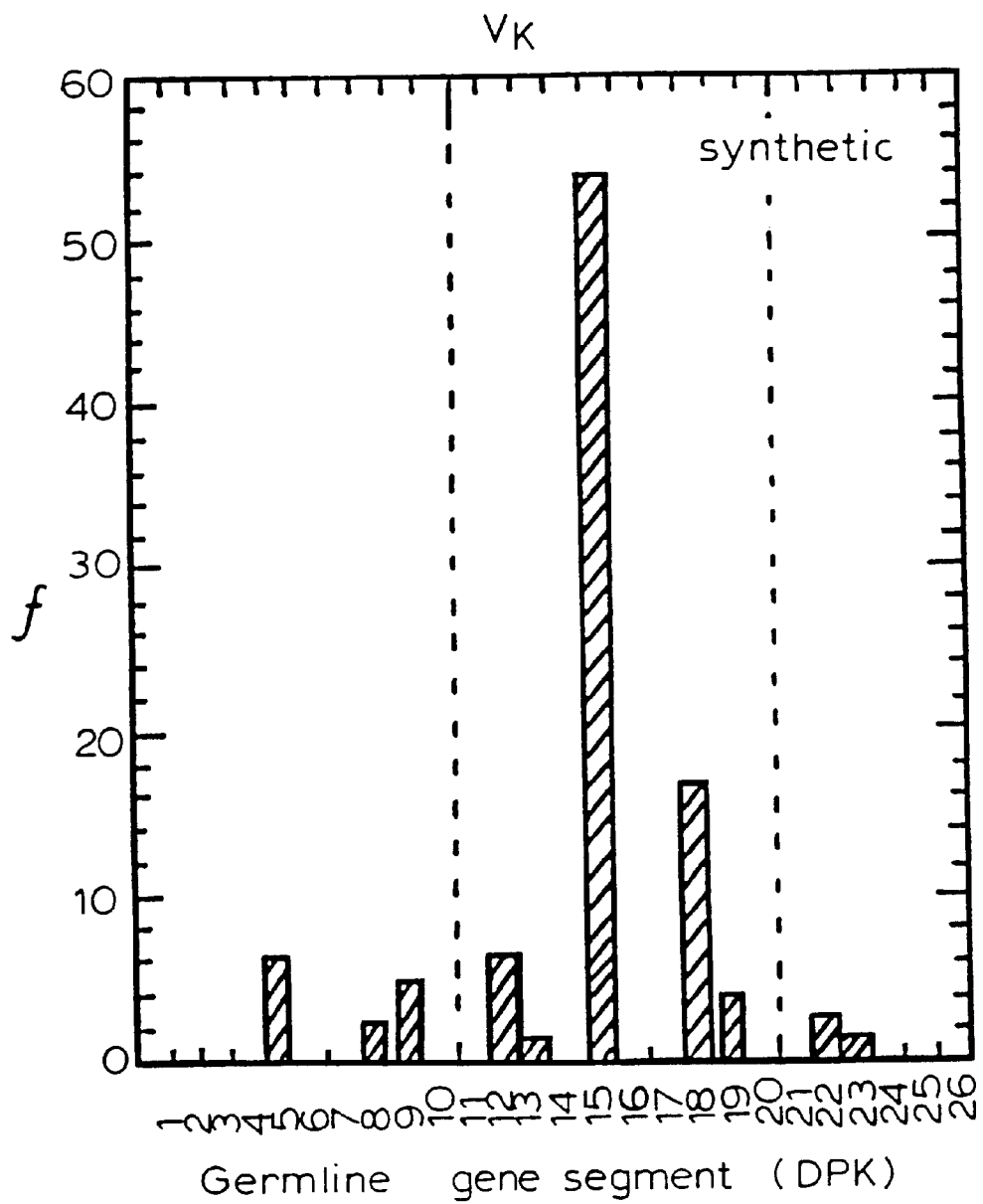
Figure 9D:
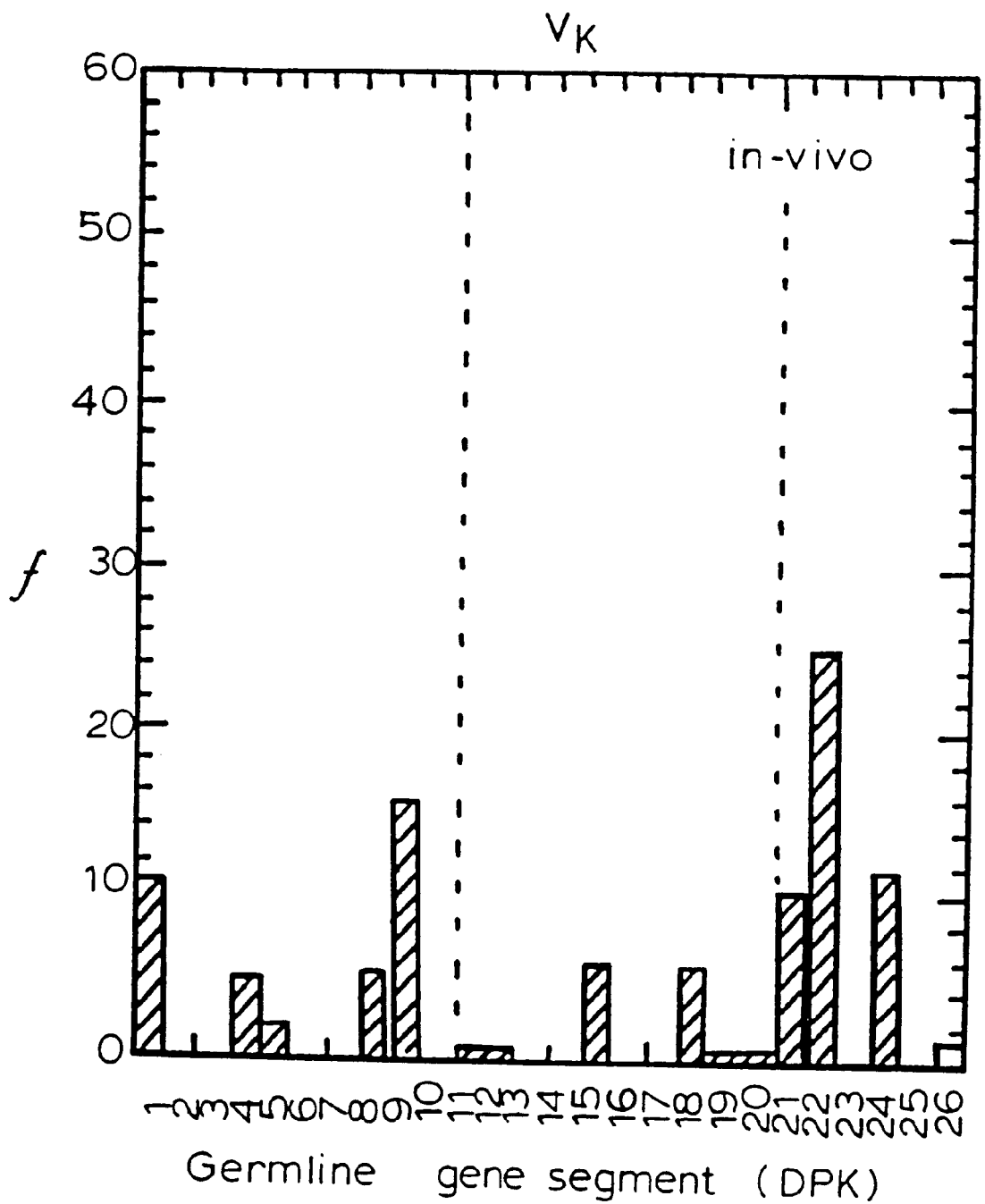
Figure 9E:
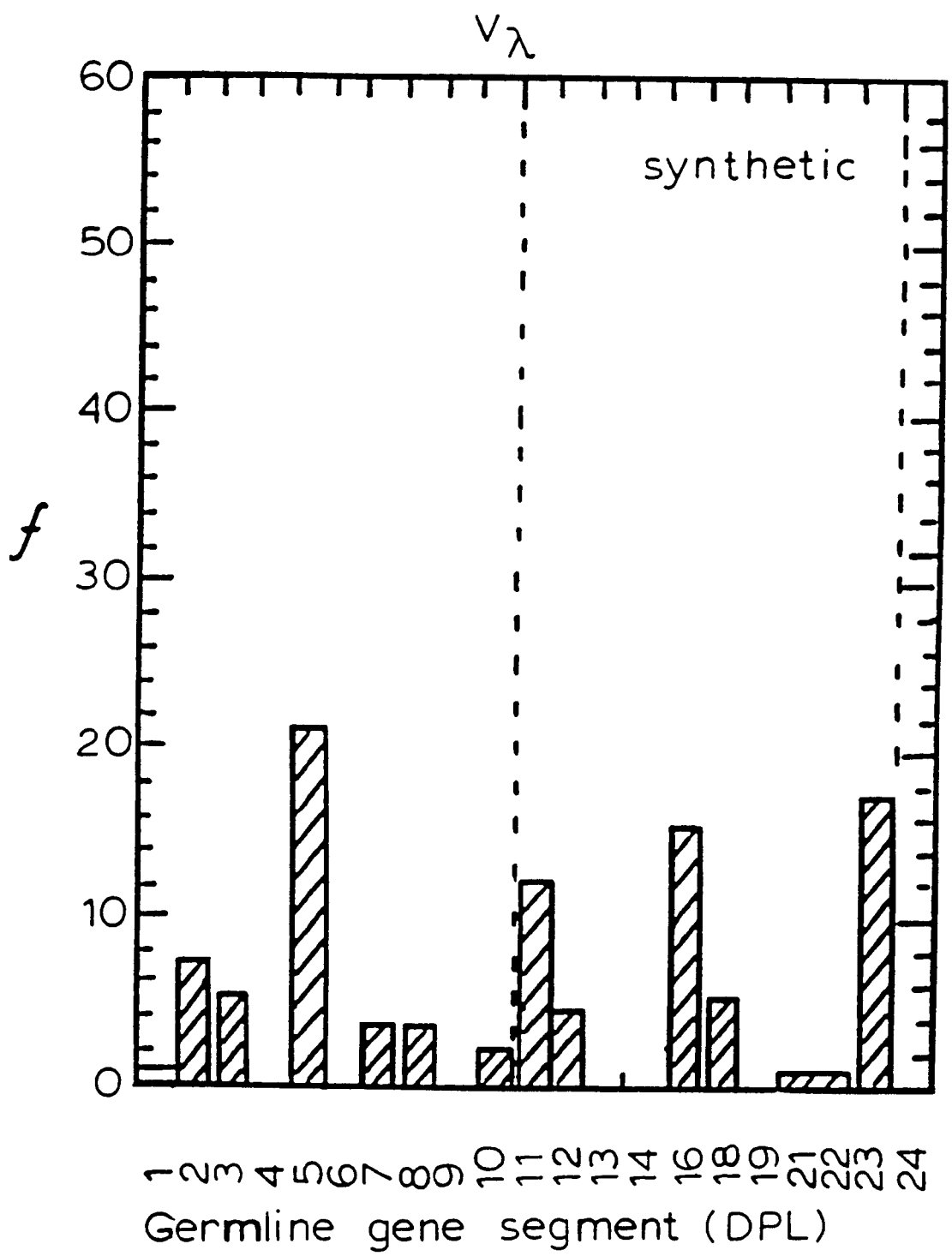
Figure 9F:
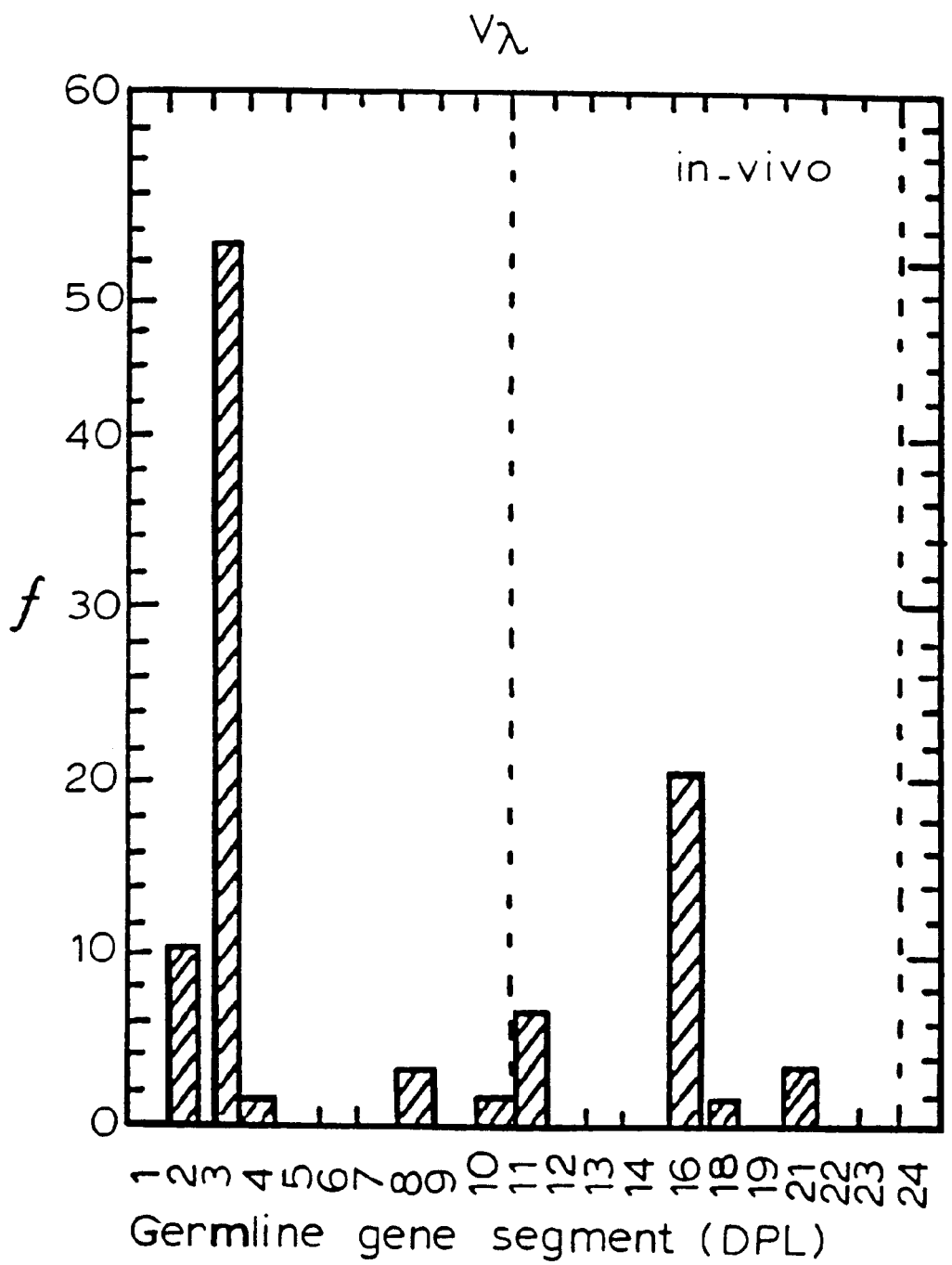
Figure 10A:
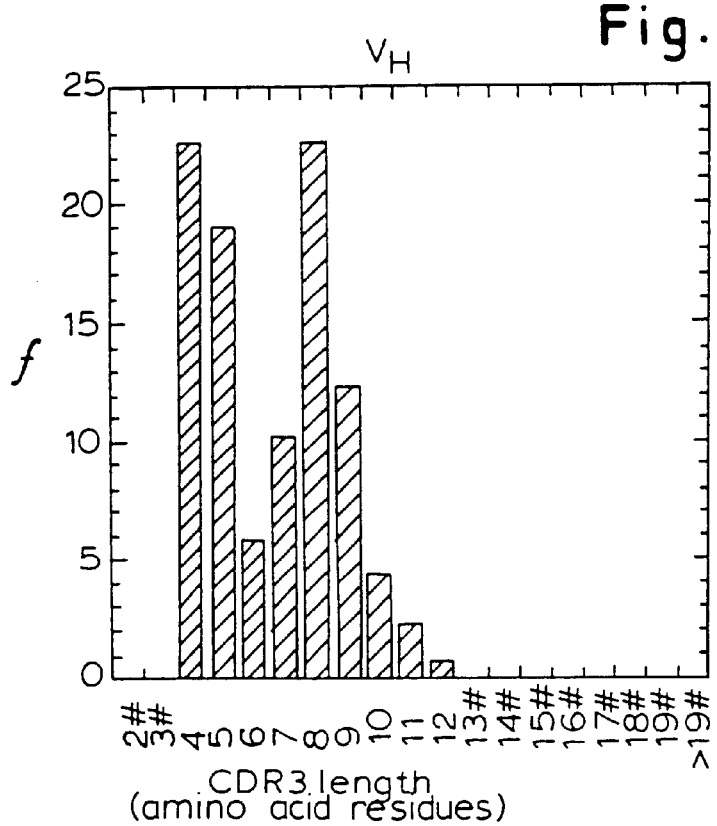
Figure 10B:
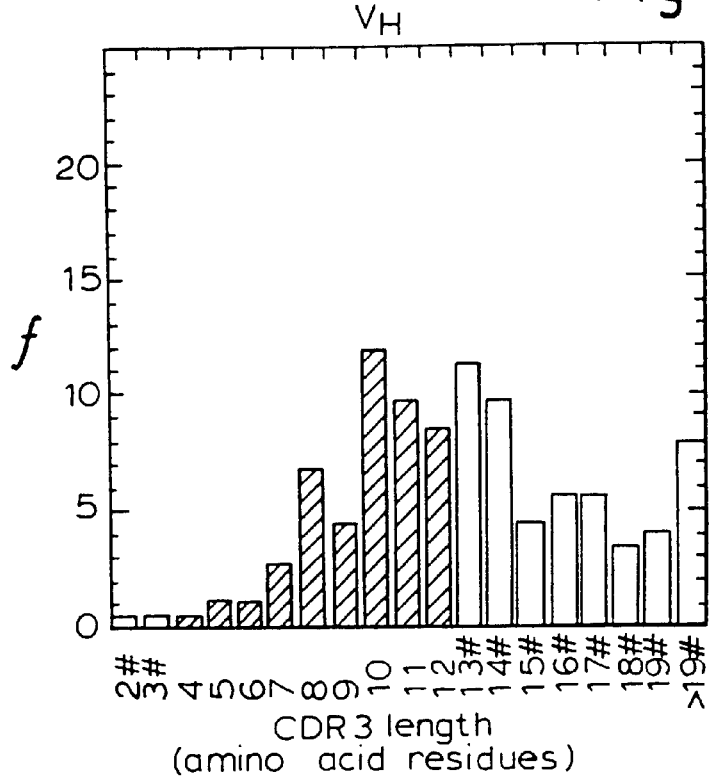
Figure 10C:
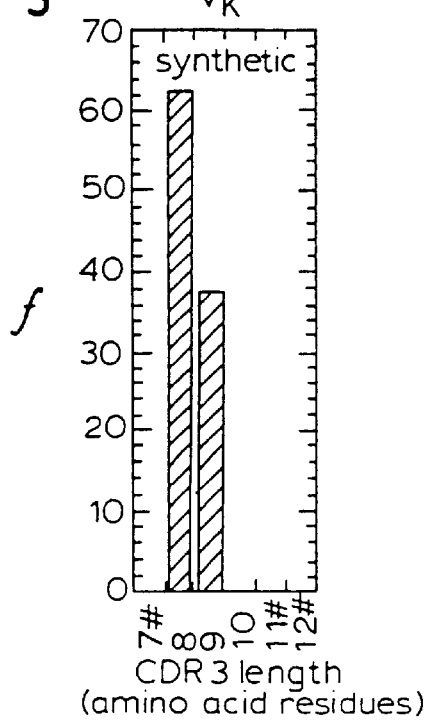
Figure 10E:
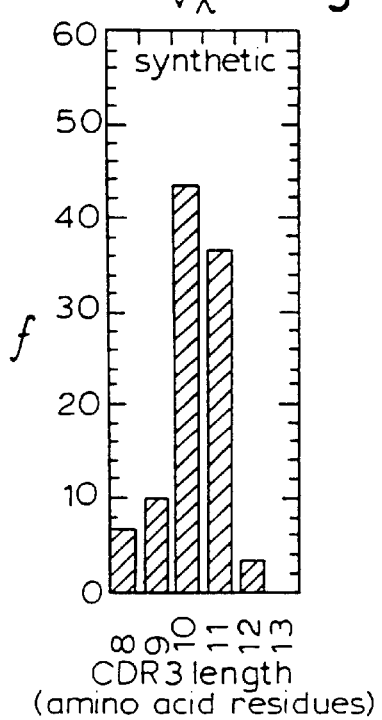
Figure 10D:
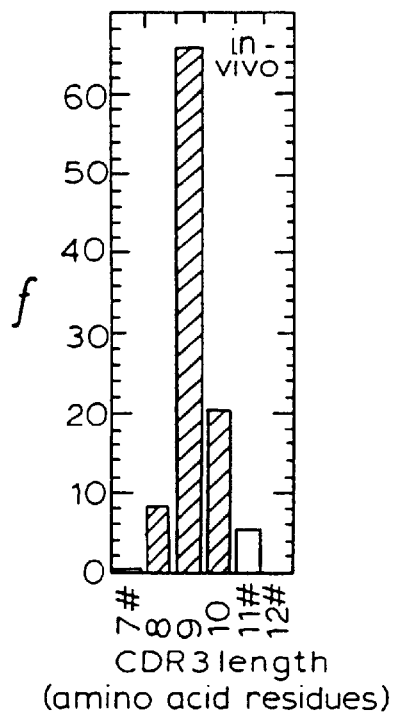
Figure 10F:
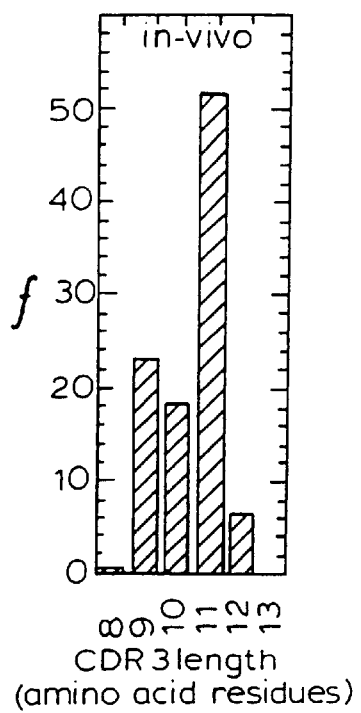

Fab fragments against 4 antigens of the kringle-serine protease family—hepatocyte growth factor/scatter factor (HGF/SF), plasmin, urokinase-type plasminogen activator (u-PA), or tissue-type plasminogen activator (t-PA)—as members of a family of related proteins were characterized. Binding of "polyclonal" phage was detected after three rounds of selection, and proved to be specific, despite homologies between the members of this family (FIG. 8).

Fab fragments against the mouse monoclonal antibody NQ11/7.22 (Griffiths et al., Nature, 312:271–275 (1984)) was characterized (Table 2), as the binding could be mapped to the variable regions, to the Fc region and to the remaining portions. of the monoclonal antibody (Table 3). The repertoire selected on the mouse monoclonal antibody NQ11/7.22 (γ1,κ; Griffiths et al., Nature, 312:271–275 (1984)) was sub-cloned after the second, third and fourth round of selection for production of soluble Fab fragments. 161 out of 384 clones bound to NQ11/7.22 (see above), and were further mapped by binding to MOPC21 (an unrelated mouse γ1, κ monoclonal antibody; Sigma); mouse Fc fragment (Jackson); and NQ11/7.22 zero-linker diabody (containing only the heavy and light chain variable domains; Holliger et al., Proc. Natl. Acad. Sci. USA, 90:6444–6448 (1993)). All proteins were coated at 10 µg/ml in 50 mM NaHCO$_3$ (pH 8.3). Eleven different Fab fragments identified by sequencing (Table 3) were thereby directly mapped to binding to the Fv (idiotypic) or Fc regions, or to the remaining portions of the monoclonal antibody.

Segment Usage of Selected Heavy and Light Chains The phage selected from the large (6.5×10$^{10}$ clones) repertoire by binding to antigen were characterised by DNA sequencing using the procedures below.

Sequencing of Antibody V-Genes

Clones, toothpicked from frozen glycerol stocks, were amplified by PCR using Taq polymerase. Reactions (50 µl) were pre-soaked for 10 min. at 94° C. and then cycled 25 times (94° C. for 1 min., 55° C. for 1 min., 72° C. for 30 sec.). The primers were Ck.lib.seq and LMB3 for kappa chain amplification; Cl.lib.seq and LMB3 for lambda chain amplification; and CH1.lib.seq and pelBback for heavy chain amplification (Table 6). Aliquots of the product were analysed on a 1.3% agarose gel. The remaining product was purified using Magic PCR Preps (Promega).

20 µl PCR cycle sequencing reactions with fluorescent dideoxy chain terminators (Applied Biosystems) (25 cycles: 96° C. for 30 sec., 50° C. for 15 sec., 60° C. for 4 min.) were carried out according to the manufacturer's instructions. 200 ng of the purified PCR product from above was used as template with the following primers: Ck.lib.seq for kappa chains, Cl.lib.seq for lambda chains and CH1.lib.seq for heavy chains (Table 6).

The sequencing reactions were analysed on an Applied Biosystems 373A Automated DNA Sequencer. Sequence analysis was performed using SeqEd (Applied Biosystems) and MacVector (IBI Kodak, New Haven, Conn.).

Many of the clones were different: 137 unique antigen-binding Fab fragments (with differing light or heavy chain protein sequences) were identified from a total of 215 clones sequenced (Table 3). A range of V-gene segments were seen: 17 of the 49 $V_H$ segments, 10 of the 26 $V_k$ segments, and 9 of the 21 $V_\lambda$ segments (see FIG. 9).

Each of the major heavy and light chain families were represented (Chuchana et al., Eur. J. Immunol., 20:1317–1325 (1990); Kabat et al., Sequences of proteins of immunological interest, 5th edit., U.S. Dept. of Health and Human Services, Bethesda (1991); Williams, S. C. and Winter, G., Eur. J. Immunol., 23:1456–1461 (1993)), but not all the minor families. Thus $V_H$ segments were seen from families 1, 3, 4 and 5, but not 2 and 6; $V_k$ segments from subgroups 1, 2, 3 and 4, but not from 6; and $V_\lambda$ segments from families 1, 2, 3, 7 and 8, but not 9. The heavy chain $V_H$ segment DP-45 (included in the repertoire, but located on chromosome 16 outside the major locus on chromosome 14) was found in two Fab fragments (Table 3 and FIG. 9A) binding to NIP-BSA.

Some V-gene segments ($V_H$ segments DP-7, DP-38, DP47 and DP-67; $V_k$ segment DPK-15; and $V_\lambda$ segment DPL-3) were seen frequently in the synthetic chains: of these only the $V_H$ segment DP-47. is common in natural antibodies. Conversely, some segments (like $V_H$ segments DP-63 and DP-71; $V_k$ segments DPK-1 and DPK-21; and $V_\lambda$ segments DPL-5 and DPL-23) that are common in natural antibodies were not seen in the synthetic chains (FIG. 9). Thus, except for DP-47, the pattern of usage of the segments from the synthetic repertoire, summed over the limited number of antigens, appears to differ from the usage in vivo.

Distribution of CDR3 Lengths

The lengths and sequences of the CDR3 loops in the selected Fab fragments (Table 3; FIG. 10) were analyzed.

All the heavy chain CDR3 lengths included in the synthetic repertoire were present. The four residue loops almost all include a glycine residue, presumably to make the tight turn. However the distribution of the heavy chain CDR3 lengths, biased towards short lengths, contrasts with natural antibodies. This appears to be especially characteristic of the synthetic Fab fragments binding to hapten-BSA conjugates; those fragments binding to protein antigen appear to have longer CDR3 lengths. The distribution of CDR3 lengths for the synthetic λ light chains was similar to natural antibodies, but differed for the k light chains, with no loops of 10 residues seen in the synthetic chains.

Pairings of Heavy and Light Chains

The distribution of heavy and light chain pairings (FIG. 11) identified some 52 different segment pairings among the 137 unique clones.

Several $V_H$-gene segments were found paired with several $V_k$- and $V_\lambda$ gene segments, for example DP-7, DP-38, DP-47 and DP-67, were each found in combination with several different light chain segments. Likewise the light chain segments DPK-15 and DPL-3 were found in combination with several heavy chain segments. Not surprisingly these segments correspond to those used with higher frequency (see above). The usage of V-gene segments differs for antibodies of different specificity, and the pattern of pairings provides a "fingerprint", readily distinguishing the "response" to different antigens. Some pairings, for example DP-47 with DPK-15, and DP-47 with DPL-16, were also present in Fab fragments of different specificities.

There were also several examples of "promiscuous" pairings (Clackson et al., Nature, 352:624–628 (1991)), chains that bind to the same antigen with any of several partner chains (Table 3). For example, in the Fab fragments binding to NIP-BSA, the same heavy chain sequence (DP-38 segment with CDR3 of sequence AGTL) was paired with 6 different light chains of Vk2, Vλ1 and Vλ3 families (segments DPK-12, DPL-3 and DPL-16 respectively). Likewise in Fab fragments binding to FITC-BSA, the same light chain sequence (DPK-15 segment with CDR3 of sequence MQALQTRT) was paired with 15 different heavy chains of VH1, VH3 and VH4 families (DP-7, DP-47 and DP-67 segments respectively).

Purification of Fabs and Affinity Determination

Several pUC119His6mycXba clones encoding NIP and fluorescein -specific Fab fragments were chosen at random for affinity determination. A one liter culture of E. coli TG1 (Gibson, T. J., PhD thesis, University of Cambridge (1984)) harbouring each plasmid was grown and Fab expression induced with IPTG as (De Bellis et al., Nucleic Acids Res., 18:1311 (1990)). After induction, the culture was shaken for 3 hours at 25° C. and the Fab fragments harvested from the periplasm essentially as in Breitling et al., Gene, 104:147–153 (1991).

The antibodies were purified by immobilised metal (chelate) affinity chromatography (IMAC) (Hochuli et al., Bio/Technology, 6:1321–1325 (1988); Hoffmann et al., Nucleic Acids Res., 19:6337–6338 (1991)). The pooled "periplasmic fraction" and "osmotic shock fraction" were passed over a 5 ml Ni-NTA resin (Diagen) according to the manufacturers instructions. The column was washed with 50 mM sodium phosphate buffer pH 7.5, 500 mM NaCl, 35 mM imidazole and the protein was eluted by applying 50 mM sodium phosphate buffer pH 7.5, 500 mM NaCl, 100 mM imidazole. The eluted protein was dialysed against 2×3 liters PBS for about 24 hours. The dialysed fractions were then analysed by SDS-polyacrylamide gel electrophoresis (Laemmli, U. K., Nature, 227:680–685 (1970)) under non-reducing conditions and the concentration determined spectrophotometrically (assuming $A_{280nm}$ of 1.0=0.7 mg/ml).

Affinities of the purified Fabs were determined by fluorescence quench titration with free hapten (Eisen, H. N., Meth. Med. Research, 10:115–121 (1964)) essentially as described by (Foote et al., Nature, 352:530–532 (1991)). The haptens used were fluorescein (Sigma) or 3-iodo-4-hydroxy-5-nitrophenyl-acetyl caproic acid (NIP-CAP). All measurements were made with a Hitachi F4500 spectrofluorimeter, using an excitation wavelength of 280 nm and monitoring emission at 340 nm. Antibody (1.0 ml) in PBS was placed in a 10 mm×10 mm cuvette in the instrument, mixed continually using a magnetic stir-bar, and held at 20° C. Hapten additions were made automatically using a 50 µl gastight syringe (Hamilton) driven by a Microlab M syringe controller (Hamilton). The titrations and data collection were performed automatically using a Dell 433/L computer interfaced with the syringe controller (through an RS-232 interface) and the spectrofluorimeter (through an IEEE interface and an instrument driver supplied by the manufacturer). The computer was programmed in QuickBasic (Microsoft). Data were averaged from 2 to 5 runs.

The binding of three of the Fab fragments binding protein antigens were analysed by SPR using the BIAcore system. (Pharmacia Biosensor). The active concentrations of purified Fab fragments NML1 (anti-NQ11/7.22 Fv); NML9 (anti-mouse g1 Fc) and MH22 (anti-HGF/SF) were determined by the measurement of mass transport-limited binding slopes (Karlsson et al., J. Immunol. Methods, 145:229–240 (1991)). The antibody NQ11/7.22 was purified from ascites by affinity chromatography (Mäkelä et al., J. Exp. Med., 148:1644–1660 (1978)) and 990 RU immobilised on the biochip by chemical coupling with NHS/EDC (Johnsson et al., Anal. Biochem., 198:268–277 (1991); Chaiken et al., Anal. Biochem., 201:197–210 (1992)). HGF/SF was immobilised on the biochip after biotinylation. Thus 3.8 kRU of immobilised streptavidin (O'Shannessy et al., Anal. Biochem., 205:132–136 (1992)) was used to capture 2800 RU HGF which had been biotinylated with biotin-LC-hydrazide (Pierce) after periodate oxidation of the carbohydrate using a protocol based on (O'Shannessy, D. J., Meth. Enzymol., 184:162–166 (1990)), but with 20 mM $Na_2SO_3$ to quench excess periodate (Weber et al., Biochem. Biophys. Res. Commun., 65:1298–1302 (1975)). After capture the hydrazone bond between the biotin and the HGF was stabilised by reduction with sodium cyanoborohydride (0.1M in 0.1M Na acetate pH4: 40 µl at 2 ul/min). The fragments were passed over the surface at 5 µl/min at 25° in concentrations ranging from 2 to 400 nM, and the dissociation constant determined by Scatchard analysis of the equilibrium binding, and on- and off-rate constants by a kinetics analysis software (Pharmacia Biosensor) (Karlsson et .al.,J. Immunol. Methods, 145:229–240 (1991); Chaiken et al., Anal. Biochem., 201:197–210 (1992)).

Affinities of Selected Antibodies

Soluble Fab fragments were produced and purified via their hexahistidine tag by immobilised metal chelate affinity chromatography (IMAC), with typical yields of 100 to 500

μg/l. From the large (6.5×10¹⁰ clones) repertoire, we measured the affinities of several Fab fragments binding to soluble NIP-CAP or fluorescein by fluorescence quench titration (Eisen, H. N., *Meth. Med. Research*, 10:115–121 (1964)). The affinities ($K_d$) of the Fab fragments ranged from 3.8 to 217 nM (Table 4A). This shows that high affinity anti-hapten antibodies can be isolated directly from large antibody repertoires. Three Fab fragments binding to the haptens NIP-CAP and fluorescein after selection of a small fraction (10⁷ clones) of the repertoire on NIP-BSA or FITC-BSA were characterized. By contrast these affinities ($K_d$) ranged from 0.8 to 12 mM (Table 4B).

Kinetics and affinity of Fab fragments (from the 6.5×10¹⁰ clone repertoire) binding to immobilised monoclonal antibody NQ11/7.22 and HGF/SF were measured by surface plasma resonance (Table 4A). For the Fab fragments against the variable region (NML1) and the Fc portion (NML9) of antibody NQ11/7.22, the binding affinities were determined both by on-and off-rate analysis and by Scatchard plots of equilibrium binding to be in the range 30–60 nM. FIG. 12 shows the analysis of affinity of Fab NML1 by SPR. Binding of the Fab to a sensor chip surface coated with mouse monoclonal antibody NQ11/7.22. For each concentration of antibody (C, nM), the equilibrium binding signal (Req, in resonance units) was plotted against the Req/C. The slope gives the binding affinity ($K_d$) as 32.3 nM.

For NML1, the on-rate was calculated as $6.4 \times 10^5$ $M^{-1}$ $s^{-1}$ and the off-rate as $2.2 \times 10^{-2}$ $s^{-1}$; for NML9 as $5.2 \times 10^5$ $M^{-1}$ $s^{-1}$ and $3 \times 10^{-2}$ $s^{-1}$ respectively. However for the Fab fragment (MH22) against HGF/SF, Scatchard analysis indicated several classes of binding sites, with affinities from micro- to nanomolar. At low Fab concentrations (<40 nM), where high affinity interactions predominate, the affinity could be estimated as 7 nM from an initial on-rate of $1.7-1.9 \times 10^6$ $M^{-1}$ $s^{-1}$, and off-rate of $1.3 \times 10^{-2}$ $s^{-1}$.

In the immune system, antibodies with moderate affinities are selected from primary repertoires, and their affinities improved step-wise by rounds of somatic mutation and selection. However theoretical arguments based on the idea of "shape space" have suggested that larger and more diverse repertoires should give rise to higher affinity antibodies (Perelson et al., *J. Theor. Biol.*, 81:645–670 (1979)). The probability (P) that an epitope is recognised by at least one antibody in a repertoire depends on the probability (p) that an antibody recognises a random epitope with an affinity above a threshold value, and on the number of antibodies (N) according to the equation $P=1-e^{-Np}$ (Perelson et al., *J. Theor. Biol.*, 81:645–670 (1979)). This predicts, as expected, that the larger the repertoire, the greater the chances of finding a high affinity antibody. However it does not provide an explicit relation between repertoire size and affinity.

Here a repertoire of phage antibodies was used as an "artificial immune system" to explore the possibility of isolating high affinity antibodies directly from a very large primary antibody repertoire. The efficiency of transfection of DNA into bacteria has limited the size of phage antibody repertoires to <10⁹ clones. This was overcome by the use of combinatorial infection and in vivo recombination. Bacteria harbouring a repertoire of heavy chains (encoded on a plasmid replicon), were infected with phage encoding a repertoire of light chains, and the heavy chain genes translocated to the phage replicon by recombination within the bacterium. By this means, repertoire of 6.5×10¹⁰ clones was made and included, antibodies to a range of antigens and haptens (Table 2) with affinities <10 nM (Table 4A).

With a smaller repertoire (10⁷ clones) only antibodies of moderate affinities (>800 nM) were found, in agreement with earlier work in which antibody fragments isolated from smaller repertoires (10⁷–10⁸ clones) were found to have affinities of 700 nM for the hapten NIP (Hoogenboom et al., *J. Mol. Biol.*, 227:381–388 (1992)), and 140 nM for the hapten fluorescein (Barbas et al., *Proc. Natl. Acad. Sci. USA*, 89:4457–4461 (1992c); Barbas et al., *Gene*, 137:57–62 (1993)). The characterisation of repertoires of different sizes (and of known diversity) should help in defining the explicit relation between repertoire size and affinity.

As shown in FIG. 13, the binding affinities of secondary response (hypermutated) mouse monoclonal antibodies to the haptens NIP and fluorescein were similar to those of human Fab fragments isolated directly from the large repertoire.

Only a single mouse anti-NIP antibody has been described (Lucisano-Valim et al., *Clin. Exp. Immunol.*, 84:1–8 (1991)) with an affinity ($K_d$ 5.6 nM) similar to the best human Fab fragment ($K_d$ 4.0 nM; Table 4A).

However, eight mouse monoclonal antibodies have been described with higher affinities for fluorescein than the best human Fab fragment ($K_d$ 3.8 nM; Table 4A), the best of these (4-4-20) with an affinity of 0.19 nM (Bedzyk et al., *Molec. Immunol.*, 23:1319–1328 (1986)).

It is quite possible that antibody fragments with even higher affinities are present in the repertoire, as the selection process was designed to capture antibody fragments with a range of binding affinities to antigen, including those with only moderate affinity. Thus, advantage was taken of the binding avidity of multiple Fab fragments on the surface of the phage (by using phage rather than phagemid vectors) and short wash times to retain phage with fast dissociation kinetics.

Also for selections on immunotubes we used a high coating density of antigen was used to favour rebinding of the phage, and for selections with soluble biotinylated antigen a relatively high concentration of antigen (50 nM) was used to try to include even those phage with moderate equilibrium constants (Hawkins et al., *J. Mol. Biol.*, 226:889–896 (1992)). The present invention also contemplates the selection of higher affinity antibodies from this repertoire by more stringent selection The phage repertoire was not only large, but also highly diverse. It was assembled from the majority of V-gene segments used in vivo, including all the major $V_H$ and $V_l$ families, and $V_k$ subgroups. The segments included all the major heavy and light chain CDR1 and CDR2 loop conformations (Chothia et al., *J. Mol. Biol.*, 227:799–817 (1992); Chothia et al., 1989; Chothia et al., *J. Mol. Biol.*, 227:799–817 (1992)), and the CDR3 loops were made of diverse sequences and lengths. The chains were paired at random (Huse et al., *Science*, 246:1275–1281 (1989)), creating diverse pairings. The repertoire was sufficiently large that several pairings of a single heavy or light chain could be isolated from the repertoire. Such chain "promiscuity" is characteristic of repertoires derived from the mRNA from immune sources (see for example Clackson et al., *Nature*, 352:624–628 (1991)) and reflects the chances of a chain making multiple pairings, which in turn depends on the frequency of the chain and the size of the repertoire.

In the antibodies binding to the haptens, the combinations of heavy and light chain segments appeared to be restricted. For example, the antibodies binding to soluble hapten NIP-CAP (Table 4A) mainly utilised the heavy chain segment DP-38 and the light chain segment DPL-3, and included a four residue heavy chain CDR3 loop with a distinctive motif, X-Gly-X-X. This is reminiscent of the restricted response seen with mouse antibodies raised by immunisation with the hapten 4-hydroxy-3-nitrophenyl acetate (NP): the immune response in C57BL/6 mice is dominated by antibodies with λ1 light chains paired with heavy chains encoded by the V186.2 $V_H$ segment and the DF116.1 D segment (Bothwell et al., Cell, 24:625–637 (1981); Cumano, A. and Rajewsky, K., Eur. J. Immunol., 15:512–520 (1985)).

Figure 1:
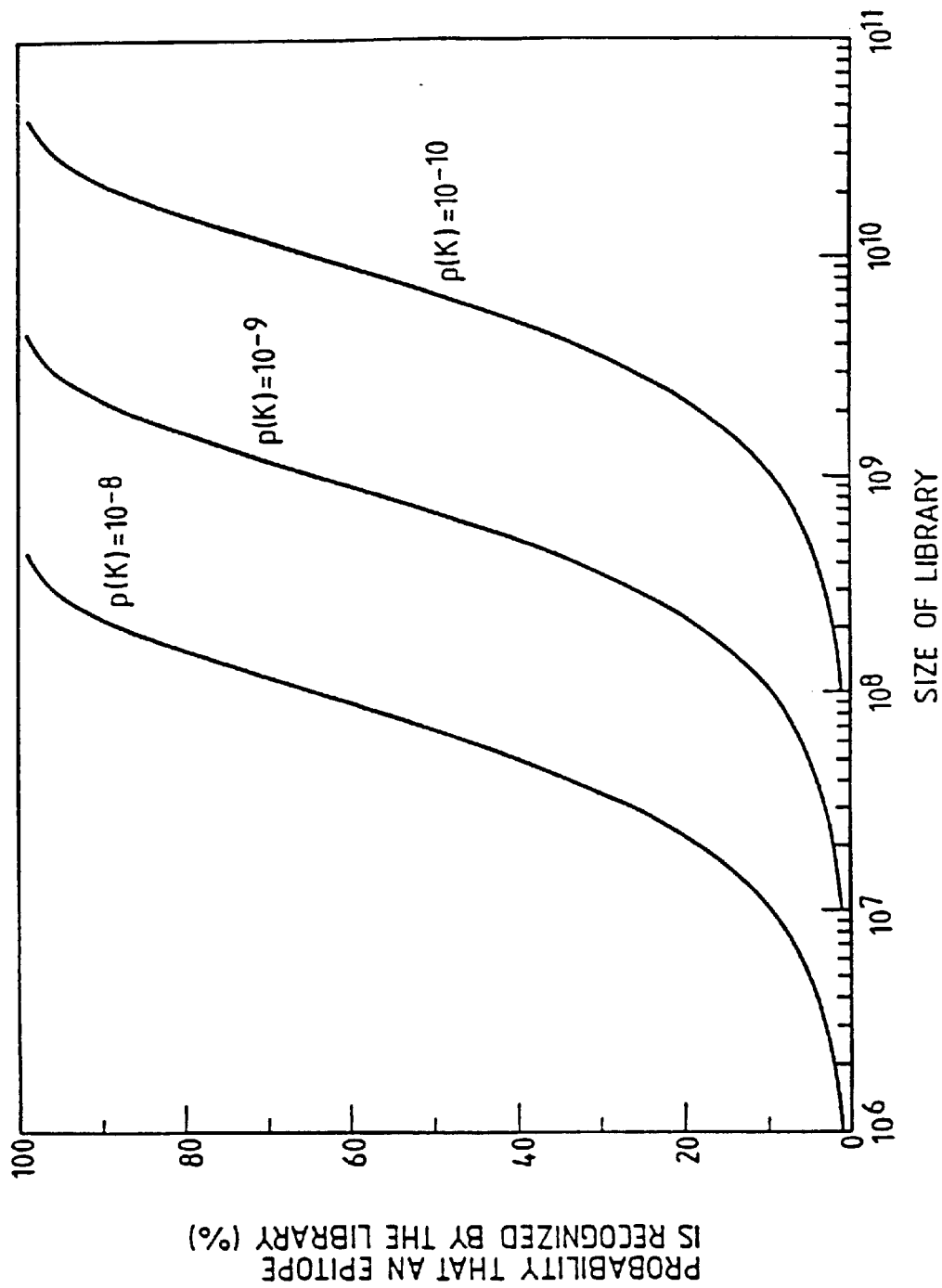
FIG. 1 shows plots of the probability of isolating an antibody with a given p[K] value against the size of a library.
Figure 2:
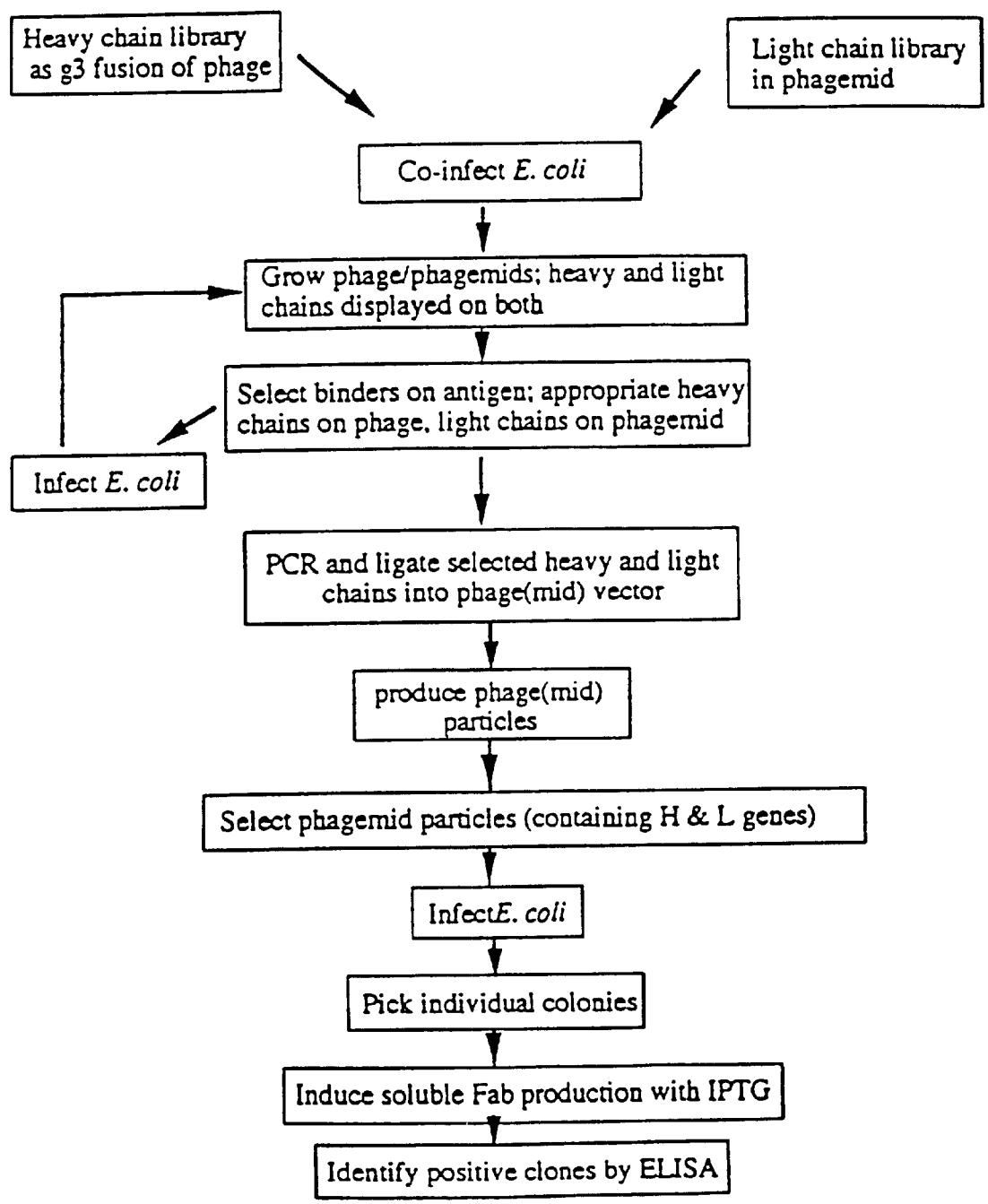
FIG. 2 outlines a strategy to clone heavy chain as g3 fusion on phage, light chain being expressed as soluble fragments from a phagemid.

As in vivo, only a few segments contributed to most of the "response". However the usage of V-gene segments found in the selected Fab fragments from the artificial repertoire differed from that of antibodies from natural repertoires (FIG. 11). This might reflect a different representation of segments in the primary repertoire, or the high frequency of sequences from phage antibodies directed against hapten-conjugates. Nevertheless it would be expected. that the artificial repertoire to be shaped by different selection pressures to those that operate in vivo, leading to a different spectrum of binding sites. If "holes" exist in the natural. repertoire, they may be absent in an artificial repertoire and vice versa. Despite the differences in segment usage between the natural and synthetic antibodies, there is one striking similarity: the heavy chain segment DP-47 is the most commonly used segment in both. In vivo, it has been suggested that pre-B cells displaying DP-47 heavy chains are selected by binding to autoantigen (Schwartz et al., Immunol. Today, 15:27–32 (1994)). We suggest that the usage of DP47 reflects a more fundamental property of this segment; the structure of the binding site may be more capable of accomodating a wider diversity of antigens than other segments (FIG. 1).

It is thus clear that human antibodies with affinities in the nanomolar range, and specific for protein antigens and haptens, can be derived directly from large and diverse synthetic phage antibody repertoires. The binding affinities are typical of somatically mutated mouse antibodies produced in vivo, and presumably could be improved further through rounds of "chain shuffling" (Marks et al., Bio/Technology, 10:779–783 (1992b)) or point mutagenesis (Hawkins et al., J. Mol. Biol., 226:889–896 (1992)) to create binding specificities and affinities outside the reach of the immune system both of which are comprehended for usee in the practice of the present invention. In addition, the use of synthetic phage antibody repertoires based on V-gene segments to simulate natural immune systems may provide further insights into immune strategy, for example in helping to. define the relation between affinity and repertoire size, or the relation between the structures of the antigen binding sites and the usage of V, D and J-segments, CDR3 lengths and junctional diversity.

EXAMPLE 4

Construction by Recombination in the loxP Format of a Large Phage Display Repertoire of Fab Fragments Derived from the Tonsils of Unimmunised Human and Selection of Antibodies This example describes the construction by recombination in the loxP format of a large phage display repertoire, containing about $8.24 \times 10^{11}$ independent clones, of Fab fragments derived from the tonsils of an unimmunised human. The isolation of clones expressing Fab fragments against the human self antigens TGFβ1 and TNFα is described.

Preparation of cDNA Template

Tonsil B cells were isolated from freshly removed (processed within 2 hours) whole tonsils provided by Addenbrookes Hospital, Hills Road, Cambridge, U.K. Each tonsil was processed as follows. Tonsils were placed in a petri dish containing 5 ml of PBS and macerated with a scalpel blade to release the cells. The suspension was transferred to a fresh tube and large debris allowed to sediment under gravity for 5 minutes. The cell suspension was then overlaid onto 10 ml of Lymphoprep in a 50 ml polypropylene tube (Falcon) and centrifuged at 1000×g for 20 minutes at room temperature (no brake) and cells at the interface harvested with a glass pipette. These cells were diluted to a final volume of 50 ml in RPMI medium at 37° C. and centrifuged at 500×g for 15 minutes at. room temperature. The supernatant was aspirated and the the cells washed. another two times with RPMI.

Polyadenylated RNA was prepared from pelleted cells using the "Quickprep™ mRNA Kit" (Pharmacia Biotech, Milton Keynes, U.K.). The entire output of cells from one tonsil (ca. $1.10^6$ cells) was processed using one Oligo(dT)-Cellulose Spun column and processed exactly as described in the accompanying protocol. MRNA was ethanol precipitated as described and resuspended in 40ml RNase free water.

The cDNA synthesis reaction was set up using the "First-Strand cDNA Synthesis Kit (Pharmacia Biotech, Milton Keynes, U.K.) as follows:

RNA-20 μl (heated to 67° C. 10 minutes before use)

1st strand buffer-11 μl

DTT solution-1 μl pd(N)$_6$ primer-1 μl

After gentle mixing, the reaction was incubated at 37° C. for 1 hour.

Construction of Naive Heavy Chain Repertoires

Human VH genes were amplified from tonsil cDNA using the nine family-based back primers (VH1b/7a -6a back Sfi, which introduce a Sfi I site at the 5'-end, Table 1) together with an equimolar mixture of the four JH forward primers (JH 1-2, 3, 4-5, 6, for; Marks et al., 1991). Thus, nine primary PCR amplifications were performed. Each reaction mixture (50 μl) comprised 2 μl cDNA template, 25 pmol back primer, 25 pmol forward primers, 250 μM dNTPs, 1.5 mM MgCl$_2$, 50 mM KCl, 10 mM Tris-HCL pH 8.3 and 2.5 u of Taq polymerase (Boehringer). The reaction mixture was overlaid with mineral (paraffin) oil and was cycled 30 times (94 ° C. for 1 min, 55° C. for 1 min, 72° C. for 1 min) using a Techne thermal cycler. The products were purified on a 1% (w/v) agarose gel, isolated from the gel using "Geneclean" (Bio 101 Inc.) and resuspended in 15 μl of water. The nine amplified products were then individually re-amplified for 30 cycles (94° C. for 1 min, 55° C. for 1 min, 72° C. for 1 min) using 2 μl purified VH as the template under the same reaction conditions as above but using an equimolar mixture of four JH forward Xho primers (which incorporate an Xho I site, JH 1-2, 3, 4-5, 6, for Xho) together with a flanking primer corresponding to the Sfi I site (Sfi Pri, Table 1). The resulting PCR products were combined to form a tonsil-derived VH pool.

The tonsil VH pool was digested with Sfi I and Xho I, gel purified using "Geneclean" (Bio 101 Inc.), and 200 ng ligated to 600 ng of Sfi I and Xho I digested pCantab 6 (see WO94/13804 incorporated herein by reference) using an Amersham ligation kit. The ligation mixes were first extracted with phenol and then with chloroform prior to ethanol precipitation in the presence of 20 μg of glycogen as a carrier to ensure quantitative recovery of the ligated material. Ligated DNA was electroporated into TG1 cells as previously described (Marks et al., J. Mol. Biol., 222:581–597 (1991)). Briefly, the ligated DNAs were resuspended in 24 μl of water, and 4 μl samples were electroporated into 100 μl aliquots of electro-competent E. coli TG1.

Cells were grown in SOC for 1 hr and plated on 2YT agar with 100 µg/ml ampicillin and 2% glucose in 243×243 mm dishes (Nunc) and then grown overnight at 30° C. Colonies were scraped off the plates into 2YT containing 15% glycerol for storage at −70° C. as library stocks.

The tonsil heavy chain repertoire was calculated to have ca. $7.4 \times 10^7$ independent recombinants, which by Bst NI fingerprinting (Clackson et al., *Nature*, 352:624–628 (1991)) were shown to be extremely diverse.

loxP Donor Vector

The plasmid 'donor' vector pUC19-2lox VHdel is as described in example 3 except that an Apa LI restriction site was deleted from CH1. To achieve this the pUC19-2lox VHdel was digested with the restriction endonucleases Eco RI and Hind III. The insert fragment was recovered from a 1% agarose-TAE gel following electrophoretic separation using the Geneclean kit (Bio 101) and cloned into Eco R1/Hind III digested pUC119 using the Amersham Ligation Kit. The ligation product was transformed into electro-competent TG1 cells.

The oligonucleotide loxP CH1ΔApa (Table 7) was synthesised for use with the Oligo-directed Mutagenesis System Version 2.1 (Amersham) to facilitate the removal of the Apa LI restriction site. Single-stranded DNA was prepared from pUC119-2lox VHdel according to Sambrook et al (1989) and mutagenesis carried out as described in the Amersham mutagenesis kit. Constructs were sequenced to determine those in which the Apa LI site had been removed. One of these constructs was digested with Eco RI and Hind III and the insert cloned back into pUC19 as described earlier. The resulting plasmid was designated pUC19CHIΔApa.

Sub-Cloning of Vh Repertoire

The Vh repertoire was generated by sub-cloning from the repertoire constructed earlier in pCANTAB6 ($7.4 \times 10^7$ clones). DNA prepared from this repertoire was digested with Sfi I and Xho I and the vector and insert separated electrophoretically on a 1% TAE-agarose gel. The insert fragment was excised and eluted using the Geneclean kit (Bio 101). pUC19CHIΔApa was digested sequentially with Sfi I, Xho I and PstI and purified on a Chromaspin column (Clontech). Vector and insert were ligated with the Amersham ligation kit as described earlier. The ligation product was extracted with phenol and precipitated as described earlier then used to transform electro-competent TG1 cells containing the pACYC ara Cre plasmid (example 5; 'araCre TG1'). $4 \times 10^7$ colonies were produced when plated on 2YTAG(2%) agar plates. A total of 10 ml 2YTAG(2%) was used to scrape the plates and thus recover the colonies. This plate scrape was used directly in the infection step.

Construction of Naive Light Chain Repertoires

Kappa and lambda light chain genes were amplified separately. Kappa light chain genes were amplified from tonsil cDNA using each of the six family-based back primers (VK 1b-6 back, Table 2) in conjunction with the kappa constant. domain primer, CK for (Table 2). Thus, six primary PCR amplifications were performed for kappa light chain genes. Lambda light chain genes were amplified from tonsil cDNA using each of the eleven family-based back primers (VL 1a-9 back, Table 3) in conjunction with an equimolar mixture of the lambda constant. domain primers, CL $2^+$ for and CL $7^+$ for (Table 3). Thus, eleven primary PCR amplifications were performed for kappa light chain genes. In each case, 50 µl reaction mixes containing 2 1 µl of tonsil-derived cDNA, 25 pmol back primer, 25 pmol forward primers, 250 µM dNTPs, 1.5 mM MgCl₂, 50 mM KCl, 10 mM Tris-HCL pH 8.3 and 2.5 u of Taq polymerase (Boehringer). The reaction mixture was overlaid with mineral (paraffin) oil and was cycled 30 times (94° C. for 1 min, 55° C. for 1 min, 72° C. for 1 min) using a Techne thermal cycler. The products were purified. on a 1% (w/v) agarose gel, isolated. from the gel using "Geneclean" (Bio 101 inc.) and resuspended in 15 µl of water.

To introduce Apa LI and Asc I restriction sites at the 5'- and 3'-ends respectively of the light chains, further PCR amplification was performed on each of the six kappa and eleven lambda preparations. Kappa light chain genes were amplified using the appropriate kappa back Apa primer (kappa 1b-6 back Apa, Table 2) in conjunction with the kappa constant domain primer, CK for Asc (Table 2). Lambda light chain genes were amplified using the appropriate lambda back Apa primer (lambda 1a-9 back Apa, Table 4) in conjunction with an equimolar mixture of the lambda constant domain primers, CL $2^+$ for Asc and CL $7^+$ for Asc (Table 4). Reaction conditions were as described above except that 2 µl of the appropriate purified primary PCR product was used as the template. The products were purified on a 1% (w/v) agarose gel, isolated from the gel using "Geneclean" (Bio 101 inc.) and combined to form a kappa and a lambda light chain pool.

A further PCR amplification was performed on the kappa and lambda preparations to introduce a Not I site at the 3'-end. The light chain genes were amplified using Apa Pri (Table 2) and Asc/Not Pri (Table 2) using the reaction conditions described above. The lambda and kappa products were digested with Asc I and Not I purified on a 1% (w/v) agarose gel, isolated from the gel using "Geneclean" (Bio 101 inc.) and 100 ng of each was ligated to 400 ng of Asc I and Not I digested pCantab 3 using an Amersham ligation kit. Ligation, electroporation and growth were as described for the VH repertoire construction.

The lambda and kappa light chain repertoires in pCantab 3 were each calculated to have ca. $5 \times 10^6$ independent recombinants, which by Bst NI fingerprinting (Clackson et al., *Nature*, 352:624–628 (1991)) were shown to be extremely diverse.

DNA was prepared from the lambda and kappa repertoires in pCantab 3, digested with Apa LI and Asc I, the light chain fragments separated from the vector on a 1% (w/v) agarose gel and isolated from the gel using "Geneclean" (Bio 101 inc.). In each case, 100 ng of light chain fragments were ligated to 1 µg of Asc I and Apa LII digested fdDOG-2lox using an Amersham ligation kit. Ligation and electroporation conditions were as described for the VH repertoire construction. After electroporation, cells were grown in SOC for 1 hr and plated on 2YT agar with 12.5 µg/ml tetracycline in 243×243 mm dishes (Nunc) and then grown overnight at 30° C. Colonies were scraped off the plates into 2YT containing 15% glycerol for storage at −70° C. as library stocks.

The kappa and lambda light chain repertoires in fdDOG-2lox were calculated to have ca. $1.7 \times 10^6$ and $3.5 \times 10^6$ independent recombinants respectively,again, Bst NI fingerprinting indicates that both libraries were extremely diverse.

Production and Purification of Phage from VI Repertoire

500 µl aliquots of the kappa and lambda light chain repertoire glycerol stocks (described earlier) were used to infect 500 ml each of 2YTtet and grown 16 h at 30° C. Cells were pelletted by centrifugation and the supernatant from each added to 150 ml ice-cold 20% PEG/2.5MNaCl and mixed. This was incubated on ice for 3 h. The PEG precipitated phage were recovered by centrifugation and the phage pellets resuspended in 13 ml TE. Caesium chloride was added to a final concentration of 0.5 g/ml and transferred to ultracentrifuge tubes. The tubes were centrifuged at 45000 rpm for 24 h in a Vti65 rotor. The resulting phage band was recovered into 1 ml TE. Approximately $5 \times 10^{12}$ infective phage particles were produced for both the kappa and lambda repertoires.

Infection 4 ml of the fresh plate scrape of the Vh repertoire in araCre TG1 cells (described earlier) were used to infect 8×11 aliquots of 2YTAGC prewarmed to 37° C. This was incubated at 37° C. with vigorous shaking (300 rpm) to $OD_{600nm}$ 0.4 then infected with a total of $10^{13}$ phage particles (lambda and kappa). Infection was carried out stationery at 37° C. for 15 min., followed by gentle shaking (200 rpm) at 37° C. for 15 min. Cells were centrifuged, resuspended in 81 2YTCATara (which consists of 2YT plus 25 µg/ml chloramphenicol, 100 µg/ml ampicillin, 12.5 µg/ml tetracycline and 0.05% arabinose) and incubated at 30° C. and 300 rpm for 24 h. Cells were removed prior to overnight incubation for titration, indicating a library size of $8.24 \times 10^{11}$ independent clones.

Following overnight growth approximately $10^{13}$ viable cells were present in the 81 of media. This was centrifuged and the cells resuspended in 150 ml 2YT. To the resuspended cells, 75 ml 50% glycerol was added and mixed in gently for 4 h at 4° C. then at −70° C. until required for regrowth.

Growth of Repertoire

A 125 ml aliquot of the glycerol stock was used to innoculate 251 media containing tetracyclin at 12.5 µg/ml and grown for 24 h at 37° C. with vigorous stirring (500 rpm). Cells were pelleted by centrifugation and the phage in the supernatant precipitated by the addition of PEG8000 to a final concentration of 5% and sodium chloride to a final concentration of 0.5M and incubation at 4° C. 16 h. The phage were pelleted by centrifugation and resuspended in 100 ml TE. The phage were titred with TG1 cells indicating there to be a total of $1.15 \times 10^{15}$ infectious phage particles.

Selection of Antibodies from the Repertoire

The phage repertoire was selected for binders to human TGFβ1, by three rounds of biopanning on immunotubes coated at 5 µg/ml, and to human TNFα, by four rounds of selection of biotinylated antigen at a range of concentrations from 0.3 nM to 500 nM on streptavidin-coated paramagnetic beads, using the methods described in example 3. Phage ELISA in 96 well plates, performed as described in example 3, indicated that clones had been selected which express Fab fragments specific to TGFβ and TNFα and show no cross-reactivity with an uncoated well. Sequencing of the clones expressing Fab fragments specific to TGFβ shows there to be at least 10 different clones.

EXAMPLE 5

Construction of the Plasmid Pacycaracre Expressing Cre Recombinase Under the Control of an Arabinose Promotor In the work described in this example, a plasmid was constructed in which Cre recombinase is expressed under the control of a promoter inducible by arabinose. The origin used p15A makes it suitable for use in combination with plasmids with ColE1 origin and with phage or phagemids with phage origins.

A fragment was amplified by PCR from pUC119 (Vieira et al., *Methods in Enzymol.* 153:3–11 (1987)) using the primers lacfor2 and lacback2. This fragment extended from within the lacI gene fragment (inactive) to the polylinker of pUC119 and the primers incorporate a series of restriction sites at both ends of the fragment.

This PCR fragment was cut with PvuII and KasI and re-cloned into pUC119 digested with the same enzymes to generate pUC119lacipoly.

pARA14 (Cagnon et al., *Protein Engineering* 4:843–847 (1991)) was digested with SacI and NcoI to release a fragment containing the araC gene and the promoter-operator region of araB. This fragment was ligated into pUC119lacipoly cut with the same enzymes to generate pUC119ara.

The Cre recombinase gene was amplified by PCR from bacteriophage P1Cm c1. 100 r⁻m⁻ (Yarmolinsky et al. *J. Bacteriol.*, 171:4785–4791 (1989)) using the primers "crefor" and "creback". After digestion with BsaI and KpnI this fragment was ligated into pUC119ara cut with NcoI and KpnI to generate pUC119araCre.

Finally, the PvuII-HindIII fragment of pUC119araCre containing the araC gene and the Cre recombinase gene under the control of the promoter-operator region of araB was subcloned into pACYC184 (Chang et al., *J. Bacteriol.*, 134, 1141–1156 (1987)) cut with BsaBI and HindIII, thereby replacing the tetracycline resistance gene of pACYC184. The plasmid produced (pACYCaraCre) thus contains the an arabinose inducible Cre gene on a plasmid with a p15A origin of replication. This plasmid can coexist in *E. coli* with both the heavy chain donor vector (which has a ColE1 origin) and with the acceptor vector (which has a filamentous phage origin) as is useful for the generation of a large phage display library in the loxP format as described in example 4.

EXAMPLE 6

Derivation of New Mutant loxP Sites and Construction of a Two Replicon Cloning System Incorporating 3 loxP Sites The use of further lox sites in addition to the two lox sites loxP and loxP 511 used in examples 1 to 4 allows increased control and flexibility in the use of the loxP recombination system. It facilitates, for example, chain shuffling of light and heavy chains for affinity maturation of antibody fragments and the transfer of light and heavy chain gene pairs, which have been selected by display on the surface of filamentous bacteriophage for binding to antigen, into a soluble expression vector.

In order to construct a system containing more lox sites new loxP sites suitable for controlled recombination were derived and their properties tested as described in this example.

Derivation of New Mutant loxP Sites

A screening system was devised for deriving the sequences of novel mutant loxP sites which could recombine with themselves efficiently but not with the wild type (WT) and mutant 511 loxP sites (described by Hoess et al., *Nucleic Acids Res.*, 14:2287–2300 (1986)). This was developed by engineering a library of degenerate loxP sites into the plasmid pBS+(Stratagene, Cambridge, UK) to create pBS+ loxP mut (FIG. 14). Degeneracy was incorporated at the 4 positions indicated below because these sites have been identified as those responsible for the specificity of recombination between loxP sites (Hoess et al., supra). The degeneracy was incorporated in PCR primers used to amplify the tetracycline resistant genes prior to cloning in the construction of pBS+loxP mut.

```
loxP WT          ATAACTTCGTATAATGTATGCTATACGAAGTTAT (SEQ ID NO:1)

Degenerate loxP  .......NN..NN....... (SEQ ID NO:597)
```

In pBS+loxP mut the wild type (WT) and mutant (511) loxP sites flank the heavy chain gene of NQ10.12.5 (Griffiths et al., *Nature* 312:271–275 (1984)) while loxP WT and one of the degenerate loxP sites flank a kanamycin resistance gene. In turn, this degenerate loxP site and another degenerate loxP site flank the tetracycline resistance gene. A library was generated by electroporation of this plasmid into *E. coli*. These *E. coli* were subjected to the conditions of recombination mediated by phage in *E. coli* as described in example 1 but without the presence of the phage replicon fdDOG-2lox, tetracycline and with only 12 hours growth in the presence of phage P1. Plasmid DNA was prepared from the recombination culture and electroporated into *E. coil* and plated on TYE with ampicillin and kanamycin to eliminate those plasmids which had undergone recombination between the degenerate loxP sites and the WT or 511 sites.

1000 single colonies were replica picked onto TYE agar with tetracycline. Tetracycline sensitive colonies were selected since they had undergone recombination between their degenerate P sites. The resulting loxP site was sequenced using primer MRB1 (5'-ATTGTCGCACCTGATTGC-3')(SEQ ID NO: 598 using methods described in example 3. Four sequences were obtained as shown in Table 8 along with the WT and 511 sites.

Testing the Recombination Properties of Four Mutant loxP Sites

The screening experiment described above does not allow for the determination of the sequences of the two degenerate loxP sites present in pBS+loxP mut but only of the recombined product. To check that the sites identified recombined efficiently when two identical sites are present and to assess further their efficiency of recombination with the wild-type (WT) and mutant (511) loxP sites, a further screen was developed. The WT and 511 loxP sites of vector pUC 19-2lox (example 1) were adapted to test several combinations of existing and new loxP sites for efficiency of recombination.

The anti-phOX VH gene in pUC19-2lox was replaced by a tetracycline resistance gene (tetR) cloned SfiI-NotI to create. pUC-2loxTET (see FIG. 15). loxP sites were introduced as appropriate to create 21 combinations of loxP sites flanking the tetracycline resistance gene, including 511/WT as a negative control for recombination, and WT/WT as a positive control for recombination. These plasmids were subject to the conditions of recombination mediated by phage P1 in *E. coli* as described in example 1 but without the presence of the phage replicon fdDOG-2lox, tetracycline and with only 12 hours growth in the presence of phage P1. After overnight growth the cultures were plated out on ampicillin plates. 100 individual colonies from each culture were replica picked onto TYE plates containing tetracycline. Table 9 gives the different combinations tested and the number of teracycline resistant colonies produced in each case.

Thus all colonies from constructs containing two different loxP sites proved to be tetracycline resistant. All colonies from constructs containing two of the same loxP sites proved to be tetracycline sensitive.

Therefore, in all cases, recombination between different loxP sites was of low enough efficiency to allow enough unrecombined sites within bacteria to enable the expression of tetracycline resistance.

Several constructs which yielded only tetracycline resistant colonies were tested for the efficiency of recombination at the DNA level, i.e. the efficiency of recombination within each cell. These included constructs containing the mutant sites with the WT site and with the 511 site, and are shown in Table 3. Combinations 511/WT and WT/WT were included as negative and positive controls respectively. Thus an aliquot of the overnight cultures described above were used to prepare plasmid DNA which was electroporated into *E. coli*. 100 resulting ampicillin resistant colonies were replica picked onto TYE plates with tetracycline in each case. Table 10 gives the numbers of tetracycline sensitive colonies which corresponds to the % efficiency of recombination.

Thus, the mutant sites are very efficient at recombination with themselves but do not recombine to any. extent with the 511 site. Mutant sites vary in their ability to recombine with the WT site, and loxP 4 is the least promiscuous of the two new sites.

PCR analysis of those tetracycline resistant colonies resulting from electroporation of construct 6 revealed that 30% of the constructs had undergone an inversion event between the loxP 4 and WT sites. Sequencing of these inverts revealed that the resulting loxP sites consisted of chimeric sequences comprising the 5' end of one loxP site joined to the reverse complement sequence of the 3' end of the other loxP site (see FIG. 16) and thus may be non-functional in further recombination events.

Testing the Efficiency of Recombination Between Ywo Replicons in a 3-lox System

The 2-loxP system described by Waterhouse et al. was adapted to include a third loxP site at the 5' end of the Ck gene which replaced the anti-phOx light chain from NQ10.12.5 (see FIG. 17). A donor vector was also created containing light chain from NQ10.12.5 flanked at the 5' end by the new loxP site, and at the 3' end by loxP 511. Four versions of this system were created corresponding to each of the new loxP sites 1, 2, 3 and 4 where both fd3lox and the pUC19-2lox light chain donor had the same mutant loxP sites. Recombinations were carried out in each case as in example 1.

Harvested phage were used to infect *E. coli*, and these were plated on tetracycline TYE plates. 100 individual colonies in each case were PCR screened using fdPCRback and Ck.lib.seq (see FIG. 14 and Table 6 for primer sequences). Phage replicons which had recombined with the donor vector such that they now contained NQ10.12.5 light chain were detected by a larger amplification product in PCR. Table 11 gives the number of phage colonies which had recombined in this way which corresponds to the efficiency of recombination. Hence loxP 4 is the least promiscuous of the four sites (loxP 1-4).

In addition, the efficiency of each of the fd3lox constructs were tested for the efficiency of recombination of the heavy chain gene mediated by sites 511 and WT with donor vector pUC19-2lox as in Waterhouse et al. Efficiencies of heavy chain gene recombination were comparable to those seen by Waterhouse et al. Production of functional phage with binding activity towards phOX was demonstrated for fd3lox constructs encoding the NQ10.12.5 Fab. In this case VHCH1 of NQ10.12.5 replaced a-TNF-H in fd3lox and phage ELISA was performed as in example 3.

The derivation of mutant loxP sites as described in this example enables the construction of a 3lox vector system as comprehended by the present invention which further increases the ease of use and flexibility of a recombination system employing loxP.

EXAMPLE 7

Use of the loxP System to Recombine Genes Encoding VH and VL Domains to Form a Single Chain Molecule, the loxP Sequence Encoding Part of the Linker Peptide Site-specific recombination allows two sequences of nucleic acids to be cloned separately as a libraries and to be subsequently brought together by recombination. In order to recombine VH and VL genes into a continuous open reading frame, amino acid sequences encoded within the loxP sequences are used. In addition to the wild type loxP sequence, a number of new loxP sequences have been identified and have been shown to be functional in recombination (example 6, Table 8). These encode different amino acid sequences as shown in FIG. 18. the work described in this example demonstrates the use of these new loxP sites as linkers in single chain Fv fragments and shows them to be compatible with expression.

Two different loxP sites were used as a scFv linkers, each consisting of 15 amino acids encoded by loxP 1 and loxP 4.

The clone #G6 encoding a single chain Fv fragment specific for the hapten NIP (3-iodo-4-hydroxy-5-nitrophenyl-acetate) was used as a model (this clone was derived from a phage display library of synthetic scFv fragments and has the following features VH: germline DP38, CDR3: AGTL and VL: germline DPK12, CDR3; MQSIQLPT). The loxP linkers were introduced by ligation of a pair of oligonucleotides into the fd vector (using oligonucleotides #3749 & 3750 to introduce loxP 1 and oligonucleotides #4120 & 4121 for loxP 4 (Table 1), in which the loxP site is flanked by XhoI at the 5' end and ApaLI at the 3' end. The resulting constructs fdSc1/3 and fdSc4/3 encode scFvs with the linkers VH-ITSYNINYTKLSSAL-VL, in the case of loxP 1 and VH-ITSYNIAYTKLSSAL-VL, in the case of loxP 4 (FIG. 18). In FIG. 18, the two alternative loxP 1 and loxP 4 linkers between the VH and VL domains are underlined and CDRs are in bold and italics. The loxP 3 linker between the VL-NIP and gene III protein is also shown. The constructs were used to transform TG1 and phage displaying scFv fragments were prepared as described in example 3. The amino acids encoded by loxP 1 and loxP 4 were compatible with successful display of anti-NIP scFv on the surface of the bacteriophage. These constructs yielded phage titers in excess of $10^{10}$ TU/ml. Binding to antigen was demonstrated by phage ELISA on plates coated with 10 $\mu$g/ml NIP-BSA as described in example 3 and resulted in an absorbance reading of over 3.

To test recombination between loxP sites the VH gene from the clone D10 (VH: DP53, CDR3: PWARGTD) was inserted into two donor vectors, pD511/4 and pD511/1 (FIG. 19). Recombinations were performed in vivo using the bacterial strain TG-1 bearing a pACYC plasmid containing the cre recombinase gene under the control of the arabinose promoter and selectable by chloramphenicol resistance, (TG1 pACYCaraCre; example 5). Shuffling the VH gene into fd containing a single chain Fv fragment with a loxP 1 linker (fdsc1/3; FIG. 19) was performed by transforming TG pACYCaraCre with pD511/1 donor vector containing VH-D10 and then infecting with fdSc1/3 containing the genes encoding the variable domains, VH-G1 and VL-G1. Recombination is allowed to continue at 30° C. overnight. Recombined phage from the bacterial supernatant were used to infect TG-1. As a result of recombination between the loxP 511 sites of donor and acceptor and between the loxP 1 sites of the donor and acceptor, the recombined fd phage contains VH-D10 while keeping the original VL-G1. Successful recombination was analyzed by PCR screening of individual fd phage clone colonies by amplification using oligonucleotides that prime specifically on the sequences encoding the VL-G1 and VH-D10 CDR3s present in the donor vectors. Thus, a PCR product is only observed when recombination has occurred.

To test recombination of the light chain, a construct was made where the VL-G1 of the fdSc1/3 was exchanged with VL-D10 (DPK-21; CDR2, QQYNNWLST) and various loxP sites between VH and VL genes and between VL and gene III were used to give the acceptor vectors fdSc1/3-D10, fdSc4/3-D10, fdSc4/1-D10, and fdSc4/WT-D10 (see FIG. 19). The light chain VL-G1 gene was cloned into the donor vectors pD1/3, pD4/3, pD4/1, or pD4/WT (see FIG. 19). These donor vectors were transformed into Tg1 pACYCara-Cre and infected with fdSc1/3-D10, fdSc4/3-D10, fdSc4/1-D10 or fd4/WT-D10 respectively. In this case successful recombination resulted in fd phage having a single chain Fv containing VH-G1 and VL-G1. PCR screening for successful recombinant was performed using oligonucleotides which prime specifically on the VL-G1 and VH-G1 CDR3s, recombination being indicated by the presence of a PCR product on agarose gel electrophoresis.

FIG. 20 summarizes the results of the recombination experiments (upper lines of pairs). For instance, when pD511/4 is recombined into fdSc4/WT there is 54% recombination and where pD4/WT was recombined into the same vector, there is 82% recombination. Thus, the loxP sites present in an open reading frame may be used to construct single chain Fv molecules by recombination and to shuffle VH or VL genes. In a further experiment, the same acceptor vectors were used together with the donor vectors pEX511/WT, pEX511/1, and pEX511/3 (see FIG. 19). In this case, recombination is between outer loxP sites which flank an intervening loxP site. No recombination was found. The intervening sequence appears to interfere with recombination at the two outer loxP sites.

Subsequent experiments have shown that successful recombination may be obtained when a cassette, with the loxP 511 and loxP 4 genes flanking a single chain Fv clone with a loxP WT recombination site included in the region linking the VH and VL genes, was transferred into pEX511/4, indicating that it is possible to get recombination at the two outer loxP sites when there is an intervening site.

This example demonstrates the utility of the loxP site to bring together two-variable domain genes into a single open reading frame in single chain Fv construction and shuffling experiments.

The foregoing examples are presented by way of illustration and are in no way intended to limit the scope of the invention as set out in the appended claims.

TABLE 1

OLIGONUCLEOTIDE SEQUENCES

ALL WRITTEN 5'->3'
A) Primers for first strand cDNA synthesis

TABLE 1-continued

OLIGONUCLEOTIDE SEQUENCES

Human IgM Constant Region Primer
HuIgMFOR      5'-TGG AAG AGG CAC GTT CTT TTC TTT-3'
Human kappa Constant Region Primer
HUCKFORCYS    5'-ACA CTC TCC CCT GTT GAA GCT CTT-3'
Human lambda Constant Region Primer
HUCLFORCYS    5'-TGA ACA TTC TGT AGG GGC CAC TGT
              CTT-3'

B) Heavy chain primary PCR
VH Primers
HuVH1aBACK    5'-CAG GTG CAG CTG GTG CAG TCT GG-3'
HuVH2aBACK    5'-CAG GTC AAC TrA AGG GAG TCT GG-3'
HuVH3aBACK    5'-GAG GTG CAG CTG GTG GAG TCT GG-3'
HuVH4aBACK    5'-CAG GTG CAG CTG CAG GAG TCG GG-3'
HuVH5aBACK    5'-GAG GTG CAG CTG TrG CAG TCT GC-3'
HuVH6aBACK    5'-CAG GTA CAG CTG CAG CAG TCA GG-3'
Forward Primer
HuIgMFOR      5'-TGG AAG AGG CAC GTT CTT TTC TTT-3'

C) Heavy chain reamplification with restriction site
primers
VH Back Primers
HuVH1aBACKSfi 5'-GTC CTC GCA ACT GCG GCC CAG CCG
              GCC ATG GCC CAG GTG CAG CTG GTG
              CAG TCT GG-3'

HuVH2aBACKSfi 5'-GTC CTC GCA ACT GCG GCC CAG CCG
              GCC ATG GCC CAG GTC AAC TTA AGG
              GAG TCT GG-3'

HuVH3aBACKSfi 5'-GTC CTC GCA ACT GCG GCC CAG CCG
              GCC ATG GCC GAG GTG CAG CTG GTG
              GAG TCT GG-3'

HuVH4aBACKSfi 5'-GTC CTC GCA ACT GCG GCC CAG CCG
              GCC ATG GCC CAG GTG CAG CTG CAG
              GAG TCG GG-3'

HuVH5aBACKSfi 5'-GTC CTC GCA ACT GCG GCC CAG CCG
              GCC ATG GCC CAG GTG CAG CTG TTG
              CAG TCT GG-3'

HuVH6aBACKSfi 5'-GTC CTC GCA ACT GCG GCC CAG CCG
              GCC ATG GCC CAG GTA CAG CTG CAG
              CAG TCA GG-3'
Forward primer
HCM1FONO      5'-CCA CGA TTC TGC GGC CGC CAC TGG
              AAG AGG CAC GTT CTT TTT D) Kappa chain primary PCR
Back primers
SYNKB1        5'-GAC ATC CAG (A/T)TG ACC CAG-3'
SYNKB2        5'-GTC ATC TGG ATG ACC CAG-3'
SYNKB3        5'-GCC ATC CAG ATG ACC CAG-3'
SYNKB4        5'-GAT (A/G)TT GTG ATG ACT CAG-3'
SYNKB5        5'-GA(T/G) ATT GTG ATG ACC CAG-3'
SYNKB6        5'-GAA ATT GTG TTG ACG CAG-3'
SYNKB7        5'-GAA ATA GTG ATG ACG CAG-3'
SYNKB8        5'-GAC ATC GTG. ATG ACC CAG-3'
SYNKB9        5'-CAG CAG GGC AAT AAG CAC-3'
SYNKB10       5'-CAT CAG AGT AGT AGT TTA C-3'
SYNKB11       5'-AAC ATC CAG ATG ACC CAG-3'
SYNKB12       5'-GAA ATT GTA ATG ACA CAG-3'
Forward Primer
HUCKFORCYS    see above E) Kappa chain reamplification with primers con-
taining restriction sites
Back primers
SYNKB1Apa     5'-CAT GAC CAC AGT GCA CTT GAC
              ATC CAG (A/K)TG ACC CAG-3'
SYNKB2Apa     5'-CAT GAC CAC AGT GCA CTT GTC ATC
              TGG ATG ACC CAG-3
SYNKB3Apa     5'-CAT GAC CAC AGT GCA CTT GCC ATC
              CAG ATG ACC CAG-3'
SYNKB4Apa     5'-CAT GAC CAC AGT GCA CTT GAT
              (A/G)TT GTG ATG ACT CAG-3'

SYNKB5Apa     5'-CAT GAC CAC AGT GCA CTT GA (T/G)
              ATT GTG ATG ACC CAG-3'
SYNKB6Apa     5'-CAT GAC CAC AGT GCA CTT GAA ATT
              GTG TTG ACG CAG-3'
SYNKB7Apa     5'-CAT GAC CAC AGT GCA CTT GAA ATA
              GTG ATG ACG CAG-3'
SYNKB8Apa     5'-CAT GAC CAC AGT GCA CTT GAC ATC
              GTG ATG ACC CAG-3'
SYNKB9Apa     5'-CAT GAC CAC AGT GCA CTT CAG CAG
              GGC AAT AAG CAC-3'
SYNKB10Apa    5'-CAT GAC CAC AGT GCA CTT CAT CAG
              AGT AGT AGT TTA-3'
SYNKB11Apa    5'-CAT GAC CAC AGT GCA CTT AAC ATC
              CAG ATG ACC CAG-3'
SYNKB12Apa    5'-CAT GAC CAC AGT GCA CTT GAA ATT
              GTA ATG ACA CAG-3'

Forward primers
HUCKFORCYSNOT 5'-GAG TCA TTC TCG ACT TGC GGC
              CGC ACA CTC TCC CCT GTT GAA
              GCT CTT-3'

F) LAmbda chain primary PCR
Back primers
DPVL1a        5'-CAG TCT GTG (T/C)TG ACG CAG
              CCG CC-3'
DPVL1b        5'-CAG TCT GTC GTG ACG CAG CCG CC-3'
DPVL1c        5'-CAG TCT GTG CTG ACT CAG CCA CC-3'
DPVL2         5'-CA(G/A) TCT GCC CTG ACT CAG CCT-3'
DPVL3a        5'-TCT TCT GAG CTG ACT CAG GAC CC-3'
DPVL3b        5'-TCC TAT GAG CTG ACT CAG CCA CC-3'
DPVL7/8       5'-CAG (A/G)CT GTG GTG AC(T/C) CAG
              GAG CC-3'
DRVL9         5'-C(A/T)G CCT GTG CTG ACT CAG
              CC(A/C) CC-3'
Forward primer
HUCLFORCYS    see above G) Lambda chain reamplification with primers con-
taining restriction sites
Back primers
DPVL1aApa     5'-CAT GAC CAC AGT GCA CTT CAG TCT
              GTG (T/C)TG ACG CAG CCG CC-3'
DPVL1bApa     5'-CAT GAC CAC AGT GCA CTT CAG TCT
              GTC GTG ACG CAG CCG CC-3'
DPVL1cApa     5'-CAT GAC CAC AGT GCA CTT CAG TCT
              GTG CTG ACT CAG CCA CC-3'
DPVL2Apa      5'-CAT GAC CAC AGT GCA CTT CA(G/A) TCT
              GCC CTG ACT CAG CCT-3'
DPVL3aApa     5'-CAT GAC CAC AGT GCA CTT TCT TCT
              GAG CTG ACT CAG GAC CC-3'
DPVL3bApa     5'-CAT GAC CAC AGT GCA CTT TCC TAT
              GAG CTG ACT CAG CCA CC-3'
DPVL7/8 Apa   5'-CAT GAC CAC AGT GCA CTT CAG
              (A/G)CT GTG GTG AC(T/C) CAG GAG CC-3'
DPVL9Apa      5'-CAT GAC CAC AGT GCA CTT C(A/T)G
              CCT GTG CTG ACT CAG CC(A/C) CC-3'

Forward primers
HUCLFORCYS    5'-GAG TCA TTC TCG ACT TGC GGC
              CGC TGA ACA TTC TGT AGG GGC
              CAC TGT CTT-3'

R) Other primers/probes
VHNQ10PR      5'-ATA GCC CCC GTA ATC TCT TGC-3
FDPCRBACK     5'-GCB ATG GTT GTT GTC ATT GTC GGC-3
LMB3          5'-CAG GAA ACA GCT ATG AC-3

TABLE 2

BINDING SPECIFICITIES ISOLATED HAPTENS 3-iodo-4-hydroxy-5-nitrophenyl-acetate (NIP)
Fluorescein

TABLE 2-continued

BINDING SPECIFICITIES ISOLATED HAPTENS 2-phenyloxazol-5-one (phOx)
N-(Carboxymethyl)-4-[(p-nitrobenzyloxyphosphoryl)-butyramide]
N-[2-hydroxy-3-(4-nitrophenyl)]-propyl-L-prolyl-glycine Foreign Antigens

| | |
|---|---|
| Serum albumin (BSA) | (Bovine) |
| Tubulin | (Bovine) |
| Calmodulin | (Bovine) |
| Hepatocyte growth factor/scatter factor (HGV/SF) | (Murine) |
| Monoclonal antibody NQ11/7.22 | (Murine) |
| FixL | (*Bradyrhizobium japonicum*) |
| Acetolactate synthase (ALS) | (*Brassice napus*) |
| Lol pII | (*Lolium perenne*) |
| Gene product of CDC4 | (*Schizosacharomyces pombe*) |
| Gene product of CDC8 | (*Schizosacharomyces pombe*) |
| Maltose binding protein | (*Escherichia coli*) |
| gp120 | (HIV-1) |
| gp11 | (T4 phage) |
| gp9 | (T4 phage) |

Human Antigens

Tumour necrosis factor α (TNFα)
Thyroglobulin
High affinity IgE receptor (FcERI)
Plasmin
Tissue-type plasminogen activator (t-PA)
Urokinase-type plasminogen activator (u-PA)
Carcinoembryonic antigen (CEA)
c-erb B2
Tau40
Elongation factor 1α (EF-1α)
Calreticulin
Calnexin
Ferritin light chain
Factor VIII
U1 snRNA
U1A protein
U1C protein

TABLE 3

CDR3 SEQUENCE AND GERMLINE V-GENE SEGMENTS FROM ANTIGEN-BINDING CLONES

| Antigen[a] | Clone | Heavy Chain[b] | | | Light Chain[c] | | | Selection method and round[d] | No. of copies[e] |
|---|---|---|---|---|---|---|---|---|---|
| | | Family | Segment | CDR3[f] | Family | Segment | CDR3[f] | | |
| NIP-BSA | G09 | VH3 | DP-38 | AGTL | Vλ1 | DPL-3 | AAWDDSLV | M4 | 1 |
| NIP-BSA | E01 | VH3 | DP-38 | AGTL | Vκ2 | DPK-12 | MQSIQLPT | M3/4 | 2 |
| NIP-BSA | G10 | VH3 | DP-38 | AGTL | Vκ2 | DPK-12 | MQSIQLPAT | M4 | 1 |
| NIP-BSA | G04 | VH3 | DP-38 | AGTL | Vλ1 | DPL-3 | AAWDDGLSLV | M4 | 1 |
| NIP-BSA | H08 | VH3 | DP-38 | AGTL | Vλ1 | DPL-3 | AAWDDSLSGV | M4 | 1 |
| NIP-BSA | G07 | VH3 | DP-38 | AGTL | Vλ3 | DPL-16 | NSRDSSGSVRV | M4 | 1 |
| NIP-BSA | C09 | VH3 | DP-38 | GGKD | Vλ7 | DPL-18 | LLYYGGAYV | Im4 | 1 |
| NIP-BSA | F03 | VH1 | DP-10 | GGRL | Vλ3 | DPL-16 | NSRDSSGVSRV | M3 | 1 |
| NIP-BSA | E07 | VH3 | DP-38 | GGTQ | Vλ1 | DPL-3 | AAWDDSLV | M3 | 1 |
| NIP-BSA | H05 | VH3 | DP-38 | GGTQ | Vλ1 | DPL-3 | AAWDDSLPYV | M4 | 1 |
| NIP-BSA | H03 | VH3 | DP-38 | HGQH | Vλ1 | DPL-3 | AAWDDSLCPEFV | M4 | 1 |
| NIP-BSA | H01 | VH3 | DP-38 | KGSE | Vλ1 | DPL-3 | AAWDDSLAWFV | M4 | 1 |
| NIP-BSA | A12 | VH3 | DP-47 | KGWS | Vλ1 | DPL-4 | LAWDTSPRWV | Im3 | 1 |
| NIP-BSA | A10 | VH3 | DP-47 | KGWS | Vλ1 | DPL-2 | TAWDDSLAVV | Im3 | 1 |
| NIP-BSA | D08 | VH3 | DP-47 | KGWS | Vλ3 | DPL-16 | NSRDSSGNHRV | Im4 | 1 |
| NIP-BSA | G02 | VH3 | DP-49 | LGKA | Vκ3 | DPK-22 | QQYGSSQRT | M4 | 1 |
| NIP-BSA | E06 | VH3 | DP-38 | NGYF | Vλ1 | DPL-3 | AAWDDSLRLV | M3 | 1 |
| NIP-BSA | D03 | VH3 | DP-49 | PRGY | Vλ1 | DPL-3 | AAWDDSLRLV | Im4 | 1 |
| NIP-BSA | B02 | VH3 | DP-46 | MYMRS | Vκ2 | DPK-18 | MQGTHWRPT | Im3 | 1 |
| NIP-BSA | E02 | VH3 | DP-46 | MYRSV | Vκ2 | DPK-18 | MQGKHWPLT | M3 | 1 |
| NIP-BSA | A06 | VH3 | DP-42 | NGGHV | Vλ1 | DPL-3 | AAWDDSLGF | Im3 | 1 |
| NIP-BSA | D05 | VH3 | DP-47 | PAGSR | Vκ2 | DPK-18 | MQGTHRRAT | Im4 | 1 |
| NIP-BSA | A04 | VH3 | DP-38 | PATRS | Vκ2 | DPK-15 | MQALQTPLT | Im3 | 1 |
| NIP-BSA | F06 | VH3 | DP-47 | PFATF | Vκ2 | DPK-18 | MRGTHRRAT | M3 | 1 |
| NIP-BSA | E08 | VH3 | DP-51 | PFLAH | Vκ2 | DPK-18 | MQGTHWHPT | M3 | 1 |
| NIP-BSA | C05 | VH3 | DP-32 | PLGAH | Vκ2 | DPK-15 | MQALQSPT | Im4 | 1 |
| NIP-BSA | E12 | VH3 | DP-47 | PMRGV | Vκ2 | DPK-18 | MQGTHRRAT | M3 | 1 |
| NIP-BSA | E05 | VH3 | DP-38 | PNGDQ | Vλ1 | DPL-3 | AAWDDSLAFV | M3 | 1 |

TABLE 3-continued

CDR3 SEQUENCE AND GERMLINE V-GENE SEGMENTS
FROM ANTIGEN-BINDING CLONES

| Antigen[a] | Clone | Heavy Chain[b] Family | Segment | CDR3[f] | Light Chain[c] Family | Segment | CDR3[f] | Selection method and round[d] | No. of copies[e] |
|---|---|---|---|---|---|---|---|---|---|
| NIP-BSA | E04 | VH3 | DP-38 | POTRR | Vκ2 | DPK-15 | MQALQTPT | M3 | 1 |
| NIP-BSA | A08 | VH3 | DP-47 | PRLPR | Vκ1 | DPK-9 | QQSYSTRT | Im3 | 1 |
| NIP-BSA | E10 | VH5 | DP-73 | PSGNV | Vκ2 | DPK-19 | MQGTHWPFT | M3 | 1 |
| NIP-BSA | A05 | VH1 | DP-25 | QGLRN | Vκ2 | DPK-15 | MQALQTPLT | Im3 | 1 |
| NIP-BSA | D06 | VH3 | DP-47 | RGHKA | Vκ2 | DPK-18 | MQGTHWPAT | Im4 | 1 |
| NIP-BSA | D02 | VH3 | DP-51 | SRGDS | Vλ1 | DPL-3 | AAWDDSLRSV | Im4 | 1 |
| NIP-BSA | F01 | VH3 | DP-47 | TFSPQ | Vκ2 | DPK-18 | MQGTHRRAT | M3 | 1 |
| NIP-BSA | B03 | VH3 | DP-47 | SFRRNL | Vλ1 | DPL-3 | AAWDDSLLV | Im3 | 1 |
| NIP-BSA | A11 | VH3 | DP-58 | SFRRNL | Vλ3 | DPL-16 | DSWDNSLVSPV | Im3 | 1 |
| NIP-BSA | C04 | VH3 | DP-38 | PGYRGTR | Vκ2 | DPK-15 | MQALQSPT | Im4 | 2 |
| NIP-BSA | D07 | VH3 | DP-38 | PGYRGTR | Vκ2 | DPK-12 | MQSIQLPT | Im4 | 1 |
| NIP-BSA | D01 | VH3 | DP-38 | PGYRGTR | Vκ2 | DPK-15 | MQALQSPAT | Im4 | 1 |
| NIP-BSA | C10 | VH3 | DP-38 | PGYRGTR | Vκ2 | DPK-15 | MQALQTPVT | Im4 | 1 |
| NIP-BSA | C11 | VH3 | DP-38 | PGYRGTR | Vλ1 | DPL-3 | AAWDDSLSAYV | Im4 | 1 |
| NIP-BSA | F04 | VH3 | DP-45 | RAINGQR | Vλ3 | DPL-16 | NSRDSSGRBNV | M3 | 1 |
| NIP-BSA | B04 | VH3 | DP-47 | RRGSTRY | Vκ2 | DPK-15 | MQALRTRT | Im3 | 1 |
| NIP-BSA | F05 | VH3 | DP-38 | VNSRFAT | Vλ3 | DPL-16 | NSRDSSGVSRV | M3 | 1 |
| NIP-BSA | E11 | VH4 | DP-67 | IKFRSSSI | Vκ2 | DPK-19 | MQGTHWPFT | M3 | 1 |
| NIP-BSA | H06 | VH4 | DP-67 | SFAKAFDY | Vλ1 | DPL-3 | AAWDDSLPYV | M4 | 1 |
| NIP-BSA | E09 | VH4 | DP-67 | SFAKAFDY | Vλ3 | DPL-16 | NSRDSSGSVRV | M3 | 1 |
| NIP-BSA | C02 | VH1 | DP-7 | SKRTSFDY | Vκ2 | DPK-18 | MQGTHWHPT | Im4 | 1 |
| NIP-BSA | G08 | VH3 | DP-47 | SLFSKFDY | Vλ3 | DPL-16 | NSRDSSGVSRV | M4 | 1 |
| NIP-BSA | A07 | VH3 | DP-47 | SVLSLFDY | Vλ1 | DPL-3 | AAWDDSLFYPV | Im3 | 1 |
| NIP-BSA | C03 | VH3 | DP-45 | SYMRGMRN | Vλ3 | DPL-16 | NSRDSSGNHRV | Im4 | 1 |
| NIP-BSA | A02 | VH3 | DP-42 | HRRAYYMIP | Vκ2 | DPK-18 | MQGTHWPVT | Im3 | 1 |
| NIP-BSA | A09 | VH4 | DP-67 | IGKLSQPTS | Vκ2 | DPK-18 | MQGTHWRPT | Im3 | 1 |
| NIP-BSA | E03 | VH3 | DP-47 | RSGVRMLID | Vκ2 | DPK-18 | MQGTHWRT | M3 | 1 |
| NQ11 (Fc) | NML7 | VH3 | DP-47 | KWGG | Vλ1 | DPL-2 | AAWDDSLLGSV | Im2 | 1 |
| NQ11 (Fc) | NML9 | VH1 | DP-14 | GTGLDG | Vλ2 | DPL-10 | CSYAGSSYV | Im2 | 1 |
| NQ11 (Fc) | NML8 | VH3 | DP-47 | KFGNNM | Vλ3 | DPK-23 | QQDYNLLT | Im2 | 1 |
| NQ11 (Fv) | NML1 | VH3 | DP-47 | ASSPFVLQ | Vλ8 | DPL-21 | VLYMGSGSAV | Im2/3/4 | 25 |
| NQ11 | NML3 | VH3 | DP-7/3[g] | YKSLSFDY | Vκ2 | DPK-13 | MQRIEFPNT | Im2 | 1 |
| NQ11 | NML5 | VH1 | DP-10 | AANYSKAHI | Vλ1 | DPL-2 | AAWDDSLACAV | Im2/3 | 4 |
| NQ11 (Fv) | NML2 | VH3 | DP-47 | RSWDGGMVD | Vκ1 | DPK-5 | QQANSFRT | Im2 | 1 |
| NQ11 (Fc) | NML11 | VH3 | DP-3 | SKLWVTFDY | Vλ1 | DPL-8/2[g] | AAWDDSLSRPV | Im3 | 1 |
| NQ11 (Fc) | NML6 | VH3 | DP-3 | SKLWVTFDY | Vλ1 | DPI-2 | AAWDDSLSRPV | Im2/3/4 | 34 |
| NQ11 | NML4 | VH3 | DP-3 | AKQSGVECLT | Vλ1 | DPI-3 | AAWDDSLYNV | Im2 | 2 |
| NQ11 (Fc) | NML10 | VH3 | DP-3 | SKYPLAWTLS | Vλ1 | DPI-2 | AAWDDSLNRNV | Im2 | 1 |
| FITC-BSA | B01 | VH3 | DP-47 | ALRR | Vκ2 | DPK-15 | MQVLQTRT | Im3 | 1 |
| FITC-BSA | B06 | VH3 | DP-47 | GGRV | Vκ2 | DPK-15 | MQALQTRT | Im3 | 1 |
| FITC-BSA | A03 | VH3 | DP-47 | IGQF | Vλ1 | DPL-3 | AAWDDSLAFV | Im3/4 | 4 |
| FITC-BSA | D10 | VH3 | DP-47 | KAKT | Vκ2 | DPK-15 | MQALQTRT | Im4 | 1 |
| FITC-BSA | G06 | VH3 | DP-47 | KSAI | Vκ2 | DPK-15 | MQALQTRT | M 4 | 1 |
| FITC-BSA | H03 | VH3 | DP-47 | KSRW | Vκ1 | DPK-9 | QQSYSTRM | M 4 | 1 |
| FITC-BSA | D12 | VH3 | DP-47 | KSTV | Vκ2 | DPK-15 | MQALRTRT | Im4 | 1 |
| FITC-BSA | A08 | VH3 | DP-47 | LNRK | Vκ2 | DPK-15 | MQALQTRT | Im3/4 | 4 |
| FITC-BSA | D08 | VH3 | DP-47 | RHGS | Vκ2 | DPK-15 | MQALRTRT | Im4 | 1 |
| FITC-BSA | G07 | VH3 | DP-47 | RKRH | Vκ2 | DPK-15 | MQALQTLT | M 4 | 1 |
| FITC-BSA | H05 | VH3 | DP-47 | RSKT | Vκ2 | DPK-15 | MQALQTRT | M 4 | 1 |
| FITC-BSA | H02 | VH3 | DP-47 | RWSF | Vλ1 | DPL-3 | AAWDDSLV | M 4 | 1 |
| FITC-BSA | E06 | VH3 | DP-47 | AKFRL | Vκ2 | DPK-15 | MQALRTRT | M 3 | 1 |
| FITC-BSA | E11 | VH3 | DP-47 | AYHGR | Vκ2 | DPK-15 | MQALQTRT | M 3 | 1 |
| FITC-BSA | C02 | VH3 | DP-47 | GKVLG | Vκ2 | DPK-15 | MQALQTPT | Im4 | 1 |
| FITC-BSA | B02 | VH3 | DP-47 | GKVLG | Vκ2 | DPK-15 | MRALQTPT | Im3/4 | 2 |
| FITC-BSA | E07 | VH3 | DP-47 | GSSRT | Vλ1 | DPL-3 | AAWDDSLPGYV | M 3 | 1 |
| FITC-BSA | E08 | VH3 | DP-47 | KRMDG | Vκ2 | DPK-15 | MQALQTRT | M 3 | 1 |
| FITC-BSA | A10 | VH1 | DP-10 | LKRGH | Vλ1 | DPL-3 | AAWDDSLGFV | Im3 | 1 |
| FITC-BSA | D09 | VH3 | DP-47 | LRREY | Vκ2 | DPK-15 | MQALRTRT | Im4 | 1 |
| FITC-BSA | G12 | VH3 | DP-47 | RAGRD | Vλ1 | DPL-3 | AAWDDSLFLV | M 4 | 1 |
| FITC-BSA | D03 | VH3 | DP-47 | LKSAYK | Vκ2 | DPK-15 | MQALQTPT | Im4 | 1 |
| FITC-BSA | C12 | VH3 | DP-47 | LNVRPK | Vκ2 | DPK-15 | MQALQTRT | Im4 | 1 |
| FITC-BSA | B10 | VH3 | DP-47 | SRGKSM | Vκ2 | DPK-15 | MQALRTRT | Im3 | 1 |
| FITC-BSA | E09 | VH3 | DP-47 | IRFRNAT | Vκ2 | DPK-15 | MQALRTRT | M 3 | 1 |
| FITC-BSA | B09 | VH3 | DP-47 | LKTSTPV | Vκ2 | DPK-15 | MRALQTPT | Im3/4 | 2 |
| FITC-BSA | G10 | VH3 | DP-47 | LSRAFTM | Vκ2 | DPK-15 | MQALRTRT | M 4 | 1 |
| FITC-BSA | E03 | VH3 | DP-47 | LSRAFTM | Vκ2 | DPK-15 | MQALQTRT | M 3 | 1 |
| FITC-BSA | B07 | VH4 | DP-67 | AQRKYFDY | Vκ2 | DPK-12 | MQSIQLRT | Im3 | 1 |
| FITC-BSA | D01 | VH4 | DP-67 | DLRKHFDY | Vκ1 | DPK-9 | QQSYSTRT | Im4 | 1 |
| FITC-BSA | E10 | VH4 | DP-67 | DRWRVFDY | Vλ1 | DPL-2 | AAWDDSLSIV | M 3 | 1 |
| FITC-BSA | A09 | VH1 | DP-14 | KGLRLFDY | Vλ1 | DPK-3 | AAWDDSLV | Im3 | 1 |
| FITC-BSA | G08 | VH3 | DP-58 | KKYQSAAR | Vκ2 | DPK-19 | MQGTHWPT | M 4 | 1 |

TABLE 3-continued

CDR3 SEQUENCE AND GERMLINE V-GENE SEGMENTS
FROM ANTIGEN-BINDING CLONES

| Antigen[a] | Clone | Heavy Chain[b] | | | Light Chain[c] | | | Selection method and round[d] | No. of copies[e] |
|---|---|---|---|---|---|---|---|---|---|
| | | Family | Segment | CDR3[f] | Family | Segment | CDR3[f] | | |
| FITC-BSA | B03 | VH4 | DP-67 | KTRRRFDY | Vκ2 | DPK-15 | MQALHTRT | Im3 | 1 |
| FITC-BSA | C03 | VH4 | DP-67 | KTRRRFDY | Vκ2 | DPK-15 | MQALQTRT | Im4 | 1 |
| FITC-BSA | G11 | VH3 | DP-47 | PYAKRFDY | Vκ2 | DPK-15 | MQALQTRT | M 4 | 1 |
| FITC-BSA | G03 | VH3 | DP-47 | RFARSFDY | Vλ3 | DPL-16 | NSRDSSGSV | M 4 | 3 |
| FITC-BSA | A04 | VH4 | DP-67 | RSFVGYEI | Vλ1 | DPL-3 | AAWDDSLV | Im3 | 2 |
| FITC-BSA | D06 | VH4 | DP-67 | RWGRTFDY | Vκ2 | DPK-15 | MQALQTRT | Im4 | 1 |
| FITC-BSA | C06 | VH1 | DP-7 | SQKRLITG | Vκ2 | DPK-15 | MQALQTRT | Im4 | 1 |
| FITC-BSA | C01 | VH1 | DP-7 | SQKRLITG | Vκ3 | DPK-22 | QQYGSSPYT | Im4 | 1 |
| FITC-BSA | H04 | VH4 | DP-67 | SRKRAFDY | Vκ2 | DPK-15 | MQALQTRT | M 4 | 1 |
| FITC-BSA | C08 | VH4 | DP-67 | SWVSGFDY | Vκ1 | DPK-9 | QQSYSTRT | Im4 | 2 |
| FITC-BSA | D04 | VH1 | DP-7 | SYHRTFDY | Vκ1 | DPK-5 | QQANSFAAT | Im4 | 1 |
| FITC-BSA | C05 | VH1 | DP-7 | SYHRTFDY | Vκ1 | DPK-5 | QQANSFPAT | Im4 | 1 |
| FITC-BSA | D05 | VH1 | DP-7 | THSKTFDY | Vλ8 | DPL-21 | VLYMGSGVYV | Im4 | 1 |
| FITC-BSA | B12 | VH3 | DP-47 | TRSSSYGE | Vκ2 | DPK-15 | MQALRTRT | Im3 | 1 |
| FITC-BSA | B04 | VH4 | DP-66 | WSRETNYS | Vλ1 | DPL-3 | AAWDDSLWSAV | Im3 | 1 |
| FITC-BSA | A07 | VH3 | DP-47 | RTRGALPRN | Vλ1 | DPL-3 | AAWDDSLPRRLV | Im3 | 1 |
| FITC-BSA | A02 | VH3 | DP-47 | YRFSAPPRD | Vλ1 | DPL-3 | AAWDDSLPSGV | Im3 | 1 |
| FITC-BSA | E04 | VH3 | DP-47 | RFNRLSPRRA | Vκ2 | DPK-15 | MQALQTRT | M 3 | 1 |
| FITC-BSA | B05 | VH1 | DP-25 | SSVMGRVPVM | Vκ2 | DPK-15 | MQALQTLT | Im3 | 1 |
| FITC-BSA | E05 | VH3 | DP-47 | TSGKLHSPRT | Vλ1 | DPL-3 | AAWDDGLLRV | M 3 | 1 |
| FITC-BSA | D11 | VH5 | DP-73 | GRGRPSMAYDV | Vλ1 | DPL-3 | AAWDDSLALV | Im4 | 1 |
| FITC-BSA | B08 | VH3 | DP-47 | RSGVSRKVYTI | Vκ2 | DPK-15 | MQALRTRT | Im3 | 1 |
| Plasmin | MP01 | VH3 | DP-47 | MTPQFFDY | Vκ2 | DPL-15 | MRALQTPT | Im4 | 1 |
| Plasmin | MP02 | VH4 | DP-67 | SAYSYFDY | Vλ3 | DPL-16 | NSRDSSGFQLV | Im4 | 1 |
| t-PA | MT09 | VH1 | DP-7 | DSGLGDPAL | Vλ2 | DPL-11 | SSYTSSSTLV | Im4 | 1 |
| t-PA | MT03 | VH1 | DP-7 | DSGLGEPAL | Vλ2 | DPL-11 | SSYTSSSTLG | Im4 | 1 |
| t-PA | MT06 | VH1 | DP-7 | DSGLGEPAL | Vλ2 | DPL-11 | SSYTSSSTLV | Im4 | 1 |
| t-PA | MT01 | VH1 | DP-7 | ESGLGDPAL | Vλ2 | DPL-11 | SSYTSSSTLV | Im4 | 1 |
| t-PA | MT07 | VH3 | DP-47 | TSRLKAHPS | Vλ1 | DPL-8 | QSYDSNLRV | Im4 | 1 |
| u-PA | MU02 | VH3 | DP-47 | TSRLEAHPR | Vκ2 | DPK-15 | MRALQTPT | Im4 | 1 |
| u-PA | MU01 | VH3 | DP-47 | TSRLKAHPS | Vκ1 | DPK-8 | QQLNSYPT | Im4 | 1 |
| u-PA | MU03 | VH3 | DP-47 | TSRLKAHPS | Vλ3 | DPL-16 | NSRDSSGFQLV | Im4 | 1 |
| HGF/SF | MH10 | VH3 | DP-47 | GRQSRL | Vκ1 | DPK-5 | QQANSFPIT | Im4 | 1 |
| HGF/SF | NH19 | VH3 | DP-42 | KFPHFGD | Vκ1 | DPK-8 | QQLNSYPT | Im4 | 1 |
| HGF/SF | MH22 | VH3 | DP-42 | KFPHFGD | Vκ1 | DPK-5 | QQANSFPIT | Im4 | 4 |

[a]The region of the monoclonal antibody NQ11/7.22 (NQ11) bound by the Fab is indicated (Fv or Fc region); three Fabs bound neither fragment and therefore probably interacted with the CH1, Cκ or hinge region. Hapten-BSA binding clones listed did not bind BSA alone.
[b]Human germline VH gene segments (Tomlinson et al., J. Mol. Biol., 227:776–798 (1992)) are assigned to families as (Kabat et al., Sequences of proteins of immunological interest, 5th edit., U.S. Dept. of Health and Human Services, Bethesda (1991)).
[c]Human germline Vκ gene segments (Cox et al., Eur. J. Immunol., in press (1994)) are assigned to subgroups as (Kabat et al., Sequences of proteiens of immunological interest, 5th edit., U.S. Dept. of Health and Human Services, Bethesda (1991)) and human germline Vλ gene segments (Williams et al., Eur. J. Immunol., 23:1456–1461 (1993)) are assigned to families as (Chuchana et al., Eur. J. Immunol., 20:1317–1325 (1990)).
[d]Im, selected using antigen-coated Immunotubes; M, selected using biotinylated antigen and streptavidin-coated paramagnetic beads. Numbers refer to how many rounds of selection the library had undergone when Fabs with the sequence indicated were isolated.
[e]The number of independent clones which were isolated with the same sequence.
[f]CDR3 (complementarity determining region 3) for both heavy and light chains are as defined by (Kabat et al., Seqences of protiens of immunological interest, 5th edit., U.S. Dept. of Health and Human Services, Bethesda (1991)).
[g]These genes appear to have been created by cross-overs between two V-genes during PCR amplification.

TABLE 4

SEQUENCES AND AFFINITIES OF FAB FRAGMENTS

A. Fabs from $6.5 \times 10^{10}$ repertoire

| Antigen | Clone | Heavy Chain | | Light Chain | | $K_d$ (nM) |
|---|---|---|---|---|---|---|
| | | Segment | CDR3 | Segment | CDR3 | |
| NIP-CAP | NIP-G6 | DP-38 | AGTL | DPK-12 | MQSIQLPT | 4.0(±0.1) |
| NIP-CAP | NIP-G10[a] | DP-38 | AGTL | DPK-12 | MQSIQLPAT | 5.4(±0.2) |
| NIP-CAP | NIP-H1[a] | DP-38 | KGSE | DPL-3 | AAWDDSLAWFV | 11.3(±0.4) |
| NIP-CAP | NIP-C11 | DP-38 | PGYRGTR | DPL-3 | AAWDDSLSAYV | 16.5(±0.5) |
| NIP-CAP | NIP-H3[a] | DP-38 | HGQH | DPL-3 | AAWDDSLCPEFV | 19.7(±1.7) |
| NIP-CAP | NIP-G11[a] | DP-47 | PLNSKKNTTTQ | DPL-3 | AAWDDSLFYV | 20.1(±3.6) |
| NIP-CAP | NIP-G9[a] | DP-38 | AGTL | DPL-3 | AAWDDSLV | 22.0(±1.0) |
| NIP-CAP | NIP-E5[a] | DP-38 | PNGDQ | DPL-3 | AAWDDSLAFV | 22.1(±0.8) |

TABLE 4-continued

SEQUENCES AND AFFINITIES OF FAB FRAGMENTS

| | | | | | | |
|---|---|---|---|---|---|---|
| NIP-CAP | NIP-E7[a] | DP-38 | GGTQ | DPL-3 | AAWDDSLV | 29.8(±1.1) |
| NIP-CAP | NIP-A4 | DP-38 | PATRS | DPK-15 | MQALQTPLT | 48(±1) |
| NIP-CAP | NIP-C9 | DP-38 | GGKD | DPL-18 | LLYYGGAYV | 59(±3) |
| Fluorescein | FITC-B4 | DP-66 | WSRETNYS | DPL-3 | AAWDDSLWSAV | 3.8(±0.4) |
| Fluorescein | FITC-A4 | DP-67 | RSFVGYEI | DPL-3 | AAWDDSLV | 14.3(±2.0) |
| Fluorescein | FITC-B11 | DP-47 | IGQF | DPL-3 | AAWDDSLAFV | 24.1(±0.8) |
| Fluorescein | FITC-B7 | DP-67 | AQRKYFDY | DPK-12 | MQSIQLRT | 151(±3) |
| Fluorescein | FITC-A2 | DP-47 | YRFSAPPRD | DPL-3 | AAWDDSLPSGV | 217(±16) |
| NQ11 (Fv) | NML1 | DP-47 | ASSPFVLQ | DPL-21 | VLYMGSGSAV | $32^s$ and $34^r$ |
| NQ11 (Fc) | NML9 | DP-14 | GTGLDG | DPL-10 | CSYAGSSYV | $41^s$ and $58^r$ |
| HGF/SF | MH22 | DP-42 | KFPHFGD | DPK-5 | QQANSFPIT | $7^r$ |

B. Fabs from $1 \times 10^7$ repertoire

| | | Heavy Chain | | Light Chain | | |
|---|---|---|---|---|---|---|
| Antigen | Clone | Gene | CDR3 | Gene | CDR3 | $K_d$ ($\mu$M) |
| NIP-CAP | sNIP-D10 | DP-53 | PWARGTD | DPK-21 | QQYNNWLST | 8(±0.6) |
| NIP-CAP | sNIP-F3[a] | DP-47 | NYNAAFDY | DPL-21 | VLYMGSGHRV | 12(±1.3) |
| Fluorescein | sFITC-C2 | DP-67 | SGVRGLMT | DPK-9 | QQSYSTRT | 0.82(±0.14) |

Affinities ($K_d$) for haptens were determined by fluorescence quench titration. Affinities ($K_d$) for protein antigens were determined by SPR, by Scatchard analysis[s], and from analysis of the rate constants[r]. All clones were derived from selections on Immunotubes except for those marked[a] which were derived from selections using magnetic beads. The residues in the light chain CDR3 regions encoded by randomised codons are underlined.

Affinities ($K_d$) for haptens were determined by fluorescence quench titration. Affinities ($K_d$) for protein antigens were determined by SPR, by Scatchard analysis[s], and from analysis of the rate constants[r]. All clones were derived from selections on Immunotubes except for those marked[a] which were derived from selections using magnetic beads. The residues in the light chain CDR3 regions encoded by randomised codons are underlined.

TABLE 5

DETERMINATION OF REPERTOIRE SIZE

Total number of colony forming units

| Sample Point | No antibiotic | amp[R] | tet[R] | chlor[R] | amp[R] + tet[R] | tet[R] + chlor[R] | amp[R] + tet[R] + chlor[R] |
|---|---|---|---|---|---|---|---|
| 1 | | $1.7 \times 10^9$ | | | | | |
| 2 | $3.4 \times 10^{10}$ | $2.3 \times 10^{10}$ | | | | | |
| 3 | $6.5 \times 10^{11}$ ($\lambda$) | | $1.0 \times 10^{11}$ ($\lambda$) | | $1.9 \times 10^{11}$ ($\lambda$) | | |
| | $7.3 \times 10^{11}$ ($\kappa$) | | $1.1 \times 10^{11}$ ($\kappa$) | | $8.0 \times 10^{10}$ ($\kappa$) | | |
| 4 | $9.5 \times 10^{10}$ ($\lambda$) | $2.2 \times 10^{11}$ ($\lambda$) | $4.5 \times 10^{10}$ ($\lambda$) | $6.0 \times 10^{10}$ ($\lambda$) | $3.0 \times 10^{10}$ ($\lambda$) | $2.0 \times 10^{10}$ ($\lambda$) | $3.0 \times 10^{10}$ ($\lambda$) |
| | $2.9 \times 10^{11}$ ($\kappa$) | $2.8 \times 10^{11}$ ($\kappa$) | $7.5 \times 10^{10}$ ($\kappa$) | $2.8 \times 10^{11}$ ($\kappa$) | $3.0 \times 10^{10}$ ($\kappa$) | $4.5 \times 10^{10}$ ($\kappa$) | $3.5 \times 10^{10}$ ($\kappa$) |
| 5 | | | | | | | |
| 6 | $3.1 \times 10^{11}$ ($\lambda$) | | | | | | $1.6 \times 10^{11}$ ($\lambda$) |
| | $3.5 \times 10^{11}$ ($\kappa$) | | | | | | $9.5 \times 10^{10}$ ($\kappa$) |
| 7 | | | | | | | |

Sample Point 1 Size of pUC19-21oxVHlib innoculum from frozen stock $1.7 \times 10^9$ Sample Point 2 Size of pUC19-21oxVHlib innoculum from overnight culture $2.3 \times 10^{10}$ Sample Point 3 Number of E. coli containing pUC19-21oxVHlib infected with fdDOG-21oxVλlib .91 $\times 10^{11}$ ($\lambda$)

Number of E. coli containing pUC19-21oxVHlib infected with fdDOG-21oxVκlib $8.0 \times 10^{10}$ ($\kappa$)

Sample Point 4 Number of E. coli containing pUC and fdDOG replicons co-infected with phage P1 $3.0 \times 10^{10}$ ($\lambda$) $3.5 \times 10^{10}$ ($\kappa$)

Sample Point 5 Titre of fdDOG phage (t.u.) immediately after P1 infection and centrifugation $9.9 \times 10^9$ ($\lambda$) $1.2 \times 10^{10}$ ($\kappa$)

Sample Point 6 Number of viable E. coli containing pUC, fdDOG and P1 replicons after 24 hours $1.6 \times 10^{11}$ ($\lambda$) $9.5 \times 10^{10}$ ($\kappa$)

Sample Point 7 Titre of fdDOG phage (t.u.) after 24 hours $1.1 \times 10^{13}$ t.u. ($\lambda$) $3.0 \times 10^{13}$ t.u. ($\kappa$)

Sample point, see Methods; amp[R], ampicillin resisitant; tet[R], tetracyclin resisitant; chlor[R], chloramphenicol resistant;

TABLE 6

OLIGONUCLEOTIDES USED IN PREPARATION OF SYNTHETIC loxP REPERTOIRE

A. Re-cloning of synthetic human VH repertoires into pUC19-2loxVHdel
pUC-reverse 5'-AGC GGA TAA CAA TTT CAC ACA GG
JH-Xho-FOR 5'-GCC TGA ACC GCC TCC ACC <u>ACT CGA GA</u>CGGT GAC CAG GGT ACC TTG GCC CCA B. Construction of synthetic human kappa chain repertoires
1. Amplification of human Cκ
CκFOR 5'-CTG CTA TTA TCG <u>GGC GCG CCT</u> TTA TTA ACA CTC TCC CCT GTT GAA GCT CTT TGT GAC GGG
DPK1,4,5,6,7,8,9,11
CκLink 5'-ACG TTC GGC CAA GGG ACC AAG STG GAA ATC AAA CGT ACT GTG GCT GCA CCA TCT GTC
DPK10

2. Human Vκ back primers
SYNκB1 5'-CAT GAC CAC <u>AGT GCA C</u>TT GAC ATC CAG WTG ACC CAG
DPK1,4,5,6,7,8,9,11
SYNκB2 5'-CAT GAC CAC <u>AGT GCA C</u>TT GTC ATC TGG ATG ACC CAG
DPK10
SYNκB3 5'-CAT GAC CAC <u>AGT GCA C</u>TT GCC ATC CAG ATG ACC CAG
DPK3
SYNκB4 5'-CAT GAC CAC <u>AGT GCA C</u>TT GAT RTT GTG ATG ACT CAG
DPK15,18,19
SYNκB5 5'-CAT GAC CAC <u>AGT GCA C</u>TT GAK ATT GTG ATG ACC CAG
DPK12,13,14,16,17
SYNκB6 5'-CAT GAC CAC <u>AGT GCA C</u>TT GAA ATT GTG TTG ACG CAG
DPK20,22
SYNκB7 5'-CAT GAC CAC <u>AGT GCA C</u>TT GAA ATA GTG ATG ACG CAG
DPK21
SYNκB8 5'-CAT GAC CAC <u>AGT GCA C</u>TT GAC ATC GTG ATG ACC CAG
DPK24
SYNκB9 5'-CAT GAC CAC <u>AGT GCA C</u>TT GAT GTT GTG ATG ACA CAG
DPK25
SYNκB10 5'-CAT GAC CAC <u>AGT GCA C</u>TT GAA ATT GTG CTG ACT CAG
DPK26
SYNκB11 5'-CAT GAC CAC <u>AGT GCA C</u>TT AAC ATC CAG ATG ACC CAG
DPK2
SYNκB12 5'-CAT GAC CAC <u>AGT GCA C</u>TT GAA ATT GTA ATG ACA CAG
DPK23

3. Human Vκ forward primers encoding synthetic CDR3δ
DPK1FOR 5'-CTT GGT CCC TTG GCC GAA CGT (MNN)$_{0-2}$ NNG GAG ATT ATC ATA CTG TTG AC
DPK1
DPK2FOR 5'-CTT GGT CCC TTG GCC GAA CGT (MNN)$_{0-2}$ NNG GTA ACT ATT ATG CTG TAG AC
DPK2
DPK3FOR 5'-CTT GGT CCC TTG GCC GAA CGT (MNN)$_{0-2}$ NNG GTA ATT GTA ATC TTG TAG AC
DPK3
DPK4FOR 5'-CTT GGT CCC TTG GCC GAA CGT (MNN)$_{0-2}$ NNG GGC ACT GTT ATA CTT TTG AC
DPK4
DPK5/6FOR 5'-CTT GGT CCC TTG GCC GAA CGT (MNN)$_{0-2}$ NNG GAA ACT GTT AGC CTG TTG AC
DPK5,6
DPK7FOR 5'-CTT GGT CCC TTG GCC GAA CGT (MNN)$_{0-2}$ NNG GTA ATT ATA CTG TTG GC
DPK7
DPK8FOR 5'-CTT GGT CCC TTG GCC GAA CGT (MNN)$_{0-2}$ NNG GTA ATT ATT AAG CTG TTG AC
DPK8

TABLE 6-continued

OLIGONUCLEOTIDES USED IN PREPARATION OF SYNTHETIC loxP REPERTOIRE

DPK9FOR 5'-CTT GGT CCC TTG GCC GAA CGT (MNN)$_{0-2}$ NNG GGT ACT GTA ACT CTG TTG AC
DPK9
DPK10FOR 5'-CTT GGT CCC TTG GCC GAA CGT (MNN)$_{0-2}$ NNG GAA ACT ATA ATA CTG TTG AC
DPK10
DPK11FOR 5'-CTT GGT CCC TTG GCC GAA CGT (MNN)$_{0-2}$ NNG GGT ATT GTA AGT CCG TTG AC
DPK11
DPK12FOR 5'-CTT GGT CCC TTG GCC GAA CGT (MNN)$_{0-2}$ NNG AAG CTG TAT ACT TTG CAT GC
DPK12
DPK13FOR 5'-CTT GGT CCC TTG GCC GAA CGT (MNN)$_{0-2}$ NNG AAA CTC TAT ACG TTG CAT GC
DPK13
DPK14FOR 5'-CTT GGT CCC TTG GCC GAA CGT (MNN)$_{0-2}$ NNG ATC TTG TGC ATC TTG CAT GC
DPK14
DPK15FOR 5'-CTT GGT CCC TTG GCC GAA CGT (MNN)$_{0-2}$ NNG AGT TTG TAG AGC TTG CAT GC
DPK15
DPK16FOR 5'-CTT GGT CCC TTG GCC GAA CGT (MNN)$_{0-2}$ NNG AAA TTG TGT AGC TTG CAT GC
DPK16
DPK17FOR 5'-CTT GGT CCC TTG GCC GAA CGT (MNN)$_{0-2}$ NNG AAA TTG TGT AGC TTG CGT GC
DPK17
DPK18/19FOR 5'-CTT GGT CCC TTG GCC GAA CGT (MNN)$_{0-2}$ NNG CCA GTG TGT ACC TTG CAT GC
DPK18,19
DPK20/22FOR 5'-CTT GGT CCC TTG GCC GAA CGT (MNN)$_{0-2}$ NNG TGA GCT ACC ATA CTG CTG AC
DPK20,22
DPK21FOR 5'-CTT GGT CCC TTG GCC GAA CGT (MNN)$_{0-2}$ NNG CCA GTT ATT ATA CTG CTG AC
DPK21
DPK23FOR 5'-CTT GGT CCC TTG GCC GAA CGT (MNN)$_{0-2}$ NNG TAA GTT ATA ATC CTG CTG AC
DPK23
DPK24FOR 5'-CTT GGT CCC TTG GCC GAA CGT (MNN)$_{0-2}$ NNG AGT ACT ATA ATA TTG CTG AC
DPK24
DPK25FOR 5'-CTT GGT CCC TTG GCC GAA CGT (MNN)$_{0-2}$ NNG GTG CTT ATT GCC CTG CTG AC
DPK25
DPK26FOR 5'-CTT GGT CCC TTG GCC GAA CGT (MNN)$_{0-2}$ NNG TAA ACT ACT ACT CTG ATG AC
DPK26

C. Construction of synthetic human lambda chain repertoires
1. Amplification of human Cλ2
CL2FOR1 5'-<u>GGA ATT C</u>GG GGT GAG GGT TGA GAA
CL2BACK1 5'- CCC CC<u>A AGC TTC</u> TGC CCC TCA TCC
CL2BACK2 5'- GTA TTC GGC GGA GGG ACC AAG CTG ACC GTC CTA GGT CAG CCC AAG GCT GCC CCC TCG GTC ACT
HUCλFORCYSASCNOT 5'-GAG TCA TTC TCG ACT TGC GGC CGC CTG CTA TTA TCG <u>GGC GCG CCT</u> TTA TTA TGA ACA TTC TGT AGG GGC CAC TGT CTT 2. Human Vλ back primers
DPVλ1a 5'-CAT GAC CAC <u>AGT GCA C</u>TT CAG TCT GTG YTG ACG CAG CCG CC
DPL4,5,8,9
DPVλ1b 5'-CAT GAC CAC <u>AGT GCA C</u>TT CAG TCT GTC GTG ACG CAG CCG CC
DPL6,7
DPVλ1c 5'-CAT GAC CAC <u>AGT GCA C</u>TT CAG TCT GTG CTG ACT CAG CCA CC
DPL1,2,3
DPVλ2 5'-CAT GAC CAC <u>AGT GCA C</u>TT CAR TCT GCC CTG ACT CAG CCT
DPL10,11,12,13,14
DPVλ3a 5'-CAT GAC CAC <u>AGT GCA C</u>TT TCT TCT GAG CTG ACT CAG GAC CC
DPL16

TABLE 6-continued

OLIGONUCLEOTIDES USED IN PREPARATION OF SYNTHETIC loxP REPERTOIRE

| Primer | Sequence |
|---|---|
| DPVλ3b | 5'-CAT GAC CAC <u>AGT GCA CTT</u> TCC TAT GAG CTG ACT CAG CCA CC<br>DPL23 |
| DPVλ7/8 | 5'-CAT GAC CAC <u>AGT GCA CTT</u> CAG RCT GTG GTG ACY CAG GAG CC<br>DPL22,24 |
| DPVλ9 | 5'-CAT GAC CAC <u>AGT GCA CTT</u> CWG CCT GTG CTG ACT CAG CCM CC<br>DPL18,19,21 |

3. Human Vλ foward primers encoding synthetic CDR3δ

| Primer | Sequence |
|---|---|
| DPL1/2/3V/JFOR | 5'-CTT GGT CCC TCC GCC GAA TAC (MNN)$_{0-5}$ --- CAG GCT GTC ATC CCA TGC TGC ACA GTA<br>DPL1,2,3 |
| DPL4V/JFOR | 5'-CTT GGT CCC TCC GCC GAA TAC (MNN)$_{0-3}$ --- CGG GCT GGT ATC CCA TGC<br>DPL4 |
| DPL4V/JFORa | 5'-CTT GGT CCC TCC GCC GAA TAC (MNN)$_{0-2}$ TCT CGG GCT GGT ATC CCA TGC TAA GCA GTA<br>DPL4 |
| DPL5V/JFOR | 5'-CTT GGT CCC TCC GCC GAA TAC (MNN)$_{0-3}$ --- CAG GCT GCT ATC CCA TGT<br>DPL5 |
| DPL5V/JFORa | 5'-CTT GGT CCC TCC GCC GAA TAC (MNN)$_{0-4}$ ACT CAG GCT GCT ATC CCA TGT TCC GCA CTA<br>DPL5 |
| DPL6/7/8V/JFOR | 5'-CTT GGT CCC TCC GCC GAA TAC (MNN)$_{0-3}$ --- CAG GCT GCT GTC ATA GGA<br>DPL6,7,8 |
| DPL6/7/8V/JFORa | 5'-CTT GGT CCC TCC GCC GAA TAC (MNN)$_{0-2}$ ACT CAG GCT GCT GTC ATA GGA CTG GCA GTA<br>DPL6,7,8 |
| DPL9V/JFOR | 5'-CTT GGT CCC TCC GCC GAA TAC (MNN)$_{0-3}$ --- CAG GCT GTT ATC CCA TGC<br>DPL9 |
| DPL9V/JFORa | 5'-CTT GGT CCC TCC GCC GAA TAC (MNN)$_{0-1}$ ATT CAG GCT GTT ATC CCA TGC TTT GCA GTA<br>DPL9 |
| DPL10V/JFOR | 5'-CTT GGT CCC TCC GCC GAA TAC (MNN)$_{0-3}$ --- GCT ACT ACC TGC ATA TGA<br>DPL10 |
| DPL11/13V/JFOR | 5'-CTT GGT CCC TCC GCC GAA TAC (MNN)$_{0-3}$ --- GCT GCT GCT TGT ATA TRA GCT GCA GTA<br>DPL11,13 |
| DPL11/13V/JFORa | 5'-CTT GGT CCC TCC GCC GAA TAC (MNN)$_{0-2}$ AGT GCT GCT GCT TGT ATA TRA GCT GCA GTA<br>DPL11,13 |
| DPL12V/JFOR | 5'-CTT GGT CCC TCC GCC GAA TAC (MNN)$_{0-3}$ --- GTA GCT GCT GCA ATA TGA<br>DPL12 |
| DPL14V/JFOR | 5'-CTT GGT CCC TCC GCC GAA TAC (MNN)$_{0-3}$ --- GTA ACT ACT TGA ATA TAA<br>DPL14 |
| DPL14V/JFORa | 5'-CTT GGT CCC TCC GCC GAA TAC (MNN)$_{0-2}$ AGT GTA ACT ACT TGA ATA TAA GCT GCA GTG<br>DPL14 |
| DPL16V/JFOR | 5'-CTT GGT CCC TCC GCC GAA TAC (MNN)$_{0-3}$ --- ACC ACT GCT GTC CCG GGA<br>DPL16 |
| DPL16V/JFORa | 5'-CTT GGT CCC TCC GCC GAA TAC (MNN)$_{0-2}$ ATG GTT ACC ACT GCT GTC CCG GGA GTT ACA<br>DPL16 |
| DPL18V/JFOR | 5'-CTT GGT CCC TCC GCC GAA TAC (MNN)$_{0-3}$ AGC ACC ACC ATA GTA GAG CAG<br>DPL18 |
| DPL19V/JFOR | 5'-CTT GGT CCC TCC GCC GAA TAC (MNN)$_{0-3}$ --- AGC ACC ACT ATA GGA GAG<br>DPL19 |
| DPL21V/JFOR | 5'-CTT GGT CCC TCC GCC GAA TAC (MNN)$_{0-3}$ GCC ACT ACC CAT ATA CAG<br>DPL21 |
| DPL22V/JFOR | 5'-CTT GGT CCC TCC GCC GAA TAC (MNN)$_{0-1}$ GAA GTT GCT CCC ACT GCC ATG GTC TGC CCC<br>DPL22 |
| DPL23V/JFOR | 5'-CTT GGT CCC TCC GCC GAA TAC (MNN)$_{0-3}$ --- AGT GCT GCT GTC CCA CGC CTG ACA GTA<br>DPL23 |
| DPL24V/JFOR | 5'-CTT GGT CCC TCC GCC GAA TAC (MNN)$_{0-3}$ GAC TTG GCC ATC AAT CGT GTG GCT CTC TCC<br>DPL24 |

D. Sub-cloning of selected repertoires for expression of soluble Fab fragments

| Primer | Sequence |
|---|---|
| fdSEQ1 | 5'-GAA TTT TCT GTA TGA GG |
| G3LXbaGTGBaCk | 5'-GTC CTC GCA ACT TGC <u>TCT AGA</u> CAA TTT CAC AGT AAG GAG GTT TAA CTT GTG AAA AAA TTA TTA TTC GCA ATT |

E. Sequencing and probing

| Primer | Sequence |
|---|---|
| TNFCDR3PRB | 5'-CCT TGG AAG GCA GCA GC |
| Cκ.lib.seq | 5'-CAA CTG CTC ATC AGA TGG CG |
| Cλ.lib.seq | 5'-GTG GCC TTG TTG GCT TGA AGC |
| CH1.lib.seq | 5'-GGT GCT CTT GGA GGA GGG TGC |
| pelBback | 5'-GAA ATA CCT ATT GCC TAC GG |
| LMB3 | 5'-CAG GAA ACA GCT ATG AC |
| fdpCRback | 5'-GCG ATG GTT GTT GTC ATT GTC GGC |

A = adenosine; C = cytosine; G = guanine; T = thymidine; Y = C or T; R = A or G; W = A or T; S = G or C; K = T or G; M = C or A
Restriction sites are underlined. Primer names are to the left of the sequences and the V-gene segments amplified to the right.

TABLE 7

OLIGONUCLEOTIDES USED IN PREPARATION OF THE
TONSIL loxP REPERTOIRE (i) Oligonucleotide primers used for PCR of human VH genes VH1b/7a back Sfi
5'-GTC CTC GCA ACT GCG GCC CAG CCG GCC ATG GCC CAG (AG)TG
CAG CTG GTG CA(AG) TCT GG-3'

VH1c back Sfi
5'-GTC CTC GCA ACT GCG GCC CAG CCG GCC ATG GCC (GC)AG GTC
CAG CTG GT(AG) CAG TCT GG-3'

VH2b back Sfi
5'-GTC CTC GCA ACT GCG GCC CAG CCG GCC ATG GCC CAG (AG)TC
ACC TTG AAG GAG TCT GG-3'

VH 3b back Sfi
5'-GTC CTC GCA ACT GCG GCC CAG CCG GCC ATG GCC (GC)AG GTG
CAG CTG GTG GAG TCT GG-3'

VH3c back Sfi
5'-GTC CTC GCA ACT GCG GCC CAG CCG GCC ATG GCC GAG GTG CAG
CTG GTG GAG (AT)C(TC) GG-3'

VH4b back Sfi
5'-GTC CTC GCA ACT GCG GCC CAG CCG GCC ATG GCC CAG GTG CAG
CTA CAG CAG TGG GG-3'

VH4c back Sfi
5'-GTC CTC GCA ACT GCG GCC CAG CCG GCC ATG GCC CAG (GC)TG
CAG CTG CAG GAG TC(GC) GG-3'

VH5b back Sfi
5'-GTC CTC GCA ACT GCG GCC CAG CCG GCC ATG GCC GA(AG) GTG
CAG CTG GTG CAG TCT GG-3'

VH 6a back Sfi
5'-GTC CTC GCA ACT GCG GCC CAG CCG GCC ATG GCC CAG GTA CAG
CTG CAG CAG TCA GG-3'

JH for 1-2 Xho
5'-ACC GCC TCC ACC ACT CGA GAC GGT GAC CAG GGT GCC
(TC)(TC)(TG) GCC CCA-3'

JH for 3 Xho
5'-ACC GCC TCC ACC ACT CGA GAC GGT GAC CAT TGT CCC
(TC)(TC)(TG) GCC CCA-3'

JH for 4-5 Xho
5'-ACC GCC TCC ACC ACT CGA GAC GGT GAC CAG GGT TCC
(TC)(TC)(TG) GCC CCA-3'

JH for 6 Xho
5'-ACC GCC TCC ACC ACT CGA GAC GGT GAC CGT GGT CCC
(TC)(TC)(TG) CCC CCA-3'

Sfi Pri
5-GTC CTC GCA ACT GCG GCC CAG CCG GCC ATG GCC-3'

(ii) Oligonucleotide primers used for PCR of human kappa
genes

Hu k 1b back
5'-GAC ATC CAG (AT)TG ACC CAG TCT CC-3'

Hu k 2 back
5'-GAT GTT GTG ATG ACT CAG TCT CC-3'

Hu k 3b back
5'-GAA ATT GTG (AT)TG AC(AG) CAG TCT CC-3'

Hu k 4b back
5'-GAT ATT GTG ATG ACC CAC ACT CC-3'

Hu k 5 back
5'-GAA ACG ACA CTC ACG CAG TCT CC-3'

Hu k 6 back

TABLE 7-continued

OLIGONUCLEOTIDES USED IN PREPARATION OF THE TONSIL loxP REPERTOIRE

5'-GAA ATT GTG CTG ACT CAG TCT CC-3'

Hu Ck for
5'-ACA CTC TCC CCT GTT GAA GCT CTT-3'

Hu k 1b back Apa
5'-ACC GCC TCC ACC AGT GCA CTT GAC ATC CAG (AT)TG ACC CAG TCT CC-3'

Hu k 2 back Apa
5'-ACC GCC TCC ACC AGT GCA CTT GAT GTT GTG ATG ACT CAG TCT CC-3'

Hu k 3b back Apa
5'-ACC GCC TCC ACC AGT GCA CTT GAA ATT GTG (AT)TG AC(AG) CAG TCT CC-3'

Hu k 4b back Apa
5'-ACC GCC TCC ACC AGT GCA CTT GAT ATT GTG ATG ACC CAG ACT CC-3'

Hu k 5 back Apa
5'-ACC GCC TCC ACC AGT GCA CTT GAA ACG ACA CTC ACG CAG TCT CC-3'

Hu k 6 back Apa
5'-ACC GCC TCC ACC AGT GCA CTT GAA ATT GTG CTG ACT CAG TCT CC-3'

Hu Ck for Asc
5'-ACC GCC TCC ACC GGG CGC GCC TTA TTA ACA CTC TCC CCT GTT GAA GCT CTT-3

Apa Pri
5'-ACC GCC TCC ACC AGT GCA-3'

Asc/Not Pri
5'-GAG TCA TTC TCG ACT TGC GGC CGC ACC GCC TCC ACC GGG CGC GCC TTA TTA-3'

(iii) Oligonucleotide primers used for primary PCR of human lambda genes

Hu λ 1a back
5'-CAG TCT GTG CTG ACT CAG CCA CC-3'

Hu λ 1b back
5'-CAG TCT GTG (TC)TG ACG CAG CCG CC-3'

Hu λ 1c back
5'-CAG TCT GTC GTG ACG CAG CCG CC-3'

Hu λ 2 back
5'-CA(AG) TCT GCC CTG ACT CAG CCT-3'

Hu λ 3a back
5'-TCC TAT G(AT)G CTG ACT CAG CCA CC-3'

Hu λ 3b back
5'-TCT TCT GAG CTG ACT CAG GAC CC-3'

Hu λ 4 back
5'-CAC GTT ATA CTG ACT CAA CCG CC-3'

Hu λ 5 back
5'-CAG GCT GTG CTG ACT CAG CCG TC-3'

Hu λ 6 back
5'-AAT TTT ATG CTG ACT CAG CCC CA-3'

Hu λ 7/8 back
5'-CAG (AG)CT GTG GTG AC(TC) CAG GAG CC-3'

Hu λ 9 back
5'-C(AT)G CCT GTG CTG ACT CAG CC(AC) CC-3'

TABLE 7-continued

OLIGONUCLEOTIDES USED IN PREPARATION OF THE
TONSIL loxP REPERTOIRE

Hu Cλ 2⁺for
5'-TGA ACA TTC TGT AGG GGC CAC TG-3'

Hu Cλ 7⁺for
5'-AGA GCA TTC TGC AGG GGC CAC TG-3' iv) Oligonucleotide primers used for pullthrough PCR of human lambda genes

Hu λ 1a back Apa
5'-ACC GCC TCC ACC AGT GCA CAG TCT GTG CTG ACT CAG CCA CC-

Hu λ 1b back Apa
5'-ACC GCC TCC ACC AGT GCA CAG TCT GTG (TC)TG ACG CAG CCG CC-3'

Hu λ 1c back Apa
5'-ACC GCC TCC ACC AGT GCA CAG TCT GTC GTG ACG CAG CCG CC-3'

Hu λ 2 back Apa
5'-ACC GCC TCC ACC AGT GCA CA(AG) TCT GCC CTG ACT CAG CCT-3'

Hu λ 3a back Apa
5'-ACC GCC TCC ACC AGT GCA CTT TCC TAT G(AT)G CTG ACT CAG CCA CC-3'

Hu λ 3b back Apa
5'-ACC GCC TCC ACC AGT GCA CTT TCT TCT GAG CTG ACT CAG GAC CC-3'

Hu λ 4 back Apa
5'-ACC GCC TCC ACC AGT GCA CAC GTT ATA CTG ACT CAA CCG CC-3'

Hu λ 5 back Apa
5'-ACC GCC TCC ACC AGT GCA CAG GCT GTG CTG ACT CAG CCG TC-3'

Hu λ 6 back Apa
5'-ACC GCC TCC ACC AGT GCA CTT AAT TTT ATG CTG ACT CAG CCC.CA-3'

Hu λ 7/8 back Apa
5'-ACC GCC TCC ACC AGT GCA CAG (AG)CT GTG GTG AC(TC) CAG GAG CC-3'

Hu λ 9 back Apa
5'-ACC GCC TCC ACC AGT GCA C(AT)G CCT GTG CTG ACT CAG CC(AC) CC-3'

Hu Cλ 2⁺for Asc
5'-ACC GCC TCC ACC GGG CGC GCC TTA TTA TGA ACA TTC TGT AGG GGC CAC TG-3'

Hu Cλ 7⁺for Asc
5'-ACC GCC TCC ACC GGG CGC GCC TTA TTA AGA GCA TTC TGC AGG GGC CAC TG-3'

(v) Other oligonucleotides used loxP CHIΔApa: 5'-CGG GAA GGT GTG GAC GCC GCT GGT C-3'

TABLE 7-continued

OLIGONUCLEOTIDES USED IN PREPARATION OF THE
TONSIL loxP REPERTOIRE

```
lacfor2:    5'-GAG TCA TTC TCG GGC GCC CCT TGG GAA TTC
            GCA TGT TCA AAG CTT GGC GTA ATC ATG GTC
            AT -3' lacback2:   5'-GTC CTC GCA ACT CAG CTG CAT ATG GAG CTC
            GTT CAG TGC CCA TGG TCA GAG TCG GGT ACC
CGA CAG GTT TCC CGA CTG GAA AGC
            GGG -3' crefor:     5'-CTG ACA GCC AGT GGT ACC TAT CAA CTA ATT
            ATA GCA ATC ATT TAC GCG-3' creback:    5'-GTC GAG AGG GCT GGT CTC CCA TGC CAA TTT
CAC AGT AAG
GAG GTT TAA
CTT ATG TCC
AAT TTA
CTG ACC GTA CAC CAA AAT-3'
```

TABLE 8

SEQUENCES OF MUTANT 511, 1, 2, 3 AND 4 AND WT loxP SITES

Dots represent nucleotide identity with the WT site, and the nucleotide substitutions are indicated in the mutant sites.

| loxP WT | ATAACTTCGTATAATGTATGCTATACGAAGTTAT |
|---|---|
| loxP 511 | ....................A.............. |
| loxP 1 | ...............A..AA............... |
| loxP 2 | ...............C..AC............... |
| loxP 3 | ..............CA..CC............... |
| loxP 4 | ..............CA..GC............... |

TABLE 9

COMBINATIONS OF loxP SITES FLANKING THE TETRACYCLINE RESISTANT GENE IN PUC2LOXTET AND THE NUMBER OF TETRACYCLINE RESISTANT COLONIES DERIVED FROM DIFFERENT CONSTRUCTS AFTER EXPOSURE TO THE CONDITIONS OF RECOMBINATION

| Construct | 5' loxP site | 3' loxP site | No. tet. resistantes |
|---|---|---|---|
| 1 | WT | WT | 0 |
| 2 | WT | 511 | 100 |
| 3 | WT | 1 | 100 |
| 4 | WT | 2 | 100 |
| 5 | WT | 3 | 100 |
| 6 | WT | 4 | 100 |
| 7 | 511 | 1 | 100 |
| 8 | 511 | 2 | 100 |
| 9 | 511 | 3 | 100 |
| 10 | 511 | 4 | 100 |
| 11 | 511 | 1 | 100 |
| 12 | 1 | 1 | 0 |
| 13 | 1 | 2 | 100 |
| 14 | 1 | 3 | 100 |
| 15 | 1 | 4 | 100 |
| 16 | 2 | 2 | 0 |
| 17 | 2 | 3 | 100 |
| 18 | 2 | 4 | 100 |
| 19 | 3 | 3 | 0 |
| 20 | 3 | 4 | 100 |
| 21 | 4 | 4 | 100 |

TABLE 10

% EFFICIENCY OF RECOMBINATION OF CONSTRUCTS 1–11 AS DETERMINED BY THE NUMBER OF TETRACYCLINE SENSITIVE COLONIES DERIVED FROM SINGLE PLASMIDS

| Construct | 5' loxP site | 3' loxP site | percent recombinant |
|---|---|---|---|
| 1 | WT | WT | 100 |
| 2 | WT | 511 | 0 |
| 3 | WT | 1 | 28 |
| 4 | WT | 2 | 36 |
| 5 | WT | 3 | 5 |
| 6 | WT | 4 | 2 |
| 7 | 511 | 1 | 0 |
| 8 | 511 | 2 | 0 |
| 9 | 511 | 3 | 0 |
| 10 | 511 | 4 | 0 |
| 11 | 511 | 1 | 0 |

TABLE 11

% EFFICIENCY OF RECOMBINATION OF NQ10.12.5 LIGHT CHAIN INTO FD3LOX.

| 3rd loxP site | % efficiency of recombination |
|---|---|
| 1 | 10 |
| 2 | 17 |

TABLE 11-continued

% EFFICIENCY OF RECOMBINATION OF NQ10.12.5
LIGHT CHAIN INTO FD3LOX.

| 3rd loxP site | % efficiency of recombination |
|---|---|
| 3 | 10 |
| 4 | 67 |

We claim:

1. Recombinant vectors produced by a method which comprises:

causing or allowing recombination between (a) first vectors comprising nucleic acid encoding a population of first polypeptide chain of a specific binding pair member; and (b) second vectors comprising nucleic acid encoding a population of a second polypeptide chain of a specific binding pair member, at least one of said populations being genetically diverse, the recombination resulting in recombinant vectors each of which comprises nucleic acid encoding a said first polypeptide chain and a said second polypeptide chain, the recombination being promoted by inclusion in said first and second vectors of sequences at which site-specific recombination occurs, each of the first vectors and each of the second vectors including a first site-specific recombination sequence and a second site-specific recombination sequence different from the first, site-specific recombination taking place preferentially between first site-specific recombination sequences on different vectors and between second site-specific recombination sequences on different vectors compared with a first site-specific recombination sequence and a second site-specific recombination sequence on the same vector.

2. Recombinant vectors according to claim 1 wherein said first vectors each encode a polypeptide fusion of said first polypeptide chain and a component of a replicable genetic display package and the recombination results in recombinant vectors each of which comprises nucleic acid encoding a said polypeptide fusion and a said second polypeptide chain, and wherein said recombinant vectors are capable of being packaged into replicable genetic display packages using said replicable genetic display package component.

3. Recombinant vectors according to claim 1 wherein the recombination is intracellular.

4. Recombinant vectors according to claim 1 comprising nucleic acid encoding a single chain sbp member resulting from recombination between first and second vectors.

5. Recombinant vectors according to claim 1 wherein said first polypeptide chain is an immunoglobulin heavy chain variable region and said second polypeptide chain is an immunoglobulin light chain variable region, or said first polypeptide chain is an immunoglobulin light chain variable region and said second polypeptide chain is an immunoglobulin heavy chain variable region.

6. Recombinant vectors according to claim 1 wherein one of said first and second site-specific recombination sequences is loxP and the second site-specific recombination sequence is a mutant coliphage P1 loxP sequence.

7. Recombinant vectors according to claim 1 wherein the site-specific recombination sequences are selected from the group consisting of loxP, loxP 511, loxP 1, loxP 2, loxP 3 and loxP 4, whose sequences are shown in Table 8.

8. Recombinant vectors according to claim 1 wherein each first vector includes a first site-specific recombination sequence , a second site-specific recombination sequence different from the first and a third site-specific recombination sequence different from the first and second and which has a frequency of recombination with the first site-specific recombination sequence which is low compared with the frequency of recombination between first site-specific recombination and a frequency of recombination w with the second d site-specific recombination sequence which is low compared with the frequency of recombination between second site-specific recombination sequence which is low compared with the frequency of recombination between second site-specific recombination sequences, and each second vector includes a said first and a said second site-specific recombination sequence, site-specific recombination sequences on different vectors and between second site-specific recombination sequences on different vectors compared with a first site-specific recombination sequence and a second site-specific recombination sequence on the same vector.

9. Recombinant vectors according to claim 8 wherein following said site-specific recombination, resultant recombinant vectors are recombined with third vectors including a said first and a said third site-specific recombination sequence, site-specific recombination taking place preferentially between first site-specific recombination sequences on different vectors and between third site-specific recombination sequences on different vectors compared with a first site-specific recombination sequence and a third site-specific recombination sequence on the same vector.

10. Recombinant vectors according to claim 9 wherein said population of a second polypeptide chain of a specific binding pair member is genetically diverse.

11. Recombinant vectors according to claim 8 wherein said first, second and third site-specific recombination sequences are selected from the group consisting of loxP, loxP 511, loxP 2, loxP 3, and loxP 4, whose sequences are shown in Table 8.

12. Recombinant vectors according to claim 1 wherein the recombination takes place in vitro.

13. Recombinant vectors according to claim 1 wherein the first vectors are phages or phagemids and the second vectors are plasmids, or the first vectors are plasmids and the second vectors are phages or phagemids.

14. Recombinant vectors according to claim 8 wherein the recombination takes place in a bacterial host which replicates the recombinant vector preferentially over the first vectors and the second vectors.

15. Recombinant vectors according to claim 14 wherein the recombination takes place in a bacterial host which replicates plasmids preferentially over phages or phagemids, or which replicates phages or phagemids preferentially over plasmids.

16. Recombinant vectors according to claim 15 wherein said bacterial host is a PolA strain of E. coli or of another gram-negative bacterium.

17. Recombinant vectors according to claim 2 wherein said replicable genetic display packages are secreted bacteriophage.

18. Recombinant vectors according to claim 4 wherein said resulting recombinant vectors encode a fusion of said single chain sbp member and a component of a replicable genetic display package and wherein said recombinant vectors are capable of being packaged into replicable genetic display packages using said replicable genetic display package components.

19. Recombinant vectors according to claim 18 wherein said replicable genetic display packages are secreted bacteriophage.

20. Recombinant vectors according to claim 8 wherein said first vectors each encode a fusion of a said first polypeptide chain and a component of a replicable genetic display package and the recombination results in recombinant vectors each of which comprises nucleic acid encoding a said fusion and a said second polypeptide chain, and wherein said recombinant vectors are capable of being packaged into replicable genetic display packages using said replicable genetic display package component.

21. The method of claim 20 wherein said replicable genetic display packages are secreted bacteriophage.

22. Recombinant vectors produced by a method comprising:
    causing or allowing recombination between (a) first vectors comprising nucleic acid encoding a specific binding pair (sbp) member and (b) second vectors, the vectors comprising site-specific recombination sequences and the site-specific recombination sequences of the first vectors flanking the nucleic acid encoding a specific binding pair member, each of the first vectors and each of the second vectors including a first site-specific recombination sequence and a second site-specific recombination sequence different from the first, site-specific recombination taking place preferentially between first site-specific recombination sequences on different vectors and between second site-specific recombination sequences on different vectors compared with a first site-specific recombination sequence and a second site-specific recombination sequence on the same vector, thereby producing recombinant vectors.

23. Recombinant vectors according to claim 22 wherein the recombination takes place intracellularly.

24. Recombinant vectors according to claim 22 wherein the first vectors comprise nucleic acid encoding a genetically diverse population of sbp members.

25. Recombinant vectors according to claim 22 wherein the second vectors comprise nucleic acid for expression of the sbp member following recombination.

26. Recombinant vectors according to claim 22 wherein the second vectors comprise nucleic acid for expression of a fusion of the sbp member and a component of a replicable genetic display package following recombination.

27. Recombinant vectors according to claim 22 wherein one of said first and second site-specific recombination sequences is loxP and the second site-specific recombination sequence is a mutant coliphage P1 loxP sequence.

28. Recombinant vectors according to claim 22 wherein the site-specific recombination sequences are selected from the group consisting of loxP, loxP 511, loxP 1, loxP 2, loxP 3, and loxP 4, whose sequences are shown in Table 8.

29. Recombinant vectors according to claim 22 wherein nucleic acid encoding the sbp member in each first vector is flanked by a first site-specific recombination sequence and a second site-specific recombination sequence different from the first, and wherein the sbp member comprises two polypeptide chains and nucleic acid encoding each polypeptide chain is separated by a third site-specific recombination sequence different from the first and second, the third site-specific recombinant sequence having a frequency of recombination with the first site-specific recombination sequence which is low compared with the frequency of recombination between first site-specific recombination sequences and a frequency of recombination with the second site-specific recombination sequence which is low compared with the frequency of recombination between second site-specific recombination sequences, and wherein each second vector includes a said first and a said second site-specific recombination sequence, site-specific recombination taking place preferentially between first site-specific recombination sequences on different vectors and between second site-specific recombination sequences on different vectors compared with a first site-specific recombination sequence and a second site-specific recombination sequence on the same vector.

30. Recombinant vectors according to claim 29 wherein the site-specific recombination sequences are selected from the group consisting of loxP, loxP 511, loxP 1, loxP 2, loxP 3, and loxP 4, whose sequences are shown in Table 8.

31. Recombinant vectors according to claim 29 wherein the first vectors are provided by recombination between (i) vectors comprising nucleic acid encoding a first polypeptide chain flanked by two site-specific recombination sequences wherein one is a said first site-specific recombination sequence and the other is a said third site-specific recombination sequence and (ii) vectors comprising nucleic acid enclosing a second polypeptide chain flanked by two site-specific recombination sequences wherein one is a third site-specific recombination sequence and the other is a said second site-specific recombination sequence and further comprising a said first site-specific recombination sequence, recombination taking place preferentially between first site-specific recombination sequences on different vectors and between third site-specific recombination sequences on different vectors compared with a first site-specific recombination sequence and a third site-specific recombination sequence on the same vector.

32. Recombinant vectors according to claim 29 wherein the site-specific recombination sequences are selected from the group consisting of loxP, loxP 511, loxP 1, loxP 2, loxP 3, and loxP 4, whose sequences are shown in Table 8.

33. Replicable genetic display packages produced by a method comprising expressing from recombinant vectors according to claim 2, said polypeptide fusions and said second polypeptide chains, producing replicable genetic display packages which display at their surface said first and second polypeptide chains and which each comprise nucleic acid encoding a said first polypeptide chain and a said second polypeptide chain.

34. Replicable genetic display packages produced by a method comprising expressing from recombinant vectors according to claim 18 said fusions, producing replicable genetic display packages which display at their surface said single chain sbp members and which each comprise nucleic acid encoding a said single chain sbp member.

35. Replicable genetic display packages produced by a method comprising expressing from recombinant vectors according to claim 20 said fusions and said second polypeptide chains, producing replicable genetic display packages which display at their surface said first and second polypeptide chains and which each comprise nucleic acid encoding a said single chain sbp member.

36. Replicable genetic display packages produced by a method comprising expressing from recombinant vectors according to claim 26 said fusions, producing replicable genetic display packages which display at their surface a specific binding pair member and which each comprise nucleic acid encoding a specific binding pair member.

* * * * *

SEQUENCE LISTING (1) GENERAL INFORMATION:

(iii) NUMBER OF SEQUENCES: 602

(2) INFORMATION FOR SEQ ID NO:1:

(i) SEQUENCE CHARACTERISTICS:
      (A) LENGTH: 34 base pairs
      (B) TYPE: nucleic acid
      (C) STRANDEDNESS: double
      (D) TOPOLOGY: circular (xi) SEQUENCE DESCRIPTION: SEQ ID NO:1:

ATAACTTCGT ATAATGTATG CTATACGAAG TTAT                                34

(2) INFORMATION FOR SEQ ID NO:2:

(i) SEQUENCE CHARACTERISTICS:
      (A) LENGTH: 34 base pairs
      (B) TYPE: nucleic acid
      (C) STRANDEDNESS: double
      (D) TOPOLOGY: circular (xi) SEQUENCE DESCRIPTION: SEQ ID NO:2:

ATAACTTCGT ATAATGTATA CTATACGAAG TTAT                                34

(2) INFORMATION FOR SEQ ID NO:3:

(i) SEQUENCE CHARACTERISTICS:
      (A) LENGTH: 34 base pairs
      (B) TYPE: nucleic acid
      (C) STRANDEDNESS: double
      (D) TOPOLOGY: circular (xi) SEQUENCE DESCRIPTION: SEQ ID NO:3:

ATAACTTCGT ATAATATAAA CTATACGAAG TTAT                                34

(2) INFORMATION FOR SEQ ID NO:4:

(i) SEQUENCE CHARACTERISTICS:
      (A) LENGTH: 34 base pairs
      (B) TYPE: nucleic acid
      (C) STRANDEDNESS: double
      (D) TOPOLOGY: circular (xi) SEQUENCE DESCRIPTION: SEQ ID NO:4:

ATAACTTCGT ATAATCTAAC CTATACGAAG TTAT                                34

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: double
        (D) TOPOLOGY: circular (xi) SEQUENCE DESCRIPTION: SEQ ID NO:5:

```
ATAACTTCGT ATAACATACC CTATACGAAG TTAT                                   34
```

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: double
        (D) TOPOLOGY: circular (xi) SEQUENCE DESCRIPTION: SEQ ID NO:6:

```
ATAACTTCGT ATAACATAGC CTATACGAAG TTAT                                   34
```

(2) INFORMATION FOR SEQ ID NO:7:

(i) SEQUENCE CHARACTERISTICS:
        (A) LENGTH: 116 base pairs
        (B) TYPE: nucleic acid
        (C) STRANDEDNESS: double
        (D) TOPOLOGY: circular (xi) SEQUENCE DESCRIPTION: SEQ ID NO:7:

```
GGAGAGTGTT AATAAGGCGC GCCAAAGCTT CCTTAATATA ACTTCGTATA ATGTATACTA        60
TACGAAGTTA TTAGGTCGCA TGCAAATTCT ATTTCAAGGA GACAGTCATA ATGAAA          116
```

(2) INFORMATION FOR SEQ ID NO:8:

(i) SEQUENCE CHARACTERISTICS:
        (A) LENGTH: 116 base pairs
        (B) TYPE: nucleic acid
        (C) STRANDEDNESS: double
        (D) TOPOLOGY: circular (xi) SEQUENCE DESCRIPTION: SEQ ID NO:8:

```
AACAGCTATG ACCATGATTA CGCCAAGCTT CCTTAATATA ACTTCGTATA ATGTATACTA        60
TACGAAGTTA TTAGGTCGCA TGCAAATTCT ATTTCAAGGA GACAGTCATA ATGAAA          116
```

(2) INFORMATION FOR SEQ ID NO:9:

(i) SEQUENCE CHARACTERISTICS:
        (A) LENGTH: 118 base pairs
        (B) TYPE: nucleic acid
        (C) STRANDEDNESS: double
        (D) TOPOLOGY: circular (xi) SEQUENCE DESCRIPTION: SEQ ID NO:9:

```
AAAGAACGTG CCTCTTCCAG TGGCGGCCGC CCTTAATATA ACTTCGTATA ATGTATGCTA        60
TACGAAGTTA TTAGGTCTGG CCGCAGAAAC TGTTGAAAGT TGTTTAGCAA AACCTCAT        118
```

(2) INFORMATION FOR SEQ ID NO:10:

(i) SEQUENCE CHARACTERISTICS:
        (A) LENGTH: 39 amino acids
        (B) TYPE: amino acid
        (C) STRANDEDNESS: single
        (D) TOPOLOGY: linear (xi) SEQUENCE DESCRIPTION: SEQ ID NO:10:

Lys Asn Val Pro Leu Pro Val Ala Ala Ala Leu Asn Ile Thr Ser Tyr
1               5                   10                  15

Asn Val Cys Tyr Thr Lys Leu Leu Gly Leu Ala Ala Glu Thr Val Glu
            20                  25                  30

Ser Cys Leu Ala Lys Pro His
        35

(2) INFORMATION FOR SEQ ID NO:11:

(i) SEQUENCE CHARACTERISTICS:
        (A) LENGTH: 118 base pairs
        (B) TYPE: nucleic acid
        (C) STRANDEDNESS: double
        (D) TOPOLOGY: circular (xi) SEQUENCE DESCRIPTION: SEQ ID NO:11:

GAAAGTTGAC CCCAAATCTT CAGCGGCCGC CCTTAATATA ACTTCGTATA ATGTATGCTA        60

TACGAAGTTA TTAGGTCTGG CCGCAGAACA AAAACTCATC TCAGAAGAGG ATCTGAAT        118

(2) INFORMATION FOR SEQ ID NO:12:

(i) SEQUENCE CHARACTERISTICS:
        (A) LENGTH: 39 amino acids
        (B) TYPE: amino acid
        (C) STRANDEDNESS: single
        (D) TOPOLOGY: linear (xi) SEQUENCE DESCRIPTION: SEQ ID NO:12:

Lys Val Asp Pro Lys Ser Ser Ala Ala Ala Leu Asn Ile Thr Ser Tyr
1               5                   10                  15

Asn Val Cys Tyr Thr Lys Leu Leu Gly Leu Ala Ala Glu Gln Lys Leu
            20                  25                  30

Ile Ser Glu Glu Asp Leu Asn
        35

(2) INFORMATION FOR SEQ ID NO:13:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:13:

Val Tyr Tyr Cys Ala Arg
1               5

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:14:

Trp Gly Gln Gly Thr Leu
1               5

(2) INFORMATION FOR SEQ ID NO:15:

(i) SEQUENCE CHARACTERISTICS:
        (A) LENGTH: 48 base pairs (B) TYPE: nucleic acid
        (C) STRANDEDNESS: single
        (D) TOPOLOGY: linear (xi) SEQUENCE DESCRIPTION: SEQ ID NO:15:

GTGTATTACT GTGCAAGANN KNNKNNKNNK TGGGGCCAAG GTACCCTG         48

(2) INFORMATION FOR SEQ ID NO:16:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:16:

GTGTATTACT GTGCAAGANN KNNKNNKNNK NNKTGGGGCC AAGGTACCCT G     51

(2) INFORMATION FOR SEQ ID NO:17:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:17:

GTGTATTACT GTGCAAGANN KNNKNNKNNK NNKNNKTGGG GCCAAGGTAC CCTG  54

(2) INFORMATION FOR SEQ ID NO:18:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:18:

GTGTATTACT GTGCAAGANN KNNKNNKNNK NNKNNKNNKT GGGGCCAAGG TACCCTG  57

(2) INFORMATION FOR SEQ ID NO:19:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:19:

GTGTATTACT GTGCAAGANN KNNKNNKNNK NNKNNKNNKN NKTGGGGCCA AGGTACCCTG  60

(2) INFORMATION FOR SEQ ID NO:20:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO:20:

GTGTATTACT GTGCAAGANN KNNKNNKNNK NNKNNKNNKN NKNNKTGGGG CCAAGGTACC  60
CTG                                                               63

(2) INFORMATION FOR SEQ ID NO:21:

(i) SEQUENCE CHARACTERISTICS:

(A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:21:

GTGTATTACT GTGCAAGANN KNNKNNKNNK NNKNNKNNKN NKNNKNNKTG GGGCCAAGGT    60

ACCCTG    66

(2) INFORMATION FOR SEQ ID NO:22:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:22:

GTGTATTACT GTGCAAGANN KNNKNNKNNK NNKNNKNNKN NKNNKNNKNN KTGGGGCCAA    60

GGTACCCTG    69

(2) INFORMATION FOR SEQ ID NO:23:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:23:

GTGTATTACT GTGCAAGANN KNNKNNKNNK NNKNNKNNKN NKNNKNNKNN KNNKTGGGGC    60

CAAGGTACCC TG    72

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:24:

Tyr Tyr Cys Gln Lys Tyr Asn Ser Ala
1               5

(2) INFORMATION FOR SEQ ID NO:25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:25:

TATTACTGTC AAAAGTATAA CAGTGCCCNN ACGTTCGGC    39

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:26:

```
TATTACTGTC AAAAGTATAA CAGTGCCCNN NNKACGTTCG GC                42
```

(2) INFORMATION FOR SEQ ID NO:27:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:27:

```
TATTACTGTC AAAAGTATAA CAGTGCCCNN NNKNNKACGT TCGGC             45
```

(2) INFORMATION FOR SEQ ID NO:28:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:28:

```
Tyr Tyr Cys Cys Ser Tyr Ala Gly Ser Tyr
1               5                   10
```

(2) INFORMATION FOR SEQ ID NO:29:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:29:

```
TATTACTGCT GCTCATATGC AGGCAGCTAC GTATTCGGC                    39
```

(2) INFORMATION FOR SEQ ID NO:30:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:30:

```
TATTACTGCT GCTCATATGC AGGCAGCTAC NNKGTATTCG GC                42
```

(2) INFORMATION FOR SEQ ID NO:31:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:31:

```
TATTACTGCT GCTCATATGC AGGCAGCTAC NNKNNKGTAT TCGGC             45
```

(2) INFORMATION FOR SEQ ID NO:32:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:32:

```
TATTACTGCT GCTCATATGC AGGCAGCTAC NNKNNKNNKG TATTCGGC                    48
```

(2) INFORMATION FOR SEQ ID NO: 33:

(i) SEQUENCE CHARACTERISTICS:
        (A) LENGTH: 30 base pairs
        (B) TYPE: nucleic acid
        (C) STRANDEDNESS: double
        (D) TOPOLOGY: circular (xi) SEQUENCE DESCRIPTION: SEQ ID NO: 33:

```
CACAGTGCAC AGTAATAAAC TGTGGCTGCA                                        30
```

(2) INFORMATION FOR SEQ ID NO: 34:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO: 34:

His Ser Ala Gln
1

(2) INFORMATION FOR SEQ ID NO: 35:

(i) SEQUENCE CHARACTERISTICS:
        (A) LENGTH: 33 base pairs
        (B) TYPE: nucleic acid
        (C) STRANDEDNESS: double
        (D) TOPOLOGY: circular (xi) SEQUENCE DESCRIPTION: SEQ ID NO: 35:

```
AGGGGAGAGT GTTAATAAGG CGCGCCAAAG CTT                                    33
```

(2) INFORMATION FOR SEQ ID NO: 36:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO: 36:

Arg Gly Glu Cys
1

(2) INFORMATION FOR SEQ ID NO: 37:

(i) SEQUENCE CHARACTERISTICS:
        (A) LENGTH: 70 base pairs
        (B) TYPE: nucleic acid
        (C) STRANDEDNESS: double
        (D) TOPOLOGY: circular (xi) SEQUENCE DESCRIPTION: SEQ ID NO: 37:

```
GCGGCCCAGC CGGCCATGGC CCAGGTGCAG CTGCAGGTCG ACCTCGAGCG CCTCCACCAA        60

GGGCCCATCG                                                              70
```

(2) INFORMATION FOR SEQ ID NO: 38:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 38:

Ala Ala Gln Pro Ala Met Ala Gln Val Gln Leu Gln Val Asp
1               5                   10

(2) INFORMATION FOR SEQ ID NO:39:

(i) SEQUENCE CHARACTERISTICS:
        (A) LENGTH: 48 base pairs
        (B) TYPE: nucleic acid
        (C) STRANDEDNESS: double
        (D) TOPOLOGY: circular (ix) FEATURE:
        (A) NAME/KEY: CDS
        (B) LOCATION: 1..48

(xi) SEQUENCE DESCRIPTION: SEQ ID NO:39:

AAG GTG GAC AAG AAA GTT GAG CCC AAA TCT TGT GCG GCC GCC CTT AAT    48
Lys Val Asp Lys Lys Val Glu Pro Lys Ser Cys Ala Ala Ala Leu Asn
1               5                   10                  15

(2) INFORMATION FOR SEQ ID NO:40:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:40:

Lys Val Asp Lys Lys Val Glu Pro Lys Ser Cys Ala Ala Ala Leu Asn
1               5                   10                  15

(2) INFORMATION FOR SEQ ID NO:41:

(i) SEQUENCE CHARACTERISTICS:
        (A) LENGTH: 125 base pairs
        (B) TYPE: nucleic acid
        (C) STRANDEDNESS: double
        (D) TOPOLOGY: circular (ix) FEATURE:
        (A) NAME/KEY: CDS
        (B) LOCATION: 45..113

(xi) SEQUENCE DESCRIPTION: SEQ ID NO:41:

AAGCTTCTAG AATCGCCATT AGCGATGTCT CGAGTCTGGC AGAG GCG GCC GCA GAA    56
                                                      Ala Ala Ala Glu
                                                                    1

CAA AAA CTC ATC TCA GAA GAG GAT CTG AAT GGG GCC GCA CAT CAC CAT    104
Gln Lys Leu Ile Ser Glu Glu Asp Leu Asn Gly Ala Ala His His His
  5              10                  15                  20

CAT CAC CAT TAATAAGAAT TC                                          125
His His His (2) INFORMATION FOR SEQ ID NO:42:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:42:

Ala Ala Ala Glu Gln Lys Leu Ile Ser Glu Glu Asp Leu Asn Gly Ala

```
                     1               5                  10                 15
Ala His His His His His His
                    20

(2) INFORMATION FOR SEQ ID NO:43:

(i) SEQUENCE CHARACTERISTICS:
        (A) LENGTH: 45 base pairs
        (B) TYPE: nucleic acid
        (C) STRANDEDNESS: double
        (D) TOPOLOGY: circular (ix) FEATURE:
        (A) NAME/KEY: CDS
        (B) LOCATION: 1..45

(xi) SEQUENCE DESCRIPTION: SEQ ID NO:43:

GCG GGT ACG TTG TGG GGC CAA GGT ACC CTG GTC ACC GTC TCG AGC      45
Ala Gly Thr Leu Trp Gly Gln Gly Thr Leu Val Thr Val Ser Ser
 1               5                  10                 15

(2) INFORMATION FOR SEQ ID NO:44:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:44:

Ala Gly Thr Leu Trp Gly Gln Gly Thr Leu Val Thr Val Ser Ser
 1               5                  10                 15

(2) INFORMATION FOR SEQ ID NO:45:

(i) SEQUENCE CHARACTERISTICS:
        (A) LENGTH: 45 base pairs
        (B) TYPE: nucleic acid
        (C) STRANDEDNESS: double
        (D) TOPOLOGY: circular (ix) FEATURE:
        (A) NAME/KEY: CDS
        (B) LOCATION: 1..45

(xi) SEQUENCE DESCRIPTION: SEQ ID NO:45:

ATA ACT TCG TAT AAT ATA AAC TAT ACG AAG TTA TCG AGT GCA CTT      45
Ile Thr Ser Tyr Asn Ile Asn Tyr Thr Lys Leu Ser Ser Ala Leu
 1               5                  10                 15

(2) INFORMATION FOR SEQ ID NO:46:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:46:

Ile Thr Ser Tyr Asn Ile Asn Tyr Thr Lys Leu Ser Ser Ala Leu
 1               5                  10                 15

(2) INFORMATION FOR SEQ ID NO:47:

(i) SEQUENCE CHARACTERISTICS:
        (A) LENGTH: 45 base pairs
        (B) TYPE: nucleic acid
```

(C) STRANDEDNESS: double
                (D) TOPOLOGY: circular (ix) FEATURE:
                (A) NAME/KEY: CDS
                (B) LOCATION: 1..45

(xi) SEQUENCE DESCRIPTION: SEQ ID NO:47:

```
ATA ACT TCG TAT AAC ATA GCC TAT ACG AAG TTA TCG AGT GCA CTT          45
Ile Thr Ser Tyr Asn Ile Ala Tyr Thr Lys Leu Ser Ser Ala Leu
 1               5                  10                  15
```

(2) INFORMATION FOR SEQ ID NO:48:

(i) SEQUENCE CHARACTERISTICS:
                (A) LENGTH: 15 amino acids
                (B) TYPE: amino acid
                (D) TOPOLOGY: linear (ii) MOLECULE TYPE: protein (xi) SEQUENCE DESCRIPTION: SEQ ID NO:48:

```
Ile Thr Ser Tyr Asn Ile Ala Tyr Thr Lys Leu Ser Ser Ala Leu
 1               5                  10                  15
```

(2) INFORMATION FOR SEQ ID NO:49:

(i) SEQUENCE CHARACTERISTICS:
                (A) LENGTH: 24 base pairs
                (B) TYPE: nucleic acid
                (C) STRANDEDNESS: double
                (D) TOPOLOGY: circular (ix) FEATURE:
                (A) NAME/KEY: CDS
                (B) LOCATION: 1..24

(xi) SEQUENCE DESCRIPTION: SEQ ID NO:49:

```
GAG ATT GTG ATG ACC CAG ACT CCA                                      24
Glu Ile Val Met Thr Gln Thr Pro
 1               5
```

(2) INFORMATION FOR SEQ ID NO:50:

(i) SEQUENCE CHARACTERISTICS:
                (A) LENGTH: 8 amino acids
                (B) TYPE: amino acid
                (D) TOPOLOGY: linear (ii) MOLECULE TYPE: protein (xi) SEQUENCE DESCRIPTION: SEQ ID NO:50:

```
Glu Ile Val Met Thr Gln Thr Pro
 1               5
```

(2) INFORMATION FOR SEQ ID NO:51:

(i) SEQUENCE CHARACTERISTICS:
                (A) LENGTH: 117 base pairs
                (B) TYPE: nucleic acid
                (C) STRANDEDNESS: double
                (D) TOPOLOGY: circular (ix) FEATURE:
                (A) NAME/KEY: CDS
                (B) LOCATION: 1..117

(xi) SEQUENCE DESCRIPTION: SEQ ID NO:51:

```
ATG CAA AGT ATA CAG CTT CCA ACG TTC GGT CAA GGG ACC AAG GTG GAA      48
Met Gln Ser Ile Gln Leu Pro Thr Phe Gly Gln Gly Thr Lys Val Glu
```

```
         1               5                  10                 15
ATC GGC GCG CCA ATC GAG GGA AGG ATA ACT TCG TAT AAC ATA CCC TAT         96
Ile Gly Ala Pro Ile Glu Gly Arg Ile Thr Ser Tyr Asn Ile Pro Tyr
                    20                  25                  30

ACG AAG TTA TTA GCG GCC GCA                                            117
Thr Lys Leu Leu Ala Ala Ala
            35
```

(2) INFORMATION FOR SEQ ID NO:52:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:52:

```
Met Gln Ser Ile Gln Leu Pro Thr Phe Gly Gln Gly Thr Lys Val Glu
  1               5                  10                  15

Ile Gly Ala Pro Ile Glu Gly Arg Ile Thr Ser Tyr Asn Ile Pro Tyr
                    20                  25                  30

Thr Lys Leu Leu Ala Ala Ala
            35
```

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:53:

TGGAAGAGGC ACGTTCTTTT CTTT                        24

(2) INFORMATION FOR SEQ ID NO:54:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:54:

ACACTCTCCC CTGTTGAAGC TCTT                        24

(2) INFORMATION FOR SEQ ID NO:55:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:55:

TGAACATTCT GTAGGGGCCA CTGTCTT                    27

(2) INFORMATION FOR SEQ ID NO:56:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:56:

CAGGTGCAGC TGGTGCAGTC TGG                                              23

(2) INFORMATION FOR SEQ ID NO:57:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:57:

CAGGTCAACT TAAGGGAGTC TGG                                              23

(2) INFORMATION FOR SEQ ID NO:58:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:58:

GAGGTGCAGC TGGTGGAGTC TGG                                              23

(2) INFORMATION FOR SEQ ID NO:59:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:59:

CAGGTGCAGC TGCAGGAGTC GGG                                              23

(2) INFORMATION FOR SEQ ID NO:60:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:60:

GAGGTGCAGC TGTTGCAGTC TGC                                              23

(2) INFORMATION FOR SEQ ID NO:61:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:61:

CAGGTACAGC TGCAGCAGTC AGG                                              23

(2) INFORMATION FOR SEQ ID NO:62:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:62:

GTCCTCGCAA CTGCGGCCCA GCCGGCCATG GCCCAGGTGC AGCTGGTGCA GTCTGG        56

(2) INFORMATION FOR SEQ ID NO:63:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:63:

GTCCTCGCAA CTGCGGCCCA GCCGGCCATG GCCCAGGTCA ACTTAAGGGA GTCTGG        56

(2) INFORMATION FOR SEQ ID NO:64:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:64:

GTCCTCGCAA CTGCGGCCCA GCCGGCCATG GCCGAGGTGC AGCTGGTGGA GTCTGG        56

(2) INFORMATION FOR SEQ ID NO:65:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:65:

GTCCTCGCAA CTGCGGCCCA GCCGGCCATG GCCCAGGTGC AGCTGCAGGA GTCGGG        56

(2) INFORMATION FOR SEQ ID NO:66:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:66:

GTCCTCGCAA CTGCGGCCCA GCCGGCCATG GCCCAGGTGC AGCTGTTGCA GTCTGC        56

(2) INFORMATION FOR SEQ ID NO:67:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:67:

GTCCTCGCAA CTGCGGCCCA GCCGGCCATG GCCCAGGTAC AGCTGCAGCA GTCAGG        56

(2) INFORMATION FOR SEQ ID NO:68:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:68:

CCACGATTCT GCGGCCGCCA CTGGAAGAGG CACGTTCTTT TCTTT                45

(2) INFORMATION FOR SEQ ID NO:69:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:69:

GACATCCAGW TGACCCAG                                              18

(2) INFORMATION FOR SEQ ID NO:70:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:70:

GTCATCTGGA TGACCCAG                                              18

(2) INFORMATION FOR SEQ ID NO:71:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:71:

GCCATCCAGA TGACCCAG                                              18

(2) INFORMATION FOR SEQ ID NO:72:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:72:

GATRTTGTGA TGACTCAG                                              18

(2) INFORMATION FOR SEQ ID NO:73:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:73:

GAKATTGTGA TGACCCAG                                              18

(2) INFORMATION FOR SEQ ID NO:74:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:74:

GAAATTGTGT TGACGCAG                                              18

(2) INFORMATION FOR SEQ ID NO:75:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:75:

GAAATAGTGA TGACGCAG                                              18

(2) INFORMATION FOR SEQ ID NO:76:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:76:

GACATCGTGA TGACCCAG                                              18

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:77:

CAGCAGGGCA ATAAGCAC                                              18

(2) INFORMATION FOR SEQ ID NO:78:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:78:

CATCAGAGTA GTAGTTTAC                                             19

(2) INFORMATION FOR SEQ ID NO:79:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:79:

AACATCCAGA TGACCCAG                                              18

(2) INFORMATION FOR SEQ ID NO:80:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:80:

GAAATTGTAA TGACACAG                                              18

(2) INFORMATION FOR SEQ ID NO:81:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:81:

CATGACCACA GTGCACTTGA CATCCAGWTG ACCCAG                              36

(2) INFORMATION FOR SEQ ID NO:82:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:82:

CATGACCACA GTGCACTTGT CATCTGGATG ACCCAG                              36

(2) INFORMATION FOR SEQ ID NO:83:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:83:

CATGACCACA GTGCACTTGC CATCCAGATG ACCCAG                              36

(2) INFORMATION FOR SEQ ID NO:84:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:84:

CATGACCACA GTGCACTTGA TRTTGTGATG ACTCAG                              36

(2) INFORMATION FOR SEQ ID NO:85:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:85:

CATGACCACA GTGCACTTGA KATTGTGATG ACCCAG                              36

(2) INFORMATION FOR SEQ ID NO:86:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:86:

CATGACCACA GTGCACTTGA AATTGTGTTG ACGCAG                              36

(2) INFORMATION FOR SEQ ID NO:87:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:87:

CATGACCACA GTGCACTTGA AATAGTGATG ACGCAG        36

(2) INFORMATION FOR SEQ ID NO:88:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:88:

CATGACCACA GTGCACTTGA CATCGTGATG ACCCAG        36

(2) INFORMATION FOR SEQ ID NO:89:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:89:

CATGACCACA GTGCACTTCA GCAGGGCAAT AAGCAC        36

(2) INFORMATION FOR SEQ ID NO:90:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:90:

CATGACCACA GTGCACTTCA TCAGAGTAGT AGTTTAC        37

(2) INFORMATION FOR SEQ ID NO:91:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:91:

CATGACCACA GTGCACTTAA CATCCAGATG ACCCAG        36

(2) INFORMATION FOR SEQ ID NO:92:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:92:

CATGACCACA GTGCACTTGA AATTGTAATG ACACAG        36

(2) INFORMATION FOR SEQ ID NO:93:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (xi) SEQUENCE DESCRIPTION: SEQ ID NO:93:

GAGTCATTCT CGACTTGCGG CCGCACACTC TCCCCTGTTG AAGCTCTT        48

(2) INFORMATION FOR SEQ ID NO:94:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:94:

CAGTCTGTGY TGACGCAGCC GCC        23

(2) INFORMATION FOR SEQ ID NO:95:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:95:

CAGTCTGTCG TGACGCAGCC GCC        23

(2) INFORMATION FOR SEQ ID NO:96:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:96:

CAGTCTGTGC TGACTCAGCC ACC        23

(2) INFORMATION FOR SEQ ID NO:97:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:97:

CARTCTGCCC TGACTCAGCC T        21

(2) INFORMATION FOR SEQ ID NO:98:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:98:

TCTTCTGAGC TGACTCAGGA CCC        23

(2) INFORMATION FOR SEQ ID NO:99:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:99:

TCCTATGAGC TGACTCAGCC ACC                                              23

(2) INFORMATION FOR SEQ ID NO:100:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:100:

CAGRCTGTGG TGACYCAGGA GCC                                              23

(2) INFORMATION FOR SEQ ID NO:101:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:101:

CWGCCTGTGC TGACTCAGCC MCC                                              23

(2) INFORMATION FOR SEQ ID NO:102:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:102:

CATGACCACA GTGCACTTCA GTCTGTGYTG ACGCAGCCGC C                          41

(2) INFORMATION FOR SEQ ID NO:103:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:103:

CATGACCACA GTGCACTTCA GTCTGTCGTG ACGCAGCCGC C                          41

(2) INFORMATION FOR SEQ ID NO:104:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO:104:

CATGACCACA GTGCACTTCA GTCTGTGCTG ACTCAGCCAC C                          41

(2) INFORMATION FOR SEQ ID NO:105:

(i) SEQUENCE CHARACTERISTICS:

(A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:105:

CATGACCACA GTGCACTTCA RTCTGCCCTG ACTCAGCCT                    39

(2) INFORMATION FOR SEQ ID NO:106:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:106:

CATGACCACA GTGCACTTTC TTCTGAGCTG ACTCAGGACC C                 41

(2) INFORMATION FOR SEQ ID NO:107:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:107:

CATGACCACA GTGCACTTTC CTATGAGCTG ACTCAGCCAC C                 41

(2) INFORMATION FOR SEQ ID NO:108:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:108:

CATGACCACA GTGCACTTCA GRCTGTGGTG ACYCAGGAGC C                 41

(2) INFORMATION FOR SEQ ID NO:109:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:109:

CATGACCACA GTGCACTTCW GCCTGTGCTG ACTCAGCCMC C                 41

(2) INFORMATION FOR SEQ ID NO:110:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:110:

GAGTCATTCT CGACTTGCGG CCGCTGAACA TTCTGTAGGG GCCACTGTCT T       51

(2) INFORMATION FOR SEQ ID NO:111:

(i) SEQUENCE CHARACTERISTICS:
        (A) LENGTH: 21 base pairs (B) TYPE: nucleic acid
        (C) STRANDEDNESS: single
        (D) TOPOLOGY: linear (xi) SEQUENCE DESCRIPTION: SEQ ID NO:111:

ATAAGCCCCG TAATCTCTTG C                                              21

(2) INFORMATION FOR SEQ ID NO:112:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:112:

GCBATGGTTG TTGTCATTGT CGGC                                           24

(2) INFORMATION FOR SEQ ID NO:113:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:113:

CAGGAAACAG CTATGAC                                                   17

(2) INFORMATION FOR SEQ ID NO:114:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:114:

AGCGGATAAC AATTTCACAC AGG                                            23

(2) INFORMATION FOR SEQ ID NO:115:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:115:

GCCTGAACCG CCTCCACCAC TCGAGACGGT GACCAGGGTA CCTTGGCCCC A              51

(2) INFORMATION FOR SEQ ID NO:116:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:116:

CTGCTATTAT CGGGCGCGCC TTTATTAACA CTCTCCCCTG TTGAAGCTCT TTGTGACGGG     60

(2) INFORMATION FOR SEQ ID NO:117:

(i) SEQUENCE CHARACTERISTICS:
        (A) LENGTH: 57 base pairs
        (B) TYPE: nucleic acid (C) STRANDEDNESS: single
        (D) TOPOLOGY: linear (xi) SEQUENCE DESCRIPTION: SEQ ID NO:117:

ACGTTCGGCC AAGGGACCAA GSTGGAAATC AAACGTACTG TGGCTGCACC ATCTGTC          57

(2) INFORMATION FOR SEQ ID NO:118:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:118:

CATGACCACA GTGCACTTGA CATCCAGWTG ACCCAG          36

(2) INFORMATION FOR SEQ ID NO:119:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:119:

CATGACCACA GTGCACTTGT CATCTGGATG ACCCAG          36

(2) INFORMATION FOR SEQ ID NO:120:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:120:

CATGACCACA GTGCACTTGC CATCCAGATG ACCCAG          36

(2) INFORMATION FOR SEQ ID NO:121:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:121:

CATGACCACA GTGCACTTGA TRTTGTGATG ACTCAG          36

(2) INFORMATION FOR SEQ ID NO:122:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:122:

CATGACCACA GTGCACTTGA KATTGTGATG ACCCAG          36

(2) INFORMATION FOR SEQ ID NO:123:

(i) SEQUENCE CHARACTERISTICS:
        (A) LENGTH: 36 base pairs
        (B) TYPE: nucleic acid
        (C) STRANDEDNESS: single (D) TOPOLOGY: linear (xi) SEQUENCE DESCRIPTION: SEQ ID NO:123:

CATGACCACA GTGCACTTGA AATTGTGTTG ACGCAG                               36

(2) INFORMATION FOR SEQ ID NO:124:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:124:

CATGACCACA GTGCACTTGA AATAGTGATG ACGCAG                               36

(2) INFORMATION FOR SEQ ID NO:125:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:125:

CATGACCACA GTGCACTTGA CATCGTGATG ACCCAG                               36

(2) INFORMATION FOR SEQ ID NO:126:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:126:

CATGACCACA GTGCACTTGA TGTTGTGATG ACACAG                               36

(2) INFORMATION FOR SEQ ID NO:127:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:127:

CATGACCACA GTGCACTTGA AATTGTGCTG ACTCAG                               36

(2) INFORMATION FOR SEQ ID NO:128:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:128:

CATGACCACA GTGCACTTAA CATCCAGATG ACCCAG                               36

(2) INFORMATION FOR SEQ ID NO:129:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:129:

CATGACCACA GTGCACTTGA AATTGTAATG ACACAG                                    36

(2) INFORMATION FOR SEQ ID NO:130:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:130:

CTTGGTCCCT TGGCCGAACG TNNGGAGATT ATCATACTGT TGAC                           44

(2) INFORMATION FOR SEQ ID NO:131:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:131:

CTTGGTCCCT TGGCCGAACG TMNNNNGGAG ATTATCATAC TGTTGAC                        47

(2) INFORMATION FOR SEQ ID NO:132:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:132:

CTTGGTCCCT TGGCCGAACG TMNNMNNNNG GAGATTATCA TACTGTTGAC                     50

(2) INFORMATION FOR SEQ ID NO:133:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:133:

CTTGGTCCCT TGGCCGAACG TNNGGTAACT ATTATGCTGT AGAC                           44

(2) INFORMATION FOR SEQ ID NO:134:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:134:

CTTGGTCCCT TGGCCGAACG TMNNNNGGTA ACTATTATGC TGTAGAC                        47

(2) INFORMATION FOR SEQ ID NO:135:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:135:

CTTGGTCCCT TGGCCGAACG TMNNMNNNNG GTAACTATTA TGCTGTAGAC              50

(2) INFORMATION FOR SEQ ID NO:136:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:136:

CTTGGTCCCT TGGCCGAACG TNNGGTAATT GTAATCTTGT AGAC                    44

(2) INFORMATION FOR SEQ ID NO:137:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:137:

CTTGGTCCCT TGGCCGAACG TMNNNNGGTA ATTGTAATCT TGTAGAC                 47

(2) INFORMATION FOR SEQ ID NO:138:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:138:

CTTGGTCCCT TGGCCGAACG TMNNMNNNNG GTAATTGTAA TCTTGTAGAC              50

(2) INFORMATION FOR SEQ ID NO:139:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:139:

CTTGGTCCCT TGGCCGAACG TNNGGGCACT GTTATACTTT TGAC                    44

(2) INFORMATION FOR SEQ ID NO:140:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:140:

CTTGGTCCCT TGGCCGAACG TMNNNNGGGC ACTGTTATAC TTTTGAC                 47

(2) INFORMATION FOR SEQ ID NO:141:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:141:

```
CTTGGTCCCT TGGCCGAACG TMNNMNNNNG GGCACTGTTA TACTTTTGAC           50

(2) INFORMATION FOR SEQ ID NO:142:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:142:

CTTGGTCCCT TGGCCGAACG TNNGGAAACT GTTAGCCTGT TGAC                 44

(2) INFORMATION FOR SEQ ID NO:143:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:143:

CTTGGTCCCT TGGCCGAACG TMNNNNGGAA ACTGTTAGCC TGTTGAC              47

(2) INFORMATION FOR SEQ ID NO:144:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:144:

CTTGGTCCCT TGGCCGAACG TMNNMNNNNG GAAACTGTTA GCCTGTTGAC           50

(2) INFORMATION FOR SEQ ID NO:145:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:145:

CTTGGTCCCT TGGCCGAACG TNNGGTAACT ATTATACTGT TGGC                 44

(2) INFORMATION FOR SEQ ID NO:146:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:146:

CTTGGTCCCT TGGCCGAACG TMNNNNGGTA ACTATTATAC TGTTGGC              47

(2) INFORMATION FOR SEQ ID NO:147:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:147:
```

```
CTTGGTCCCT TGGCCGAACG TMNNMNNNNG GTAACTATTA TACTGTTGGC         50
```

(2) INFORMATION FOR SEQ ID NO:148:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:148:

```
CTTGGTCCCT TGGCCGAACG TNNGGTAACT ATTAAGCTGT TGAC               44
```

(2) INFORMATION FOR SEQ ID NO:149:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:149:

```
CTTGGTCCCT TGGCCGAACG TMNNNNGGTA ACTATTAAGC TGTTGAC            47
```

(2) INFORMATION FOR SEQ ID NO:150:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:150:

```
CTTGGTCCCT TGGCCGAACG TMNNMNNNNG GTAACTATTA AGCTGTTGAC         50
```

(2) INFORMATION FOR SEQ ID NO:151:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:151:

```
CTTGGTCCCT TGGCCGAACG TNNGGGTACT GTAACTCTGT TGAC               44
```

(2) INFORMATION FOR SEQ ID NO:152:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:152:

```
CTTGGTCCCT TGGCCGAACG TMNNNNGGGT ACTGTAACTC TGTTGAC            47
```

(2) INFORMATION FOR SEQ ID NO:153:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:153:

```
CTTGGTCCCT TGGCCGAACG TMNNMNNNNG GGTACTGTAA CTCTGTTGAC         50
```

(2) INFORMATION FOR SEQ ID NO:154:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:154:

CTTGGTCCCT TGGCCGAACG TNNGGAAACT ATAATACTGT TGAC           44

(2) INFORMATION FOR SEQ ID NO:155:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:155:

CTTGGTCCCT TGGCCGAACG TMNNNNGGAA ACTATAATAC TGTTGAC       47

(2) INFORMATION FOR SEQ ID NO:156:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:156:

CTTGGTCCCT TGGCCGAACG TMNNMNNNNG GAAACTATAA TACTGTTGAC    50

(2) INFORMATION FOR SEQ ID NO:157:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:157:

CTTGGTCCCT TGGCCGAACG TNNGGGCATT GTAAGTCCGT TGAC           44

(2) INFORMATION FOR SEQ ID NO:158:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:158:

CTTGGTCCCT TGGCCGAACG TMNNNNGGGC ATTGTAAGTC CGTTGAC       47

(2) INFORMATION FOR SEQ ID NO:159:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:159:

CTTGGTCCCT TGGCCGAACG TMNNMNNNNG GCATTGTAA GTCCGTTGAC    50

(2) INFORMATION FOR SEQ ID NO:160:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:160:

CTTGGTCCCT TGGCCGAACG TNNGAAGCTG TATACTTTGC ATGC          44

(2) INFORMATION FOR SEQ ID NO:161:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:161:

CTTGGTCCCT TGGCCGAACG TMNNNNGAAG CTGTATACTT TGCATGC         47

(2) INFORMATION FOR SEQ ID NO:162:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:162:

CTTGGTCCCT TGGCCGAACG TMNNMNNNNG AAGCTGTATA CTTTGCATGC      50

(2) INFORMATION FOR SEQ ID NO:163:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:163:

CTTGGTCCCT TGGCCGAACG TNNGAAACTC TATACGTTGC ATGC          44

(2) INFORMATION FOR SEQ ID NO:164:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:164:

CTTGGTCCCT TGGCCGAACG TMNNNNGAAA CTCTATACGT TGCATGC         47

(2) INFORMATION FOR SEQ ID NO:165:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:165:

CTTGGTCCCT TGGCCGAACG TMNNMNNNNG AAACTCTATA CGTTGCATGC      50

(2) INFORMATION FOR SEQ ID NO:166:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:166:

CTTGGTCCCT TGGCCGAACG TNNGATCTTG TGCATCTTGC ATGC          44

(2) INFORMATION FOR SEQ ID NO:167:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:167:

CTTGGTCCCT TGGCCGAACG TMNNNNGATC TTGTGCATCT TGCATGC       47

(2) INFORMATION FOR SEQ ID NO:168:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:168:

CTTGGTCCCT TGGCCGAACG TMNNMNNNNG ATCTTGTGCA TCTTGCATGC    50

(2) INFORMATION FOR SEQ ID NO:169:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:169:

CTTGGTCCCT TGGCCGAACG TNNGAGTTTG TAGAGCTTGC ATGC          44

(2) INFORMATION FOR SEQ ID NO:170:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:170:

CTTGGTCCCT TGGCCGAACG TMNNNNGAGT TTGTAGAGCT TGCATGC       47

(2) INFORMATION FOR SEQ ID NO:171:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:171:

CTTGGTCCCT TGGCCGAACG TMNNMNNNNG AGTTTGTAGA GCTTGCATGC    50

(2) INFORMATION FOR SEQ ID NO:172:

(i) SEQUENCE CHARACTERISTICS:
       (A) LENGTH: 44 base pairs
       (B) TYPE: nucleic acid
       (C) STRANDEDNESS: single
       (D) TOPOLOGY: linear (xi) SEQUENCE DESCRIPTION: SEQ ID NO:172:

CTTGGTCCCT TGGCCGAACG TNNGAAATTG TGTAGCTTGC ATGC                44

(2) INFORMATION FOR SEQ ID NO:173:

(i) SEQUENCE CHARACTERISTICS:
       (A) LENGTH: 47 base pairs
       (B) TYPE: nucleic acid
       (C) STRANDEDNESS: single
       (D) TOPOLOGY: linear (xi) SEQUENCE DESCRIPTION: SEQ ID NO:173:

CTTGGTCCCT TGGCCGAACG TMNNNNGAAA TTGTGTAGCT TGCATGC             47

(2) INFORMATION FOR SEQ ID NO:174:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:174:

CTTGGTCCCT TGGCCGAACG TMNNMNNNNG AAATTGTGTA GCTTGCATGC          50

(2) INFORMATION FOR SEQ ID NO:175:

(i) SEQUENCE CHARACTERISTICS:
       (A) LENGTH: 44 base pairs
       (B) TYPE: nucleic acid
       (C) STRANDEDNESS: single
       (D) TOPOLOGY: linear (xi) SEQUENCE DESCRIPTION: SEQ ID NO:175:

CTTGGTCCCT TGGCCGAACG TNNGAAATTG TGTAGCTTGC GTGC                44

(2) INFORMATION FOR SEQ ID NO:176:

(i) SEQUENCE CHARACTERISTICS:
       (A) LENGTH: 47 base pairs
       (B) TYPE: nucleic acid
       (C) STRANDEDNESS: single
       (D) TOPOLOGY: linear (xi) SEQUENCE DESCRIPTION: SEQ ID NO:176:

CTTGGTCCCT TGGCCGAACG TMNNNNGAAA TTGTGTAGCT TGCGTGC             47

(2) INFORMATION FOR SEQ ID NO:177:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO:177:

CTTGGTCCCT TGGCCGAACG TMNNMNNNNG AAATTGTGTA GCTTGCGTGC          50

(2) INFORMATION FOR SEQ ID NO:178:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (xi) SEQUENCE DESCRIPTION: SEQ ID NO:178:

CTTGGTCCCT TGGCCGAACG TNNGCCAGTG TGTACCTTGC ATGC                              44

(2) INFORMATION FOR SEQ ID NO:179:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (xi) SEQUENCE DESCRIPTION: SEQ ID NO:179:

CTTGGTCCCT TGGCCGAACG TMNNNNGCCA GTGTGTACCT TGCATGC                           47

(2) INFORMATION FOR SEQ ID NO:180:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (xi) SEQUENCE DESCRIPTION: SEQ ID NO:180:

CTTGGTCCCT TGGCCGAACG TMNNMNNNG CCAGTGTGTA CCTTGCATGC                         50

(2) INFORMATION FOR SEQ ID NO:181:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (xi) SEQUENCE DESCRIPTION: SEQ ID NO:181:

CTTGGTCCCT TGGCCGAACG TNNGTGAGCT ACCATACTGC TGAC                              44

(2) INFORMATION FOR SEQ ID NO:182:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (xi) SEQUENCE DESCRIPTION: SEQ ID NO:182:

CTTGGTCCCT TGGCCGAACG TMNNNNGTGA GCTACCATAC TGCTGAC                           47

(2) INFORMATION FOR SEQ ID NO:183:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (xi) SEQUENCE DESCRIPTION: SEQ ID NO:183:

CTTGGTCCCT TGGCCGAACG TMNNMNNNG TGAGCTACCA TACTGCTGAC                         50

(2) INFORMATION FOR SEQ ID NO:184:

(i) SEQUENCE CHARACTERISTICS:

(A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:184:

CTTGGTCCCT TGGCCGAACG TNNGCCAGTT ATTATACTGC TGAC                         44

(2) INFORMATION FOR SEQ ID NO:185:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:185:

CTTGGTCCCT TGGCCGAACG TMNNNNGCCA GTTATTATAC TGCTGAC                      47

(2) INFORMATION FOR SEQ ID NO:186:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:186:

CTTGGTCCCT TGGCCGAACG TMNNMNNNNG CCAGTTATTA TACTGCTGAC                   50

(2) INFORMATION FOR SEQ ID NO:187:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:187:

CTTGGTCCCT TGGCCGAACG TNNGTAAGTT ATAATCCTGC TGAC                         44

(2) INFORMATION FOR SEQ ID NO:188:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:188:

CTTGGTCCCT TGGCCGAACG TMNNNNGTAA GTTATAATCC TGCTGAC                      47

(2) INFORMATION FOR SEQ ID NO:189:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:189:

CTTGGTCCCT TGGCCGAACG TMNNMNNNNG TAAGTTATAA TCCTGCTGAC                   50

(2) INFORMATION FOR SEQ ID NO:190:

(i) SEQUENCE CHARACTERISTICS:
        (A) LENGTH: 44 base pairs (B) TYPE: nucleic acid
        (C) STRANDEDNESS: single
        (D) TOPOLOGY: linear (xi) SEQUENCE DESCRIPTION: SEQ ID NO:190:

CTTGGTCCCT TGGCCGAACG TNNGAGTACT ATAATATTGC TGAC              44

(2) INFORMATION FOR SEQ ID NO:191:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:191:

CTTGGTCCCT TGGCCGAACG TMNNNNGAGT ACTATAATAT TGCTGAC           47

(2) INFORMATION FOR SEQ ID NO:192:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:192:

CTTGGTCCCT TGGCCGAACG TMNNMNNNNG AGTACTATAA TATTGCTGAC        50

(2) INFORMATION FOR SEQ ID NO:193:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:193:

CTTGGTCCCT TGGCCGAACG TNNGGTGCTT ATTGCCCTGC TGAC              44

(2) INFORMATION FOR SEQ ID NO:194:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:194:

CTTGGTCCCT TGGCCGAACG TMNNNNGGTG CTTATTGCCC TGCTGAC           47

(2) INFORMATION FOR SEQ ID NO:195:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:195:

CTTGGTCCCT TGGCCGAACG TMNNMNNNNG GTGCTTATTG CCCTGCTGAC        50

(2) INFORMATION FOR SEQ ID NO:196:

(i) SEQUENCE CHARACTERISTICS:
        (A) LENGTH: 44 base pairs
        (B) TYPE: nucleic acid

```
            (C) STRANDEDNESS: single
            (D) TOPOLOGY: linear (xi) SEQUENCE DESCRIPTION: SEQ ID NO:196:

CTTGGTCCCT TGGCCGAACG TNNGTAAACT ACTACTCTGA TGAC                44

(2) INFORMATION FOR SEQ ID NO:197:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (xi) SEQUENCE DESCRIPTION: SEQ ID NO:197:

CTTGGTCCCT TGGCCGAACG TMNNNNGTAA ACTACTACTC TGATGAC             47

(2) INFORMATION FOR SEQ ID NO:198:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (xi) SEQUENCE DESCRIPTION: SEQ ID NO:198:

CTTGGTCCCT TGGCCGAACG TMNNMNNNNG TAAACTACTA CTCTGATGAC          50

(2) INFORMATION FOR SEQ ID NO:199:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:199:

GGAATTCGGG GTGAGGGTTG AGAA                                     24

(2) INFORMATION FOR SEQ ID NO:200:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:200:

CCCCCAAGCT TCTGCCCCTC ATCC                                     24

(2) INFORMATION FOR SEQ ID NO:201:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (xi) SEQUENCE DESCRIPTION: SEQ ID NO:201:

GTATTCGGCG GAGGGACCAA GCTGACCGTC CTAGGTCAGC CCAAGGCTGC CCCCTCGGTC   60

ACT                                                            63

(2) INFORMATION FOR SEQ ID NO:202:

(i) SEQUENCE CHARACTERISTICS:
            (A) LENGTH: 78 base pairs
```

(B) TYPE: nucleic acid
        (C) STRANDEDNESS: single
        (D) TOPOLOGY: linear (xi) SEQUENCE DESCRIPTION: SEQ ID NO:202:

GAGTCATTCT CGACTTGCGG CCGCCTGCTA TTATCGGGCG CGCCTTTATT ATGAACATTC    60

TGTAGGGGCC ACTGTCTT    78

(2) INFORMATION FOR SEQ ID NO:203:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:203:

CATGACCACA GTGCACTTCA GTCTGTGYTG ACGCAGCCGC C    41

(2) INFORMATION FOR SEQ ID NO:204:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:204:

CATGACCACA GTGCACTTCA GTCTGTCGTG ACGCAGCCGC C    41

(2) INFORMATION FOR SEQ ID NO:205:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:205:

CATGACCACA GTGCACTTCA GTCTGTGCTG ACTCAGCCAC C    41

(2) INFORMATION FOR SEQ ID NO:206:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:206:

CATGACCACA GTGCACTTCA RTCTGCCCTG ACTCAGCCT    39

(2) INFORMATION FOR SEQ ID NO:207:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:207:

CATGACCACA GTGCACTTTC TTCTGAGCTG ACTCAGGACC C    41

(2) INFORMATION FOR SEQ ID NO:208:

(i) SEQUENCE CHARACTERISTICS:

(A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:208:

CATGACCACA GTGCACTTTC CTATGAGCTG ACTCAGCCAC C            41

(2) INFORMATION FOR SEQ ID NO:209:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:209:

CATGACCACA GTGCACTTCA GRCTGTGGTG ACYCAGGAGC C            41

(2) INFORMATION FOR SEQ ID NO:210:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:210:

CATGACCACA GTGCACTTCW GCCTGTGCTG ACTCAGCCMC C            41

(2) INFORMATION FOR SEQ ID NO:211:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:211:

CTTGGTCCCT CCGCCGAATA CCAGGCTGTC ATCCCATGCT GCACAGTA     48

(2) INFORMATION FOR SEQ ID NO:212:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:212:

CTTGGTCCCT CCGCCGAATA CMNNCAGGCT GTCATCCCAT GCTGCACAGT A    51

(2) INFORMATION FOR SEQ ID NO:213:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:213:

CTTGGTCCCT CCGCCGAATA CMNNMNNCAG GCTGTCATCC CATGCTGCAC AGTA  54

(2) INFORMATION FOR SEQ ID NO:214:

(i) SEQUENCE CHARACTERISTICS:
        (A) LENGTH: 57 base pairs (B) TYPE: nucleic acid
        (C) STRANDEDNESS: single
        (D) TOPOLOGY: linear (xi) SEQUENCE DESCRIPTION: SEQ ID NO:214:

CTTGGTCCCT CCGCCGAATA CMNNMNNMNN CAGGCTGTCA TCCCATGCTG CACAGTA    57

(2) INFORMATION FOR SEQ ID NO:215:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:215:

CTTGGTCCCT CCGCCGAATA CMNNMNNMNN MNNCAGGCTG TCATCCCATG CTGCACAGTA    60

(2) INFORMATION FOR SEQ ID NO:216:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO:216:

CTTGGTCCCT CCGCCGAATA CMNNMNNMNN MNNMNNCAGG CTGTCATCCC ATGCTGCACA    60

GTA    63

(2) INFORMATION FOR SEQ ID NO:217:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:217:

CTTGGTCCCT CCGCCGAATA CCGGGCTGGT ATCCCATGC    39

(2) INFORMATION FOR SEQ ID NO:218:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:218:

CTTGGTCCCT CCGCCGAATA CMNNCGGGCT GGTATCCCAT GC    42

(2) INFORMATION FOR SEQ ID NO:219:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:219:

CTTGGTCCCT CCGCCGAATA CMNNMNNCGG GCTGGTATCC CATGC    45

(2) INFORMATION FOR SEQ ID NO:220:

(i) SEQUENCE CHARACTERISTICS:

(A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:220:

CTTGGTCCCT CCGCCGAATA CMNNMNNMNN CGGGCTGGTA TCCCATGC                48

(2) INFORMATION FOR SEQ ID NO:221:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:221:

CTTGGTCCCT CCGCCGAATA CTCTCGGGCT GGTATCCCAT GCTAAGCAGT A            51

(2) INFORMATION FOR SEQ ID NO:222:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:222:

CTTGGTCCCT CCGCCGAATA CMNNTCTCGG GCTGGTATCC CATGCTAAGC AGTA         54

(2) INFORMATION FOR SEQ ID NO:223:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:223:

CTTGGTCCCT CCGCCGAATA CMNNMNNTCT CGGGCTGGTA TCCCATGCTA AGCAGTA      57

(2) INFORMATION FOR SEQ ID NO:224:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:224:

CTTGGTCCCT CCGCCGAATA CCAGGCTGCT ATCCCATGT                          39

(2) INFORMATION FOR SEQ ID NO:225:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:225:

CTTGGTCCCT CCGCCGAATA CMNNCAGGCT GCTATCCCAT GT                      42

(2) INFORMATION FOR SEQ ID NO:226:

(i) SEQUENCE CHARACTERISTICS:
        (A) LENGTH: 45 base pairs (B) TYPE: nucleic acid
            (C) STRANDEDNESS: single
            (D) TOPOLOGY: linear (xi) SEQUENCE DESCRIPTION: SEQ ID NO:226:

CTTGGTCCCT CCGCCGAATA CMNNMNNCAG GCTGCTATCC CATGT                45

(2) INFORMATION FOR SEQ ID NO:227:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (xi) SEQUENCE DESCRIPTION: SEQ ID NO:227:

CTTGGTCCCT CCGCCGAATA CMNNMNNMNN CAGGCTGCTA TCCCATGT             48

(2) INFORMATION FOR SEQ ID NO:228:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (xi) SEQUENCE DESCRIPTION: SEQ ID NO:228:

CTTGGTCCCT CCGCCGAATA CACTCAGGCT GCTATCCCAT GTTCCGCACT A         51

(2) INFORMATION FOR SEQ ID NO:229:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (xi) SEQUENCE DESCRIPTION: SEQ ID NO:229:

CTTGGTCCCT CCGCCGAATA CMNNACTCAG GCTGCTATCC CATGTTCCGC ACTA      54

(2) INFORMATION FOR SEQ ID NO:230:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (xi) SEQUENCE DESCRIPTION: SEQ ID NO:230:

CTTGGTCCCT CCGCCGAATA CMNNMNNACT CAGGCTGCTA TCCCATGTTC CGCACTA   57

(2) INFORMATION FOR SEQ ID NO:231:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (xi) SEQUENCE DESCRIPTION: SEQ ID NO:231:

CTTGGTCCCT CCGCCGAATA CMNNMNNMNN ACTCAGGCTG CTATCCCATG TTCCGCACTA   60

(2) INFORMATION FOR SEQ ID NO:232:

(i) SEQUENCE CHARACTERISTICS:
            (A) LENGTH: 63 base pairs
            (B) TYPE: nucleic acid (C) STRANDEDNESS: single
            (D) TOPOLOGY: linear (xi) SEQUENCE DESCRIPTION: SEQ ID NO:232:

CTTGGTCCCT CCGCCGAATA CMNNMNNMNN MNNACTCAGG CTGCTATCCC ATGTTCCGCA        60

CTA                                                                     63

(2) INFORMATION FOR SEQ ID NO:233:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:233:

CTTGGTCCCT CCGCCGAATA CCAGGCTGCT GTCATAGGA                               39

(2) INFORMATION FOR SEQ ID NO:234:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:234:

CTTGGTCCCT CCGCCGAATA CMNNCAGGCT GCTGTCATAG GA                           42

(2) INFORMATION FOR SEQ ID NO:235:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (xi) SEQUENCE DESCRIPTION: SEQ ID NO:235:

CTTGGTCCCT CCGCCGAATA CMNNMNNCAG GCTGCTGTCA TAGGA                        45

(2) INFORMATION FOR SEQ ID NO:236:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (xi) SEQUENCE DESCRIPTION: SEQ ID NO:236:

CTTGGTCCCT CCGCCGAATA CMNNMNNMNN CAGGCTGCTG TCATAGGA                     48

(2) INFORMATION FOR SEQ ID NO:237:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (xi) SEQUENCE DESCRIPTION: SEQ ID NO:237:

CTTGGTCCCT CCGCCGAATA CACTCAGGCT GCTGTCATAG GACTGGCAGT A                 51

(2) INFORMATION FOR SEQ ID NO:238:

(i) SEQUENCE CHARACTERISTICS:
            (A) LENGTH: 54 base pairs (B) TYPE: nucleic acid
(C) STRANDEDNESS: single
(D) TOPOLOGY: linear (xi) SEQUENCE DESCRIPTION: SEQ ID NO:238:

CTTGGTCCCT CCGCCGAATA CMNNACTCAG GCTGCTGTCA TAGGACTGGC AGTA                54

(2) INFORMATION FOR SEQ ID NO:239:

(i) SEQUENCE CHARACTERISTICS:
(A) LENGTH: 57 base pairs
(B) TYPE: nucleic acid
(C) STRANDEDNESS: single
(D) TOPOLOGY: linear (xi) SEQUENCE DESCRIPTION: SEQ ID NO:239:

CTTGGTCCCT CCGCCGAATA CMNNMNNACT CAGGCTGCTG TCATAGGACT GGCAGTA             57

(2) INFORMATION FOR SEQ ID NO:240:

(i) SEQUENCE CHARACTERISTICS:
(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:240:

CTTGGTCCCT CCGCCGAATA CCAGGCTGTT ATCCCATGC                                 39

(2) INFORMATION FOR SEQ ID NO:241:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:241:

CTTGGTCCCT CCGCCGAATA CMNNCAGGCT GTTATCCCAT GC                             42

(2) INFORMATION FOR SEQ ID NO:242:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO:242:

CTTGGTCCCT CCGCCGAATA CMNNMNNCAG GCTGTTATCC CATGC                          45

(2) INFORMATION FOR SEQ ID NO:243:

(i) SEQUENCE CHARACTERISTICS:
(A) LENGTH: 48 base pairs
(B) TYPE: nucleic acid
(C) STRANDEDNESS: single
(D) TOPOLOGY: linear (xi) SEQUENCE DESCRIPTION: SEQ ID NO:243:

CTTGGTCCCT CCGCCGAATA CMNNMNNMNN CAGGCTGTTA TCCCATGC                       48

(2) INFORMATION FOR SEQ ID NO:244:

(i) SEQUENCE CHARACTERISTICS:
(A) LENGTH: 51 base pairs
(B) TYPE: nucleic acid (C) STRANDEDNESS: single
            (D) TOPOLOGY: linear (xi) SEQUENCE DESCRIPTION: SEQ ID NO:244:

CTTGGTCCCT CCGCCGAATA CATTCAGGCT GTTATCCCAT GCTTTGCAGT A           51

(2) INFORMATION FOR SEQ ID NO:245:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (xi) SEQUENCE DESCRIPTION: SEQ ID NO:245:

CTTGGTCCCT CCGCCGAATA CMNNATTCAG GCTGTTATCC CATGCTTTGC AGTA        54

(2) INFORMATION FOR SEQ ID NO:246:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:246:

CTTGGTCCCT CCGCCGAATA CGCTACTACC TGCATATGA                         39

(2) INFORMATION FOR SEQ ID NO:247:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:247:

CTTGGTCCCT CCGCCGAATA CMNNGCTACT ACCTGCATAT GA                     42

(2) INFORMATION FOR SEQ ID NO:248:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (xi) SEQUENCE DESCRIPTION: SEQ ID NO:248:

CTTGGTCCCT CCGCCGAATA CMNNMNNGCT ACTACCTGCA TATGA                  45

(2) INFORMATION FOR SEQ ID NO:249:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (xi) SEQUENCE DESCRIPTION: SEQ ID NO:249:

CTTGGTCCCT CCGCCGAATA CMNNMNNMNN GCTACTACCT GCATATGA               48

(2) INFORMATION FOR SEQ ID NO:250:

(i) SEQUENCE CHARACTERISTICS:
            (A) LENGTH: 48 base pairs
            (B) TYPE: nucleic acid
            (C) STRANDEDNESS: single (D) TOPOLOGY: linear (xi) SEQUENCE DESCRIPTION: SEQ ID NO:250:

CTTGGTCCCT CCGCCGAATA CGCTGCTGCT TGTATATRAG CTGCAGTA                48

(2) INFORMATION FOR SEQ ID NO:251:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:251:

CTTGGTCCCT CCGCCGAATA CMNNGCTGCT GCTTGTATAT RAGCTGCAGT A             51

(2) INFORMATION FOR SEQ ID NO:252:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:252:

CTTGGTCCCT CCGCCGAATA CMNNMNNGCT GCTGCTTGTA TATRAGCTGC AGTA          54

(2) INFORMATION FOR SEQ ID NO:253:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:253:

CTTGGTCCCT CCGCCGAATA CMNNMNNMNN GCTGCTGCTT GTATATRAGC TGCAGTA       57

(2) INFORMATION FOR SEQ ID NO:254:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:254:

CTTGGTCCCT CCGCCGAATA CAGTGCTGCT GCTTGTATAT RAGCTGCAGT A             51

(2) INFORMATION FOR SEQ ID NO:255:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:255:

CTTGGTCCCT CCGCCGAATA CMNNAGTGCT GCTGCTTGTA TATRAGCTGC AGTA          54

(2) INFORMATION FOR SEQ ID NO:256:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:256:

CTTGGTCCCT CCGCCGAATA CMNNMNNAGT GCTGCTGCTT GTATATRAGC TGCAGTA        57

(2) INFORMATION FOR SEQ ID NO:257:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:257:

CTTGGTCCCT CCGCCGAATA CGTAGCTGCC TGCATATGA        39

(2) INFORMATION FOR SEQ ID NO:258:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:258:

CTTGGTCCCT CCGCCGAATA CMNNGTAGCT GCCTGCATAT GA        42

(2) INFORMATION FOR SEQ ID NO:259:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:259:

CTTGGTCCCT CCGCCGAATA CMNNMNNGTA GCTGCCTGCA TATGA        45

(2) INFORMATION FOR SEQ ID NO:260:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:260:

CTTGGTCCCT CCGCCGAATA CMNNMNNMNN GTAGCTGCCT GCATATGA        48

(2) INFORMATION FOR SEQ ID NO:261:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:261:

CTTGGTCCCT CCGCCGAATA CGTAACTACT TGAATATAA        39

(2) INFORMATION FOR SEQ ID NO:262:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:262:

CTTGGTCCCT CCGCCGAATA CMNNGTAACT ACTTGAATAT AA                42

(2) INFORMATION FOR SEQ ID NO:263:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:263:

CTTGGTCCCT CCGCCGAATA CMNNMNNGTA ACTACTTGAA TATAA             45

(2) INFORMATION FOR SEQ ID NO:264:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:264:

CTTGGTCCCT CCGCCGAATA CMNNMNNMNN GTAACTACTT GAATATAA          48

(2) INFORMATION FOR SEQ ID NO:265:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:265:

CTTGGTCCCT CCGCCGAATA CAGTGTAACT ACTTGAATAT AAGCTGCAGT G      51

(2) INFORMATION FOR SEQ ID NO:266:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:266:

CTTGGTCCCT CCGCCGAATA CMNNAGTGTA ACTACTTGAA TATAAGCTGC AGTG   54

(2) INFORMATION FOR SEQ ID NO:267:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:267:

CTTGGTCCCT CCGCCGAATA CMNNMNNAGT GTAACTACTT GAATATAAGC TGCAGTG    57

(2) INFORMATION FOR SEQ ID NO:268:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:268:

CTTGGTCCCT CCGCCGAATA CACCACTGCT GTCCCGGGA                    39

(2) INFORMATION FOR SEQ ID NO:269:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:269:

CTTGGTCCCT CCGCCGAATA CMNNACCACT GCTGTCCCGG GA                42

(2) INFORMATION FOR SEQ ID NO:270:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:270:

CTTGGTCCCT CCGCCGAATA CMNNMNNACC ACTGCTGTCC CGGGA             45

(2) INFORMATION FOR SEQ ID NO:271:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:271:

CTTGGTCCCT CCGCCGAATA CMNNMNNMNN ACCACTGCTG TCCCGGGA          48

(2) INFORMATION FOR SEQ ID NO:272:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:272:

CTTGGTCCCT CCGCCGAATA CATGGTTACC ACTGCTGTCC CGGGAGTTAC A      51

(2) INFORMATION FOR SEQ ID NO:273:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:273:

CTTGGTCCCT CCGCCGAATA CMNNATGGTT ACCACTGCTG TCCCGGGAGT TACA   54

(2) INFORMATION FOR SEQ ID NO:274:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:274:

```
CTTGGTCCCT CCGCCGAATA CMNNMNNATG GTTACCACTG CTGTCCCGGG AGTTACA           57
```

(2) INFORMATION FOR SEQ ID NO:275:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:275:

```
CTTGGTCCCT CCGCCGAATA CAGCACCACC ATAGTAGAGC AG                          42
```

(2) INFORMATION FOR SEQ ID NO:276:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:276:

```
CTTGGTCCCT CCGCCGAATA CMNNAGCACC ACCATAGTAG AGCAG                       45
```

(2) INFORMATION FOR SEQ ID NO:277:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:277:

```
CTTGGTCCCT CCGCCGAATA CMNNMNNAGC ACCACCATAG TAGAGCAG                    48
```

(2) INFORMATION FOR SEQ ID NO:278:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:278:

```
CTTGGTCCCT CCGCCGAATA CMNNMNNMNN AGCACCACCA TAGTAGAGCA G                51
```

(2) INFORMATION FOR SEQ ID NO:279:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:279:

```
CTTGGTCCCT CCGCCGAATA CAGCACCACT ATAGGAGAG                              39
```

(2) INFORMATION FOR SEQ ID NO:280:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:280:

```
CTTGGTCCCT CCGCCGAATA CMNNAGCACC ACTATAGGAG AG                          42
```

(2) INFORMATION FOR SEQ ID NO:281:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:281:

CTTGGTCCCT CCGCCGAATA CMNNMNNAGC ACCACTATAG GAGAG               45

(2) INFORMATION FOR SEQ ID NO:282:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:282:

CTTGGTCCCT CCGCCGAATA CMNNMNNMNN AGCACCACTA TAGGAGAG           48

(2) INFORMATION FOR SEQ ID NO:283:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:283:

CTTGGTCCCT CCGCCGAATA CGCCACTACC CATATACAG                     39

(2) INFORMATION FOR SEQ ID NO:284:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:284:

CTTGGTCCCT CCGCCGAATA CMNNGCCACT ACCCATATAC AG                 42

(2) INFORMATION FOR SEQ ID NO:285:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:285:

CTTGGTCCCT CCGCCGAATA CMNNMNNGCC ACTACCCATA TACAG               45

(2) INFORMATION FOR SEQ ID NO:286:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:286:

CTTGGTCCCT CCGCCGAATA CMNNMNNMNN GCCACTACCC ATATACAG           48

(2) INFORMATION FOR SEQ ID NO:287:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:287:

CTTGGTCCCT CCGCCGAATA CGAAGTTGCT CCCACTGCCA TGGTCTGCCC C          51

(2) INFORMATION FOR SEQ ID NO:288:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:288:

CTTGGTCCCT CCGCCGAATA CMNNGAAGTT GCTCCCACTG CCATGGTCTG CCCC      54

(2) INFORMATION FOR SEQ ID NO:289:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:289:

CTTGGTCCCT CCGCCGAATA CAGTGCTGCT GTCCCACGCC TGACAGTA             48

(2) INFORMATION FOR SEQ ID NO:290:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:290:

CTTGGTCCCT CCGCCGAATA CMNNAGTGCT GCTGTCCCAC GCCTGACAGT A       51

(2) INFORMATION FOR SEQ ID NO:291:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:291:

CTTGGTCCCT CCGCCGAATA CMNNMNNAGT GCTGCTGTCC CACGCCTGAC AGTA      54

(2) INFORMATION FOR SEQ ID NO:292:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:292:

CTTGGTCCCT CCGCCGAATA CMNNMNNMNN AGTGCTGCTG TCCCACGCCT GACAGTA   57

(2) INFORMATION FOR SEQ ID NO:293:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:293:

CTTGGTCCCT CCGCCGAATA CGACTTGGCC ATCAATCGTG TGGCTCTCTC C        51

(2) INFORMATION FOR SEQ ID NO:294:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:294:

CTTGGTCCCT CCGCCGAATA CMNNGACTTG GCCATCAATC GTGTGGCTCT CTCC     54

(2) INFORMATION FOR SEQ ID NO:295:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:295:

GAATTTTCTG TATGAGG        17

(2) INFORMATION FOR SEQ ID NO:296:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:296:

GTCCTCGCAA CTTGCTCTAG ACAATTTCAC AGTAAGGAGG TTTAACTTGT GAAAAAATTA     60

TTATTCGCAA TT        72

(2) INFORMATION FOR SEQ ID NO:297:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:297:

CCTTGGAAGG CAGCAGC        17

(2) INFORMATION FOR SEQ ID NO:298:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:298:

CAACTGCTCA TCAGATGGCG        20

(2) INFORMATION FOR SEQ ID NO:299:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:299:

GTGGCCTTGT TGGCTTGAAG C                                      21

(2) INFORMATION FOR SEQ ID NO:300:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:300:

GGTGCTCTTG GAGGAGGGTG C                                      21

(2) INFORMATION FOR SEQ ID NO:301:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:301:

GAAATACCTA TTGCCTACGG                                        20

(2) INFORMATION FOR SEQ ID NO:302:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:302:

CAGGAAACAG CTATGAC                                            17

(2) INFORMATION FOR SEQ ID NO:303:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:303:

GCGATGGTTG TTGTCATTGT CGGC                                  24

(2) INFORMATION FOR SEQ ID NO:304:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:304:

Ala Gly Thr Leu
1

(2) INFORMATION FOR SEQ ID NO:305:

(i) SEQUENCE CHARACTERISTICS:
       (A) LENGTH: 4 amino acids
       (B) TYPE: amino acid
       (C) STRANDEDNESS: single
       (D) TOPOLOGY: linear (xi) SEQUENCE DESCRIPTION: SEQ ID NO:305:

Gly Gly Lys Asp
1

(2) INFORMATION FOR SEQ ID NO:306:

(i) SEQUENCE CHARACTERISTICS:
       (A) LENGTH: 4 amino acids
       (B) TYPE: amino acid
       (C) STRANDEDNESS: single
       (D) TOPOLOGY: linear (xi) SEQUENCE DESCRIPTION: SEQ ID NO:306:

Gly Gly Arg Leu
1

(2) INFORMATION FOR SEQ ID NO:307:

(i) SEQUENCE CHARACTERISTICS:
       (A) LENGTH: 4 amino acids
       (B) TYPE: amino acid
       (C) STRANDEDNESS: single
       (D) TOPOLOGY: linear (xi) SEQUENCE DESCRIPTION: SEQ ID NO:307:

Gly Gly Thr Gln
1

(2) INFORMATION FOR SEQ ID NO:308:

(i) SEQUENCE CHARACTERISTICS:
       (A) LENGTH: 4 amino acids
       (B) TYPE: amino acid
       (C) STRANDEDNESS: single
       (D) TOPOLOGY: linear (xi) SEQUENCE DESCRIPTION: SEQ ID NO:308:

His Gly Gln His
1

(2) INFORMATION FOR SEQ ID NO:309:

(i) SEQUENCE CHARACTERISTICS:
       (A) LENGTH: 4 amino acids
       (B) TYPE: amino acid
       (C) STRANDEDNESS: single
       (D) TOPOLOGY: linear (xi) SEQUENCE DESCRIPTION: SEQ ID NO:309:

Lys Gly Ser Glu
1

(2) INFORMATION FOR SEQ ID NO:310:

(i) SEQUENCE CHARACTERISTICS:
       (A) LENGTH: 4 amino acids
       (B) TYPE: amino acid
       (C) STRANDEDNESS: single
       (D) TOPOLOGY: linear (xi) SEQUENCE DESCRIPTION: SEQ ID NO:310:

Lys Gly Trp Ser
1

(2) INFORMATION FOR SEQ ID NO:311:

(i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO:311:

Leu Gly Lys Ala
1

(2) INFORMATION FOR SEQ ID NO:312:

(i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO:312:

Asn Gly Tyr Phe
1

(2) INFORMATION FOR SEQ ID NO:313:

(i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO:313:

Pro Arg Gly Tyr
1

(2) INFORMATION FOR SEQ ID NO:314:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:314:

Met Tyr Met Arg Ser
1               5

(2) INFORMATION FOR SEQ ID NO:315:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:315:

Met Tyr Arg Ser Val
1               5

(2) INFORMATION FOR SEQ ID NO:316:

(i) SEQUENCE CHARACTERISTICS:

```
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:316:

Asn Gly Gly His Val
1               5

(2) INFORMATION FOR SEQ ID NO:317:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:317:

Pro Ala Gly Ser Arg
1               5

(2) INFORMATION FOR SEQ ID NO:318:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:318:

Pro Ala Thr Arg Ser
1               5

(2) INFORMATION FOR SEQ ID NO:319:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:319:

Pro Phe Ala Thr Phe
1               5

(2) INFORMATION FOR SEQ ID NO:320:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:320:

Pro Phe Leu Ala His
1               5

(2) INFORMATION FOR SEQ ID NO:321:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:321:

Pro Leu Gly Ala His
1               5
```

(2) INFORMATION FOR SEQ ID NO:322:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:322:

Pro Met Arg Gly Val
1               5

(2) INFORMATION FOR SEQ ID NO:323:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:323:

Pro Asn Gly Asp Gln
1               5

(2) INFORMATION FOR SEQ ID NO:324:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:324:

Pro Thr Arg Arg
1

(2) INFORMATION FOR SEQ ID NO:325:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:325:

Pro Arg Leu Pro Arg
1               5

(2) INFORMATION FOR SEQ ID NO:326:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:326:

Pro Ser Gly Asn Val
1               5

(2) INFORMATION FOR SEQ ID NO:327:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:327:

Gln Gly Leu Arg Asn
1               5

(2) INFORMATION FOR SEQ ID NO:328:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:328:

Arg Gly His Lys Ala
1               5

(2) INFORMATION FOR SEQ ID NO:329:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:329:

Ser Arg Gly Asp Ser
1               5

(2) INFORMATION FOR SEQ ID NO:330:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:330:

Thr Phe Ser Pro Gln
1               5

(2) INFORMATION FOR SEQ ID NO:331:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:331:

Ser Phe Arg Arg Asn Leu
1               5

(2) INFORMATION FOR SEQ ID NO:332:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:332:

Pro Gly Tyr Arg Gly Thr Arg
1               5

(2) INFORMATION FOR SEQ ID NO:333:

```
    (i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:333:

Arg Ala Ile Asn Gly Gln Arg
1               5

(2) INFORMATION FOR SEQ ID NO:334:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:334:

Arg Arg Gly Ser Thr Arg Tyr
1               5

(2) INFORMATION FOR SEQ ID NO:335:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:335:

Ala Ala Trp Asp Asp Ser Leu Val
1               5

(2) INFORMATION FOR SEQ ID NO:336:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:336:

Met Gln Ser Ile Gln Leu Pro Thr
1               5

(2) INFORMATION FOR SEQ ID NO:337:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:337:

Met Gln Ser Ile Gln Leu Pro Ala Thr
1               5

(2) INFORMATION FOR SEQ ID NO:338:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:338:

Ala Ala Trp Asp Asp Gly Leu Ser Leu Val
```

1               5                   10

(2) INFORMATION FOR SEQ ID NO:339:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:339:

Ala Ala Trp Asp Asp Ser Leu Ser Gly Val
1               5                   10

(2) INFORMATION FOR SEQ ID NO:340:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:340:

Asn Ser Arg Asp Ser Ser Gly Ser Val Arg Val
1               5                   10

(2) INFORMATION FOR SEQ ID NO:341:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:341:

Leu Leu Tyr Tyr Gly Gly Ala Tyr Val
1               5

(2) INFORMATION FOR SEQ ID NO:342:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:342:

Asn Ser Arg Asp Ser Ser Gly Val Ser Arg Val
1               5                   10

(2) INFORMATION FOR SEQ ID NO:343:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:343:

Ala Ala Trp Asp Asp Ser Leu Val
1               5

(2) INFORMATION FOR SEQ ID NO:344:

(i) SEQUENCE CHARACTERISTICS:
        (A) LENGTH: 10 amino acids
        (B) TYPE: amino acid
        (C) STRANDEDNESS: single (D) TOPOLOGY: linear (xi) SEQUENCE DESCRIPTION: SEQ ID NO:344:

Ala Ala Trp Asp Asp Ser Leu Pro Tyr Val
1               5                   10

(2) INFORMATION FOR SEQ ID NO:345:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:345:

Ala Ala Trp Asp Asp Ser Leu Cys Pro Glu Phe Val
1               5                   10

(2) INFORMATION FOR SEQ ID NO:346:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:346:

Ala Ala Trp Asp Asp Ser Leu Ala Trp Phe Val
1               5                   10

(2) INFORMATION FOR SEQ ID NO:347:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:347:

Leu Ala Trp Asp Thr Ser Pro Arg Trp Val
1               5                   10

(2) INFORMATION FOR SEQ ID NO:348:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:348:

Thr Ala Trp Asp Asp Ser Leu Ala Val Val
1               5                   10

(2) INFORMATION FOR SEQ ID NO:349:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:349:

Asn Ser Arg Asp Ser Ser Gly Asn His Arg Val
1               5                   10

(2) INFORMATION FOR SEQ ID NO:350:

```
    (i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:350:

Gln Gln Tyr Gly Ser Ser Gln Arg Thr
1               5

(2) INFORMATION FOR SEQ ID NO:351:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:351:

Ala Ala Trp Asp Asp Ser Leu Arg Leu Val
1               5                   10

(2) INFORMATION FOR SEQ ID NO:352:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:352:

Met Gln Gly Thr His Trp Arg Pro Thr
1               5

(2) INFORMATION FOR SEQ ID NO:353:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:353:

Met Gln Gly Lys His Trp Pro Leu Thr
1               5

(2) INFORMATION FOR SEQ ID NO:354:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:354:

Ala Ala Trp Asp Asp Ser Leu Gly Phe
1               5

(2) INFORMATION FOR SEQ ID NO:355:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:355:
```

```
Met Gln Gly Thr His Arg Arg Ala Thr
1               5
```

(2) INFORMATION FOR SEQ ID NO:356:

(i) SEQUENCE CHARACTERISTICS:
       (A) LENGTH: 9 amino acids
       (B) TYPE: amino acid
       (C) STRANDEDNESS: single
       (D) TOPOLOGY: linear (xi) SEQUENCE DESCRIPTION: SEQ ID NO:356:

```
Met Gln Ala Leu Gln Thr Pro Leu Thr
1               5
```

(2) INFORMATION FOR SEQ ID NO:357:

(i) SEQUENCE CHARACTERISTICS:
       (A) LENGTH: 9 amino acids
       (B) TYPE: amino acid
       (C) STRANDEDNESS: single
       (D) TOPOLOGY: linear (xi) SEQUENCE DESCRIPTION: SEQ ID NO:357:

```
Met Arg Gly Thr His Arg Arg Ala Thr
1               5
```

(2) INFORMATION FOR SEQ ID NO:358:

(i) SEQUENCE CHARACTERISTICS:
       (A) LENGTH: 9 amino acids
       (B) TYPE: amino acid
       (C) STRANDEDNESS: single
       (D) TOPOLOGY: linear (xi) SEQUENCE DESCRIPTION: SEQ ID NO:358:

```
Met Gln Gly Thr His Trp His Pro Thr
1               5
```

(2) INFORMATION FOR SEQ ID NO:359:

(i) SEQUENCE CHARACTERISTICS:
       (A) LENGTH: 8 amino acids
       (B) TYPE: amino acid
       (C) STRANDEDNESS: single
       (D) TOPOLOGY: linear (xi) SEQUENCE DESCRIPTION: SEQ ID NO:359:

```
Met Gln Ala Leu Gln Ser Pro Thr
1               5
```

(2) INFORMATION FOR SEQ ID NO:360:

(i) SEQUENCE CHARACTERISTICS:
       (A) LENGTH: 9 amino acids
       (B) TYPE: amino acid
       (C) STRANDEDNESS: single
       (D) TOPOLOGY: linear (xi) SEQUENCE DESCRIPTION: SEQ ID NO:360:

```
Met Gln Gly Thr His Arg Arg Ala Thr
1               5
```

(2) INFORMATION FOR SEQ ID NO:361:

(i) SEQUENCE CHARACTERISTICS:
       (A) LENGTH: 10 amino acids
       (B) TYPE: amino acid

```
        (C) STRANDEDNESS: single
        (D) TOPOLOGY: linear (xi) SEQUENCE DESCRIPTION: SEQ ID NO:361:

Ala Ala Trp Asp Asp Ser Leu Ala Phe Val
1               5                   10

(2) INFORMATION FOR SEQ ID NO:362:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:362:

Met Gln Ala Leu Gln Thr Pro Thr
1               5

(2) INFORMATION FOR SEQ ID NO:363:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:363:

Gln Gln Ser Tyr Ser Thr Arg Thr
1               5

(2) INFORMATION FOR SEQ ID NO:364:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:364:

Met Gln Gly Thr His Trp Pro Phe Thr
1               5

(2) INFORMATION FOR SEQ ID NO:365:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:365:

Met Gln Ala Leu Gln Thr Pro Leu Thr
1               5

(2) INFORMATION FOR SEQ ID NO:366:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:366:

Met Gln Gly Thr His Trp Pro Ala Thr
1               5
```

(2) INFORMATION FOR SEQ ID NO:367:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:367:

```
Ala Ala Trp Asp Asp Ser Leu Arg Ser Val
1               5                  10
```

(2) INFORMATION FOR SEQ ID NO:368:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:368:

```
Ala Ala Trp Asp Asp Ser Leu Leu Val
1               5
```

(2) INFORMATION FOR SEQ ID NO:369:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:369:

```
Asp Ser Trp Asp Asn Ser Leu Val Ser Pro Val
1               5                  10
```

(2) INFORMATION FOR SEQ ID NO:370:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:370:

```
Met Gln Ala Leu Gln Ser Pro Thr
1               5
```

(2) INFORMATION FOR SEQ ID NO:371:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:371:

```
Met Gln Ser Ile Gln Leu Pro Thr
1               5
```

(2) INFORMATION FOR SEQ ID NO:372:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:372:

```
Met Gln Ala Leu Gln Ser Pro Ala Thr
1               5
```

(2) INFORMATION FOR SEQ ID NO:373:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:373:

```
Met Gln Ala Leu Gln Thr Pro Val Thr
1               5
```

(2) INFORMATION FOR SEQ ID NO:374:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:374:

```
Ala Ala Trp Asp Asp Ser Leu Ser Ala Tyr Val
1               5                   10
```

(2) INFORMATION FOR SEQ ID NO:375:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:375:

```
Asn Ser Arg Asp Ser Ser Gly Arg Asx Asn Val
1               5                   10
```

(2) INFORMATION FOR SEQ ID NO:376:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:376:

```
Met Gln Ala Leu Arg Thr Arg Thr
1               5
```

(2) INFORMATION FOR SEQ ID NO:377:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:377:

```
Val Asn Ser Arg Phe Ala Thr
1               5
```

(2) INFORMATION FOR SEQ ID NO:378:

(i) SEQUENCE CHARACTERISTICS:
        (A) LENGTH: 8 amino acids (B) TYPE: amino acid
        (C) STRANDEDNESS: single
        (D) TOPOLOGY: linear (xi) SEQUENCE DESCRIPTION: SEQ ID NO:378:

Ile Lys Phe Arg Ser Ser Ser Ile
1               5

(2) INFORMATION FOR SEQ ID NO:379:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:379:

Ser Phe Ala Lys Ala Phe Asp Tyr
1               5

(2) INFORMATION FOR SEQ ID NO:380:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:380:

Ser Lys Arg Thr Ser Phe Asp Tyr
1               5

(2) INFORMATION FOR SEQ ID NO:381:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:381:

Ser Leu Phe Ser Lys Phe Asp Tyr
1               5

(2) INFORMATION FOR SEQ ID NO:382:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:382:

Ser Val Leu Ser Leu Phe Asp Tyr
1               5

(2) INFORMATION FOR SEQ ID NO:383:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:383:

Ser Tyr Met Arg Gly Met Arg Asn
1               5

(2) INFORMATION FOR SEQ ID NO:384:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:384:

His Arg Arg Ala Tyr Tyr Met Ile Pro
1          5

(2) INFORMATION FOR SEQ ID NO:385:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:385:

Ile Gly Lys Leu Ser Gln Pro Thr Ser
1          5

(2) INFORMATION FOR SEQ ID NO:386:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:386:

Arg Ser Gly Val Arg Met Leu Ile Asp
1          5

(2) INFORMATION FOR SEQ ID NO:387:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:387:

Lys Trp Gly Gly
1

(2) INFORMATION FOR SEQ ID NO:388:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:388:

Gly Thr Gly Leu Asp Gly
1          5

(2) INFORMATION FOR SEQ ID NO:389:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:389:

Lys Phe Gly Asn Asn Met
1               5

(2) INFORMATION FOR SEQ ID NO:390:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:390:

Ala Ser Ser Pro Phe Val Leu Gln
1               5

(2) INFORMATION FOR SEQ ID NO:391:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:391:

Tyr Lys Ser Leu Ser Phe Asp Tyr
1               5

(2) INFORMATION FOR SEQ ID NO:392:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO:392:

Ala Ala Asn Tyr Ser Lys Ala His Ile
1               5

(2) INFORMATION FOR SEQ ID NO:393:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO:393:

Arg Ser Trp Asp Gly Gly Met Val Asp
1               5

(2) INFORMATION FOR SEQ ID NO:394:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO:394:

Ser Lys Leu Trp Val Thr Phe Asp Tyr
1               5

(2) INFORMATION FOR SEQ ID NO:395:

(i) SEQUENCE CHARACTERISTICS:

```
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:395:

Ala Lys Gln Ser Gly Val Glu Cys Leu Thr
1               5                   10

(2) INFORMATION FOR SEQ ID NO:396:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:396:

Ser Lys Tyr Pro Leu Ala Trp Thr Leu Ser
1               5                   10

(2) INFORMATION FOR SEQ ID NO:397:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:397:

Ala Leu Arg Arg
1

(2) INFORMATION FOR SEQ ID NO:398:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:398:

Gly Gly Arg Val
1

(2) INFORMATION FOR SEQ ID NO:399:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:399:

Ile Gly Gln Phe
1

(2) INFORMATION FOR SEQ ID NO:400:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:400:

Lys Ala Lys Thr
1
```

(2) INFORMATION FOR SEQ ID NO:401:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:401:

Lys Ser Ala Ile
1

(2) INFORMATION FOR SEQ ID NO:402:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:402:

Lys Ser Arg Trp
1

(2) INFORMATION FOR SEQ ID NO:403:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:403:

Lys Ser Thr Val
1

(2) INFORMATION FOR SEQ ID NO:404:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:404:

Leu Asn Arg Lys
1

(2) INFORMATION FOR SEQ ID NO:405:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:405:

Arg His Gly Ser
1

(2) INFORMATION FOR SEQ ID NO:406:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:406:

Arg Lys Arg His
1

(2) INFORMATION FOR SEQ ID NO:407:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:407:

Arg Ser Lys Thr
1

(2) INFORMATION FOR SEQ ID NO:408:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:408:

Arg Trp Ser Phe
1

(2) INFORMATION FOR SEQ ID NO:409:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:409:

Ala Lys Phe Arg Leu
1               5

(2) INFORMATION FOR SEQ ID NO:410:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:410:

Ala Tyr His Gly Arg
1               5

(2) INFORMATION FOR SEQ ID NO:411:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:411:

Gly Lys Val Leu Gly
1               5

(2) INFORMATION FOR SEQ ID NO:412:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:412:

Gly Ser Ser Arg Thr
1               5

(2) INFORMATION FOR SEQ ID NO:413:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:413:

Lys Arg Met Asp Gly
1               5

(2) INFORMATION FOR SEQ ID NO:414:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:414:

Leu Lys Arg Gly His
1               5

(2) INFORMATION FOR SEQ ID NO:415:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:415:

Leu Arg Arg Glu Tyr
1               5

(2) INFORMATION FOR SEQ ID NO:416:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:416:

Arg Ala Gly Arg Asp
1               5

(2) INFORMATION FOR SEQ ID NO:417:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:417:

Leu Lys Ser Ala Tyr Lys

```
1               5

(2) INFORMATION FOR SEQ ID NO:418:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:418:

Leu Asn Val Arg Pro Lys
1               5

(2) INFORMATION FOR SEQ ID NO:419:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:419:

Ser Arg Gly Lys Ser Met
1               5

(2) INFORMATION FOR SEQ ID NO:420:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:420:

Ile Arg Phe Arg Asn Ala Thr
1               5

(2) INFORMATION FOR SEQ ID NO:421:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:421:

Leu Lys Thr Ser Thr Pro Val
1               5

(2) INFORMATION FOR SEQ ID NO:422:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:422:

Leu Ser Arg Ala Phe Thr Met
1               5

(2) INFORMATION FOR SEQ ID NO:423:

(i) SEQUENCE CHARACTERISTICS:
        (A) LENGTH: 8 amino acids
        (B) TYPE: amino acid
        (C) STRANDEDNESS: single
```

```
        (D) TOPOLOGY: linear (xi) SEQUENCE DESCRIPTION: SEQ ID NO:423:

Ala Gln Arg Lys Tyr Phe Asp Tyr
1               5

(2) INFORMATION FOR SEQ ID NO:424:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:424:

Asn Ser Arg Asp Ser Ser Gly Val Ser Arg Val
1               5                   10

(2) INFORMATION FOR SEQ ID NO:425:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:425:

Met Gln Gly Thr His Trp Pro Phe Thr
1               5

(2) INFORMATION FOR SEQ ID NO:426:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:426:

Ala Ala Trp Asp Asp Ser Leu Pro Tyr Val
1               5                   10

(2) INFORMATION FOR SEQ ID NO:427:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:427:

Asn Ser Arg Asp Ser Ser Gly Ser Val Arg Val
1               5                   10

(2) INFORMATION FOR SEQ ID NO:428:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:428:

Met Gln Gly Thr His Trp His Pro Thr
1               5

(2) INFORMATION FOR SEQ ID NO:429:
```

(i) SEQUENCE CHARACTERISTICS:
            (A) LENGTH: 11 amino acids
            (B) TYPE: amino acid
            (C) STRANDEDNESS: single
            (D) TOPOLOGY: linear (xi) SEQUENCE DESCRIPTION: SEQ ID NO:429:

Ala Ala Trp Asp Asp Ser Leu Phe Tyr Pro Val
1               5                   10

(2) INFORMATION FOR SEQ ID NO:430:

(i) SEQUENCE CHARACTERISTICS:
            (A) LENGTH: 11 amino acids
            (B) TYPE: amino acid
            (C) STRANDEDNESS: single
            (D) TOPOLOGY: linear (xi) SEQUENCE DESCRIPTION: SEQ ID NO:430:

Asn Ser Arg Asp Ser Ser Gly Asn His Arg Val
1               5                   10

(2) INFORMATION FOR SEQ ID NO:431:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO:431:

Met Gln Gly Thr His Trp Pro Val Thr
1               5

(2) INFORMATION FOR SEQ ID NO:432:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO:432:

Met Gln Gly Thr His Trp Arg Pro Thr
1               5

(2) INFORMATION FOR SEQ ID NO:433:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:433:

Met Gln Gly Thr His Trp Arg Thr
1               5

(2) INFORMATION FOR SEQ ID NO:434:

(i) SEQUENCE CHARACTERISTICS:
            (A) LENGTH: 11 amino acids
            (B) TYPE: amino acid
            (C) STRANDEDNESS: single
            (D) TOPOLOGY: linear (xi) SEQUENCE DESCRIPTION: SEQ ID NO:434:

```
Ala Ala Trp Asp Asp Ser Leu Leu Gly Ser Val
1               5                   10
```

(2) INFORMATION FOR SEQ ID NO:435:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:435:

```
Cys Ser Tyr Ala Gly Ser Ser Tyr Val
1               5
```

(2) INFORMATION FOR SEQ ID NO:436:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:436:

```
Gln Gln Asp Tyr Asn Leu Leu Thr
1               5
```

(2) INFORMATION FOR SEQ ID NO:437:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:437:

```
Val Leu Tyr Met Gly Ser Gly Ser Ala Val
1               5                   10
```

(2) INFORMATION FOR SEQ ID NO:438:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:438:

```
Met Gln Arg Ile Glu Phe Pro Asn Thr
1               5
```

(2) INFORMATION FOR SEQ ID NO:439:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:439:

```
Ala Ala Trp Asp Asp Ser Leu Ala Cys Ala Val
1               5                   10
```

(2) INFORMATION FOR SEQ ID NO:440:

(i) SEQUENCE CHARACTERISTICS:
        (A) LENGTH: 8 amino acids
        (B) TYPE: amino acid

```
        (C) STRANDEDNESS: single
        (D) TOPOLOGY: linear (xi) SEQUENCE DESCRIPTION: SEQ ID NO:440:

Gln Gln Ala Asn Ser Phe Arg Thr
1               5

(2) INFORMATION FOR SEQ ID NO:441:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:441:

Ala Ala Trp Asp Asp Ser Leu Ser Arg Pro Val
1               5                   10

(2) INFORMATION FOR SEQ ID NO:442:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:442:

Ala Ala Trp Asp Asp Ser Leu Tyr Asn Val
1               5                   10

(2) INFORMATION FOR SEQ ID NO:443:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:443:

Ala Ala Trp Asp Asp Ser Leu Asn Arg Asn Val
1               5                   10

(2) INFORMATION FOR SEQ ID NO:444:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:444:

Met Gln Val Leu Gln Thr Arg Thr
1               5

(2) INFORMATION FOR SEQ ID NO:445:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:445:

Met Gln Ala Leu Gln Thr Arg Thr
1               5
```

(2) INFORMATION FOR SEQ ID NO:446:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:446:

Ala Ala Trp Asp Asp Ser Leu Ala Phe Val
1               5                   10

(2) INFORMATION FOR SEQ ID NO:447:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:447:

Met Gln Ala Leu Gln Thr Arg Thr
1               5

(2) INFORMATION FOR SEQ ID NO:448:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:448:

Gln Gln Ser Tyr Ser Thr Arg Met
1               5

(2) INFORMATION FOR SEQ ID NO:449:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:449:

Met Gln Ala Leu Arg Thr Arg Thr
1               5

(2) INFORMATION FOR SEQ ID NO:450:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:450:

Met Gln Ala Leu Gln Thr Leu Thr
1               5

(2) INFORMATION FOR SEQ ID NO:451:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:451:

```
Ala Ala Trp Asp Asp Ser Leu Val
1               5
```

(2) INFORMATION FOR SEQ ID NO:452:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:452:

```
Met Gln Ala Leu Gln Thr Pro Thr
1               5
```

(2) INFORMATION FOR SEQ ID NO:453:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:453:

```
Met Arg Ala Leu Gln Thr Pro Thr
1               5
```

(2) INFORMATION FOR SEQ ID NO:454:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:454:

```
Ala Ala Trp Asp Asp Ser Leu Pro Gly Tyr Val
1               5                   10
```

(2) INFORMATION FOR SEQ ID NO:455:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:455:

```
Ala Ala Trp Asp Asp Ser Leu Gly Phe Val
1               5                   10
```

(2) INFORMATION FOR SEQ ID NO:456:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:456:

```
Met Gln Ala Leu Arg Thr Arg Thr
1               5
```

(2) INFORMATION FOR SEQ ID NO:457:

(i) SEQUENCE CHARACTERISTICS:
        (A) LENGTH: 10 amino acids (B) TYPE: amino acid
        (C) STRANDEDNESS: single
        (D) TOPOLOGY: linear (xi) SEQUENCE DESCRIPTION: SEQ ID NO:457:

Ala Ala Trp Asp Asp Ser Leu Phe Leu Val
1               5                  10

(2) INFORMATION FOR SEQ ID NO:458:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:458:

Met Gln Ala Leu Gln Thr Pro Thr
1               5

(2) INFORMATION FOR SEQ ID NO:459:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:459:

Met Gln Ala Leu Arg Thr Arg Thr
1               5

(2) INFORMATION FOR SEQ ID NO:460:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:460:

Met Arg Ala Leu Gln Thr Pro Thr
1               5

(2) INFORMATION FOR SEQ ID NO:461:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:461:

Met Gln Ala Leu Gln Thr Arg Thr
1               5

(2) INFORMATION FOR SEQ ID NO:462:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:462:

Met Gln Ser Ile Gln Leu Arg Thr
1               5

(2) INFORMATION FOR SEQ ID NO:463:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:463:

Asp Leu Arg Lys His Phe Asp Tyr
1          5

(2) INFORMATION FOR SEQ ID NO:464:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:464:

Asp Arg Trp Arg Val Phe Asp Tyr
1          5

(2) INFORMATION FOR SEQ ID NO:465:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:465:

Lys Gly Leu Arg Leu Phe Asp Tyr
1          5

(2) INFORMATION FOR SEQ ID NO:466:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:466:

Lys Lys Tyr Gln Ser Ala Ala Arg
1          5

(2) INFORMATION FOR SEQ ID NO:467:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:467:

Lys Thr Arg Arg Arg Phe Asp Tyr
1          5

(2) INFORMATION FOR SEQ ID NO:468:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:468:

Pro Tyr Ala Lys Arg Phe Asp Tyr
1               5

(2) INFORMATION FOR SEQ ID NO:469:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:469:

Arg Phe Ala Arg Ser Phe Asp Tyr
1               5

(2) INFORMATION FOR SEQ ID NO:470:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:470:

Arg Ser Phe Val Gly Tyr Glu Ile
1               5

(2) INFORMATION FOR SEQ ID NO:471:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:471:

Arg Trp Gly Arg Thr Phe Asp Tyr
1               5

(2) INFORMATION FOR SEQ ID NO:472:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:472:

Ser Gln Lys Arg Leu Ile Thr Gly
1               5

(2) INFORMATION FOR SEQ ID NO:473:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:473:

Ser Arg Lys Arg Ala Phe Asp Tyr
1               5

(2) INFORMATION FOR SEQ ID NO:474:

(i) SEQUENCE CHARACTERISTICS:

```
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:474:

Ser Trp Val Ser Gly Phe Asp Tyr
1               5

(2) INFORMATION FOR SEQ ID NO:475:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:475:

Ser Tyr His Arg Thr Phe Asp Tyr
1               5

(2) INFORMATION FOR SEQ ID NO:476:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:476:

Thr His Ser Lys Thr Phe Asp Tyr
1               5

(2) INFORMATION FOR SEQ ID NO:477:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:477:

Thr Arg Ser Ser Ser Tyr Gly Glu
1               5

(2) INFORMATION FOR SEQ ID NO:478:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:478:

Trp Ser Arg Glu Thr Asn Tyr Ser
1               5

(2) INFORMATION FOR SEQ ID NO:479:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:479:

Arg Thr Arg Gly Ala Leu Pro Arg Asn
1               5
```

(2) INFORMATION FOR SEQ ID NO:480:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:480:

Tyr Arg Phe Ser Ala Pro Pro Arg Asp
1               5

(2) INFORMATION FOR SEQ ID NO:481:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:481:

Arg Phe Asn Arg Leu Ser Pro Arg Arg Ala
1               5                   10

(2) INFORMATION FOR SEQ ID NO:482:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:482:

Ser Ser Val Met Gly Arg Val Pro Val Met
1               5                   10

(2) INFORMATION FOR SEQ ID NO:483:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:483:

Thr Ser Gly Lys Leu His Ser Pro Arg Thr
1               5                   10

(2) INFORMATION FOR SEQ ID NO:484:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:484:

Gly Arg Gly Arg Pro Ser Met Ala Tyr Asp Val
1               5                   10

(2) INFORMATION FOR SEQ ID NO:485:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:485:

Arg Ser Gly Val Ser Arg Lys Val Tyr Thr Ile
1               5                   10

(2) INFORMATION FOR SEQ ID NO:486:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:486:

Met Thr Pro Gln Phe Phe Asp Tyr
1               5

(2) INFORMATION FOR SEQ ID NO:487:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:487:

Ser Ala Tyr Ser Tyr Phe Asp Tyr
1               5

(2) INFORMATION FOR SEQ ID NO:488:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:488:

Asp Ser Gly Leu Gly Asp Pro Ala Leu
1               5

(2) INFORMATION FOR SEQ ID NO:489:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:489:

Asp Ser Gly Leu Gly Glu Pro Ala Leu
1               5

(2) INFORMATION FOR SEQ ID NO:490:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:490:

Glu Ser Gly Leu Gly Asp Pro Ala Leu
1               5

(2) INFORMATION FOR SEQ ID NO:491:

(i) SEQUENCE CHARACTERISTICS:
    (A) LENGTH: 9 amino acids
    (B) TYPE: amino acid
    (C) STRANDEDNESS: single
    (D) TOPOLOGY: linear (xi) SEQUENCE DESCRIPTION: SEQ ID NO:491:

Thr Ser Arg Leu Lys Ala His Pro Ser
1               5

(2) INFORMATION FOR SEQ ID NO:492:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:492:

Thr Ser Arg Leu Glu Ala His Pro Arg
1               5

(2) INFORMATION FOR SEQ ID NO:493:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:493:

Thr Ser Arg Leu Lys Ala His Pro Ser
1               5

(2) INFORMATION FOR SEQ ID NO:494:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:494:

Gly Arg Gln Ser Arg Leu
1               5

(2) INFORMATION FOR SEQ ID NO:495:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:495:

Lys Phe Pro His Phe Gly Asp
1               5

(2) INFORMATION FOR SEQ ID NO:496:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:496:

Gln Gln Ser Tyr Ser Thr Arg Thr 1               5

(2) INFORMATION FOR SEQ ID NO:497:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:497:

Ala Ala Trp Asp Asp Ser Leu Ser Ile Val
1               5                   10

(2) INFORMATION FOR SEQ ID NO:498:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:498:

Ala Ala Trp Asp Asp Ser Leu Val
1               5

(2) INFORMATION FOR SEQ ID NO:499:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:499:

Met Gln Gly Thr His Trp Pro Thr
1               5

(2) INFORMATION FOR SEQ ID NO:500:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:500:

Met Gln Ala Leu His Thr Arg Thr
1               5

(2) INFORMATION FOR SEQ ID NO:501:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:501:

Met Gln Ala Leu Gln Thr Arg Thr
1               5

(2) INFORMATION FOR SEQ ID NO:502:

(i) SEQUENCE CHARACTERISTICS:
        (A) LENGTH: 9 amino acids
        (B) TYPE: amino acid
        (C) STRANDEDNESS: single (D) TOPOLOGY: linear (xi) SEQUENCE DESCRIPTION: SEQ ID NO:502:

Asn Ser Arg Asp Ser Ser Gly Ser Val
1               5

(2) INFORMATION FOR SEQ ID NO:503:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:503:

Gln Gln Tyr Gly Ser Ser Pro Tyr Thr
1               5

(2) INFORMATION FOR SEQ ID NO:504:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:504:

Gln Gln Ser Tyr Ser Thr Arg Thr
1               5

(2) INFORMATION FOR SEQ ID NO:505:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:505:

Gln Gln Ala Asn Ser Phe Ala Ala Thr
1               5

(2) INFORMATION FOR SEQ ID NO:506:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:506:

Gln Gln Ala Asn Ser Phe Pro Ala Thr
1               5

(2) INFORMATION FOR SEQ ID NO:507:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:507:

Val Leu Tyr Met Gly Ser Gly Val Tyr Val
1               5                   10

(2) INFORMATION FOR SEQ ID NO:508:

```
        (i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:508:

Met Gln Ala Leu Arg Thr Arg Thr
1               5

(2) INFORMATION FOR SEQ ID NO:509:

(i) SEQUENCE CHARACTERISTICS:
            (A) LENGTH: 11 amino acids
            (B) TYPE: amino acid
            (C) STRANDEDNESS: single
            (D) TOPOLOGY: linear (xi) SEQUENCE DESCRIPTION: SEQ ID NO:509:

Ala Ala Trp Asp Asp Ser Leu Trp Ser Ala Val
1               5                   10

(2) INFORMATION FOR SEQ ID NO:510:

(i) SEQUENCE CHARACTERISTICS:
            (A) LENGTH: 12 amino acids
            (B) TYPE: amino acid
            (C) STRANDEDNESS: single
            (D) TOPOLOGY: linear (xi) SEQUENCE DESCRIPTION: SEQ ID NO:510:

Ala Ala Trp Asp Asp Ser Leu Pro Arg Arg Leu Val
1               5                   10

(2) INFORMATION FOR SEQ ID NO:511:

(i) SEQUENCE CHARACTERISTICS:
            (A) LENGTH: 11 amino acids
            (B) TYPE: amino acid
            (C) STRANDEDNESS: single
            (D) TOPOLOGY: linear (xi) SEQUENCE DESCRIPTION: SEQ ID NO:511:

Ala Ala Trp Asp Asp Ser Leu Pro Ser Gly Val
1               5                   10

(2) INFORMATION FOR SEQ ID NO:512:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:512:

Met Gln Ala Leu Gln Thr Arg Thr
1               5

(2) INFORMATION FOR SEQ ID NO:513:

(i) SEQUENCE CHARACTERISTICS:
            (A) LENGTH: 10 amino acids
            (B) TYPE: amino acid
            (C) STRANDEDNESS: single
            (D) TOPOLOGY: linear (xi) SEQUENCE DESCRIPTION: SEQ ID NO:513:
```

```
Ala Ala Trp Asp Asp Gly Leu Leu Arg Val
1               5                   10

(2) INFORMATION FOR SEQ ID NO:514:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:514:

Ala Ala Trp Asp Asp Ser Leu Ala Leu Val
1               5                   10

(2) INFORMATION FOR SEQ ID NO:515:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:515:

Met Arg Ala Leu Gln Thr Pro Thr
1               5

(2) INFORMATION FOR SEQ ID NO:516:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:516:

Asn Ser Arg Asp Ser Ser Gly Phe Gln Leu Val
1               5                   10

(2) INFORMATION FOR SEQ ID NO:517:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:517:

Ser Ser Tyr Thr Ser Ser Ser Thr Leu Val
1               5                   10

(2) INFORMATION FOR SEQ ID NO:518:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:518:

Ser Ser Tyr Thr Ser Ser Ser Thr Leu Gly
1               5                   10

(2) INFORMATION FOR SEQ ID NO:519:

(i) SEQUENCE CHARACTERISTICS:
        (A) LENGTH: 9 amino acids
        (B) TYPE: amino acid
```

```
            (C) STRANDEDNESS: single
            (D) TOPOLOGY: linear (xi) SEQUENCE DESCRIPTION: SEQ ID NO:519:

Gln Ser Tyr Asp Ser Asn Leu Arg Val
1               5

(2) INFORMATION FOR SEQ ID NO:520:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:520:

Met Arg Ala Leu Gln Thr Pro Thr
1               5

(2) INFORMATION FOR SEQ ID NO:521:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:521:

Gln Gln Leu Asn Ser Tyr Pro Thr
1               5

(2) INFORMATION FOR SEQ ID NO:522:

(i) SEQUENCE CHARACTERISTICS:
            (A) LENGTH: 11 amino acids
            (B) TYPE: amino acid
            (C) STRANDEDNESS: single
            (D) TOPOLOGY: linear (xi) SEQUENCE DESCRIPTION: SEQ ID NO:522:

Asn Ser Arg Asp Ser Ser Gly Phe Gln Leu Val
1               5                   10

(2) INFORMATION FOR SEQ ID NO:523:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO:523:

Gln Gln Ala Asn Ser Phe Pro Ile Thr
1               5

(2) INFORMATION FOR SEQ ID NO:524:

(i) SEQUENCE CHARACTERISTICS:
            (A) LENGTH: 8 amino acids
            (B) TYPE: amino acid
            (C) STRANDEDNESS: single
            (D) TOPOLOGY: linear (xi) SEQUENCE DESCRIPTION: SEQ ID NO:524:

Gln Gln Leu Asn Ser Tyr Pro Thr
1               5
```

```
(2) INFORMATION FOR SEQ ID NO:525:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:525:

Pro Leu Asn Ser Lys Lys Asn Thr Thr Thr Gln
1               5                   10

(2) INFORMATION FOR SEQ ID NO:526:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:526:

Trp Ser Arg Glu Thr Asn Tyr Ser
1               5

(2) INFORMATION FOR SEQ ID NO:527:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:527:

Ala Ser Ser Pro Phe Val Leu Gln
1               5

(2) INFORMATION FOR SEQ ID NO:528:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:528:

Met Gln Ser Ile Gln Leu Pro Thr
1               5

(2) INFORMATION FOR SEQ ID NO:529:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:529:

Met Gln Ser Ile Gln Leu Pro Ala Thr
1               5

(2) INFORMATION FOR SEQ ID NO:530:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:530:
```

```
Ala Ala Trp Asp Asp Ser Leu Phe Tyr Val
1               5                   10
```

(2) INFORMATION FOR SEQ ID NO:531:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:531:

```
Pro Trp Ala Arg Gly Thr Asp
1               5
```

(2) INFORMATION FOR SEQ ID NO:532:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:532:

```
Asn Tyr Asn Ala Ala Phe Asp Tyr
1               5
```

(2) INFORMATION FOR SEQ ID NO:533:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:533:

```
Ser Gly Val Arg Gly Leu Met Thr
1               5
```

(2) INFORMATION FOR SEQ ID NO:534:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:534:

```
Gln Gln Tyr Asn Asn Trp Leu Ser Thr
1               5
```

(2) INFORMATION FOR SEQ ID NO:535:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:535:

```
Val Leu Tyr Met Gly Ser Gly His Arg Val
1               5                   10
```

(2) INFORMATION FOR SEQ ID NO:536:

(i) SEQUENCE CHARACTERISTICS:
        (A) LENGTH: 56 base pairs (B) TYPE: nucleic acid
        (C) STRANDEDNESS: single
        (D) TOPOLOGY: linear (xi) SEQUENCE DESCRIPTION: SEQ ID NO:536:

GTCCTCGCAA CTGCGGCCCA GCCGGCCATG GCCCAGRTGC AGCTGGTGCA RTCTGG        56

(2) INFORMATION FOR SEQ ID NO:537:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:537:

GTCCTCGCAA CTGCGGCCCA GCCGGCCATG GCCSAGGTCC AGCTGGTRCA GTCTGG        56

(2) INFORMATION FOR SEQ ID NO:538:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:538:

GTCCTCGCAA CTGCGGCCCA GCCGGCCATG GCCCAGRTCA CCTTGAAGGA GTCTGG        56

(2) INFORMATION FOR SEQ ID NO:539:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:539:

GTCCTCGCAA CTGCGGCCCA GCCGGCCATG GCCSAGGTGC AGCTGGTGGA GTCTGG        56

(2) INFORMATION FOR SEQ ID NO:540:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:540:

GTCCTCGCAA CTGCGGCCCA GCCGGCCATG GCCGAGGTGC AGCTGGTGGA GWCYGG        56

(2) INFORMATION FOR SEQ ID NO:541:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:541:

GTCCTCGCAA CTGCGGCCCA GCCGGCCATG GCCCAGGTGC AGCTACAGCA GTGGGG        56

(2) INFORMATION FOR SEQ ID NO:542:

(i) SEQUENCE CHARACTERISTICS:
        (A) LENGTH: 56 base pairs
        (B) TYPE: nucleic acid

```
        (C) STRANDEDNESS: single
        (D) TOPOLOGY: linear (xi) SEQUENCE DESCRIPTION: SEQ ID NO:542:

GTCCTCGCAA CTGCGGCCCA GCCGGCCATG GCCCAGSTGC AGCTGCAGGA GTCSGG      56

(2) INFORMATION FOR SEQ ID NO:543:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:543:

GTCCTCGCAA CTGCGGCCCA GCCGGCCATG GCCGARGTGC AGCTGGTGCA GTCTGG      56

(2) INFORMATION FOR SEQ ID NO:544:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:544:

GTCCTCGCAA CTGCGGCCCA GCCGGCCATG GCCCAGGTAC AGCTGCAGCA GTCAGG      56

(2) INFORMATION FOR SEQ ID NO:545:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:545:

ACCGCCTCCA CCACTCGAGA CGGTGACCAG GGTGCCYYKG CCCCA                  45

(2) INFORMATION FOR SEQ ID NO:546:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:546:

ACCGCCTCCA CCACTCGAGA CGGTGACCAT TGTCCCYYKG CCCCA                  45

(2) INFORMATION FOR SEQ ID NO:547:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:547:

ACCGCCTCCA CCACTCGAGA CGGTGACCAG GGTTCCYYKG CCCCA                  45

(2) INFORMATION FOR SEQ ID NO:548:

(i) SEQUENCE CHARACTERISTICS:
        (A) LENGTH: 45 base pairs
        (B) TYPE: nucleic acid
        (C) STRANDEDNESS: single
```

(D) TOPOLOGY: linear (xi) SEQUENCE DESCRIPTION: SEQ ID NO:548:

ACCGCCTCCA CCACTCGAGA CGGTGACCGT GGTCCCYYKC CCCCA        45

(2) INFORMATION FOR SEQ ID NO:549:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO:549:

GTCCTCGCAA CTGCGGCCCA GCCGGCCATG GCC        33

(2) INFORMATION FOR SEQ ID NO:550:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:550:

GACATCCAGW TGACCCAGTC TCC        23

(2) INFORMATION FOR SEQ ID NO:551:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:551:

GATGTTGTGA TGACTCAGTC TCC        23

(2) INFORMATION FOR SEQ ID NO:552:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:552:

GAAATTGTGW TGACRCAGTC TCC        23

(2) INFORMATION FOR SEQ ID NO:553:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:553:

GATATTGTGA TGACCCACAC TCC        23

(2) INFORMATION FOR SEQ ID NO:554:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:554:

GAAACGACAC TCACGCAGTC TCC                                                         23

(2) INFORMATION FOR SEQ ID NO:555:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:555:

GAAATTGTGC TGACTCAGTC TCC                                                         23

(2) INFORMATION FOR SEQ ID NO:556:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:556:

ACACTCTCCC CTGTTGAAGC TCTT                                                        24

(2) INFORMATION FOR SEQ ID NO:557:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (xi) SEQUENCE DESCRIPTION: SEQ ID NO:557:

ACCGCCTCCA CCAGTGCACT TGACATCCAG WTGACCCAGT CTCC                                  44

(2) INFORMATION FOR SEQ ID NO:558:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (xi) SEQUENCE DESCRIPTION: SEQ ID NO:558:

ACCGCCTCCA CCAGTGCACT TGATGTTGTG ATGACTCAGT CTCC                                  44

(2) INFORMATION FOR SEQ ID NO:559:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (xi) SEQUENCE DESCRIPTION: SEQ ID NO:559:

ACCGCCTCCA CCAGTGCACT TGAAATTGTG WTGACRCAGT CTCC                                  44

(2) INFORMATION FOR SEQ ID NO:560:

(i) SEQUENCE CHARACTERISTICS:
            (A) LENGTH: 44 base pairs
            (B) TYPE: nucleic acid
            (C) STRANDEDNESS: single
            (D) TOPOLOGY: linear

```
    (xi) SEQUENCE DESCRIPTION: SEQ ID NO:560:

ACCGCCTCCA CCAGTGCACT TGATATTGTG ATGACCCAGA CTCC                44

(2) INFORMATION FOR SEQ ID NO:561:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:561:

ACCGCCTCCA CCAGTGCACT TGAAACGACA CTCACGCAGT CTCC                44

(2) INFORMATION FOR SEQ ID NO:562:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:562:

ACCGCCTCCA CCAGTGCACT TGAAATTGTG CTGACTCAGT CTCC                44

(2) INFORMATION FOR SEQ ID NO:563:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:563:

ACCGCCTCCA CCGGGCGCGC CTTATTAACA CTCTCCCCTG TTGAAGCTCT T         51

(2) INFORMATION FOR SEQ ID NO:564:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:564:

ACCGCCTCCA CCAGTGCA                                             18

(2) INFORMATION FOR SEQ ID NO:565:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:565:

GAGTCATTCT CGACTTGCGG CCGCACCGCC TCCACCGGGC GCGCCTTATT A         51

(2) INFORMATION FOR SEQ ID NO:566:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:566:
```

```
CAGTCTGTGC TGACTCAGCC ACC                                              23

(2) INFORMATION FOR SEQ ID NO:567:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:567:

CAGTCTGTGY TGACGCAGCC GCC                                              23

(2) INFORMATION FOR SEQ ID NO:568:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:568:

CAGTCTGTCG TGACGCAGCC GCC                                              23

(2) INFORMATION FOR SEQ ID NO:569:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:569:

CARTCTGCCC TGACTCAGCC T                                                21

(2) INFORMATION FOR SEQ ID NO:570:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:570:

TCCTATGWGC TGACTCAGCC ACC                                              23

(2) INFORMATION FOR SEQ ID NO:571:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:571:

TCTTCTGAGC TGACTCAGGA CCC                                              23

(2) INFORMATION FOR SEQ ID NO:572:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:572:
```

```
CACGTTATAC TGACTCAACC GCC                                                23
```

(2) INFORMATION FOR SEQ ID NO:573:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:573:

```
CAGGCTGTGC TGACTCAGCC GTC                                                23
```

(2) INFORMATION FOR SEQ ID NO:574:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:574:

```
AATTTTATGC TGACTCAGCC CCA                                                23
```

(2) INFORMATION FOR SEQ ID NO:575:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:575:

```
CAGRCTGTGG TGACYCAGGA GCC                                                23
```

(2) INFORMATION FOR SEQ ID NO:576:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:576:

```
CWGCCTGTGC TGACTCAGCC MCC                                                23
```

(2) INFORMATION FOR SEQ ID NO:577:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:577:

```
TGAACATTCT GTAGGGGCCA CTG                                                23
```

(2) INFORMATION FOR SEQ ID NO:578:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:578:

```
AGAGCATTCT GCAGGGGCCA CTG                                                23
```

(2) INFORMATION FOR SEQ ID NO:579:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:579:

ACCGCCTCCA CCAGTGCACA GTCTGTGCTG ACTCAGCCAC C          41

(2) INFORMATION FOR SEQ ID NO:580:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:580:

ACCGCCTCCA CCAGTGCACA GTCTGTGYTG ACGCAGCCGC C          41

(2) INFORMATION FOR SEQ ID NO:581:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:581:

ACCGCCTCCA CCAGTGCACA GTCTGTCGTG ACGCAGCCGC C          41

(2) INFORMATION FOR SEQ ID NO:582:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:582:

ACCGCCTCCA CCAGTGCACA RTCTGCCCTG ACTCAGCCT            39

(2) INFORMATION FOR SEQ ID NO:583:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:583:

ACCGCCTCCA CCAGTGCACT TTCCTATGWG CTGACTCAGC CACC       44

(2) INFORMATION FOR SEQ ID NO:584:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:584:

ACCGCCTCCA CCAGTGCACT TTCTTCTGAG CTGACTCAGG ACCC       44

(2) INFORMATION FOR SEQ ID NO:585:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:585:

ACCGCCTCCA CCAGTGCACA CGTTATACTG ACTCAACCGC C                                41

(2) INFORMATION FOR SEQ ID NO:586:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:586:

ACCGCCTCCA CCAGTGCACA GGCTGTGCTG ACTCAGCCGT C                                41

(2) INFORMATION FOR SEQ ID NO:587:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:587:

ACCGCCTCCA CCAGTGCACT TAATTTTATG CTGACTCAGC CCCA                             44

(2) INFORMATION FOR SEQ ID NO:588:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:588:

ACCGCCTCCA CCAGTGCACA GRCTGTGGTG ACYCAGGAGC C                                41

(2) INFORMATION FOR SEQ ID NO:589:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:589:

ACCGCCTCCA CCAGTGCACW GCCTGTGCTG ACTCAGCCMC C                                41

(2) INFORMATION FOR SEQ ID NO:590:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:590:

ACCGCCTCCA CCGGGCGCGC CTTATTATGA ACATTCTGTA GGGGCCACTG                       50

(2) INFORMATION FOR SEQ ID NO:591:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO:591:

ACCGCCTCCA CCGGGCGCGC CTTATTAAGA GCATTCTGCA GGGGCCACTG        50

(2) INFORMATION FOR SEQ ID NO:592:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (xi) SEQUENCE DESCRIPTION: SEQ ID NO:592:

CGGGAAGGTG TGGACGCCGC TGGTC        25

(2) INFORMATION FOR SEQ ID NO:593:

(i) SEQUENCE CHARACTERISTICS:
      (A) LENGTH: 62 base pairs
      (B) TYPE: nucleic acid
      (C) STRANDEDNESS: single
      (D) TOPOLOGY: linear (xi) SEQUENCE DESCRIPTION: SEQ ID NO:593:

GAGTCATTCT CGGGCGCCCC TTGGGAATTC GCATGTTCAA AGCTTGGCGT AATCATGGTC        60

AT        62

(2) INFORMATION FOR SEQ ID NO:594:

(i) SEQUENCE CHARACTERISTICS:
      (A) LENGTH: 90 base pairs
      (B) TYPE: nucleic acid
      (C) STRANDEDNESS: single
      (D) TOPOLOGY: linear (xi) SEQUENCE DESCRIPTION: SEQ ID NO:594:

GTCCTCGCAA CTCAGCTGCA TATGGAGCTC GTTCAGTGCC CATGGTCAGA GTCGGGTACC        60

GCACGACAGG TTTCCCGACT GGAAAGCGGG        90

(2) INFORMATION FOR SEQ ID NO:595:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (xi) SEQUENCE DESCRIPTION: SEQ ID NO:595:

CTGACAGCCA GTGGTACCTA TCAACTAATT ATAGCAATCA TTTACGCG        48

(2) INFORMATION FOR SEQ ID NO:596:

(i) SEQUENCE CHARACTERISTICS:
      (A) LENGTH: 81 base pairs
      (B) TYPE: nucleic acid
      (C) STRANDEDNESS: single
      (D) TOPOLOGY: linear (xi) SEQUENCE DESCRIPTION: SEQ ID NO:596:

-continued

```
GTCGAGAGGG CTGGTCTCCC ATGCCAATTT CACAGTAAGG AGGTTTAACT TATGTCCAAT        60

TTACTGACCG TACACCAAAA T                                                 81
```

(2) INFORMATION FOR SEQ ID NO:597:

(i) SEQUENCE CHARACTERISTICS:
        (A) LENGTH: 34 base pairs
        (B) TYPE: nucleic acid
        (C) STRANDEDNESS: double
        (D) TOPOLOGY: circular (xi) SEQUENCE DESCRIPTION: SEQ ID NO:597:

```
ATAACTTCGT ATAANNTANN CTATACGAAG TTAT                                   34
```

(2) INFORMATION FOR SEQ ID NO:598:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:598:

```
ATTGTCGCAC CTGATTGC                                                     18
```

(2) INFORMATION FOR SEQ ID NO: 599:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO: 599:

Thr Val Ala Ala
1

(2) INFORMATION FOR SEQ ID NO: 600:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 600:

Ser Ser Ala Ser Thr Lys Gly Pro Ser
1               5